(12) United States Patent
Antipov et al.

(10) Patent No.: US 11,879,002 B2
(45) Date of Patent: *Jan. 23, 2024

(54) BI-SPECIFIC THERAPEUTIC PROTEINS, IN VIVO METHODS OF USE THEREOF AND ENCODING NUCLEIC ACIDS THEREOF

(71) Applicant: Silver Creek Pharmaceuticals, Inc., San Francisco, CA (US)

(72) Inventors: Laura D. J. Antipov, Oakland, CA (US); Shawdee Eshghi, Oakland, CA (US); Kristopher M. Kuchenbecker, Phoenix, AZ (US); Bjorn L. Millard, Orinda, CA (US); Matthew D. Onsum, El Cerrito, CA (US); Andrea D. Nickerson, San Francisco, CA (US); Timothy R. Stowe, San Francisco, CA (US); Yan Zhang, San Francisco, CA (US)

(73) Assignee: Silver Creek Pharmaceuticals, Inc., San Francisco, CA (US)

( * ) Notice: Subject to any disclaimer, the term of this patent is extended or adjusted under 35 U.S.C. 154(b) by 169 days.

This patent is subject to a terminal disclaimer.

(21) Appl. No.: 17/487,120

(22) Filed: Sep. 28, 2021

(65) Prior Publication Data

US 2022/0009991 A1 Jan. 13, 2022

Related U.S. Application Data

(60) Continuation of application No. 16/820,960, filed on Mar. 17, 2020, now Pat. No. 11,155,593, which is a division of application No. 16/026,319, filed on Jul. 3, 2018, now Pat. No. 10,633,425, which is a continuation of application No. 15/281,795, filed on Sep. 30, 2016, now Pat. No. 10,040,840.

(60) Provisional application No. 62/322,910, filed on Apr. 15, 2016, provisional application No. 62/237,889, filed on Oct. 6, 2015, provisional application No. 62/236,169, filed on Oct. 2, 2015.

(51) Int. Cl.
| | |
|---|---|
| *C07K 14/65* | (2006.01) |
| *C07K 14/47* | (2006.01) |
| *C07K 14/765* | (2006.01) |
| *A61K 38/00* | (2006.01) |

(52) U.S. Cl.
CPC .............. *C07K 14/65* (2013.01); *C07K 14/47* (2013.01); *C07K 14/765* (2013.01); *A61K 38/00* (2013.01); *C07K 2319/035* (2013.01); *C07K 2319/33* (2013.01); *C07K 2319/75* (2013.01)

(58) Field of Classification Search
CPC ...... C07K 14/65; C07K 14/47; C07K 14/765; A61K 38/00
See application file for complete search history.

(56) References Cited

U.S. PATENT DOCUMENTS

| | | | |
|---|---|---|---|
| 5,273,966 | A | 12/1993 | Sknottner-Lundin et al. |
| 5,444,045 | A * | 8/1995 | Francis .................. C07K 14/65 |
| | | | 514/4.8 |
| 5,632,986 | A | 5/1997 | Tait et al. |
| 5,679,771 | A | 10/1997 | Ballard et al. |
| 6,387,663 | B1 | 5/2002 | Hall et al. |
| 6,556,098 | B2 | 5/2003 | Chan et al. |
| 7,226,907 | B1 | 6/2007 | Zhou |
| 7,459,541 | B2 | 12/2008 | Hall et al. |
| 7,521,211 | B2 | 4/2009 | Glass |
| 7,531,318 | B2 | 5/2009 | Srivastava et al. |
| 7,576,186 | B2 | 8/2009 | Lum et al. |
| 7,612,164 | B2 | 11/2009 | Zho et al. |
| 3,067,357 | A1 | 11/2011 | Reutelingsperger et al. |
| 8,158,581 | B2 | 4/2012 | Glas et al. |
| 8,691,771 | B2 | 4/2014 | Nielsen et al. |
| 8,748,380 | B2 | 6/2014 | Plumridge et al. |
| 9,238,080 | B2 | 1/2016 | Nielsen et al. |
| 9,718,892 | B2 | 8/2017 | Nielsen et al. |
| 9,982,060 | B2 | 5/2018 | Nielsen et al. |
| 10,040,840 | B2 | 8/2018 | Antipov et al. |
| 10,407,512 | B2 | 9/2019 | Nielsen et al. |
| 10,633,425 | B2 | 4/2020 | Antipov et al. |
| 10,858,450 | B2 | 12/2020 | Nielsen et al. |
| 10,988,547 | B2 | 4/2021 | Nielsen et al. |
| 2003/0153490 | A1 | 8/2003 | Tchelingerian |
| 2004/0213738 | A1 | 10/2004 | Croll-Kalish et al. |
| 2005/0043236 | A1 | 2/2005 | Daly et al. |
| 2005/0164926 | A1 | 7/2005 | Wun |
| 2005/0287151 | A1 | 12/2005 | Glass |
| 2006/0018897 | A1 | 1/2006 | Lee et al. |
| 2006/0223753 | A1 | 10/2006 | Glass |
| 2006/0228299 | A1 | 10/2006 | Thorpe et al. |
| 2006/0275254 | A1 | 12/2006 | Kim et al. |
| 2007/0054851 | A1 | 3/2007 | Lin et al. |
| 2007/0110733 | A1 | 5/2007 | Lum |
| 2007/0172811 | A1 | 7/2007 | Srivastava et al. |
| 2007/0224119 | A1 | 9/2007 | McTavish |

(Continued)

FOREIGN PATENT DOCUMENTS

| | | |
|---|---|---|
| AU | 2008-200706 | 3/2008 |
| AU | 2015204540 | 8/2016 |

(Continued)

OTHER PUBLICATIONS

Adderson, E., et al., "Molecular analysis of polyreactive monoclonal antibodies from rheumatic carditis: human anti-N-acetylglucosamine/anti-myosin antibody V region genes," J Immunol., 161(4):2020-2031, (Aug. 15, 1998).

(Continued)

*Primary Examiner* — Robert S Landsman
(74) *Attorney, Agent, or Firm* — Greenberg Traurig, LLP; Natalie Salem; David J. Dykeman

(57) ABSTRACT

Bi-specific fusion proteins with therapeutic uses are provided, as well as pharmaceutical compositions comprising such fusion proteins, and methods for using such fusion proteins to repair or regenerate damaged or diseased tissue.

19 Claims, 15 Drawing Sheets

Specification includes a Sequence Listing.

(56) References Cited

U.S. PATENT DOCUMENTS

| | | | |
|---|---|---|---|
| 2008/0039341 | A1 | 2/2008 | Schellenberger et al. |
| 2008/0050370 | A1 | 2/2008 | Glaser et al. |
| 2008/0069823 | A1 | 3/2008 | Allison |
| 2008/0071063 | A1 | 3/2008 | Allan et al. |
| 2008/0241118 | A1 | 10/2008 | LeBowitz |
| 2009/0068181 | A1 | 3/2009 | Lee et al. |
| 2009/0093407 | A1 | 4/2009 | Hall et al. |
| 2009/0214507 | A1 | 8/2009 | Srivastava et al. |
| 2010/0055115 | A1 | 3/2010 | Lum et al. |
| 2010/0197890 | A1 | 8/2010 | McTavish |
| 2010/0291080 | A1 | 11/2010 | Lee et al. |
| 2011/0045007 | A1 | 2/2011 | Schuurman et al. |
| 2011/0059076 | A1 | 3/2011 | McDonagh et al. |
| 2011/0274658 | A1 | 11/2011 | Silver et al. |
| 2011/0293579 | A1 | 12/2011 | Nielsen et al. |
| 2012/0177652 | A1 | 7/2012 | Nielsen et al. |
| 2012/0244163 | A1 | 9/2012 | Schoeberl et al. |
| 2014/0315817 | A1 | 10/2014 | Schmidt et al. |
| 2017/0096469 | A1 | 4/2017 | Antipov et al. |
| 2019/0169258 | A1 | 6/2019 | Antipov et al. |
| 2020/0207826 | A1 | 7/2020 | Antipov et al. |
| 2021/0214463 | A1 | 7/2021 | Nielsen et al. |

FOREIGN PATENT DOCUMENTS

| | | |
|---|---|---|
| CA | 2286264 | 10/1998 |
| CA | 2768621 | 1/2011 |
| CA | 2902744 | 10/2014 |
| EP | 854884 | 7/1998 |
| EP | 1141015 | 10/2001 |
| EP | 1436316 | 7/2004 |
| EP | 2275446 | 1/2011 |
| EP | 2900255 | 8/2015 |
| WO | 1992/008495 | 5/1992 |
| WO | 1995/032003 | 11/1995 |
| WO | 1996/033698 | 10/1996 |
| WO | 2000/002587 | 1/2000 |
| WO | 2002/017951 | 3/2002 |
| WO | 2005/117973 | 12/2005 |
| WO | 2006/003488 | 1/2006 |
| WO | 2006/004910 | 1/2006 |
| WO | 2006/076525 | 7/2006 |
| WO | 2006/079120 | 7/2006 |
| WO | 2006/091209 | 8/2006 |
| WO | 2006/128125 | 11/2006 |
| WO | 2007/021494 | 2/2007 |
| WO | 2007/044887 | 4/2007 |
| WO | 2008/063424 | 5/2008 |
| WO | 2008/089567 | 7/2008 |
| WO | 2008/091209 | 8/2008 |
| WO | 2008/096158 | 8/2008 |
| WO | 2008/151005 | 12/2008 |
| WO | 2008/155134 | 12/2008 |
| WO | 2009/030720 | 3/2009 |
| WO | 2009/126920 | 10/2009 |
| WO | 2010/059315 | 5/2010 |
| WO | 2011/011071 | 1/2011 |
| WO | 2011/146902 | 11/2011 |
| WO | 2012/078153 | 6/2012 |
| WO | 2013/086785 | 6/2013 |

OTHER PUBLICATIONS

Andrades, et al., "Engineering, expression, and renaturation of a collagen-targeted human bFGF fusion protein," Growth Factors, 18:261-275, (Aug. 1999).

Askari, et al., "Effect of stromal-cell-derived factor 1 on stem-cell homing and tissue regeneration in ischaemic cardiomyopathy," Mechanisms of Disease, 362: 697-703, (Aug. 30, 2003).

Bai et al., "Tracking long-term survival of intramyocardially delivered human adipose tissue-derived stem cells using bioluminescence imaging," Molecular Imaging and Biology, 13 pages (2010).

Barbas, S., et al., "Human autoantibody recognition of DNA," Proc Natl Acad Sci U S A, 92(7):2529-2533, (Mar. 28, 1995).

Bauwens, C., et al., "Geometric control of cardiomyogenic induction in human pluripotent stem cells", Tissue Eng., Part A, (Apr. 25, 2011).

Bayne, Marvin et al., "The Roles of Tyrosines 24,31, and 60 in the High Affinity Binding of Insulin-like Growth Factor-I to the Type 1 Insulin-like Growth Factor Receptor", The Journal of Biological Chemistry, vol. 265, No. 26, Issue of Sep. 15, pp. 15648-15652, 1990.

Bersell, et al., "Neuregulin1/ErbB4 signaling induces cardiomyocyte proliferation and repair of heart injury," Cell, 138:257-270, (Jul. 24, 2009).

Black, S., "In vivo models of myocardial ischemia and reperfusion injury: application to drug discovery and evaluation," J. Pharmacol. Toxicol. Methods 43(2):153-167, (Mar.-Apr. 2000).

Bock-Marquette, et al., "Thymosin B4 activates integrin-linked kinase and promotes cardiac cell migration, survival and cardiac repair," Nature, 432:466-472, (Nov. 25, 2004).

Buerke, et al., "Cardioprotective effect of insulin-like growth factor I in myocardial ischemia followed by reperfusion," Proc. Natl. Acad. Sci. USA, 92: 8031-8035, (Aug. 1995).

Bujak, "The Role of TGF-β Signaling in Myocardial Infarction and Cardiac Remodeling", 2007, Cardiovascular Research , vol. 74. Issued 2, pp. 184-195.

Burchfield, et al., "Interleukin-10 from transplanted bone marrow mononuclear cells contributes to cardiac protection after myocardial infarction," Circulation Research, 15 pages, (Mar. 23, 2011).

Burchfield, et al., "Role of paracrine factors in stem and progenitor cell mediated cardiac repair and tissue fibrosis," Fibrogenesis and Tissue Repair, 1(4):1-11, (2008).

Burchfield, et al., "The cytoprotective effects of tumor necrosis factor are conveyed through tumor necrosis factor receptor-associated factor 2 in the heart," Circulation Heart Failure, 16 pages, (Jan. 2010).

Burrill, Devin et al., "Targeted erythropoietin selectively stimulates red blood cell expansion in vivo", Proceedings of the National Academy of Sciences of the United States of America (PNAS), vol. 113, No. 19, pp. 5245-5250, May 10, 2016.

Chen, et al . "Effects of receptor binding on plasma half-life of bifunctional transferrin fusion proteins," Molecular Pharmaceutics 8: 457-65 (2011).

Chen, et al., "Localization of monoclonal antibody TNT-1 in experimental kidney infarction of the mouse," FASEB J., 4(12):3033-3039, (Sep. 1, 1990).

Chimenti, et al., "Myocardial infarction: animal models," Methods. Mol. Med., 98:217-226, (2004).

Christman, et al., "Enhanced neovasculature formation in ischemic myocardium following delivery of pleiotrophin plasmid in a biopolymer," Biomaterials, 26:1139-1144 (2005).

Cironi, Pablo et al., "Enhancement of Cell Type Specificity by Quantitative Modulation of Chimeric Ligand", The Journal of Biological Chemistry, vol. 283, No. 13, pp. 8460-8476, Mar. 28, 2008.

Davis, "Local myocardial insulin-like growth factor 1 (IGF-1) delivery with biotinylated peptide nanofibers improves cell therapy for myocardial infarction," Proc. Natl. Acad. Sci USA, 103(21):8155-8160, (May 23, 2006).

Davletov, A. & Sudhof, T., "A single C2 domain from synaptotagmin I is sufficient for high affinity Ca2+/phospholipid binding," J. Biol. Chem., 268(35):26386-2690, (Dec. 15, 1993).

Doldan-Martelli, V. et al., "A Mathematical Model for the Rational Design of Chimeric Ligands in Selective Drug Therapies", CPT: Pharmacometrics & Systems Pharmacology (2013) 2, e26.

Dorn II, M.D., "Periostin and myocardial repair, regeneration, and recovery," The New England Journal of Medicine, 357(15):1552-1554, (Oct. 11, 2007).

Dumont, et al., "Cardiomyocyte Death Induced by Myocardial Ischemia and Reperfusion: Measurement With Recombinant Human Annexin-V in a Mouse Model ," Circulation 102(13):1564-1568, (Sep. 26, 2000).

(56) References Cited

OTHER PUBLICATIONS

Engel, et al., "FGF1/p38 MAP kinase inhibitor therapy induces cardiomyocyte mitosis, reduces scarring, and rescues function after myocardial infarction," PNAS, 103(42):15546-15551, (Oct. 17, 2006).
Fracis, G.L., et al., "Novel recombinant fusion protein analogues of insulin-like growth factor (IGF)-I indicate the relative importance of IGF-binding protein and receptor binding for enhanced biological potency", Journal of Molecular Endocrinology (1992), 8, pp. 213-223.
George, et al., "Typhostin AG-556 reduces myocardial infarct size and improves cardiac performance in the rat," Experimental and Molecular Pathology, 74:314-318 (2003).
Gnecchi, et al., "Evidence supporting paracrine hypothesis for Akt-modified mesenchymal stem cell-mediated cardiac protection and functional improvement," The FASEB Journal, 20:661-669, (Apr. 2006).
Gnecchi, et al., "Paracrine mechanisms in adult stem cell signaling and therapy," Adult Stem Cells and Paracrine Effects, 1204-1219, (Nov. 2008).
Greenberg, et al., "Chapter 7. Mouse models of ischemic angiogenesis and ischemia-reperfusion injury," Methods Enzymol., 444:159-174, (2008).
Gripenberg, et al., "A Solid Phase Enzyme-linked Immunosorbent Assay (ELISA) for the Demonstration of Antibodies against Denatured, Single-stranded DNA in Patient Sera," Scand. J. Immunol., 7(2):151-157, (Feb. 1978).
Han, et al., "Refolding of a recombinant collagen-targeted TGF-B2 fusion protein expressed in *Escherichia coli*," Protein Expression and Purification, 11:169-178 (1997).
Hashino, K., et al., "A 31-kDa Recombinant Fibronectin Cell-Binding Domain Fragment: Its Binding to Receptor, Cell Adhesive Activity, and Fusion Proteins," J. Biochem., 119(4):604-609, (Apr. 4, 1996).
Hausenloy et al., "Cardioprotective growth factors," Cardiovascular Research, 83: 179-194, (2009).
Hefta, et al., "Measuring Affinity Using Biosensors", in "Antibody engineering: A Practical Approach", pp. 99-116, Oxford University Press, 1996, Edited by McCafferty et al., (Hames B.D.eds).
Henson, et al. "Surviving cell death through epidermal growth factor (EGF) signal transduction pathways: Implications for cancer therapy", 2006, Cellular Signaling, vol. 18, pp. 2089-2097.
Hinkel et al., "Thymosin B4 is an essential paracrine factor of embryonic endothelial progenitor cell-mediated cardioprotection," Circulation, 2232-2240 (Apr. 29, 2008).
Hoberg, E., et al., "Monoclonal antibodies specific for human cardiac myosin: selection, characterization and experimental myocardial infarct imaging," Eur Heart J., 9(3):328-236, (Mar. 1988).
Hofstra, et al., "Visualisation of cell death in vivo in patients with acute myocardial infarction," The Lancet, 356(9225):209-212, (2000).
Hsieh et al., "Local controlled intramyocardial delivery of plateet-derived growth factor improves postinfarction ventricular function without pulmonary toxicity," Circulation, 637-644, (Aug. 15, 2006).
Hu et al., Stromal cell-derived factor-1a confers protection against myocardial ischemia/reperfusion injury, Molecular Cardiology, 654-663, (Aug. 7, 2007).
Ieda, et al., "Cardiac fibroblasts regulate myocardial proliferation through B1 integrin signaling," Developmental Cell, 16: 233-244 (Feb. 17, 2009).
Igarashi, K., et al., "Specific binding of a synthetic peptide derived from an antibody complementarity determining region to phosphatidylserine," J Biochem., 117(2):452-457, (Feb. 1995).
Ishikawa, et al., "Production of biologically active epidermal growth factor fusion protein with high collagen affinity," J. Biochem., 129(4): 627-633 (2001).
Jeon, et al., "Long-term and zero-order release of basic fibroblast growth factor from heparin-conjugated poly(L-lactide-co-glycolide) nanospheres and fibrin gel," Biomaterials, 27:1598-1607 (2006).

Kanashiro-Takeuchi, et al., "Cardioprotective effects of growth hormone-releasing hormone agonist after myocardial infarction," PNAS, 107(6):2604-2609, (Feb. 9, 2010).
Kardami, et al., "Fibroblast growth factor-2 and cardioprotection," Heart Fail Rev., 12:267-277 (2007).
Kawase Y. et al. "Construction and characterization of a fusion protein with epidermal growth factor and the cell-binding domain of fibronectin" FEBS letters, 298(2-3),: 126-128, 1992.
Kenis, H., et al., "Annexin A5 uptake in ischemic myocardium: demonstration of reversible phosphatidylserine externalization and feasibility of radionuclide imaging," J Nucl Med., 51(2):259-67, (Feb. 2010).
Kenis, H., et al., "Cell surface-expressed phosphatidylserine and annexin A5 open a novel portal of cell entry," J Biol Chem., 279(50):52623-52629, Epub Sep. 20, 2004, (Dec. 10, 2004).
Khaw, B., et al., "Monoclonal antibody to cardiac myosin: imaging of experimental myocardial infarction," Hybridoma, 3(1):11-23, (1984).
Klopsch, et al., "Intracardiac injection of erythropoietin induces stem cell recruitment and improves cardiac functions in a rat myocardial infarction model," J. Cell. Mol. Med. 13(4): 664-679, (2009).
Ko, Y., et al., "Gene delivery into ischemic myocardium by double-targeted lipoplexes with anti-myosin antibody and TAT peptide," Gene Ther., 16(1):52-9. Epub Aug. 14, 2008, (Jan. 2009).
Kobayashi, et al., "Effect of atrial natriuretic peptide on ischemia-reperfusion injury in a porcine total hepatic vascular exclusion model," World J. Gastroenterol., 13(25):3487-3492, (Jul. 7, 2007).
Kuhn, et al., "Periostin induces proliferation of differentiated cardiomyocytes and promotes cardiac repair," Nature Medicine, 13(8):962-969, (Aug. 2007).
Kuramochi, "Cardiac Endothelial Cells Regulate Reactive Oxygen Species-induced Cardiomyocyte Apoptosis through Neuregulin-1_/erbB4 Signaling*," J. Biol. Chem., 279(49): 51141-51147, (2004).
Laroche-Traineau, J., et al., "A human monoclonal antibody obtained from EBV-transformed B cells with specificity for myosin," Br J Haematol., 91(4):951-962, (Dec. 1995).
Laroche-Traineau, J., et al., "Analysis of the V genes coding for a monospecific human antibody to myosin and functional expression of single chain Fv fragments," FEBS Lett., 460(1):86-92, (Oct. 22, 1999).
Laroche-Traineau, J., et al., "Three-step purification of bacterially expressed human single-chain Fv antibodies for clinical applications," J Chromatogr B Biomed Sci Appl., 737(1-2):107-117, (Jan. 14, 2000).
Liang, W., et al., "ATP-containing immunoliposomes specific for cardiac myosin," Curr Drug Deliv., 1(1):1-7, (Jan. 2004).
Liu, et al., "Neuregulin-1/erbB-activation improves cardiac function and survival in models of ischemic, dilated, and viral cardiomyopathy," Journal of the American College of Cardiology, 48(7):1438-1447, (Oct. 3, 2006).
Lorts, et al., "Genetic manipulation of periostin expression in the heart does not affect myocyte content, cell cycle activity, or cardiac repair," UltraRapid Communication, e1-e7, (Jan. 2, 2009).
Marshall, K.W. & Marks, J.D. "Engineering and characterization of a novel fusion protein incorporating B7.2 and an anti-ErbB-2 single-chain antibody fragment for the activation of Jurkat T cells," Journal of Immunotherapy. Hagerstown, Md.: 1997) 24: 27-36 (2001).
Mihardja, et al., "Targeted in vivo extracellular matrix formation promotes neovascularization in a rodent model of myocardial infarction," PLoS One, 5(4):e10384 (8 pages), (Apr. 2010).
Mira, et al., "Inhibition of cytosolic phospholipase A2 by annexin V in differentiated permeabilized HL-60 cells. Evidence of crucial importance of domain I type II Ca2+-binding site in the mechanism of inhibition," J. Biol Chem., 272(16):10474-10482, (Apr. 18, 1997).
Miranda, et al., "Endothelium-dependent and -independent hepatic artery vasodilatation is not impaired in a canine model of liver ischemia-reperfusion injury," Braz. J. Med. Biol. Res., 40(6):857-865, (Jun. 2007).

(56) References Cited

OTHER PUBLICATIONS

Murray and Brown, "Measurement of association constants in ELISA. Reactions between solid-phase antibody and fluid-phase biotinylated antigen," J. Immunol. Methods., 127(1):25-28 (Feb. 20, 1990).
Nedelman, M., et al., "Rapid infarct imaging with a technetium-99m-labeled antimyosin recombinant single-chain Fv: evaluation in a canine model of acute myocardial infarction," J Nucl Med., 34(2):234-241, (Feb. 1993).
Nelson, P., et al. "Characterization of anti-myosin monoclonal antibodies," Hybridoma (Larchmt), 24(6):314-318, (Dec. 2005).
Nimni, "Polypeptide growth factors: targeted delivery systems," Biomaterials, 18(18):1201-1225, (1997).
Nishi, et al., "Collagen-binding growth factors: Production and characterization of functional fusion proteins having a collagen-binding domain," Proc. Natl. Acad. Sci. USA, 95:7018-7023, (Jun. 1998).
Pak, K., et al., "An instant kit method for labeling antimyosin Fab' with technetium-99m: evaluation in an experimental myocardial infarct model," J. Nucl Med., 33(1):144-149, (Jan. 1992).
Peter, K., et al., "Construction and functional evaluation of a single-chain antibody fusion protein with fibrin targeting and thrombin inhibition after activation by factor Xa," Circulation, 101(10):1158-1164, (Mar. 14, 2000).
Pietronave, et al., "Agonist monoclonal antibodies against HGF receptor protect cardiac muscle cells from apoptosis," Am J Physiol Heart circ Physiol, 298:H1155-H1165, (2010).
Prior, et al. "Cytotoxic Activity of a Recombinant Fusion Protein between Insulin-like Growth Factor I and Pseudomonas Exotoxin," Cancer, 174-180 (1991).
Rosenthal, et al., "Growth factor enhancement of cardiac regeneration," Cell Transplantation, 15(1):S41-S45, (2006).
Saxena, et al., "Stromal cell-derived factor-1a is cardioprotective after mocardial infarction," Molecular Cardiology, 2224-2231, (2008).
Schutters, K. & Reutelingsperger, C.P.M. "Phosphatidylserine targeting for diagnosis and treatment of human diseases," Apoptosis□: An International Journal on Programmed Cell Death. 15:1072-82, (2010).
Scott, et al. "Aiming for the heart: targeted delivery of drugs to diseased cardiac tissue," Expert Opinion on Drug Delivery, 5:459-70, (2008).
Scott, R.C. et al. "Targeted Delivery of Antibody Conjugated Liposomal Drug Carriers to Rat Myocardial Infarction," Biotechnology, 96:795-802, (2007).
Scott, R.C. et al. "Targeting VEGF-encapsulated immunoliposomes to MI heart improves vascularity and cardiac function". The FASEB Journal□: Official Publication of the Federation of American Societies for Experimental Biology, 23:3361-7, (2009).
Segers, et al., "Protein therapeutics for cardiac regeneration after myocradial infarction," J. of Cardiovasc. Trans. Res., 9 pages, (Jul. 7, 2010).
Shan, et al., "Overexpression of TRPC3 increases apoptosis but not necrosis in response to ischemia-reperfusion in adult mouse cardiomyocytes," Am. J. Physiol. Cell. Physiol., 294(3):833-841, (Mar. 2008).
Shin, et al. "Functional properties of antibody insulin-like growth factor fusion proteins," The Journal of Biological Chemistry, 269: 4979-8,5 (1994).
Shin, S.U. & Morrison, S.L., "Expression and characterization of an antibody binding specificity joined to insulin-like growth factor 1: potential applications for cellular targeting," Proceedings of the National Academy of Sciences of the United States of America, 87:5322-6, (1990).
Simeonova, P., et al., "Identification of human ventricular myosin heavy chain fragments with monoclonal antibody 2F4 in human sera after myocardial necrosis," Clin Chim Acta., 201(3):207-221, (Sep. 30, 1991).
Stamm et al. Human ortholog to mouse gene imap38 encoding an ER-localized G-protein belongs to the a gene family clustered on chromosome 7q32-36, Gene vol. 282: 159-167, 2003.
Stokes, et al., "A simple, rapid ELISA method for the detection of DNA antibodies," J. Clin. Pathol., 35(5):566-573, (May 1982).
Suleiman, et al., "Apoptosis and the cardiac action of insulin-like growth factor I," Pharmacology and Therapeutics, 114:278-294, (2007).
Sutton, R., et al., "Structure of the first C2 domain of synaptotagmin I: a novel Ca2+/phospholipid-binding fold," Cell, 80(6):929-938, (Mar. 24, 1995).
Tuan et al. "Engineering, expression and renaturation of targeted TGF-beta fusion proteins"; Connect Tissue Res. 1996;34(1):1-9.
Ueda, et al., "A potential cardioprotective role of hepatocyte growth factor in myocardial infarction in rats," Cardiovascular Research, 51:41-50, (2001).
Umeda, M., et al., "Effective production of monoclonal antibodies against phosphatidylserine: stereo-specific recognition of phosphatidylserine by monoclonal antibody," J Immunol., 143(7):2273-2279, (Oct. 1, 1989).
Ungethum, et al., "Engineered annexin A5 variants have impaired cell entry for molecular imaging of apoptosis using pretargeting strategies," J Biol Chem., 286(3):1903-10. Epub Nov. 15, 2010, (Jan. 21, 2011).
Urbanek K et al., "Myocardial regeneration by activation of multipotent cardiac stem cells in ischemic heart failure," Proc. Natl. Acad. Sci. USA, 102(24):8692-8697, (Jun. 14, 2005).
Wang, et al., "Degradable PLGA scaffolds with basic fibroblast growth factor," Texas Heart Institute Journal, 89-97, (2009).
Wassaf, et al., "High-throughput affinity ranking of antibodies using surface plasmon resonance microarrays," Anal. Biochem., 351(2):241-253, (Apr. 15, 2006).
Winter, et al. "A new bioassay for the immunocytokine L19-IL2 for simultaneous analysis of both functional moieties," Journal of Pharmaceutical and Biomedical Analysis, 54:81-6 (2011).
Yang L. et al., "Human cardiovascular progenitor cells develop from a KDR+ embryonic-stem-cell-derived population", Nature. May 22, 2008;453(7194):524-8. Epub Apr. 23, 2008.
Yeghiazarians, et al., "Injection of bone marrow cell extract into infarcted hearts results in functional improvement comparable to intact cell therapy," The American Society of Gene Therapy, 17(7):1250-1256, (Jul. 2009).
Zaruba, et al., "Synergy between CD26/DPP-IV inhibition and G-CSF improves cardiac function after acute myocardial infarction," Cell Stem Cell, 4:313-323, (Apr. 3, 2009).
Zbinden, et al., "Interanimal variability in preexisting collaterals is a major factor determining outcome in experimental angiogenesis trials," Am. J. Physiol. Heart Circ. Physiol., 292(4): H1891-H1897, (Apr. 2007).
Zentilin, et al., "Cardiomyocyte VEGFR-1 activation by VEGF-B induces compensatory hypertrophy and preserves cardiac function after myocardial infarction," The FASEB Journal, 24:1467-1478, (May 2010).
Zhang, J. et al. "Collagen-targeting vascular endothelial growth factor improves cardiac performance after myocardial infarction," Circulation, 119:1776-84, (2009).
Zhao, et al., "Neuregulins promote survival and growth of cardiac myocytes," The Journal of Biological Chemistry, 273(17):0261-10269, (Apr. 24, 1998).
Zhao, et al., "Recruitment of endogenous stem cells for tissue repair," Macromolecular Bioscience, 8:836-842, (2008).
Ziegler M et al. "The bispecific SDF1-GPVI fusion protein preserves myocardial function after transient ischemia in mice" Circulation. Feb. 7, 2012;125(5):685-96. doi: 10.1161/CIRCULATION. 111.070508. Epub Jan. 5, 2012.
Stowe, et al., Engineering Growth Factors for Cardiomyocyte Survival and Regeneration Following Ischemic Injury. American Heart Association Basic Cardiovascular Science [online Jul. 15, 2014 [retrieved Dec. 5, 2016].
International Search Report in International Application No. PCT/US2016/054744 dated Mar. 10, 2017.
Zhao, Ming, et al., 99m Tc-Labeled C2A Domain of Synaptotagmin I as a Target-Specific Molecular Probe for Noninvasive Imaging of Acute Myocardial Infarction, The Journal of Nuclear Medicine, vol. 47, No. 8, Aug. 2006, pp. 1367-1374.
O' Sullivan et al., "Potent Long-Term Cardioprotective Effects of Single Low-Dose Insulin-Like Growth Factor-1 Treatment Postmyocardial Infarction", American Heart Association—Circulation: Cardiovascular Interventions, 4:327-335, Jun. 28, 2011.
Dubaquie, Y. et al. "Total Alanine-Scanning Mutagenesis of Insulin-Like Growth Factor I (IGF-I) Identifies Differential Binding Epitopes for IGFBP-1 and IGFBP-3", Biochemistry, 1999, 38, 6386-6396.

(56) References Cited

OTHER PUBLICATIONS

Epa, V.C. et al., "Model for the Complex between the insulin-like growth factor 1 and its receptors: towards designing antagonists for the IGF-1 receptor", Protein Engineering, Design & Selection, vol. 19, No. 8, pp. 377-384, 2006.
King et al., "Production and characterization of recombinant insulin-like growth factor-I (IGF-I) and potent analogues of IGF-I, with Gly or Arg substituted for Glu3, following their expression in *Escherichia colu* as fusion proteins", Journal of Molecular Endocrinology, (1992) 8, pp. 29-41.
Loddick, S. et al., "Displacement of insulin-like growth factors from their binding proteins as a potential treatment for stroke", PNAS, vol. 95, pp. 1894-1898, Feb. 1998.
Novo Nordisk Pharmatech A/S "How Insulin and IGF-1 Bind to the receptors" retrieved from http://novonordiskpharmatech.com/how-insulin0and-igf-1-bind-to-their-receptors/ ; retrieved Dec. 16, 2016.
Tomas, F.M. et al., "IGF-I variants which bind poorly to IGF-binding proteins show more potent and prolonged hypoglycemic action that native IGF-I in pigs and marmoset monkeys", Journal of Endocrinology (1997), 155, 377-386.
Laajoki, L. et al. Solution Structure and Backbone Dynamics of Long-[ARG3] Insulin-like Growth Factor-I; Journal of Biological Chemistry, vol. 275, No. 14, pp. 10009-10015, Apr. 7, 2000.
Sendoel, et al., "Apoptotic Cell Death Under Hypoxia", Physiology, vol. 29, pp. 168-176, 2014.

\* cited by examiner

FIG. 1B

| | |
|---|---|
| Targeted, potency-reduced, IGF1-based SGFs | |
| 606 | IGF1(LR3-R37x-3x)_Ik40_mHSA_Ik40_AnxVC316S_Ik8_His6 |
| 683 | IGF1(LR3-R37x-3x)_Ik40_Fc_Ik40_AnxVmS_Ik40_AnxVC316S |
| 711 | IGF1(LR3)_Ik15_mHSA_Ik15_AnxV |
| 713 | IGF1(LR3)_Ik15_mHSA_Ik15_AnxV(ni) |
| 716 | IGF1(LR3)_Ik15_mHSA7_Ik15_AnxV(ni) |
| 727 | IGF1(LR3-R37x-3x)_Ik40_mHSA_Ik40_AnxV |
| 728 | IGF1(LR3-Y60L)_Ik15_mHSA7_Ik15_AnxV(ni) |
| 729 | IGF1(LR3)_Ik7_mHSA_Ik7_AnxV |
| 730 | IGF1(LR3-R37x-3x)_Ik15_mHSA7_Ik15_AnxV(ni) |
| 731 | IGF1(LR3-Y24L/Y31A)_Ik15_mHSA7_Ik15_AnxV(ni) |
| 732 | IGF1(LR3-Y24L)_Ik15_mHSA7_Ik15_AnxV(ni) |
| 733 | IGF1(LR3-Y31A)_Ik15_mHSA7_Ik15_AnxV(ni) |
| 734 | IGF1(LR3-Y24L/Y31A)_Ik7_mHSA7_Ik7_AnxV(ni) |
| 737 | IGF1(LR3-Y31A)_Ik7_mHSA_Ik7_AnxV |
| 739 | IGF1(LR3-Y24L)_Ik7_mHSA_Ik7_AnxV(ni) |
| 740 | IGF1(LR3-Y31A)_Ik7_mHSA_Ik7_AnxV(ni) |
| 741 | IGF1(LR3-Y60L)_Ik7_mHSA_Ik7_AnxV(ni) |
| 743 | IGF1(LR3-R37x-3X)_Ik7_mHSA_Ik7_AnxV(ni) |
| Targeted, potency-reduced, Nrg1a-based SGFs | |
| 757 | Nrg1a_Ik7_mHSA_Ik7_AnxV(ni) |
| CONTROLS: | |
| Non-targeted, potency-reduced, IGF1-based SGFs | |
| 602 | IGF

FIG. 2A

| SGF | Identity | EC$_{50}$ (nM) | Fold potency reduction compared to WT GF |
|---|---|---|---|
| n/a | wt IGF1 | 1.22 ± 0.74 | 1 ± 0.86 |
| n/a | IGF1(LR3) | 0.73 ± 0.35 | 0.6 ± 0.46 |
| 649 | IGF1(LR3)_lk40_Fc_lk40_AnxVC316S | 2.31 ± 0.13 | 1.89 ± 1.15 |
| 688 | IGF1(LR3-R37x-3x)_lk40_Fc (non-targeted control) | 2.91 ± 0.67 | 2.39 ± 1.55 |
| 703 | IGF1(LR3)_lk15_mHSA (non-targeted control) | 7.46 | 6.11 |
| 711 | IGF1(LR3)_lk15_mHSA_lk15_AnxV | 8.52 ± 3.16 | 6.98 ± 4.97 |
| 683 | IGF1(LR3-R37x-3x)_lk40_Fc_lk40_AnxVmS_lk40_AnxVC316S | 8.6 ± 1.81 | 7.05 ± 4.53 |
| 713 | IGF1(LR3)_lk15_mHSA_lk15_AnxV(ni) | 8.87 | 7.27 |
| 729 | IGF1(LR3)_lk7_mHSA_lk7_AnxV | 9.25 ± 0.38 | 7.58 ± 4.61 |
| 716 | IGF1(LR3)_lk15_mHSA7_lk15_AnxV | 11.84 ± 3.71 | 9.7 ± 6.63 |
| 704 | IGF1(LR3)_lk15_mHSA7 (non-targeted control) | 12.52 ± 4.33 | 10.26 ± 7.17 |
| 727 | IGF1(LR3-R37x-3x)_lk40_mHSA_lk40_AnxV | 22.04 ± 5.74 | 18.07 ± 11.93 |
| 602 | IGF1(LR3-R37x)_lk40_mHSA_lk8_His6 (non-targeted control) | 35.35 ± 10.46 | 28.98 ± 19.56 |
| 606 | IGF1(LR3-R37x-3x)_lk40_mHSA_lk40_AnxVC316S_lk8_His6 | 35.52 ± 19.03 | 29.11 ± 23.56 |

FIG. 2B

| SGF | Identity | EC$_{50}$ (nM) | Fold potency reduction compared to WT GF |
|---|---|---|---|
| 743 | IGF1(LR3-R37X-3X)_lk7_mHSA_lk7_AnxV(ni) | 44.2 ± 21.6 | 36.23 ± 28.22 |
| 730 | IGF1(LR3-R37x-3x)_lk15_mHSA7_lk15_AnxV(ni) | 48.49 ± 1.46 | 39.75 ± 24.14 |
| 740 | IGF1(LR3-Y31A)_lk7_mHSA_lk7_AnxV(ni) | 65.98 ± 9.65 | 54.08 ± 33.74 |
| 733 | IGF1(LR3-Y31A)_lk15_mHSA7_lk15_AnxV(ni) | 191.73 ± 135.59 | 157.16 ± 146.42 |
| 739 | IGF1(LR3-Y24L)_lk7_mHSA_lk7_AnxV(ni) | 213.15 ± 0.64 | 174.71 ± 105.97 |
| 732 | IGF1(LR3-Y24L)_lk15_mHSA7_lk15_AnxV(ni) | 231.5 ± 179.32 | 189.75 ± 186.69 |
| 728 | IGF1(LR3_Y60L)_lk15_mHSA7_lk15_AnxV(ni) | 645.6 ± 329.65 | 529.18 ± 419.57 |
| 741 | IGF1(LR3-Y60L)_lk7_mHSA_lk7_AnxV(ni) | 915 | 750 |
| 731 | IGF1(LR3-Y24L/Y31A)_lk15_mHSA7_lk15_AnxV(ni) | 2041 ± 793.37 | 1672.95 ± 1205.24 |
| n/a | wt Nrg1a | 19.28 | 1 |
| 757 | Nrg1a_lk7_mHSA_lk7_AnxV(ni) | 76.53 ± 40.55 | 3.97 |

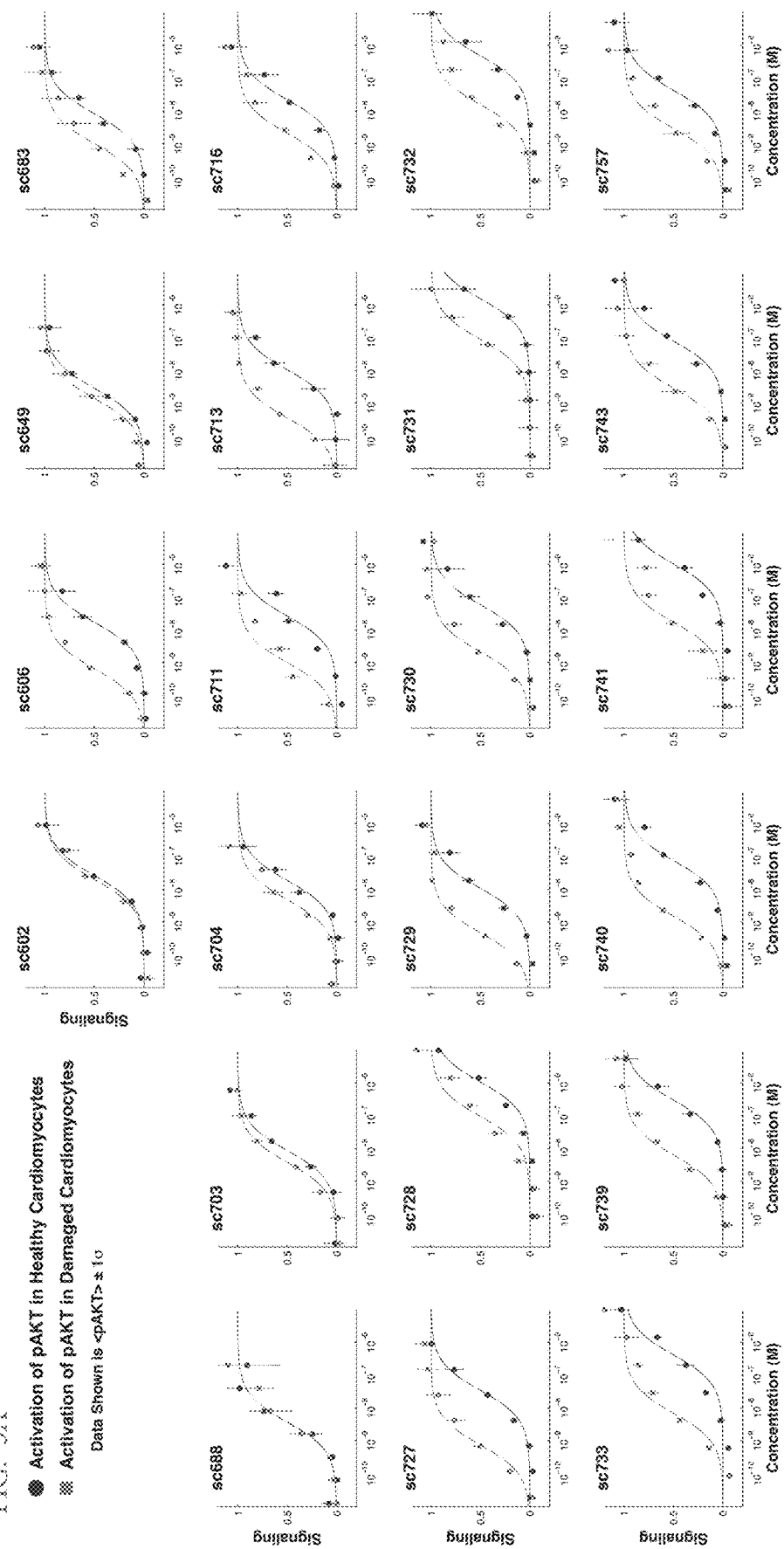

- sc776 Healthy Cardiomyocytes
- sc776 Damaged Cardiomyocytes
- sc777 Healthy Cardiomyocytes
- sc777 Damaged Cardiomyocytes

FIG. 6

| SGF | Dose | Half-life (h) | Decay Rate (1/h) |
|---|---|---|---|
| wt IGF1 | 3.2nmol/kg | 0.213 | 0.7970 |
| 727 | 16nmol/kg | 1.8184 | 0.3806 |
| 739 | 16nmol/kg | 3.2491 | 0.213 |
| 740 | 16nmol/kg | 3.6705 | 0.1885 |
| 741 | 16nmol/kg | 5.235 | 0.1322 |
| 743 | 16nmol/kg | 3.6827 | 0.1879 |
| 757 | 16nmol/kg | 4.919 | 0.1407 |

BI-SPECIFIC THERAPEUTIC PROTEINS, IN VIVO METHODS OF USE THEREOF AND ENCODING NUCLEIC ACIDS THEREOF

CROSS REFERENCE TO RELATED APPLICATIONS

This application is a continuation patent application of U.S. application Ser. No. 16/820,960, filed on Mar. 17, 2020, which is a divisional patent application of U.S. application Ser. No. 16/026,319, filed on Jul. 3, 2018, now U.S. Pat. No. 10,633,425, which is a continuation patent application of U.S. application Ser. No. 15/281,795, filed on Sep. 30, 2016, now U.S. Pat. No. 10,040,840, which claims the benefit of and priority to U.S. Provisional Application Ser. No. 62/236,169, filed Oct. 2, 2015, U.S. Provisional Application Ser. No. 62/237,889, filed Oct. 6, 2015, U.S. Provisional Application Ser. No. 62/322,910, filed Apr. 15, 2016, each of which are incorporated herein by reference in its entirety.

STATEMENT REGARDING FEDERALLY SPONSORED RESEARCH

This invention was made with government support under contract number 1R43HL124678-01A1 awarded by National Institute of Health (NIH) SBIR program. The government has certain rights in the invention.

REFERENCE TO SEQUENCE LISTING

This specification includes a sequence listing submitted herewith, which includes the file entitled 132463-010303/US_ST25.txt having the following size: 413,847 bytes which was created Sep. 30, 2016, the contents of which are incorporated by reference herein.

TECHNICAL FIELD

The present invention relates generally to proteins that have therapeutic uses, and more specifically to bi-specific proteins, pharmaceutical compositions comprising such proteins, and methods for using such proteins to repair damaged tissue.

BACKGROUND

Tissue regeneration is a multidisciplinary science in which the goal is to restore biological function of diseased or damaged tissues. Tissue regeneration addresses major clinical problems such as myocardial infarction. Myocardial infarction, commonly known as a heart attack, occurs when coronary artery obstruction cuts off the blood supply to part of the heart. The resulting lack of oxygen causes irreversible tissue damage (necrosis and apoptosis), due to the inability of the heart to sufficiently activate endogenous regeneration programs and self-repair. Such tissue damage is a leading cause of congestive heart failure, a condition in which the heart is no longer capable of effectively pumping blood and can results in kidney acute injury. In the United States, there are more than a million heart attacks every year, and nearly 5 million people are afflicted with congestive heart failure.

There are no effective treatments for regenerating damaged cardiac tissue. Current therapies for congestive heart failure focus on preventing arrhythmia, progression of arteriosclerosis and recurrent myocardial infarction, but do not address the underlying tissue damage. More than half of patients diagnosed with congestive heart failure die within five years of diagnosis.

There is, thus, a need in the art for methods for repairing or regenerating damaged tissues, and for improving the targeting of cells such as stem cells to facilitate tissue repair. The present invention fulfills these needs and provides other related advantages.

BRIEF SUMMARY OF THE INVENTION

The present invention provides bi-specific therapeutic proteins, nucleic acid molecules encoding bi-specific fusion proteins and therapeutic methods that employ such bi-specific therapeutic proteins to promote tissue survival, and/or regeneration of damaged tissue.

In some embodiments, the bi-specific fusion protein promotes tissue regeneration, cell survival, cell differentiation, inhibits apoptosis, induces cell proliferation, promotes cell growth, promotes motility of stem cells, promotes differentiation of stem cells, prevents cell damage, and/or promotes angiogenesis. In some embodiments, the tissue can be cardiac tissue, kidney tissue, bone, cartilage, joints, skin, liver tissue, pancreatic tissue, blood cells, lung tissue, brain tissue, and nervous tissue.

In other aspects, the present invention provides pharmaceutical compositions, comprising a bi-specific protein in combination with a physiologically acceptable carrier.

Within still further aspects, methods are provided for treating pathological tissue damage in a patient, comprising administering a pharmaceutical composition to a patient suffering from pathological tissue damage, and thereby decreasing pathological tissue damage in the patient.

In certain aspects, the present invention provides bi-specific proteins comprising (1) a targeting domain having a binding specificity to a target molecule associated with the outer surface of a cell of a tissue, and (2) an engineered activator domain having a binding specificity to a receptor associated with the surface of a cell of the tissue, wherein the engineered activator domain has a modified amino acid sequence of an amino acid sequence of a wild-type activator domain, wherein the engineered activator domain decreases activation of the receptor relative to the wild-type activator domain. In some embodiments, the activator domain is modified to decrease activation of the receptor relative to the wild-type activator domain by at least 3.5-fold. In some aspects, the activator domain when associated to the targeting domain in bi-specific protein exhibits a receptor activation at least twice stronger on cells containing the target molecule compared to cells that do not contain the target molecule as measured by phosphorylation of a receptor or a downstream effector molecule. In some embodiments, the bi-specific protein exhibits a receptor activation at least twice stronger on cells containing the target molecule compared to cells that do not contain the target molecule, as measured by phosphorylation of AKT.

In some embodiments, the engineered activator domain comprises the wild-type amino acid sequence modified to comprise a deletion, a substitution, an addition, an additional amino acid sequence at an N- and/or C-terminus or a combination thereof. In some embodiments, the engineered activator domain comprises a wild-type activator domain fused to a non-immunogenic protein. In some embodiments, the engineered activator domain comprises a modified amino acid sequence of an amino acid sequence of the wild-type activator domain fused to a non-immunogenic protein.

In some embodiments, the bi-specific protein further comprises a half-life modulator, wherein the half-life modulator increases the half-life of the bi-specific protein. The half-life modulator can comprise the sequence of Human Serum Albumin, Fc, scFc, Albumin binding domain, PASylation, human alpha-fetoprotein, or variants thereof.

In some embodiments, the engineered activator domain has a binding affinity to a growth factor receptor.

In some embodiments, the activator domain and targeting domain are recombinantly fused. Yet in other embodiments, the activator domain and targeting domain are chemically coupled or joined.

In some embodiments, the engineered activator domain comprises a growth factor. In some embodiments, the growth factor is IGF-1, NRG, or variants thereof.

In some embodiments, the targeting domain comprises Annexin A5 or variants thereof. In some embodiments, the Annexin A5 comprises an amino acid sequence set forth in any one of SEQ ID NOs: 1-4 or 122.

In some embodiments, the engineered activator domain comprises IGF-1 (LR3-Y31A). In some embodiments, the engineered activator domain comprises an amino acid sequence set forth in any one of SEQ ID NOs: 18, 19, 23, 24, 28, 29, or 120.

In some embodiments, the half-life modulator is Human Serum Albumin or variant thereof. In some embodiments, the Human Serum Albumin comprises an amino acid sequence set forth in any one of SEQ ID NOs: 54-56 or 124.

In some embodiments, the half-life modulator comprises Fc or variant thereof. In some embodiments, the Fc comprises an amino acid sequence set forth in any one of SEQ ID NOs: 53.

In some embodiments, the bi-specific protein further comprises a connector linking the engineered activator domain to the half-life modulator and a connector linking the half-life modulator to the targeting domain. In some embodiments, the connector comprises an amino acid sequence set forth in any one of SEQ ID NOs: 60-62 or 126-127.

In some embodiments, the engineered activator domain can be joined via a peptide bond to the amino terminus of the targeting domain. In some embodiments, the engineered activator domain can be joined via peptide bond to the carboxy terminus of the targeting domain.

In some aspects, the bi-specific protein comprises: (1) an activator domain, the activator domain comprising a growth factor, (2) a targeting domain, the targeting domain comprising a polypeptide that binds to phosphatidylserine at the outer surface of a damaged cell, the bi-specific protein having a half maximal effective concentration lower in the damaged cell ($EC50_{Damaged}$) than a healthy cell ($EC50_{Healthy}$). In some embodiments, the damaged cell can be a cell undergoing apoptosis or necrosis. In some embodiments, the growth factor is a modified IGF-1 protein (also referred herein as a variant of IGF-1). In some embodiments, the bi-specific protein comprising the IGF-1 variant has an $EC50_{Healthy}/EC50_{Damaged}$ ratio of at least 10:1.

In some embodiments, the activator domain comprises a variant of IGF-1. In some embodiments, the targeting domain comprises human Annexin A5 or variant thereof. In some embodiments, the activator domain comprises a variant of IGF-1 and the targeting domain comprises human annexin A5 or variant thereof.

In some aspects, the bi-specific protein comprises (1) an activator domain, the activator domain comprising a variant of IGF-1, (2) a targeting domain, the targeting domain comprising Annexin A5 or variant thereof, wherein the Annexin A5 or variant thereof binds to phosphatidylserine at the outer surface of a cell within damaged tissue, wherein the bi-specific protein and has a half maximal effective concentration lower in the damaged tissue ($EC50_{Damaged}$) than healthy tissue ($EC50_{Healthy}$). In some embodiments, the IGF-1 variant induces the phosphorylation of AKT. In some embodiments, the bi-specific protein comprising IGF-1 variant has an $EC50_{Healthy}/EC50_{Damaged}$ ratio of at least 10:1.

In some embodiments, the damaged tissue is an ischemic tissue. In some embodiments, the targeted cell is a apoptotic or necrotic cell.

In some embodiments, the damaged tissue is a diabetic tissue damage caused by diabetes. In some embodiments, the damaged tissue is a diabetic tissue damage caused by diabetic nephropathy. In some embodiments, the damaged tissue caused podocyte-related disorder. In some embodiments, the targeting domain is capable of binding a podocyte protein, such as nephrin (NPHS1), podoplanin (PDPN), podocalyxin (PODXL), dystroglycan (DAG1), GLEPP1 (PTPRO), NEPH1 (KIRREL), FAT atypical cadherin 1 (FAT1), cysteine rich transmembrane BMP regulator 1 (CRIM1), integrin alpha-8/beta 1 (ITGA8). In some embodiments, the IGF-1 variant has an amino acid sequence set forth in any one of SEQ ID NOs: 10-30 or 120. In some embodiments, the IGF-1 variant induces survival signaling upon binding to the IGF-1 receptor.

In some embodiments, the targeting domain comprises a molecule capable of binding phosphatidylserine. In some embodiments, the targeting domain comprises Annexin A5. In some embodiments, Annexin A5 has an amino acid sequence set forth in any one of SEQ ID NOs: 1-4 or 122.

In some embodiments, the targeting domain comprises a molecule capable of binding a binding a podocyte protein, such as nephrin (NPHS1), podoplanin (PDPN), podocalyxin (PODXL), dystroglycan (DAG1), GLEPP1 (PTPRO), NEPH1 (KIRREL), FAT atypical cadherin 1 (FAT1), cysteine rich transmembrane BMP regulator 1 (CRIM1), integrin alpha-8/beta 1 (ITGA8). In some embodiments, the targeting domain comprises an antibody capable of binding a binding a podocyte protein, such as nephrin (NPHS1), podoplanin (PDPN), podocalyxin (PODXL), dystroglycan (DAG1), GLEPP1 (PTPRO), NEPH1 (KIRREL), FAT atypical cadherin 1 (FAT1), cysteine rich transmembrane BMP regulator 1 (CRIM1), integrin alpha-8/beta 1 (ITGA8).

In some embodiments, the activator domain and the targeting domain are covalently linked by a peptide bond to form a single polypeptide.

In some embodiments, the IGF-1 variant and the Annexin A5 or variant thereof are covalently linked by a peptide bond to form a single polypeptide. In some embodiments, the variant of IGF-1 and the Annexin A5 or variant thereof are covalently linked to the peptide linker by a peptide bond to form a single polypeptide.

In some embodiments, the bi-specific protein further comprises a peptide linker. In some embodiments, the peptide linker is a half-life modulator. In some embodiments, the half-life modulator is a human serum albumin or variant thereof. In some embodiments, the half-life modulator is an Fc fragment or variant thereof. In some embodiments, the human serum albumin or variant thereof has an amino acid sequence set forth in any one of SEQ ID NOs: 54-56 or 124. In some embodiments, the Fc fragment has an amino acid sequence set forth in SEQ ID NO: 53.

In some embodiments, the activator domain is linked to the amino terminus of the peptide linker and the targeting domain is linked to the carboxy terminus of the peptide linker. In some embodiments, the activator domain is linked to the carboxy terminus of the peptide linker and the targeting domain thereof is linked to the amino terminus of the peptide linker. In some embodiments, the bi-specific protein further comprises a peptide connector between the activator domain and peptide linker and a peptide connector between the targeting domain and peptide linker.

In some embodiments, the IGF-1 variant is linked to the amino terminus of the peptide linker and the annexin A5 or variant thereof is linked to the carboxy terminus of the peptide linker. In some embodiments, the IGF-1 variant is linked to the carboxy terminus of the peptide linker and the annexin A5 or variant thereof is linked to the amino terminus of the peptide linker.

In some embodiments, the bi-specific protein further comprises a peptide connector between the IGF-1 variant and peptide linker and a peptide connector between the Annexin A5 or variant thereof and peptide linker.

In some embodiments, the peptide connector has an amino acid sequence set forth in any one of SEQ ID NOs: 60-62 or 126-127.

In some aspects of the invention, the engineered protein has an amino acid sequence recited in SEQ ID NO: 84. In some aspects of the invention, the nucleic acid has a sequence recited in SEQ ID NO: 102.

In some aspects of the invention, the engineered protein has an amino acid sequence recited in SEQ ID NO: 118. In some aspects of the invention, the nucleic acid has a sequence recited in SEQ ID NO: 119.

Aspects of the invention relate to bi-specific protein comprising: (1) an IGF-1 variant comprising an amino acid sequence set forth in any one of SEQ ID NOs: 18, 19, 23, 24, 28, 29 or 120, and (2) Annexin A5 or variant thereof comprising an amino acid sequence set forth in any one of SEQ ID NOs: 1-4 or 122.

In some embodiments, the bi-specific protein comprises a Human Serum Albumin or variant thereof comprising an amino acid sequence set forth in any one of SEQ ID NOs: 54-56 or 124. In some embodiments, the Human Serum Albumin or variant thereof is linked to a C-terminus of Annexin A5 or variant thereof and to the N-terminus of the IGF-1 variant.

In some embodiments, the bi-specific protein further comprises a connector peptide linking a N-terminus of the Human Serum Albumin or variant thereof to the C-terminus of Annexin A5 or variant thereof and a peptide linking a C-terminus of the Human Serum Albumin or variant thereof to the N-terminus of the IGF-1 variant. In some embodiments, the connector peptide comprises an amino acid sequence set forth in any one of SEQ ID NOs: 60-62 or 126-127.

In some embodiments, the bi-specific protein further comprises a leader polypeptide.

In some embodiments, the bi-specific protein further comprises polypeptide affinity tag. In some embodiments, the affinity tag is at the amino terminus of the fusion protein, at the carboxy terminus of the fusion protein, or in the middle of the fusion protein. In some embodiments, the bi-specific protein comprises a histidine-comprising polypeptide.

In some embodiments, the bi-specific protein comprises an amino acid sequence of a non-internalizing variant of human Annexin A5 and the bi-specific protein has a prolonged half-life as compared to a bi-specific protein comprising the amino acid sequence of wild-type human Annexin A5. For example, the bi-specific protein comprises an amino acid sequence set forth in SEQ ID NO: 4.

Aspects of the invention relate to bi-specific protein comprising an amino acid sequence set forth in any one of SEQ ID NOs: 67, 70, 73-86, 108, 110, 116, or 118.

The bi-specific proteins provided herein are not necessarily limited to two binding specificities. In certain embodiments, in addition to the targeting domain, the bi-specific protein comprises two or more activator domains that are linked directly or indirectly via peptide bonds. In certain embodiments, in addition to the activator domain, the bi-specific protein comprises two or more targeting domains that are linked directly or indirectly via peptide bonds.

Aspects of the invention relate to a method of promoting tissue regeneration or survival in a subject, the method comprising administering in a patient in need thereof a therapeutically effective amount of the bi-specific protein, whereby the targeting domain specifically binds to the target molecule associated with a damaged cell of a damaged tissue, thereby targeting the bi-specific fusion protein to the damaged tissue and whereby upon exposure of the activator domain to the growth factor receptor, the activator domain specifically activates the growth factor receptor so as to promote regeneration or survival of the damaged tissue.

Aspects of the invention relate to a method of treating a patient in need thereof, the method comprising providing a bi-specific, and administering in the patient a therapeutically effective amount of the bi-specific protein, wherein the bi-specific proteins binds to phosphatidylserine on the outer leaflet of the plasma membrane of a cell of a tissue and to a IGF-1 growth factor receptor at the surface of the cell of the tissue. In some embodiments, the bi-specific protein binds to molecules associated with the surface of the same cell of the tissue. In other embodiments, the bi-specific protein binds to molecules associated with the surface of different cells of the tissue.

Aspects of the invention relate to a method of promoting tissue regeneration or survival in a subject, the method comprising (a) providing a bi-specific protein having a targeting domain having a binding specificity to a target molecule associated with the outer surface of a first cell of a tissue and an engineered activator domain having a binding specificity to a receptor associated with the surface of a second cell of the tissue, wherein the engineered activator domain has a modified amino acid sequence of an amino acid sequence of a wild-type activator domain, wherein the engineered activator domain decreases activation of the receptor relative to the wild-type activator domain; and (b) administering in a patient in need thereof a therapeutically effective amount of the bi-specific protein, whereby the targeting domain targets the bi-specific fusion protein to the first cell of the tissue and whereby upon exposure of the activator domain to a growth factor receptor at the surface of a second cell, the activator domain specifically activates the growth factor receptor of so as to promote tissue regeneration, wherein the bi-specific protein exhibits a receptor activation at least twice stronger on cells containing the target molecule compared to cells that do not contain the target molecule as measured by phosphorylation of a receptor or a downstream effector molecule. In some embodiments, the first cell is an apoptotic or necrotic cell.

Aspects of the invention relate to a method of promoting tissue regeneration or survival in a subject, the method comprising (a) providing a bi-specific protein having (1) an activator domain, wherein the activator domain comprises a variant of IGF-1 and (2) a targeting domain, wherein the targeting domain comprises annexin A5 or variant thereof; and (b) administering in a patient in need thereof a therapeutically effective amount of the bi-specific protein whereby the Annexin A5 or variant thereof targets the bi-specific fusion protein to a first cell of the tissue, wherein the cell expresses phosphatidylserine on the outer leaflet of the plasma membrane, and whereby upon exposure of the IGF-1 variant to a IGF-1 receptor at the surface of a second cell, the IGF-1 variant specifically activates the IGF-1 receptor of so as to promote tissue regeneration.

In some embodiments, the targeted cell and activated cell are the same. Yet in other embodiments, the targeted cell and activated cell are different. In some embodiments, the targeted cell is a damaged cell and the activated cell is a viable cell. In some embodiments, the targeted cell is a damaged cell and the activated cell is a damaged cell.

In certain embodiments, the pathological tissue damage is heart tissue damage associated with myocardial infarction. In other embodiments, the pathological tissue damage is kidney tissue damage. In other embodiments, the pathological tissue damage is in bone, cartilage, joints, skin, liver tissue, pancreatic tissue, blood cells, lung tissue, or nervous tissue. In certain embodiments, such methods further comprise the administration of stem cells to the patient.

Also provided herein are nucleic acid molecules encoding a bi-specific fusion protein as described herein. In certain embodiments, the nucleic acid molecule is DNA, and the DNA further comprises transcriptional and translational regulatory sequences operably linked to the bi-specific fusion protein coding sequence, such that transcription and translation of the coding sequence occurs in at least one eukaryotic cell type.

These and other aspects of the present invention will become apparent upon reference to the following detailed description.

DESCRIPTION OF THE SEQUENCE LISTING

SEQ ID NO: 1 is the amino acid sequence of human annexin A5 (AnxV).

SEQ ID NO: 2 is the amino acid sequence of a variant of annexin A5 having a C316S substitution (AnxV-C316S).

SEQ ID NO: 3 is the amino acid sequence of human annexin A5 having a C316S and a C-terminal hexahistidine-comprising peptide (AnxV-C316S-6His).

SEQ ID NO: 4 is the amino acid sequence of non-internalizing variant of human annexin A5 (ni-AnxV).

SEQ ID NO: 5 is the nucleic acid sequence encoding annexin A5 (AnxV).

SEQ ID NO: 6 is the nucleic acid sequence encoding AnxV C316S.

SEQ ID NO: 7 is the nucleic acid sequence encoding AnxV C316S-6His.

SEQ ID NO: 8 is the nucleic acid sequence encoding ni-AnxV.

SEQ ID NO: 9 is the amino acid sequence of wild-type human IGF-1 (mature form).

SEQ ID NO: 10 is the amino acid sequence of a variant of human IGF-1 (IGF-1Des 1-3).

SEQ ID NO: 11 is the amino acid sequence a variant of human IGF-1 (IGF-1 LONG).

SEQ ID NO: 12 is the amino acid sequence a variant of human IGF-1 (IGF1 E3R).

SEQ ID NO: 13 is the amino acid sequence a variant of human IGF-1 (IGF1 R37X).

SEQ ID NO: 14 is the amino acid sequence of human a variant of human IGF-1 with deletion of residues 68-70 (IGF1 3X).

SEQ ID NO: 15 is the amino acid sequence of a variant of human IGF-1 (IGF-1 LR3).

SEQ ID NO: 16 is the amino acid sequence of human IGF-1 (LR3) variant comprising R37X_3X.

SEQ ID NO: 17 is the amino acid sequence of human IGF-1 (LR3) variant comprising

Y24L.

SEQ ID NO: 18 is the amino acid sequence of human IGF-1 (LR3) variant comprising Y24L_Y31A.

SEQ ID NO: 19 is the amino acid sequence of human IGF-1 (LR3) variant comprising Y31A.

SEQ ID NO: 20 is the amino acid sequence of human IGF-1 (LR3) variant comprising Y60L.

SEQ ID NO: 21 is the amino acid sequence of a variant of human IGF-1 comprising R37X_3X.

SEQ ID NO: 22 is the amino acid sequence of a variant of wild-type human IGF-1 comprising Y24L.

SEQ ID NO: 23 is the amino acid sequence of a variant of wild-type human IGF-1 comprising Y24L_Y31A.

SEQ ID NO: 24 is the amino acid sequence of a variant of wild-type human IGF-1 comprising Y31A.

SEQ ID NO: 25 is the amino acid sequence of a variant of wild-type human IGF-1 variant comprising Y60L.

SEQ ID NO: 26 is the amino acid sequence of human IGF-1 (Des1-3) variant comprising R37X_3X.

SEQ ID NO: 27 is the amino acid sequence of human IGF-1 (Des1-3) variant comprising Y24L.

SEQ ID NO: 28 is the amino acid sequence of human IGF-1 (Des1-3) variant comprising Y24L_Y31A.

SEQ ID NO: 29 is the amino acid sequence of human IGF-1 (Des1-3) variant comprising Y31A.

SEQ ID NO: 30 is the amino acid sequence of human IGF-1 (Des1-3) variant Y60L.

SEQ ID NO: 31 is the nucleic acid sequence encoding IGF-1.

SEQ ID NO: 32 is the nucleic acid sequence encoding IGF-1 (Des1-3).

SEQ ID NO: 33 is the nucleic acid sequence of human IGF1 LONG.

SEQ ID NO: 34 is the nucleic acid sequence of human IGF1 E3R.

SEQ ID NO: 35 is the nucleic acid sequence of human IGF1 R37X.

SEQ ID NO: 36 is the nucleic acid sequence of human IGF1 3X (deletion of residues 68-70).

SEQ ID NO: 37 is the nucleic acid sequence encoding IGF-1 (LR3).

SEQ ID NO: 38 is the nucleic acid sequence encoding IGF-1 (LR3) variant comprising R37X_3X.

SEQ ID NO: 39 is the nucleic acid sequence encoding IGF-1 (LR3) variant comprising

Y24L.

SEQ ID NO: 40 is the nucleic acid sequence encoding IGF-1 (LR3) variant comprising Y24L, Y31A.

SEQ ID NO: 41 is the nucleic acid sequence encoding IGF-1 (LR3) variant comprising Y31A.

SEQ ID NO: 42 is the nucleic acid sequence encoding IGF-1 (LR3) variant comprising

Y60L.

SEQ ID NO: 43 is the nucleic acid sequence encoding IGF-1 variant comprising R37X_3X.

SEQ ID NO: 44 is the nucleic acid sequence encoding IGF-1 variant comprising Y24L.

SEQ ID NO: 45 is the nucleic acid sequence encoding IGF-1 variant comprising Y24L and Y31A.

SEQ ID NO: 46 is the nucleic acid sequence encoding IGF-1 variant comprising Y31A.

SEQ ID NO: 47 is the nucleic acid sequence encoding IGF-1 variant Y60L.

SEQ ID NO: 48 is the nucleic acid sequence encoding IGF-1 (Des1-3) variant R37X_3X.

SEQ ID NO: 49 is the nucleic acid sequence encoding IGF-1 (Des1-3) variant Y24L.

SEQ ID NO: 50 is the nucleic acid sequence encoding IGF-1 (Des1-3) variant Y24L, Y31A.

SEQ ID NO: 51 is the nucleic acid sequence encoding IGF-1 (Des1-3) variant Y31A.

SEQ ID NO: 52 is the nucleic acid sequence encoding IGF-1 (Des1-3) variant Y60L.

SEQ ID NO: 53 is the amino acid sequence of Fc peptide.

SEQ ID NO: 54 is the amino acid sequence of Human Serum Albumin (HSA).

SEQ ID NO: 55 is the amino acid sequence of Human Serum Albumin variant mHSA.

SEQ ID NO: 56 is the amino acid sequence of Human Serum Albumin variant mHSA7.

SEQ ID NO: 57 is the nucleic acid sequence encoding human serum albumin HSA.

SEQ ID NO: 58 is the nucleic acid sequence encoding human serum albumin variant mHSA.

SEQ ID NO: 59 is the nucleic acid sequence encoding human serum albumin variant mHSA7.

SEQ ID NO: 60 is the amino acid sequence of the linker lk7.

SEQ ID NO: 61 is the amino acid sequence of the linker lk15.

SEQ ID NO: 62 is the amino acid sequence of the linker lk40.

SEQ ID NO: 63 is the nucleic acid sequence encoding linker lk7.

SEQ ID NO: 64 is the nucleic acid sequence encoding linker lk15.

SEQ ID NO: 65 is the nucleic acid sequence encoding linker lk40.

SEQ ID NO: 66 is the amino acid sequence of SGF 602

SEQ ID NO: 67 is the amino acid sequence of SGF 683

SEQ ID NO: 68 is the amino acid sequence of SGF 703

SEQ ID NO: 69 is the amino acid sequence of SGF604.

SEQ ID NO: 70 is the amino acid sequence of SGF606.

SEQ ID NO: 71 is the amino acid sequence of SGF649.

SEQ ID NO: 72 is the amino acid sequence of SGF688.

SEQ ID NO: 73 is the amino acid sequence of SGF711.

SEQ ID NO: 74 is the amino acid sequence of SGF713.

SEQ ID NO: 75 is the amino acid sequence of SGF716.

SEQ ID NO: 76 is the amino acid sequence of SGF727.

SEQ ID NO: 77 is the amino acid sequence of SGF728.

SEQ ID NO: 78 is the amino acid sequence of SGF729.

SEQ ID NO: 79 is the amino acid sequence of SGF730.

SEQ ID NO: 80 is the amino acid sequence of SGF731.

SEQ ID NO: 81 is the amino acid sequence of SGF732.

SEQ ID NO: 82 is the amino acid sequence of SGF733.

SEQ ID NO: 83 is the amino acid sequence of SGF739.

SEQ ID NO: 84 is the amino acid sequence of SGF740.

SEQ ID NO: 85 is the amino acid sequence of SGF741.

SEQ ID NO: 86 is the amino acid sequence of SGF743.

SEQ ID NO: 87 is the nucleic acid sequence encoding SGF604.

SEQ ID NO: 88 is the nucleic acid sequence encoding SGF606.

SEQ ID NO: 89 is the nucleic acid sequence encoding SGF649.

SEQ ID NO: 90 is the nucleic acid sequence encoding SGF688.

SEQ ID NO: 91 is the nucleic acid sequence encoding SGF711.

SEQ ID NO: 92 is the nucleic acid sequence encoding SGF713.

SEQ ID NO: 93 is the nucleic acid sequence encoding SGF716.

SEQ ID NO: 94 is the nucleic acid sequence encoding SGF727.

SEQ ID NO: 95 is the nucleic acid sequence encoding SGF728.

SEQ ID NO: 96 is the nucleic acid sequence encoding SGF729.

SEQ ID NO: 97 is the nucleic acid sequence encoding SGF730.

SEQ ID NO: 98 is the nucleic acid sequence encoding SGF731.

SEQ ID NO: 99 is the nucleic acid sequence encoding SGF732.

SEQ ID NO: 100 is the nucleic acid sequence encoding SGF733.

SEQ ID NO: 101 is the nucleic acid sequence encoding SGF739.

SEQ ID NO: 102 is the nucleic acid sequence encoding SGF740

SEQ ID NO: 103 is the nucleic acid sequence encoding SGF741.

SEQ ID NO: 104 is the nucleic acid sequence encoding SGF743.

SEQ ID NO: 105 is the amino acid sequence encoding a leader sequence.

SEQ ID NO: 106 is the nucleic acid sequence encoding a leader sequence.

SEQ ID NO: 107 is the amino acid sequence of SGF 704

SEQ ID NO: 108 is the amino acid sequence of SGF 734

SEQ ID NO: 109 is the amino acid sequence of SGF 746

SEQ ID NO: 110 is the amino acid sequence of SGF 757.

SEQ ID NO: 111 is the nucleic acid sequence encoding of SGF 704.

SEQ ID NO: 112 is the nucleic acid sequence encoding of SGF 734.

SEQ ID NO: 113 is the nucleic acid sequence encoding of SGF 746.

SEQ ID NO: 114 is the nucleic acid sequence encoding of SGF 757.

SEQ ID NO: 115 is the nucleic acid sequence encoding Fc.

SEQ ID NO: 116 is the amino acid sequence of SGF 737.

SEQ ID NO: 117 is the nucleic acid sequence of SGF 737.

SEQ ID NO: 118 is the amino acid sequence of SGF-776.

SEQ ID NO: 119 is the nucleic acid sequence of SGF-776.

SEQ ID NO: 120 is the amino acid sequence of a variant of wild-type human IGF-1 variant comprising E3R and Y31A substitutions.

SEQ ID NO: 121 is nucleic acid sequence encoding a variant of wild-type human IGF-1 variant comprising E3R and Y31A substitutions.

SEQ ID NO: 122 is the amino acid sequence of a variant of wild-type human annexin 5 comprising the amino acids 2-320 of wild type annexin 5 and the R63A, K70A, K101A, E138A, D139G, N160A and C316A substitutions.

SEQ ID NO: 123 is the nucleic acid sequence encoding a variant of human annexin 5 comprising the amino acids 2-320 of wild type annexin 5 and the R63A, K70A, K101A, E138A, D139G, N160A and C316A substitutions.

SEQ ID NO: 124 is the amino acid sequence of a variant human serum albumin comprising the amino acids 26-609 of wild type human serum albumin and the C58S and N527Q substitutions.

SEQ ID NO: 125 is the nucleic acid sequence encoding a variant human serum albumin comprising the amino acids 26-609 of wild type human serum albumin and the C58S and N527Q substitutions.

SEQ ID NO: 126 is the amino acid sequence of the linker lk7.

SEQ ID NO: 127 is the amino acid sequence of the linker aliphatic lk7.

SEQ ID NO: 128 is the amino acid sequence of anti-phosphatidylserine scFV PS4A7.

SEQ ID NO: 129 is the amino acid sequence of anti-DNA scFv SI-1.

SEQ ID NO: 130 is the amino acid sequence of anti-DNA scFv SI-22.

SEQ ID NO: 131 is the amino acid sequence of B7 scFv anti-myosin scFv antibody.

SEQ ID NO: 132 is the amino acid sequence of FD2 anti-myosin scFv antibody.

SEQ ID NO: 133 is the amino acid sequence of MCA1 anti-myosin scFv antibody.

SEQ ID NO: 134 is the amino acid sequence of MCB11 anti-myosin scFv antibody.

SEQ ID NO: 135 is the amino acid sequence of S3F51 anti-myosin scFv antibody.

SEQ ID NO: 136 is the amino acid sequence of an anti-DNA scFV antibody.

SEQ ID NO: 137 the amino acid sequence of a motif PASylation.

SEQ ID NO: 138 is the amino acid sequence of the albumin-binding domain human antibody (aldudAB).

BRIEF DESCRIPTION OF THE DRAWINGS

FIG. 1A and FIG. 1B are schematics of representative therapeutic bi-specific proteins (also referred herein as Smart Growth Factors or SGFs) and non-targeted control proteins, according to some embodiments. FIG. 1A and FIG. 1B are schematics of representative (1) targeted, potency-reduced IGF-1-based proteins, (2) targeted, potency-reduced Nrg1α-based proteins, (3) non-targeted, potency-reduced IGF-1-based proteins, (4) non-targeted, non-potency-reduced IGF-1-based proteins, (5) targeted, non-potency-reduced IGF-1-based proteins, (6) signaling arms, (7) targeting arms, (8) half-life modulators, and (9) linkers, according to some embodiments.

FIGS. 2A and 2B are tables listing therapeutic bi-specific proteins and the potency and the fold decreased potency in healthy cells compared to wild-type growth factors (wt GFs) according to some embodiments. FIGS. 2A and 2B show that engineered Growth factors according to embodiments of the invention have decreased potency (i.e., increased pAKT EC50's) compared to wild type growth factors. EC50 is defined as the concentration needed to achieve the half maximal level of pAKT signaling. iPSC-derived cardiomyocytes (CDI) were stimulated with (S)GFs for 10 min and pAKT levels were measured by ELISA. FIGS. 2A and 2B show that engineering GFs, either by addition, deletion, or mutation of amino acids or by fusing to other protein domains, causes reduced potency compared to wt GF.

FIG. 3A is a set of graphs depicting pAKT (protein kinase B) dose response in healthy and damaged cardiomyocytes using different therapeutic bi-specific proteins and non-targeted control proteins according to some embodiments. The potencies of candidate Smart Growth Factors (SGF) are measured in pluripotent stem cell derived cardiomyocytes (Cellular Dynamics International) and signaling is quantified by the accumulation of phosphorylated Akt. In order to assess the targeting of Smart Growth Factors, dose response curves are collected in Healthy and Damaged cardiomyocytes (damaged=incubation with 12.5 µg/mL doxorubicin for 24 hours to induce apoptosis). Dose response curves are subsequently fit to a three parameter EC50 activation model and the calculated EC50s are compared between the Healthy (circle, blue color) and Damaged (square, red color) contexts. In these normalized plots, the lines of best fit are shown and individual data points are depicted as filled circles or squares.

FIG. 3B shows that non-targeted, non-potency reduced molecules (e.g., 688) and non-targeted, potency-reduced molecules (e.g., 704, 602, 703) have no appreciable potency shift. Likewise, targeted, non-potency reduced molecules (e.g., 649) also have no appreciable potency shift. Only targeted, potency-reduced molecules (e.g., 606, 683, 711, 713, 716, 727, 728, 729, 730, 731, 732, 733, 739, 740, 741, 743, 757) have an appreciable (>4-fold) potency shift.

FIG. 4 shows that targeted, engineered growth factors according to embodiments of the invention reduce apoptosis in human cardiomyocytes in a dose dependent manner. Apoptosis was induced by culturing cell at 1% oxygen for 48 hours. The therapeutic bi-specific protein 740 was added at the start of the hypoxia period. Caspase 3/7 activity was measured using capsaseGlo (Promega). Fusion protein 740 significantly (p≤0.01) reduces caspase activity induced by hypoxia in human cardiomyocytes.

FIG. 5 shows that targeted engineered growth factors according to embodiments of the invention reduce hypoxia-induced cell death in human kidney proximal tubule epithelial cells while non-targeted controls show no effect. Cell death was measured by the percentage of cells staining positive for propidium iodide by flow cytometry. Cells were serum starved for 5 hours, then pre-treated with therapeutic bi-specific proteins SGFs 727, 740, 734 or non-targeted control (746) prior to placing in anaerobic pouches for 18 hours (GasPak EZ Anaerobe pouch System with indicator BD 260683). Normoxia control was treated the same way except that the control was not placed in the anaerobic pouch. All results were normalized to normoxia control. Results are the average of 2-3 independent experiments. Significance was determined by a one way ANOVA test, alpha=0.05.

FIG. 6 is a table depicting the half-life and decay rate after intravenous dosing of different therapeutic bi-specific proteins. The half-life of different therapeutic bi-specific proteins and wt IGF-1 in mice was calculated using a single compartment model. SGF 727 has the structure IGF1 (LR-3-R37X-3X)_lk40_mHSA_lk40_AnxV, whereas molecules 739-743 have the basic structure IGF1*(LR3)_lk7_mHSA_lk7_AnxV(ni), where * denotes a potency reducing deletion or mutation of IGF1. SGF757 has the structure Nrg1α_lk7_mHSA_lk7_AnxV(ni). FIG. 6 shows that targeted engineered growth factors (SGFs) according to some embodiments have longer half-lives than wild type growth factor (wt IGF1)

FIG. 7 shows that targeted, engineered growth factors (SGFs) according to some embodiments have reduced off target effects. Anx-targeted, potency-reduced IGF1 fusion proteins have significantly reduced hypoglycemia compared to untargeted, high potency IGF1 fusions proteins.

FIG. 7A is a graph depicting the time course of blood glucose levels in mice after dosing with different therapeutic bi-specific proteins. Data are shown as mg/dL glucose level. SGFs 727-743 are targeted, potency-reduced IGF1-based fusion proteins, whereas 688 is a non-targeted high-potency IGF1 fusion protein. Mice were dosed with recombinant HSA as negative control and IGF-1 (LR3 variant) as positive control.

FIG. 7B is a graph depicting the relationship between SGF potency (defined as the concentration required to achieve half maximal pAKT levels, i.e., pAKT EC50 of therapeutic bi-specific proteins) vs. 3 hr blood glucose area under the curve (AUC). FIG. 7B demonstrates that greater potency reduction (i.e., increased pAKT EC50) leads to increased 3 hr blood glucose AUC (i.e., less blood glucose reduction).

FIG. 8 shows targeted, engineered growth factors (SGFs) activate pro-survival signaling in damaged tissue in vivo. Targeted, potency reduced IGF1 fusions protein 606 activates significantly more pAKT signaling in infarcted tissue vs. remote (healthy) tissue in vivo. Selective signaling is not observed with either wt IGF1 or a non-targeted, high potency fusion protein (688).

FIG. 9A depicts an overview of the rat acute myocardial infarction (AMI) model. Overview of rat AMI model. The left anterior descending coronary artery (LAD) is tied off at the ligation point for 1 hour then loosened and reperfused during a 72 hour recovery period. Vehicle, IGF1 or SGF 606 are injected intravenously at the time of reperfusion via the lateral tail vein. After 72 hours the LAD is religated and the heart is processed for histological assessment of infarct size FIG. 9B is a graph depicting the percent area of the left ventricle that is at risk after ischemia (area at risk (AAR)/LV %) using the model shown in FIG. 9A. There was no significant difference in the size of injury produced by the surgical procedure between any of the groups as indicated by comparable size of the area at risk (AAR) with respect to the area of the left ventricle (LV).

FIG. 9C is a graph depicting the infarct/area at risk percentage in rats injured by AMI and treated with vehicle, wt IGF1, or a targeted therapeutic bi-specific protein (SGF 606). The targeted, potency-reduced SGF 606 is highly significantly efficacious in infarct size reduction at 72 hours compared to vehicle control ($p<0.001$). IGF1 is also able to significantly reduce infarct size compared to vehicle ($p<0.05$); however treatment with SGF 606 results larger infarct reduction compared to IGF1 ($p<0.05$).

DETAILED DESCRIPTION OF THE INVENTION

Figure 1A:
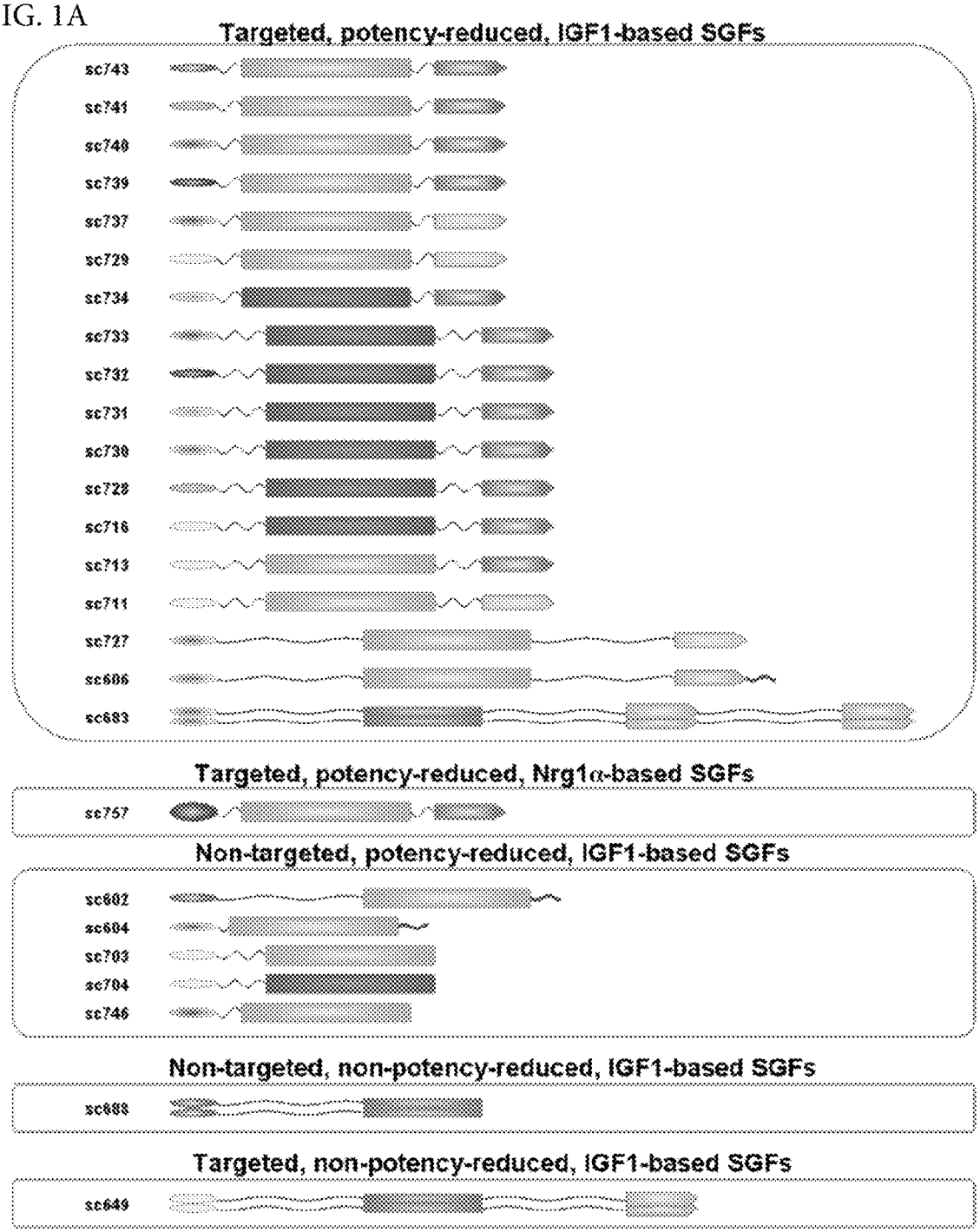
Figure 1A:
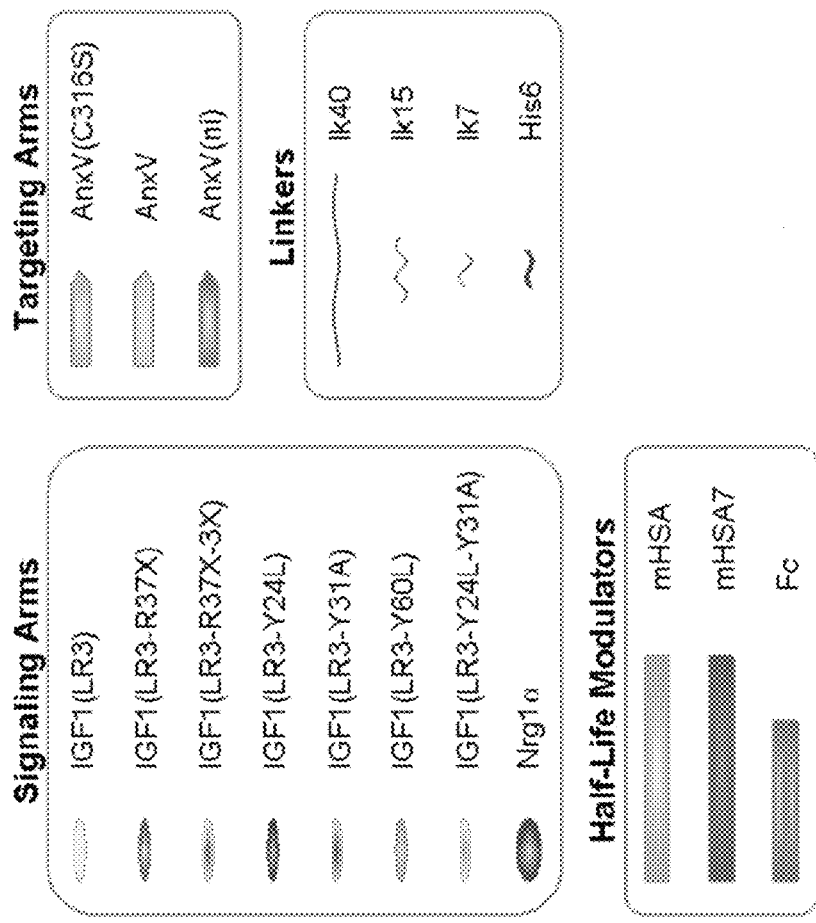

It is to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a," "an" and "the" include plural referents unless the content clearly dictates otherwise.

The term "peptide," "polypeptide" and "protein" are used interchangeably to denote a sequence polymer of at least two amino acids covalently linked by an amide bond (also referred herein as peptide bond).

The term "bi-specific," as used herein, refers to the ability of the fusion protein to interact with two different ligands. In some embodiments, the bi-specific protein interacts with a target molecule for the targeting domain and a receptor for the activator domain.

As used herein the term "target molecule" refers to any molecule that is associated with a tissue (e.g. "at risk", diseased or damaged tissue). A "target cell" is meant to be a cell to which a bi-specific protein or targeting domain thereof can specifically bind.

"Binding" or "specific binding" are used interchangeably herein and indicates that a protein (or the targeting polypeptide domain thereof or the activator domain thereof) exhibits substantial affinity for a specific molecule (e.g., targeting domain exhibits substantial affinity for a target molecule, or an activator domain exhibits substantial affinity for a molecule associated with the surface of a cell such as a growth factor receptor) or a cell or tissue bearing the molecule and is said to occur when the protein (or the targeting polypeptide domain thereof or the activator domain thereof) has a substantial affinity for a specific molecule and is selective in that it does not exhibit significant cross-reactivity with other molecules.

The term "recombinant," as used herein, means a genetic entity distinct from that generally found in nature. As applied to a polynucleotide or gene, this means that the polynucleotide is the product of various combinations of cloning, restriction and/or ligation steps, and other procedures that result in the production of a construct that is distinct from a polynucleotide found in nature.

The term "operably linked" refers to a nucleic acid sequence placed into a functional relationship with another nucleic acid sequence. A nucleic acid is "operably linked" when it is placed into a functional relationship with another nucleic acid sequence.

The term "vector," as used herein, is intended to refer to a nucleic acid molecule capable of transporting another nucleic acid to which it has been linked. One type of vector is a "plasmid," which refers to a circular double-stranded DNA loop into which additional DNA segments may be ligated. Another type of vector is a viral vector, (e.g., a replication defective retrovirus, adenovirus and adeno-associated virus) wherein additional DNA segments may be ligated into the viral genome so as to be operatively linked to a promoter (e.g., a viral promoter) that will drive the expression of a protein encoded by the DNA segment. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

The term "host cell," as used herein, is intended to refer to a cell into which an expression vector has been introduced, which cell is capable of reproducing, and preferably expressing proteins encoded by, the vector. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

"Identity," as known in the art, is a relationship between two or more polypeptide or protein sequences, as determined by comparing the sequences. In the art, "identity" also refers to the degree of sequence relatedness between polypeptides or proteins, as determined by the match between strings of such sequences. "Identity" can be readily calculated by any bioinformational methods known in the art.

The term "parent polypeptide" refers to a wild-type polypeptide and the amino acid sequence or nucleotide sequence of the wild-type polypeptide is part of a publicly accessible protein database (e.g., EMBL Nucleotide Sequence Database, NCBI Entrez, ExPasy, Protein Data Bank and the like).

The term "mutant polypeptide" or "polypeptide variant" refers to a form of a polypeptide, wherein its amino acid sequence differs from the amino acid sequence of its corresponding wild-type (parent) form, naturally existing form or any other parent form. A mutant polypeptide can contain one or more mutations, e.g., substitution, insertion, deletion, addition etc . . . which result in the mutant polypeptide.

The term "corresponding to a parent polypeptide" is used to describe a polypeptide of the invention, wherein the amino acid sequence of the polypeptide differs from the amino acid sequence of the corresponding parent polypeptide only by the presence of at least one amino acid variation. Typically, the amino acid sequences of the variant polypeptide and the parent polypeptide exhibit a high percentage of identity. In one example, "corresponding to a parent polypeptide" means that the amino acid sequence of the variant polypeptide has at least about 50% identity, at least about 60%, at least about 70%, at least about 80%, at least about 90%, at least about 95%, at least about 98% identity or at least about 99% identity to the amino acid sequence of the parent polypeptide. In another example, the nucleic acid sequence that encodes the variant polypeptide has at least about 50% identity, at least about 60%, at least about 70%, at least about 80%, at least about 90%, at least about 95%, at least about 98% identity or at least about 99% identity to the nucleic acid sequence encoding the parent polypeptide.

The term "substantial identity" or "substantial similarity," as used herein, when referring to a nucleic acid or fragment thereof, indicates that when optimally aligned with appropriate nucleotide insertions or deletions with another nucleic acid (or its complementary strand), there is nucleotide sequence identity in at least about 95 to 99% of the sequence.

The term "homologous" as used herein and relating to peptides refers to amino acid sequence similarity between two peptides. When an amino acid position in both of the peptides is occupied by identical amino acids, they are homologous at that position. As used herein, "substantially homologous" as used herein means that a sequence is at least 50% identical, and preferably at least 75% and more preferably 95% homologous to the reference peptide and which retains most or all of the activity as the sequence to which it is homologous.

The term "damaged cell" or "damaged tissue," as used herein, means and includes biological cell or tissue; for example, but not limited to, cardiovascular cell or tissue damaged or injured by trauma or chemical insult, ischemic tissue, infarcted tissue or cell or tissue damaged by any means which results in interruption of normal blood flow to the tissue.

The term "therapeutically effective amount," as used herein, means the amount of the bi-specific protein that will elicit the biological or medical response of a tissue, system, animal or human that is being sought by the researcher, veterinarian, medical doctor or other clinician.

The term "pharmaceutically acceptable," as used herein, means the carrier, diluent or excipient must be compatible with the other ingredients of the formulation and not deleterious to the recipient thereof.

Aspects of the invention relate to bi-specific therapeutic proteins, pharmacological compositions and methods for repairing or regenerating damaged or diseased tissue or cells. In some embodiments, the bi-specific therapeutic proteins can positively regulate survival of targeted cells or targeted tissue. In particular, the bi-specific therapeutic proteins, can promote survival signaling.

In some embodiments, the pharmacological compositions of the invention can further include one or more additional bioactive agents or components to aid in the treatment of damaged tissue or cells and/or facilitate the tissue regenerative process.

Aspects of the invention also encompass polynucleotides encoding the therapeutic bi-specific proteins and variants thereof that may be in the form of RNA or in the form of DNA, which DNA includes cDNA and synthetic DNA. The DNA may be double-stranded or single-stranded. The coding sequences that encode the variants of the present invention may vary as a result of the redundancy or degeneracy of the genetic code.

Aspects of the invention are directed to bi-specific therapeutic proteins comprising two binding domains, each specific for a different target molecule or "ligand". In some embodiments, the bi-specific protein comprises a targeting domain or targeting moiety and activator domain or therapeutic moiety. The term "targeting moiety", "targeting domain," or "targeting polypeptide" are used herein interchangeably and refer to molecules that selectively localize the bi-specific therapeutic in a particular tissue or region of the body. The localization can be mediated by specific recognition of molecular determinants, molecular size of the targeting domain, ionic interactions, hydrophobic interactions and the like. As used herein, the terms "therapeutic moiety," "activator domain," "activator polypeptide" and "signaling arm" are used herein interchangeably and refers to any agents useful for therapy and that are non-toxic, do not have a cytotoxic effect or are not detrimental to the cells, including, but not limited to, growth factors.

As used herein a "bi-specific protein" refers to a protein capable of specific binding to two or more different specific molecules. In some embodiments, the bi-specific protein comprises a targeting domain having a binding specificity to a first specific target molecule and an activator domain having a binding specificity to a second target molecule. In some aspects, the activator domain has a binding specificity to a receptor. In some aspects, the activator domain has a binding specificity to a receptor that modulates/promotes tissue regeneration. In some embodiments, the targeting domain serves to target the bi-specific protein to a target cell or tissue while the activator domain serves to activate a cell thereby to promote regeneration of the targeted tissue.

In some aspects, the bi-specific therapeutic proteins are chimeric proteins having a targeting polypeptide connected to an activator polypeptide. In some aspects, the bi-specific therapeutic proteins are chimeric proteins having a targeting polypeptide connected to a growth factor variant.

The targeting domain is generally used to target the bi-specific proteins to a cell of choice, also referred to as "target cell." The binding of the targeting domain to its target molecule does not induce a significant biological effect in the target cell. The activator domain binds to a second target molecule or ligand on a cell. The binding of the activator domain to its ligand is intended to modulate a specific biological effect, such as, to increase that biological activity. In some embodiments, binding of the activator domain to its ligand is intended the positively regulate survival of the targeted cells or tissue. In particular, the activator domain of the bi-specific proteins can promote survival signaling.

In some embodiments, the targeting domain and the activator domain are associated with different subunits of a multimeric protein. In some embodiments, the activator domain is cross-linked to the targeting domain. In some embodiments, the activator domain is directly or indirectly fused to the targeting domain.

It is important to note that a substitution of one amino acid residue in the activator domain may affect the characteristics of the bi-specific protein as a whole, and that overall effect may be beneficial (or detrimental) to the pharmacological potency and targeting specificity of the bi-specific protein.

In some aspects of the methods and compositions of the invention, the bi-specific therapeutic protein has an activator domain engineered to have a decreased potency as compared to wild-type activator domain. It has been observed that decreasing the potency of the activator domain can increase the selectivity of the bi-specific therapeutic protein resulting in preferential activation of cells or tissue containing the target molecule (see FIG. 3A, FIG. 3B and FIG. 3C). In some embodiments, the activator domain is a therapeutic agent. In some embodiments, the activator domain is a growth factor variant. This observed decrease in potency relative to the wild-type activator domain can be attributed to both steric hindrance of the activation domain and also a decreased rate of diffusion in the context of the larger multi-domain fusion protein. In some embodiments, the activator domain is an IGF-1 variant. In some embodiments, the activator domain is a NRG variant.

In some aspects of the methods and compositions of the invention, the bi-specific therapeutic protein has an activator domain that is fused to both a half-life modulating domain and to a targeting domain such that the activator domain possesses a decreased activation potency as compared to the wild-type activator domain. It has been observed that fusion of the activator domain to the half-life modulation and targeting domains decreases the potency of the activator domain, thereby increasing the selectivity of the bi-specific therapeutic protein resulting in preferential activation of cells or tissue containing the target molecule. This observed decrease in potency relative to the wild-type activator domain can be attributed to both steric hindrance of the activation domain and also a decreased rate of diffusion in the context of the larger multi-domain fusion protein. In some embodiments, the activator domain is a therapeutic agent. In some embodiments, the activator domain is a growth factor variant. In some embodiments, the activator domain is an IGF-1 variant. In some embodiments, the activator domain is a NRG variant.

Some embodiments of the invention provide engineered proteins having a targeting domain, an activator domain, and optionally a peptide linker or half-life modulator. In various embodiments, the invention provides variants having this level of identity to a portion of the parent polypeptide sequence, e.g., Human Insulin Growth Factor 1 (IGF-1), Annexin A5 (Anx A5 or AnxV), Human Serum Albumin (HSA), as defined herein. In various embodiments, the variant has at least about 80%, 85%, 90%, 95%, 96%, 97%, 98% or 99% sequence identity to the parent polypeptide or to a portion of the parent polypeptide sequence, e.g., IGF-1, Annexin A5, Human Serum Albumin, as defined herein.

In some aspects of the methods and compositions of the invention, the activator domain (i.e., the growth factor) of the bi-specific protein is engineered to give, when fused to the targeting domain, the bi-specific fusion protein a half-maximal effective concentration (EC50) lower in damaged cells or tissue than in healthy cells or tissue. In some embodiments, the activator domain (i.e., the growth factor) of the bi-specific protein is engineered to give, when fused to the targeting domain, the bi-specific fusion protein at least one order of magnitude lower EC50 in damaged cell or tissue than in healthy cells or tissue.

In some aspects of the methods and compositions of the invention, the targeting domain(s) of the bi-specific protein can be selected to have at least an order of magnitude higher binding affinity for its ligand than the affinity the activator domain has for its ligand. For example, the targeting domain has at least 10 times or greater affinity for its ligand than the activator domain has for its ligand. In some embodiments, the affinity of the targeting domain for its ligand is at least 15 times higher or at least 20 times or more higher, 25 times or more higher, than that of the activator domain. In some embodiments, the affinity of the targeting domain to its ligand is 30, 40, 50 or even 100 times or more higher than that the affinity of the activator domain for its ligand.

The differential potency of the activator domain and/or the differential binding affinity between the targeting domain and the activator binding domain provides surprising and previously unrecognized advantages over prior bi-specific proteins. In particular, the discovery that alteration (addition, deletion, substitution) of one or more residues of the activator domain of the bi-specific protein can result in higher specificity for target cells together with a decreased potency in the activator domain for non-target cells. Without being bound to the theory, it was assumed that due to their low EC50s (i.e., high potency), growth factors cannot be effectively targeted. According to aspects of the invention, variants of growth factors can be made with significantly decreased potency (i.e., increased EC50). These growth factor variants, when fused with high affinity targeting arms, can result in selective activation of growth factor receptors on cells or tissue containing the target molecule and substantially no activation of cells or tissue that do not contain the target molecule.

In some aspects of the invention, the targeting domain and the activator domain are directly linked. In some aspects of the invention, the targeting domain and the activator domain are indirectly linked. In some aspects of the invention, the targeting domain and the activator domain are covalently linked. Yet, in other aspects of the invention, the targeting domain and the activator domain are non-covalently associated.

The linkages between the activator moiety and the targeting moiety, the activator moiety and the half-life modulator (or peptide linker) and the targeting moiety and the half-life modulator (or peptide linker) can be covalent linkages or non-covalent linkages. The linkages can be peptide bonds formed by derivatization of the components involved with peptides and the formation of a peptide linkage between the peptides. The linkages can be non-covalent linkages, such as biotin/avidin or biotin/streptavidin linkages or specific antigen/antibody or hapten/antibody linkages.

In some embodiments, the bi-specific protein comprises (1) a targeting domain having a binding specificity to a molecule associated with a damaged cell of a tissue, wherein the molecule is intracellular in a viable cell and exposed to the extracellular space in the damaged cell; and (2) an activator domain having a binding specificity to a growth factor receptor of a cell in the tissue, wherein upon exposure of the activator domain to the growth factor receptor, the activator domain binds the growth factor receptor so as to promote regeneration or survival of the tissue. In some embodiments, the activator domain is a growth factor that is engineered to give, when fused with the targeting domain, the bi-specific fusion protein a half maximal effective concentration (EC50) lower in damaged cell or tissue than in healthy cells or tissue. In some embodiments, the activator domain is a growth factor that is engineered to give, when fused with the targeting domain, the bi-specific fusion protein at least one order of magnitude lower EC50 in damaged cell or tissue than in healthy cells or tissue.

In some embodiments, the bi-specific fusion protein comprises (1) a targeting domain having a binding specificity to a molecule associated with a damaged cell of a tissue, wherein the molecule is intracellular in a viable cell and exposed to the extracellular space in the damaged cell; (2) an activator domain having a binding specificity to a molecule associated with the surface of a cell in the tissue, wherein upon exposure of the activator domain to membrane-associated molecule, the activator domain binds the membrane-associated molecule so as to modulate regeneration of the tissue and (3) a peptide linker. In some embodiments, the activator domain is a growth factor that is engineered to give the bi-specific fusion protein a half maximal effective concentration (EC50) lower in damaged cell or tissue than in healthy cells or tissue. In some embodiments, the activator domain is a growth factor that is engineered to give the bi-specific fusion protein at least one order of magnitude lower EC50 in damaged cell or tissue than in healthy cells or tissue. In some embodiments, the linker is a non-immunogenic peptide. In some embodiments, the peptide linker is a half-life modulator capable of modulating (e.g., increasing) the half-life of the bi-specific protein.

In some embodiments, the bi-specific proteins comprises: (1) a targeting polypeptide domain that binds to an ischemia-associated molecule; and (2) a growth factor polypeptide engineered to give the bi-specific fusion protein a half maximal effective concentration (EC50) lower in ischemic cell or tissue than in healthy cells or tissue while having an affinity to a receptor at the surface of a cell in a tissue so as to promote regeneration or survival of the tissue.

In some embodiments, the bi-specific proteins comprises: (1) a targeting polypeptide domain that binds to a podocyte-associated protein; and (2) a growth factor polypeptide engineered to give the bi-specific fusion protein a half maximal effective concentration (EC50) lower in ischemic cell or tissue than in healthy cells or tissue while having an affinity to a receptor at the surface of a cell in a tissue so as to promote regeneration or survival of the tissue.

In some embodiment, the bi-specific proteins comprises (1) at least one targeting domain having a binding specificity to at least one target molecule associated with a tissue; (2) at least one an activator domain having a binding specificity to at least one molecule associated with the surface of a cell in the tissue, wherein upon exposure of the binding domain to the molecule, the binding domain binds the molecule so as to promote regeneration or survival of the tissue; and (3) optionally a peptide linker. In some embodiments, the fusion protein comprises two or more targeting domains, each targeting domain having a binding affinity to a target molecule associated with a tissue. Each of the targeting domains may have a same binding specificity (e.g., a binding specificity for the same target molecule) or a different binding specificity (e.g., a binding specificity for a different target molecule). Each of the targeting domains may have a same binding affinity or different binding affinities. In some embodiments, the protein comprises two or more activator domains. Each of the activator domains may have the same binding specificity (e.g., a binding specificity to the same receptor on the cell) or different binding specificity (e.g., a binding specificity for a different receptor on a cell). Each of the activator domains may have the same binding affinity or different binding affinities. In some embodiments, the linker is a peptide. In some embodiments, the linker is a non-immunogenic peptide. In some embodiments, the linker is a half-life modulator wherein the half-life modulator modulates the half-life of the bi-specific protein.

In certain embodiments, the bi-specific protein comprises a half-life modulator (HLM). In some embodiments, the half-life modulator is a polypeptide. The half-life modulator can have two termini, an N-terminus and a C-terminus, and is joined at one terminus via a peptide bond to the targeting polypeptide domain and is joined at the other terminus via a peptide bond to the activator domain. In other embodiments, the half-life modulator is joined at one terminus (N-terminus or C-terminus) to the activator domain or to the targeting domain. Accordingly, the half-life modulator can be at the N-terminus or at the C-terminus of the bi-specific protein. The half-life modulator may be joined to the targeting domain or the activator domain via peptide bonds.

One skilled in the art will appreciate that such bi-specific proteins can find use in tissue regeneration. In some embodiments, bi-specific fusion proteins can be used in diseased cells, following tissue or organ injury or following an event in which the cells of a tissue may be damaged. In some embodiments, the bi-specific fusion proteins can activate cells that express one or more growth factor receptors. In other embodiments, the bi-specific fusion proteins find use, for example, in recruiting cells that express one or more growth factor receptors to tissue following for example, injury, or an event in which the cells of a tissue may be damaged or may become dysfunctional.

In some aspects, administration of such bi-specific proteins may be used to facilitate repair, survival or regeneration of damaged tissue or organ. In some embodiments, the bi-specific proteins disclosed herein can find use in modulating tissue survival. For example, the bi-specific proteins can enhance or maintain the viability of a cell or tissue. In some embodiments, the bi-specific fusion proteins can activate the pro-survival or the cell survival pathway. In some embodiments, the bi-specific proteins can decrease apoptosis or decrease cell death.

In some embodiments, bi-specific proteins can have (1) a targeting polypeptide domain wherein the targeting domain binds to a target molecule thereby targeting the bi-specific fusion protein to a first cell of a tissue, and (2) an activator domain having a binding specificity to a growth factor receptor. Upon exposure of the activator domain to the growth factor receptor, the activator domain can activate the receptor of a second cell so as to promote cell recruitment, inhibition of apoptosis, induction of cell proliferation, activation of the pro-survival pathway, regeneration, and/or survival of the tissue. One skilled in the art will appreciate that the bi-specific fusion protein can bind to a first cell population and act on the same cell population (e.g. in an autocrine manner) or on a different cell population (e.g. in a paracrine manner). In some embodiments, the targeting domain binds specifically to a target molecule associated with a damaged first cell population and the activator domain binds specifically to a receptor of a second cell population of viable cells. In some embodiments, the targeting domain binds specifically to a target molecule associated with a damaged cell population and the activator domain binds specifically to a receptor of the same cell population. In some embodiments, the targeting domain binds specifically to a tissue specific target molecule at the surface of a first cell population and the activator domain acts specifically to a second cell population. In some embodiments, the targeting domain binds specifically to a tissue specific target molecule at the surface of a cell population and the activator domain acts specifically on the same cell population. The first cell can be a viable cell, or an "at risk" cell. As used herein "at risk" cell refers to a viable cell that has not yet undergone apoptosis or is not damaged but is at risk to be damaged.

In some embodiments, the bi-specific protein has two different binding domains (such targeting domain and activator domain) which bind to different molecules on different cells in a tissue or organ. Yet in some embodiments, the bi-specific protein has two different binding domains which bind to different molecules on the same target cell in a tissue, the targeting domain being selected to bind specifically a target cell and the activator domain selected to bind to a receptor (e.g., growth factor receptor) at the surface of the cell to promote tissue regeneration, cell recruitment, inhibition of apoptosis, induction of cell proliferation, activation of the pro-survival pathway, regeneration, and/or survival of the tissue.

Target Molecules

In some aspects, target molecules are exposed or enriched on the exterior of a target cell. In some embodiments, the target molecule is associated with a damaged cell, the target molecule being intracellular in a viable or undamaged cell and being exposed to the extracellular space in a damaged cell. Such molecules include, for example, molecules that are exposed in cells that undergo necrosis (such as DNA) or apoptosis (e.g., phosphatidylserine), myosin (including the tissue type-specific subtypes thereof), ICAM-1 or P-selectin. Yet in other embodiments, the target molecule is a molecule that is present or enriched at the surface of a diseased or dysfunctional cell or tissue as compared to the level detected in a healthy or functional cell or tissue. In some embodiments, the target cell is not a tumor or cancerous cell.

Cells are bounded by a plasma membrane (or cell membrane) comprising a lipid bilayer. The cell membrane may be considered to have a surface facing the cytosol (cytosolic side or interior of the cell) and a surface facing the exterior of the cell, or the extracellular space. Trans-bilayer movement of anionic phospholipids from the inner to the outer leaflet of the plasma membrane occurs during apoptosis. The anionic phospholipid-binding protein, such as Annexin A5, synaptotagmin I or lactadherin can be used to detect the presence of phosphatidylserine on the outer leaflet of the cell membrane. Phosphatidylserine is a phospholipid, that is usually restricted to the cytosolic side of the membrane in viable or undamaged cells, and that becomes exposed on the outer cell surface or to the extracellular space in damaged cells or apoptosis.

In some embodiments, the target molecule is an "ischemia-associated molecule". An "ischemia-associated molecule" is any molecule that is detected at a level that is significantly higher (e.g., at least 1.5 higher, at least 2-fold higher, at least 3-fold higher, at least 4-fold higher, at least 5-fold higher) following ischemia (which results in hypoxia) or hypoxia. Ischemia occurs when there is insufficient blood flow to provide adequate oxygenation, which results in tissue hypoxia (reduced oxygen) or anoxia (absence of oxygen) as the most severe form of hypoxia, and ultimately tissue necrosis, and apoptosis. Any suitable binding assay may be used to identify ischemia-associated molecules, including those provided herein. The increased level of molecule that is detected may be the result of upregulation or decreased turnover, or may be due to increased accessibility (e.g., resulting from cell damage) or increased extracellular exposure (e.g., trans-bilayer movement from the inner to the outer leaflet of the plasma membrane). In certain embodiments, the ischemia-associated molecule is detected in a cell of post-ischemic tissue at a significantly higher level (e.g., at least 1.5 higher, at least 2-fold higher, at least 3-fold higher, at least 4-fold higher, at least 5-fold higher) than in a cell of the same tissue that has not undergone an ischemic event (i.e., the molecule is specific to or enriched in the post-ischemic tissue). In further embodiments, the ischemia-associated molecule is associated with cell damage (i.e., the molecule is detected at a significantly higher level in cells that are damaged than in undamaged cells of the same type). Certain ischemia-associated molecules are enriched (e.g., at least 1.5 higher, at least 2-fold higher, at least 3-fold higher, at least 4-fold higher, at least 5-fold higher) in the heart after an ischemic event (or in a model system that is used to mimic ischemia in the heart). In some embodiments, the ischemia-associated molecules are about 1.5-fold enriched, about 2-fold enriched, about 3-fold enriched, about 4-fold enriched, about 5-fold enriched in the heart after an ischemic event (or in a model system that is used to mimic ischemia in the heart). In some embodiments, the ischemia-associated molecules are from about 1.5-fold to about 5 fold or more enriched in the heart after an ischemic event (or in a model system that is used to mimic ischemia in the heart). In some embodiments, the ischemia-associated molecules are from about 1.5-fold to about 2 fold, about 2-fold to about 2.5 fold, about 2.5 fold to about 3-fold, about 3-fold to about 3.5 fold, about 3.5 fold to about 4-fold, about 4-fold to about 4.5 fold, about 4.5-fold to about 5-fold, or more enriched in the heart after an ischemic event (or in a model system that is used to mimic ischemia in the heart)). In some embodiments, such molecules include molecules that are exposed on myocytes or other cardiac cells that undergo necrosis (for example, but not limited to, DNA) or apoptosis (for example, but not limited to, phosphatidylserine). In some embodiments, such molecules include molecules that are enriched in scarred heart tissue, such as collagen (collagen I, III), myosin (including the cell type-specific subtypes thereof), or other extracellular matrix proteins that are enriched in post ischemic hearts. Such molecules can be identified on the basis of enrichment following ischemia-reperfusion in vivo or in simulated ischemia-reperfusion in vitro, or following exposure to conditions such as hypoxia, decreased ATP, increased reactive oxygen species (ROS) or nitric oxide synthase (NOS) production, or serum starvation of cells cultured in vitro.

In some embodiments, the target molecule is a podocyte-associated molecule. In some embodiments, the target molecule is one of nephrin (NPHS1), podoplanin (PDPN), podocalyxin (PODXL), dystroglycan (DAG1), GLEPP1 (PTPRO), NEPH1 (KIRREL), FAT atypical cadherin 1 (FAT1), cysteine rich transmembrane BMP regulator 1 (CRIM1), integrin alpha-8/beta 1 (ITGA8).

Activator Domain

The activator domain can be any polypeptide that detectably modulates the activity of a cellular network or recruits cells from one location to another. In some embodiments, the activator domain is capable of activating signal transduction pathways by binding to a receptor at the surface a cell. In some embodiments, certain activator domains are growth factor polypeptides, or any agonist of the receptor. It will be apparent that such modulation may be an increase in the activity of the cellular network such as induction of proliferation of cells, induction of cell growth, promotion of cell survival and/or inhibition of apoptosis. In some embodiments, the activator domain can recruit other factors or cells (e.g. stem cells).

An activator domain for a particular application may be selected based on the desired therapeutic outcome. For example, to increase survival and/or for stem cell differentiation (regenerative) purposes, activator domains that comprise IGF, HGF, G-CSF, GLP-1, PDGF, SDF1, TB4, or NRG1 (or a portion or derivative thereof) may be used. To increase cell proliferation (regenerative) purposes, activator domains that comprise IGF, FGF2, G-CSF, GH, HGF, PDGF, TB4, or NRG1 (or a portion or derivative thereof) may be used. An activator domain that comprises FGF2, G-CSF, GH, HGF, SGF1, TB4, VEGF alpha, or a portion or derivative thereof, that substantially retains the ability to bind to cognate receptor, may generally be used to increase angiogenesis.

In some embodiments, the activator domain comprises a change in the amino acid sequence, the three-dimensional structure of the protein, and/or the activity of the protein, relative to the wild-type form of the protein. It will be understood that the selection of a suitable modification in the activator domain for the creation of bi-specific proteins having the desired therapeutic effect can depend on multiple factors.

In some embodiments, the activator domain is a growth factor having amino acid sequence modification relating to the wild-type growth factor (e.g. IGF-1) to decrease its binding to its natural receptor (e.g. IGF-1 receptor), to decrease its binding to binding proteins (IGF binding proteins) and/or decrease its activation of its natural receptor (e.g. IGF-1 receptor). In some embodiments, the activator domain is a growth factor having amino acid sequence modification that reduce (e.g., for about 1-5%, 5-10%, 10%-20%, about 20%-40%, about 50%, about 40%-60%, about 60%-80%, about 80%-90%, 90-95%) its binding to its natural receptor (e.g. IGF-1 receptor).

A growth factor polypeptide detectably modulates activation of a growth factor receptor. In some embodiments, the activator domain of the bi-specific protein is a growth factor, variant or derivative thereof that retains at least about 0.01% of wild-type biological activity. In some embodiments, the activator domain of the bi-specific protein is a growth factor, variant or derivatives thereof that retain at least about 0.1%, at least about 1%, at least about 10%, of wild-type biological activity. In some embodiments, the activator domain of the bi-specific protein is a growth factor, variant or derivative thereof that retains between about 0.01% to about 0.1% of wild-type biological activity. In some embodiments, the activator domain of the bi-specific protein is a growth factor, variant or derivative thereof that retains between about 0.01% to about 1% of wild-type biological activity. In some embodiments, the activator domain of the bi-specific protein is a growth factor, variant or derivative thereof that retains between about 0.01% to about 10% of wild-type biological activity. In some embodiments, the activator domain of the bi-specific protein is a growth factor, variant or derivative thereof that retains between about 0.1% to about 1% of wild-type biological activity. In some embodiments, the activator domain of the bi-specific protein is a growth factor, variant or derivative thereof that retains between about 0.1% to about 10% of wild-type biological activity. In some embodiments, the activator domain of the bi-specific protein is a growth factor, variant or derivative thereof that retains between about 01% to about 10% of wild-type biological activity. Biological activity in some embodiments can be determined by measuring activation of the corresponding growth factor receptor in appropriate cells. In some embodiments, activation may be assessed, for example, by measuring phosphorylation of receptor kinase or downstream effector proteins, such as, but not limited to, AKT, S6, ERK, JNK, mTOR, etc.

Insulin-Like Growth Factors (IGFs) and Derivatives Thereof

The insulin-like growth factors (IGFs) constitute a family of proteins having insulin-like and growth stimulating properties. The IGFs Human IGF1 is a 70 amino acids basic peptide having the protein and DNA sequences shown in SEQ ID NOs: 9 and 31, respectively. IGF-1 and IGF-1 receptor is important for cellular processes such as cell proliferation and survival. Binding of IGF-1 or variant thereof to the IGF-1 receptor stimulates kinase activity, leading to phosphorylation of multiple substrate, thereby initiating signaling cascades. IGF-1 stimulates cell proliferation and survival through activation of the AKT pathway. Upon binding of IGF-I to the IGF-1 receptor, a tyrosine kinase, phosphorylates tyrosine residues on two major substrates, IRS-1 and Shc, which subsequently signal through the Ras/Raf and PI 3-kinase/AKT pathways.

The interaction of IGF-1 (and IGF-2) with the IGF-1 receptor is regulated by IGF binding Proteins (IGFBPs). All six IGFBPs (particularly IGFBP5) have been shown to inhibit IGF action, but in some instances a stimulatory effect has been observed. At least 99% of the IGF in the circulation is normally bound to IGFBPs.

According to some embodiments, the bi-specific proteins can maintain the ability to signal through the IGF-1 receptor. The signaling ability can be determined by assessing whether a downstream intracellular target, e.g., AKT (serine/threonine protein kinase B), is phosphorylated in response to the binding of activator domain of the bi-specific protein to the receptor at the cell surface.

In some embodiments, the activator domain (also referred herein as signaling arm) is human IGF-1 or a derivative of the human IGF-1. In some embodiments, the activator domain has an amino acid sequence recited in any one of SEQ ID NOs: 9-30 or 120.

In some embodiments, the activator domain is a variant of IGF-1 that is capable of maintaining selectivity to the IGF-1 receptor by assaying for receptor phosphorylation or downstream signaling protein phosphorylation in response to the binding of the variant of IGF-1 to the IGF-1 receptor.

In some embodiments, the activator domain is a variant of IGF-1 that is modified to reduce binding to IGF-1 binding proteins (IGFBPs) relative to wild-type IGF-1 while maintaining its ability to activate the AKT pathway. In some embodiments, the IGF-1 variant can activate the IGF-1 receptor with a decreased potency for non-target cells, as assessed by pAKT EC50. EC50 is defined as the concentration needed to achieve the half maximal level of pAKT signaling.

In some embodiments, the activator domain is a derivative of the human IGF-1 and is engineered to decrease the binding of the activator domain to the IGF binding proteins which are present in the serum and other body fluid.

In some embodiments, the activator domain is a derivative of the human IGF-1 and comprises an N-terminal 13-residue extension (also referred as IGF-1 LONG, SEQ ID NO: 11), a mutation E3R (SEQ ID NO: 12) or a combination thereof (LONG E3R, also referred as LR3, SEQ ID NO: 15). In some embodiments, the IGF-1 variant comprises the E3R substitution, an N-terminal 13-residue extension, deletion of amino acids 1-3 ((Des1-3), SEQ ID NO: 10) or a combination thereof to decrease the binding of the activator domain to the IGF binding proteins which are present in the serum and other body fluid.

In some embodiments, the activator domain is a derivative of the human IGF-1 and comprises one or more of the following modifications: an N-terminal 13-residue extension (referred as IGF-1 LONG, SEQ ID NO: 11), a deletion of amino acids 1-3 (Des-1-3, SEQ ID NO: 10), a substitution replacing Arg for a Glu at the 3 position of the polypeptide (E3R, SEQ ID NO: 12), no Arginine at position 37 (R37X, SEQ ID NO: 13), a deletion of amino acids 68-70 (3X, SEQ ID NO: 14), or an N-terminal 13-residue extension and a substitution replacing Arg for a Glu at the 3 position of the wild-type polypeptide (LR3, SEQ ID NO: 15).

In some embodiments, the IGF-1 or the IGF-1 variant can comprise a substitution at one or more of the tyrosine residues. For example, the IGF-1 or IGF-1 variant (e.g. LR3, Des 1-3) can comprise one or more of the following substitutions, Y24L (SEQ ID NOs: 17, 22, and 27), Y31A (SEQ ID NOs: 19, 24 and 29), and Y60L (SEQ ID NOs: 20, 25 and 30). For example, the IGF-1 variant can comprise a Y24L substitution and a Y31A substitution (SEQ ID NOs: 18, 23 and 28). In some embodiments, one or more tyrosine residues (Y24, Y31, Y60 or combinations thereof) can be substituted for a short aliphatic amino acid. In some embodiments, one or more tyrosine residues (Y24, Y31, Y60 or combinations thereof) can be substituted for a polar amino acid. In some embodiments, one or more tyrosine residues (Y24, Y31, Y60 or combinations thereof) can be substituted for leucine, alanine, isoleucine, serine, threonine or any other amino acid.

In some embodiments, the activator domain is a derivative of the human IGF-1 comprising one or more of the following modifications: a N-terminal 13-residue extension (IGF-1 LONG), a deletion of amino acids 1-3 (Des-1-3), a substitution replacing Arg for a Glu at the 3 position of the polypeptide (E3R), no Arginine at position 37 (R37X), a deletion of amino acids 68-70 (3X), an N-terminal 13-residue extension and a substitution replacing Arg for a Glu at the 3 position of the wild-type polypeptide (LR3), substitutions of one or more of tyrosine residues (Y24, Y31, Y60 or combinations thereof (e.g. Y24L, Y31A, Y60L substitutions or combinations thereof).

In some embodiments, the activator domain is derivative of the human IGF-1 comprising a substitution at the position 3 and 31. For example, the activator domain can be derivative of the human IGF-1 comprising E3R and Y31A substitutions. In some embodiments, the activator domain has an amino acid sequence having SEQ ID NO: 120. In some embodiments, the activator domain is encoded by a nucleic acid sequence having SEQ ID NO: 121.

In some embodiments, the activator domain is derivative of the human IGF-1 comprising a mutation (e.g. substitution, deletion) at one or more residues 24 to 37.

In some embodiments, the IGF-1 variant can be modified by glycosylation of one or more glycosylation site present in the IGF-1 variant.

It is believed that the bi-specific proteins that contain IGF-1 LONG, IGF-1 LONG E3R (referred to as IGF-1 (LR3)) or IGF1 Des1-3, have decreased affinity for IGF binding proteins relative to wild-type IGF-1. In some embodiments, the IGF-1 variants of the bi-specific proteins described herein can activate the signaling pathway while having a substantially decreased interaction with the IGF-1 binding proteins relative to wild-type IGF-1.

In some embodiments, the bi-specific proteins that contain the IGF-1 variants described herein have a potency for non-target cells that is less than wild-type IGF-1 for non-target cells.

Certain activator domains that bind to growth factor receptors are provided herein in SEQ ID NOs: 9-30 and 120.

Additional peptide sequence modifications can be included, such as variations, deletions, substitutions or derivatizations of the amino acid sequence of the sequences disclosed herein, so long as the peptide has substantially the same activity or function as the unmodified peptides. Notably, a modified peptide will retain activity or function associated with the unmodified peptide, the modified peptide will generally have an amino acid sequence "substantially homologous" with the amino acid sequence of the unmodified sequence.

In some embodiments, the IGF-1 variant can have an amino acid sequence having at least about 85%, at least about 90%, at least about 95%, at least about 98% identity or at least about 99% identity to the amino acid sequence provided in SEQ ID NOs: 9-30 and 120. In some embodiments, the IGF-1 variant can have an amino acid sequence having from about 85% to about 90%, from about 90% to about 95%, from about 95% to about 98%, from about 98% identity to about 99% identity to the amino acid sequence provided in SEQ ID NOs: 9-30 and 120. In some embodiments, the IGF-1 variant can comprise 10, 20, 30, 40, 50, 60 or more consecutive amino acid of any one of amino acids in SEQ ID NOs: 9-30 or 120. In some embodiments, the IGF-1 variant can have an amino acid sequence recited in any one of SEQ ID NOs: 15-20. In some embodiments, the IGF-1 variant can have an amino acid sequence recited in any one of SEQ ID NOs: 10, or 26-30. In some embodiments, the IGF-1 variant can have an amino acid sequence recited in any one of SEQ ID NOs: 11-14, or 21-25 and 120.

In some embodiments, the bi-specific protein comprises an activator domain having a growth factor variant that is selected to give the bi-specific protein at least an order of magnitude lower EC50 in damaged tissue than in healthy tissue. For example, the bi-specific protein domain comprises a growth factor variant and has an EC50 in damaged tissue that is at least 10 times lower, at least 15 times lower, at least 20 times lower, at least 25 times lower, at least 30 times lower, at least 35 times lower, at least 40 times lower, at least 45 times lower, at least 50 times lower, at least 55 times lower, at least 60 times lower, at least 65 times lower, at least 70 times lower, at least 75 times lower, at least 80 times lower, at least 85 times lower, at least 90 times lower, at least 95 times lower, at least 100 times lower, at least 110 times lower than the EC50 in healthy tissue.

In some embodiments, the bi-specific proteins that contain the IGF-1 variants have a half maximal effective concentration (EC50) that is lower in damaged tissue than in healthy tissue. In some embodiments, the bi-specific proteins that contain the IGF-1 variants have a half maximal effective concentration (EC50) that is at least 10 times lower, at least 15 times lower, at least 20 times lower, at least 25 times lower, at least 30 times lower, at least 35 times lower, at least 40 times lower, at least 45 times lower, at least 50 times lower, at least 55 times lower, at least 60 times lower, at least 65 times lower, at least 70 times lower, at least 75 times lower, at least 80 times lower, at least 85 times lower, at least 90 times lower, at least 95 times lower, at least 100 times lower, at least 110 times lower in damaged tissue than in healthy tissue.

The binding affinity and kinetic on and off rates for binding of the bi-specific fusion protein to the receptor(s) can be measured using standard techniques and compared to other negative control molecules (fusion protein with irrelevant control activator domain, fusion protein lacking an activator domain) and positive control molecules (recombinant wild-type receptor ligand, such as a growth factor). The equilibrium and kinetic binding parameters of the bi-specific fusion protein can also be compared to the same parameters measured for the un-fused wild-type ligand to determine whether fusion of the ligand to other molecules affects the normal binding of the ligand to its corresponding receptor. Such information may be used to determine the effective dose of the bi-specific fusion protein.

A bi-specific fusion protein binds to immobilized growth factor receptor with a significantly higher affinity (e.g., at least 100-fold) than that observed for negative controls. A bi-specific fusion protein binds to immobilized growth factor receptor with a significantly higher affinity (e.g., at least 100-fold) than that observed for negative controls but with a lower affinity (e.g., at least 5-fold) than that observed for positive controls.

In addition, binding to the immobilized receptor can be competed using excess soluble polypeptide, soluble receptor, or antibodies that bind to polypeptide or receptor and block their interaction. In some embodiments, the bi-specific fusion protein binds to the growth factor receptor with an affinity within 1000-fold of the native ligand binding to its receptor.

Native growth factors can be used as activator domains. However it has been observed that bi-specific fusion proteins having growth factors having altered sequences designed to reduce potency but that retain the ability to activate the cognate growth factor receptor, can be used. In some embodiments, the bi-specific fusion proteins have a modified IGF-1 signaling arm having altered sequences designed to reduce binding or interaction with IGF-1 binding protein and/or IGF-1 receptor. Surprisingly, the bi-specific proteins having such modified growth factors have been shown to have a higher specificity to the damaged tissue targeted.

A bi-specific fusion protein (and its activator domain) further has the capacity to mediate cognate receptor activation. Such activity may be assessed, for example, cellular models. For ischemia, a cellular model of ischemia reperfusion, which uses cultured cardiomyocytes such as neonatal rat ventricular myocytes (NRVM) or induced pluripotent stem cell derived cardiomyocytes or cell lines can be used. Simulated ischemia (SI) can be initiated by metabolic inhibitors (deoxyglucose and dithionite) and metabolites (high potassium, lactate, low pH) or by hypoxia in an anaerobic chamber or hypoxic bags. Reperfusion can be simulated by resuspension in an oxygenated buffer. An in vitro adult cardiomyocyte pellet model of ischemia has been developed that provides the two primary components of ischemia—hypoxia and metabolite accumulation—in the absence of any exogenous metabolic inhibitors or metabolites. Table 1 below shows representative methods for demonstrating the ability of a bi-specific fusion protein to prevent damage of cardiomyocytes, promote growth, motility or differentiation of cardiac stem cells and/or promote repair of damaged tissue.

TABLE 1

Activity Assessment Methods

| Aspect | Assay | Reference |
|---|---|---|
| Localization and retention kinetics of activator domain | Detection of activator domain in cell lysate by ELISA<br>Detection of activator domain in cells by immunofluorescence (flow cytometry or microscopic) | Davis,.. *Proc Natl Acad Sci USA* 103(21):8155-60 (2006)<br>Urbanek, *Proc. Natl. Acad Sci. USA* 102 (24): 8692-97 (2005) |
| Signaling by activator domain | Detection of phospho-akt or phospho-ERK in cells by flow cytometry, immunofluorescence, ELISA, phospho-labeling, or Western | Davis,.. *Proc Natl Acad Sci USA* 103(21):8155-60 (2006)<br>Urbanek, *Proc. Natl. Acad Sci. USA* 102 (24): 8692-97 (2005) |
| Protection of cells against apoptosis following hypoxia or other cell stressor | AnnexinV binding by immunofluorescence or flow cytometry<br>Detection of caspase activity<br>TUNEL-assay (reduced number of TUNEL-positive cells)<br>DNA laddering<br>Cell viability<br>Enhancement of cardiomyocyte viability following exposure to $H_2O_2$ or hypoxia or chemical insult. Number of rod-shaped cells<br>pPCR assessment of gene expression | |
| Protection of cells against necrosis | Reduced necrotic area by H&E staining | |
| Reduction in scar formation | Reduction in number of fibroblastic cells in infarct area<br>Reduction collagen deposition<br>Reduction in other matrix proteins associated with scar formation | |
| Migration of CSC into the infarct area | Time dependent increase in c-kit+, sca-1+, MDR1+ cell numbers and numbers undergoing transition to small myocytes | Urbanek, *Proc. Natl. Acad. Sci. USA* 102 (24): 8692-97 (2005) |
| Myocyte mechanics and cell fusion: | Frequency of distribution of myocyte sizes<br>Peak shortening<br>Velocity of shortening and relengthening<br>Assessment of cell fusion (number of X chromosomes) | Urbanek, *Proc. Natl. Acad.Sci. USA* 102 (24): 8692-97 (2005) |
| Cardiac functional assessment | Comparison of MI-treated versus MI-untreated animals<br>LVEDP<br>LVDP<br>+dp/dT<br>LV Weight<br>Chamber Volume<br>Diastolic Wall Stress<br>Survival | Urbanek, *Proc. Natl. Acad. Sci. USA* 102 (24): 8692-97 (2005) |
| Myocardial regeneration | Composition of regenerated myocardium<br>Assessment of BrdU+ cells in infarct area in treated versus untreated animals<br>Myosin+ cells in the infarct area in treated versus untreated animals | Urbanek, *Proc. Natl. Acad. Sci. USA* 102 (24): 8692-97 (2005) |
| Cardiac structural | Infarct size<br>Fibrosis<br>Cardiomyocyte hypertrophy | Urbanek, *Proc. Natl. Acad. Sci. USA* 102 (24): 8692-97 (2005) |

In some cases, it may be desirable to assess the activity of both the activator domain and the targeting polypeptide simultaneously. An ELISA may be conveniently used for this purpose.

The substrate of the targeting polypeptide (e.g., Annexin A5) can be adsorbed to the ELISA plate, which is then blocked with appropriate BSA containing buffers. The bi-specific fusion protein can then be added, followed by addition of recombinant substrate for the activator domain (e.g., if the activator is a growth factor, then the substrate is recombinant cognate receptor or receptor fragment (ectodomain)). This substrate can either be fluorescently labeled for detection or detected using a labeled antibody to a region of the receptor that does not significantly affect ligand binding.

The in vivo activity of the engineered bi-specific fusion protein is generally assessed by detecting signaling changes in molecules that are regulated by the activator domain of the bi-specific fusion protein. This can involve changes in cell surface receptor phosphorylation status or downstream mediators such as phospho-AKT or phospho-ERK as detected by flow cytometry, immunofluorescence, ELISA, phospho-labeling, or Western analysis of treated tissues.

Other functional assessments include tests for the number of viable cells by staining and morphological identification, level of apoptosis by Annexin A5 binding (via immunofluorescence) or flow cytometry, detection of caspase activity, TUNEL-assay (reduced number of TUNEL-positive cells) or DNA laddering. In some embodiments, a bi-specific fusion protein functions in vivo if it induces a significant (e.g., at least 20%) change in the level, functional activity, or phosphorylation of the regulated molecule detected by the assay.

The repair of damaged tissue in a patient can be assessed using any clinically relevant standard. For example, repair of infarcted tissue can be measured by quantitation of cell number, such as the number of myocytes, fibroblast, or amount of scarring, or with functional assays for output or structural aspects of heart function including, LVEDP, LVDP, +dp/dT, LV Weight, Chamber Volume, and Diastolic Wall Stress. Methods for such assessments are well known and amply described in the literature. In general, a bi-specific fusion protein is said to repair damaged tissue if it results in a significant (e.g., at least 10%) change in any such clinical assessment.

Targeting Domain

In some aspects of the invention, the targeting domain is specific to a target molecule associated with a tissue (for example, an ischemia-associated molecule). In some aspects of the invention, the targeting domain of the bi-specific protein targets the bi-specific protein to a non-cancerous or non-tumor cell or tissue. In some embodiments, the targeting domain is specific to podocyte-associated molecules.

The targeting domain may be any polypeptide sequence that serves this function. In some embodiments, binding of the targeting domain to the target molecule does not have or does not modulate a biological activity. As used herein, "biological activity" refers to a defined, known activity performed by exposure of a molecule to a domain of the protein.

In some embodiments, the targeting domain is a non-antibody polypeptide, fragment thereof or variant thereof having a binding affinity to the target molecule, fragment thereof or variant thereof. In some embodiments, the targeting domain is a non-antibody polypeptide having a peptide sequence having a binding affinity to the target molecule, fragment thereof or variant thereof.

Yet in other embodiments, the targeting polypeptide domain comprises one or more antibody variable regions. One skilled in the art will appreciate that any targeting domain capable of binding directly or indirectly to the target molecule is contemplated.

Annexin A5 and Variants Thereof

In some aspects, the targeting domain is an annexin. The term "annexin" refers to any protein capable of binding to phospholipids, especially phosphatidylserine (PS), and member of the annexin family. In some embodiments, the annexin is Annexin A5 but other annexins can equally be used for producing and using the annexin variants of the invention. In some embodiments, the targeting domain is human Annexin A5 (AnxV, SEQ ID NO: 1), a functional fragment thereof, or a variant thereof. A variant of Annexin A5 has at least one amino acid in at least one position in which this amino acid is not found in the parent Annexin A5 polypeptide (wild-type, SEQ ID NO: 1). In some embodiments, the targeting domain is a variant of Annexin A5 (SEQ ID NOs: 2-4, 122). The annexin variants according may comprise one or more amino acid substitutions, deletions, or additions, wherein the amino acid substitutions, deletions, or additions do not substantially affect the ability of the Annexin A5 variant of the bi-specific protein to bind to at least one phospholipid, such as PS. In some embodiments, the Annexin A5 variant can have an amino acid sequence having at least about 85%, at least about 90%, at least about 95%, at least about 98% identity or at least about 99% identity to the amino acid sequence provided in SEQ ID NOs: 1-4, 122. In some embodiments, the Annexin A5 variant can comprise 50, 110, 200, 300, or more consecutive amino acid of any one of amino acids in SEQ ID NOs: 1-4, 122. In some embodiments, Annexin A5 is modified to reduce internalization of annexin A5 while maintaining phosphatidylserine binding affinity. In some embodiments, the annexin variant can bind to at least one phospholipid, in particular to phosphatidylserine (PS), and is not internalized into a cell or is internalized at a slower rate than wild-type annexin.

In some embodiments, one or more residues of Annexin A5 may be altered to modify binding to achieve a more favored on-rate of binding to the target molecule, or a more favored off-rate of binding to the target molecule. Some annexin variants according to the invention have amino acid sequences SEQ ID NO: 1, which is modified to inhibit the internalization into a cell. In some embodiments, the targeting domain is a non-internalizing variant of Annexin A5, (also referred as ni-Annexin A5 or ni-AnxV, SEQ ID NO: 4). In some embodiments, the non-internalizing mutant of Annexin A5 can have an amino acid sequence having at least about 85%, at least about 90%, at least about 95%, at least about 98% identity or at least about 99% identity to the amino acid sequence provided in SEQ ID NO: 4. In some embodiments, the non-internalizing mutant of Annexin A5 can have an amino acid sequence having from about 85% to about 90%, from about 90% to about 95%, from about 95% to about 98%, from about 98% to about 99% identity to the amino acid sequence provided in SEQ ID NO: 4. In some embodiments, the Annexin A5 variant can comprise 50, 110, 200, 300, or more consecutive amino acid of any one of amino acids in SEQ ID NO: 4.

Any variation of Annexin A5 that results in substantially no internalization is envisioned. It should be appreciated that the non-internalizing variant of annexin A5 can confer an extended half-life to the bi-specific protein as compared to a bi-specific protein that contains wild-type A5.

In some embodiments, variants of Annexin A5 that results in substantially no internalization can be used to extend the half-life of the annexin variant or protein associated with the annexin variant. In some embodiments, the variants of annexin A5 that results in substantially no internalization, or fusion proteins containing variants of annexin A5 that results in substantially no internalization, can have an extended half-life of 1.1 to 1.2, 1.1 to 1.3, 1.1. to 1.4, 1.1 to 1.5, 1.1 to 1.6, 1.1 to 1.7, 1.1 to 1.8, 1.1 to 1.9, 1.1 to 2 or greater as compared to wild-type annexin A5, or fusion proteins containing wild-type annexin A5. For example, the extension in half-life of a bi-specific fusion protein containing ni-Annexin A5 (SGF 740, SEQ ID NO: 84) is about 1.15-fold increased compared to a variant of this bi-specific fusion protein containing wt Annexin A5 (SGF 737). In addition, variants of Annexin A5 that result in substantially no internalization should be useful for extension of half-life of other Annexin A5-containing proteins or fusion molecules, such as those used in imaging studies or pre-targeting studies.

The terms "non-internalizing" and "substantially no internalization," as used herein, refer to a lack of internalization of a substantial amount of the bi-specific proteins of the present invention. For example, the phrase "substantially no internalization" will be understood as less than 50% of the bi-specific proteins of the present invention being internalized by a cell to which the bi-specific protein is bound, or less than 25% of the bi-specific proteins of the present invention being internalized by a cell to which the bi-specific protein is bound, or less than 10% of the bi-specific proteins of the present invention being internalized by a cell to which the bi-specific protein is bound, or less than 5% of the bi-specific proteins of the present invention being internalized by a cell to which the bi-specific protein is bound, or less than 3% of the bi-specific protein of the present invention being internalized by a cell to which the bi-specific protein is bound, or less than 1% of the bi-specific proteins of the present invention being internalized by a cell to which the bi-specific protein is bound.

As used herein, the term "corresponding to" is often used to designate the position/identity of an amino acid residue in a polypeptide (e.g., Annexin A5). Those of ordinary skill will appreciate that, for purposes of simplicity, a canonical numbering system (based on wild-type Annexin A5) is utilized herein, so that an amino acid "corresponding to" a residue at position 316, for example, need not actually be the 316th amino acid in a particular amino acid chain but rather corresponds to the residue found at position 316 in a for example Annexin A5 before the post-translational removal of the N-terminal methionine; those of ordinary skill in the art readily appreciate how to identify corresponding amino acids. In particular, it is noted that the amino acid sequence of wild-type Annexin A5 (SEQ ID NO: 1) do not start with a Methionine as the Methionine residue is cleaved during processing.

In some embodiments, Annexin A5 is modified to substitute cysteine at position 315 (corresponding to C316) with serine or alanine to reduce dimer formation. In some embodiments, the Annexin A5 variant having the substitution of cysteine at position 315 to a serine has the amino-acid sequence of SEQ ID NO: 2. In some embodiments, the Annexin A5 variant having the substitution of cysteine at position 315 to an alanine. In some embodiments, the non-internalizing mutant of Annexin A5 can have an amino acid sequence having at least about 85%, at least about 90%, at least about 95%, at least about 98% identity or at least about 99% identity to Annexin A5 modified to substitute cysteine at position 315 (corresponding to C316) with serine or alanine.

In some embodiments, variants of annexin A5 in which D143 was substituted to N, and/or E227 was substituted with A can be used (see Mira, 1997; Kenis, 2004; Kenis 2010 and Ungethum, 2010). For example, the Annexin A5 variant having the substitution of cysteine at position 315 can be modified to have a substitution at D143 and/or E227.

In some embodiments, Annexin A5 or Annexin A5 variants (for example having a substitution at C316, D143 and/or E227) are modified to comprise one or more of the following substitutions R62A, K69A, K100A, E137A, D138G, N159A, L313E (corresponding to R63A, K70A, K101A, E138A, D139G, N160A, L314E). For example, Annexin A5 having SEQ ID NO: 1 can be modified to have C315A or C315S substitution (corresponding to C316A or C316S relative to wild type Annexin A5) and one or more of the following substitutions R62A, K69A, K100A, E137A, D138G, N159A, L313E (corresponding to R63A, K70A, K101A, E138A, D139G, N160A, L314E relative to wild type Annexin A5).

In some embodiments, Annexin A5 (SEQ ID NO: 1) or Annexin A5 variants (for example having a substitution at C316, D143 and/or E227) are modified to comprise one or more of the following substitutions R62A, K69A, K100A, E137A, D138G, N159A, D143N, E227A, C315S or C315A (corresponding to R63A, K70A, K101A, E138A, D139G, D144N, N160A, E228A, C316S or C316A relative to wild type Annexin A5).

In some embodiments, the targeting domain is Annexin A5 which has been engineered to have R63A, K70A, K101A, E138A, D139G, N160A and C316A or C316S substitutions relative to wild type Annexin A5. For example, the targeting domain can have the amino acid sequence of SEQ ID NO: 122.

In some embodiments, the Annexin A5 variant comprises one or more, two, or two or more substitutions in different regions, in order to further decrease the internalization of the annexin in a cell. For example, the Annexin A5 variants may comprise R62A and K69A, R62A and K100A, R62A and E137A, R62A and D138G, R62A and N159A, R62A and K69A and K100A, R62A and K69A and E137A, etc . . . .

The annexin variants according may further comprise one or more amino acid substitutions, deletions, or additions, wherein the amino acid substitutions, deletions, or additions do not substantially affect the ability of the Annexin A5 variant of the bi-specific protein to bind to at least one phospholipid, such as PS.

Other Non-Antibody Targeting Domains:

In other embodiments, the targeting domain is synaptotagmin I, fragment thereof, or variant thereof. Synaptotagmin I (SytI) has been shown to bind phosphatidylserine in a Ca++-dependent manner with a binding affinity of about 5 to 40 nM. In some embodiments, one of the two C2 domains of synaptotagmin (e.g., C2B) can be used as the targeting domain. In some embodiments, the targeting domain is a C2 domain of Ca++-dependent membrane-targeting proteins involved in signal transduction or membrane trafficking (e.g., protein kinase C, blood coagulation factor V and VIII). In some embodiments, the targeting domain has sequence recited in SEQ ID. NO: 114 as provided in U.S. patent application Ser. No. 13/068,808, which is incorporated herein by reference in its entirety. Lactadherin, also known as milk fat globule-EGF 8, is a 45 kDa phosphatidylserine-binding glycoprotein secreted by macrophages. Lactadherin contains EGF-like domains at the amino terminus and two C-domains at the carboxy terminus. Accordingly, in some embodiments, the targeting domain comprises the C-domain of lactadherin, fragment thereof or variant thereof. In some embodiments, one or more residues of the C2 domain may be altered to modify binding to achieve a more favored on-rate of binding to the target molecule, or to achieve a more favored off-rate of binding to the target molecule. In some embodiments, the targeting domain has sequence recited in SEQ ID. NOs: 115 or 116 as provided in U.S. patent application Ser. No. 13/068,808, which is incorporated herein by reference in its entirety. In some embodiments, the targeting polypeptide domain comprises a T cell immunoglobulin mucin 1 & 4 (TIM protein). In other embodiments, the targeting polypeptide domain comprises a 3G4 antibody or antibody domain capable of binding indirectly to phosphatidylserine through plasma 2-glycoprotein 1. Yet in other embodiments, the targeting polypeptide domain comprises an anti-phosphatidylserine antibody (e.g. PS4A7, SEQ ID NO: 128) or antibody domain capable of binding phosphatidylserine as provided in U.S. patent application Ser. No. 13/068,808, which is incorporated herein by reference in its entirety.

In some embodiments, the targeting polypeptide domain comprises a polypeptide that binds to the target molecule. Representative such polypeptides comprise or have the sequences provided herein as SEQ ID NOs: 1-4 and 122.

Representative polypeptides comprise or have an amino acid sequence having at least 85%, at least about 90%, at least about 95%, at least about 98% identity or at least about 99% identity to the sequences provided as SEQ ID NOs: 1-4 and 122. Representative such polypeptides nucleic acid sequences comprise or have the sequences provided herein as SEQ ID NOs: 5-8 and 123. Representative polypeptides nucleic acid sequences can comprise or have a nucleic acid sequence having at least 85%, at least about 90%, at least about 95%, at least about 98% identity or at least about 99% identity to the sequences provided as SEQ ID NOs: 5-8 and 123.

Native polypeptide can be used as targeting domains. It will be apparent, however, that portions of such native sequences and polypeptides having altered sequences may also be used, provided that such polypeptides retain the ability to bind the target molecule with an appropriate binding affinity (Kd) as described in more details below.

Antibody Targeting Domain:

As used herein, an "antibody" is a protein consisting of one or more polypeptides substantially encoded by immunoglobulin genes. A typical antibody is a tetramer that is composed of two identical pairs of polypeptide chains, each pair having one "light" (about 25 kD) and one "heavy" chain (about 50-70 kD). "VL" and "VH" refer to these light and heavy chains respectively. An "antibody variable region" is an N-terminal region of an antibody variable chain (VL or VH) comprising amino acid residues that are primarily responsible for antigen recognition. Those of ordinary skill in the art are readily able to identify an antibody variable region and to determine the minimum size needed to confer antigen recognition. Typically, an antibody variable region comprises at least 70 amino acid residues, and more commonly at least 100 amino acid residues. A polypeptide that comprises an antibody variable region may (but need not) further comprise other light and/or heavy chain sequences, and may (but need not) further comprise sequences that are not antibody-derived. It will be apparent that the sequence of an antibody variable region may be naturally-occurring, or may be modified using standard techniques, provided that the function (antigen recognition) is retained. Certain polypeptides that comprise an antibody variable region are single chain antibodies (antibodies that exist as a single polypeptide chain), more preferably single chain Fv antibodies (scFv) in which a variable heavy chain region and a variable light chain region are joined together (directly or through a peptide linker) to form a continuous polypeptide. The scFv antibody may be chemically synthesized or may be expressed from a nucleic acid including $V_H$- and $V_L$-encoding sequences either joined directly or joined by a peptide-encoding linker.

Such single chain antibodies are also intended to be encompassed within the term "antibody".

Diabodies are also encompassed within the term "antibody". Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites. The diabodies may be chemically synthesized or may be expressed from a nucleic acid including VH- and VL-encoding sequences either joined by a peptide-encoding linker.

The "Fab region"/"Fab domain"/"Fab fragment", contains variable regions that define the specific target that the antibody can bind. Fab fragments can be produced from intact antibodies using methods known in the art, such as by proteolytic cleavage with enzymes or may be produced recombinantly, using standard recombinant DNA and protein expression technologies.

Examples of binding fragments encompassed within the term "antibody" thus include but are not limited to: (i) a Fab fragment, a monovalent fragment consisting of the VL, VH, CL and CH1 domains; (ii) F(ab)2 and F(ab')2 fragments, a bivalent fragment comprising two Fab fragments linked by a disulfide bridge at the hinge region; (iii) a Fd fragment consisting of the VH and CH1 domains; (iv) a scFv fragment consisting of the VL and VH domains of a single arm of an antibody, (v) a dAb fragment which consists of a domain; and (vi) an isolated complementarily determining region (CDR). Such antibodies may be produced from intact antibodies using methods known in the art, or may be produced recombinantly, using standard recombinant DNA and protein expression technologies.

In some embodiments, an anti-phosphatidylserine antibody, such as chimeric antibody Bavituximab that binds to phosphatidylserine can be used as a targeting domain.

In some embodiments, antibodies that bind podocyte associated proteins can be used as a targeting domain. For example, antibodies capable of biding to nephrin (NPHS1), podoplanin (PDPN), podocalyxin (PODXL), dystroglycan (DAG1), GLEPP1 (PTPRO), NEPH1 (KIRREL), FAT atypical cadherin 1 (FAT1), cysteine rich transmembrane BMP regulator 1 (CRIM1), integrin alpha-8/beta 1 (ITGA8) can be used.

Nephrin, a cell surface signaling receptor, regulates podocyte function. It is crucial podocyte molecule in the kidney glomerular filtration barrier. Nephrin is an Ig-like transmembrane protein. It is a major component of the podocyte slit diaphragm and is essential for maintaining normal glomerular permeability.

Podoplanin is a glomerular podocyte membrane mucoprotein. Podoplanin plays a role in maintaining the unique shape of podocyte foot processes and glomerular permeability. In rats, the 43-kD integral membrane protein podoplanin is localized on the surface of podocytes, and transcriptionally downregulated puromycin nephrosis.

Podocalyxin is the major sialoglycoprotein expressed on the apical membrane of the podocyte. It is involved in the regulation of both adhesion and cell morphology and cancer progression. It functions as an anti-adhesive molecule that can maintain an open filtration pathway between neighboring foot processes in the podocyte by charge repulsion. It acts as a pro-adhesive molecule, enhancing the adherence of cells to immobilized ligands, increasing the rate of migration and cell-cell contacts in an integrin-dependent manner. The protein induces the formation of apical actin-dependent microvilli. It is involved in the formation of a preapical plasma membrane subdomain to set up initial epithelial polarization and the apical lumen formation during renal tubulogenesis. It plays a role in cancer development and aggressiveness by inducing cell migration and invasion through its interaction with the actin-binding protein EZR. It affects EZR-dependent signaling events, leading to increased activities of the MAPK and PI3K pathways in cancer cells.

In kidney, dystroglycan (DG) has been shown to cover the basolateral and apical membranes of the podocyte. alpha-DG is heavily glycosylated, which is important for its binding to laminin and agrin in the glomerular basement membrane. Alpha-DG covers the whole podocyte cell membrane in the rat, and is expressed at both the basolateral and apical sides of the podocyte. This localization suggests that alpha-DG plays a dual role in the maintenance of the unique architecture of podocytes by its binding to the glomerular basement membrane, and in the maintenance of the integrity of the filtration slit, respectively. Dystroglycan was diffusely found over the entire cell surface of the podocytes.

GLEPP1 (PTPRO) is a podocyte receptor membrane protein tyrosine phosphatase located on the apical cell membrane of visceral glomerular epithelial cell and foot processes, has been used as a marker of acute podocyte injury.

NEPH1 (KIRREL) is a podocyte membrane protein of the Ig superfamily. The cytoplasmic domains of these proteins interact with the C terminus of podocin. It is expressed in kidney podocytes, cells involved in ensuring size- and charge-selective ultrafiltration.

FAT atypical cadherin 1 (FAT 1) is an essential protein for cellular polarization, directed cell migration and modulating cell-cell contact and expressed in the highly polarized podocyte cell-type.

Cysteine rich transmembrane BMP regulator 1 (CRIM1) has tissue enrichment expression in the renal glomeruli and is thought to play a role in tissue development through interactions with members of the transforming growth factor beta family, such as bone morphogenetic proteins.

Integrin alpha-8/beta 1 (ITGA8) functions in the genesis of kidney and probably of other organs by regulating the recruitment of mesenchymal cells into epithelial structures. It recognizes the sequence R-G-D in a wide array of ligands including TNC, FN1, SPP1 TGFB1, TGFB3 and VTN. NPNT is probably its functional ligand in kidney genesis. ITGA8 has been shown to accumulate in the renal glomeruli in response to renal injury, such as diabetic nephropathy.

Binding of Targeting Domain

Preferred substantial binding includes binding with a dissociation constant ($K_d$) of $10^{-6}$, $10^{-7}$, $10^{-8}$, $10^{-9}$, $10^{-10}$, $10^{-11}$, $10^{-12}$ M or better. For example, the $K_d$ of an antibody-antigen interaction indicates the concentration of antibody (expressed as molarity) at which 50% of antibody and antigen molecules are bound together at thermodynamic equilibrium. Thus, at a suitable fixed antigen concentration, 50% of a higher (i.e., stronger) affinity antibody will bind antigen molecules at a lower antibody concentration than would be required to achieve the same percent binding with a lower affinity antibody. $K_d$ is also the ratio of the kinetic on and off rates ($k_{on}$ and $k_{off}$); i.e., $K_d=k_{off}/k_{on}$. Thus, a lower $K_d$ value indicates a higher (stronger) affinity. As used herein, "better" affinities are stronger affinities, and are identified by dissociation constants of lower numeric value than their comparators, with a $K_d$ of $10^{-10}$ M being of lower numeric value and therefore representing a better affinity than a $K_d$ of $10^{-9}$ M. Affinities better (i.e., with a lower $K_d$ value and therefore stronger) than $10^{-7}$ M, preferably better than $10^{-8}$ M, are generally preferred. Values intermediate to those set forth herein are also contemplated, and preferred binding affinity can be indicated as a range of dissociation constants, for example preferred binding affinities for antibodies disclosed herein are represented by $K_d$ values ranging from $10^{-6}$ to $10^{-12}$ M (i.e., micromolar to picomolar), preferably $10^{-7}$ to $10^{-12}$ M, more preferably $10^{-8}$ to $10^{-12}$ M or better. An antibody that "does not exhibit significant cross-reactivity" is one that will not appreciably bind to an off-target antigen. For example, in one embodiment, an antibody that specifically and selectively binds to cardiac myosin will exhibit at least a two, and preferably three, or four or more orders of magnitude better binding affinity (i.e., binding exhibiting a two, three, or four or more orders of magnitude lower $K_d$ value) for cardiac myosin than for myosin molecules other than cardiac myosin or for non-myosin proteins or peptides. Binding affinity and selectivity can be determined using any art-recognized methods for determining such characteristics, including, for example, using Scatchard analysis and/or competitive (competition) binding assays.

Binding may be assessed, and $K_d$ values determined, using any of a variety of techniques that are well known in the art. For example, binding to an ischemia-associated DNA molecule is commonly assessed by coating an appropriate solid support (e.g., beads, ELISA plate or BIACORE chip) with target DNA fragments. For a targeting polypeptide domain that binds to any sequence of DNA, DNA fragments (single or double-stranded) of 10 base pairs or larger are immobilized on the solid substrate. For a targeting polypeptide domain that binds to a specific sequence or DNA complex (e.g., DNA-histone complex) the appropriate corresponding target is immobilized. Prior to adding the ischemia-associated molecule, non-specific binding sites for protein are blocked with BSA, milk, or any other appropriate blocker. Uncoated wells or wells coated with a non-target molecule serve as specificity controls. Increasing concentrations of the bi-specific fusion protein (or targeting polypeptide domain) are incubated with target-coated substrate or control substrate. A fusion protein or domain that does not bind to the target is also tested as a specificity control. Target specific, dose-dependent binding of the bi-specific fusion protein (or targeting polypeptide domain) is then assessed by measuring the amount of bi-specific fusion protein (or targeting polypeptide domain) binding to target versus controls as a function of increasing dose using standard protocols corresponding to the solid support and binding technology being used. Representative such protocols include those described in Wassaf et al., Anal. Biochem. 351(2): 241-53 (2006); Epub 2006 Feb. 10 (BIACORE); and Murray and Brown, J. Immunol. Methods. 127(1): 25-8 (1990) (ELISA). In addition, studies that vary the amount of immobilized target molecule or that include increasing levels of soluble target molecule as a competitor may also be performed to monitor binding and specificity.

The binding affinity and kinetic on and off rates for binding to the target molecule are measured using standard techniques and compared to other negative control molecules (e.g., fusion protein with irrelevant targeting polypeptide or fusion protein lacking a targeting polypeptide or fusion proteins with non-binding targeting polypeptide) and positive control molecules (e.g., parental antibody that targets the target molecule, or other antibodies or antibody fragments that are known to bind to the target molecule). For example, the non-binding targeting polypeptide can be a non-binding Annexin A5 variant, a non-binding synaptotagmin variant or a non-binding scFv.

In certain embodiments, the $K_d$ is determined using a biosensor (e.g., by surface plasmon resonance (e.g., BIAcore) or resonant mirror analysis (IAsys)). Such determinations may be performed as described by Hefta et al., Measuring Affinity Using Biosensors, in "Antibody Engineering: A Practical Approach," McCafferty et al. (eds), pp. 99-116 (Oxford University Press, 1996), and references cited therein. Briefly, kinetic on and off rates ($k_{on}$ and $k_{off}$) are determined using a sensor chip to which the ischemia-associated molecule has been coupled. To evaluate association ($k_{on}$), solutions of different concentrations of bi-specific fusion protein (or targeting polypeptide domain) flow across the chip while binding is monitored using mass sensitive detection. Using the BIAcore system (GE Healthcare; Piscataway, NJ), $k_{on}$ is the slope of the plot of dR/dt versus R, where R is the signal observed. Following binding, dissociation is observed by passing a buffer solution across the chip, and $k_{off}$ is determined in an analogous fashion. $K_d$ is then calculated using the equation:

$$K_d = k_{off}/k_{on}$$

In the context of the present invention, a bi-specific fusion protein binds to the target molecule if it binds with a $K_d$ of less than $10^{-6}$ M, preferably less than $10^{-7}$ M, $10^{-8}$ M, $10^{-9}$ M or $10^{-10}$ M. In addition, the binding of the bi-specific fusion protein to the target molecule in this assay is significantly higher (e.g., at least 2-, 10- or 100-fold higher) than binding of the bi-specific fusion protein to negative controls. Preferably, binding to the immobilized target can also be competed using excess soluble target.

As noted above, certain target molecules are specific to (or enriched in) damaged cells. Representative target molecules include but are not limited to phosphatidylserine, DNA, myosin, cardiac myosin, c-Met (HGF receptor), phosphatidylserine, P-selectin, and ICAM-1. Binding to damaged cells is conveniently demonstrated in vitro using cultured cells that are exposed to conditions that induce necrosis or apoptosis. For example, necrosis can be induced in cultured cardiomyocytes by simulated ischemia/reperfusion, and monitored using a LDH release assay, or trypan blue assay followed by subtraction of the number of cells undergoing apoptosis, essentially as described in Shan et al., *Am. J. Physiol. Cell. Physiol.* 294:833-841 (2008). This assay quantitates the total dead cells and the difference between the total and the number of apoptotic cells is attributed to necrosis, as discussed in more detail below. Conditions that induce apoptosis include exposure to $H_2O_2$ or hypoxia, and apoptosis can be monitored using any of a variety of techniques known in the art including, for example, Annexin A5 binding, cleavage of target peptide sequences by known caspases that are activated by apoptosis, or DNA laddering (measured by TUNEL assay, essentially as described in Kuramochi, *J. Biol. Chem.* 279(49): 51141-47 (2004)). Binding to the cells undergoing necrosis or apoptosis may be assessed by adding fluorescently labeled bi-specific fusion protein (or targeting polypeptide domain) or appropriate control proteins to cells following the induction of apoptosis or necrosis. After incubation of the proteins with the cells for times ranging from a few minutes to one day, the cells are washed and then the cell-bound fluorescence is measured using immunofluorescence, flow cytometry, or similar techniques. Alternatively, other methods of detecting the bound bi-specific fusion protein (or targeting polypeptide domain) may be used, including radiolabeling or using enzymes conjugated to the bi-specific fusion protein (or targeting polypeptide domain) or to antibodies that bind to the fusion protein (or targeting polypeptide domain), which is common practice in ELISA protocols. The bi-specific fusion protein (or targeting polypeptide domain) binds to target cells if significantly higher (e.g., 2-fold higher) binding to cells following ischemia (e.g., cells undergoing necrosis or apoptosis) is detected, as compared to cells that have not experienced injury (e.g., cells not undergoing apoptosis or necrosis).

In vivo targeting may be demonstrated by inducing, for example, ischemia in an animal model and comparing the level of administered bi-specific fusion protein (or targeting polypeptide domain) in a target tissue before and after ischemia. In vivo targeting to damaged cells may be demonstrated by inducing tissue damage in an animal model, administering the bi-specific fusion protein (or targeting polypeptide domain), and comparing the level of bi-specific fusion protein (or targeting polypeptide domain) in damaged versus undamaged cells. In one embodiment, the bi-specific fusion proteins are designed to target areas of tissue damage following ischemia-reperfusion injury. In such a case, demonstration of in vivo targeting may be accomplished by inducing tissue damage, preferably by a method that causes ischemia followed by re-establishment of blood supply. Numerous methods are available to do this in different tissues. For example, blood flow to the hindlimb of the mouse can be transiently blocked with a simple tourniquet. Alternatively, temporary clamp on the artery leading into the kidney can be employed. Ischemia-reperfusion injury can be induced in the heart through temporary blockage of the coronary artery as demonstrated in mice, rats, dogs, and pigs. Representative methods for inducing tissue damage in an animal model are summarized in Table 2 below.

TABLE 2

Representative Methods used to Induce Ischemia-Reperfusion Damage

| Organ or tissue | Methods used to induce damage | Reference |
| --- | --- | --- |
| Heart | Mouse: left anterior descending artery (LAD) clamped for up to 30 to minutes followed by reperfusion<br>Rat: coronary artery ligation | Dumont et al., *Circulation* 102(13):1564-8 (2000)<br>Davis, *Proc. Natl. Acad. Sci. USA* 23:103(21):8155-60 (2006) |
| Kidney | Mouse: Renal artery clamped with pediatric suture for 1-6 hrs | Chen et al., *FASEB J.* 4(12): 3033-39 (1990) |
| Liver | Dog: The hepatic pedicle and hepatic artery (close to the celiac artery) were cross-clamped with vascular clamps.<br>Pig: Details in reference | Miranda et al., *Braz. J. Med. Biol. Res.* 40(6):857-65 (2007)<br>Kobayashi et al., *World J. Gastroenterol.*13(25):3487-92 (2007) |
| Hindlimb |  | Zbinden et al., *Am. J. Physiol. Heart Circ. Physiol.* 292: H1891-H1897 (2007) |

Animal models for ischemia-reperfusion injury are further detailed in the following references:

Greenberg et al., Chapter 7. Mouse models of ischemic angiogenesis and ischemia-reperfusion injury. Methods Enzymol. 444: 159-74 (2008).

Chimenti et al., Myocardial infarction: animal models. Methods Mol. Med. 98: 217-26 (2004).

Black S C, In vivo models of myocardial ischemia and reperfusion injury: application to drug discovery and evaluation. J. Pharmacol. Toxicol. Methods 43(2): 153-67 (2000).

The specificity of targeting can be established by comparing the bi-specific fusion protein (or targeting polypeptide domain) deposition in the clamped versus unclamped kidney as shown in Chen et al., FASEB J. 4(12): 3033-39 (1990), or in the treated versus untreated hindlimb as shown in Zbinden et al., Am. J. Physiol. Heart Circ. Physiol. 292: H1891-H1897 (2007), using radiolabeled bi-specific fusion protein (or targeting polypeptide domain). Alternatively, bi-specific fusion protein (or targeting polypeptide domain) can be detected in homogenized tissue using ELISA, or can be imaged in real time using bi-specific fusion protein (or targeting polypeptide domain) labeled with the appropriate metal for imaging (e.g., Tc99, Y or Gd). Specific deposition in the damaged area of the heart can be measured as described in Dumont et al., *Circulation* 102(13): 1564-8 (2000). Representative methods for demonstrating targeting of proteins to damaged tissue are shown in Table 3 below.

the certain targeting polypeptide domains comprise a scFv antibody that binds to the target molecule. For example, the targeting domain can be an anti-DNA S1-1 scFv an anti-DNA SI-22 scFv. Representative such antibodies and scFv antibodies comprise or have the sequences provided as SEQ ID NOs: 128-136. In some embodiments, representative such antibodies and scFv antibodies nucleic acid sequences comprise or have the sequences provided as SEQ ID NOs 220-224 in U.S. patent application Ser. No. 13/068,808, which is incorporated herein by reference in its entirety.

It will be apparent that functionally related antibodies may also, or alternatively, be used as a targeting polypeptide domain. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to generate modified antibodies that mimic the properties of an original antibody by combining CDR sequences from one antibody with framework sequences from a different antibody. Such framework sequences can be obtained from public DNA databases that include germline antibody gene sequences.

Thus, one or more CDRs of a targeting polypeptide domain sequence provided herein can be used to create

TABLE 3

Demonstration of Targeting to Damaged Tissue

| Damaged organ or tissue targeted | Methods used to demonstrate targeted delivery | Reference |
| --- | --- | --- |
| Heart | Humans: Tc99 labeling of annexin A5 followed by imaging in humans using SPECT in patients with myocardial infarction followed by reperfusion attempts via angioplasty or thrombolysis | Hofstra et al., *The Lancet* 356 (9225): 209-12 (2000) |
| Heart | Mouse: Fluorescent labeling of annexin A5 in murine model of ischemia reperfusion with distribution in the myocardium detected histologically | Dumont et al., *Circulation* 102(13): 1564-8 (2000) |
| Heart | Humans: Tc99 labeling of annexin A5 followed by imaging in humans using SPECT in patients undergoing cardiac transplant rejection | Hofstra et al., *The Lancet* 356 (9225): 209-12 (2000) |
| Heart | Mouse: Fluorescently-labeled growth factor imaged in heart tissue using confocal microscopy | Urbanek, *Proc. Natl. Acad. Sci. USA* 102 (24):8692-97 (2005) |
| Damaged kidney targeted using radiolabeled antibody to DNA | Radiographs of clamped versus unclamped kidney<br>Microautoradiographs to show localization to specific cellular structures in the kidney<br>Imaging of whole mouse using I131-labeled antibody to DNA (versus labeled control)<br>Biodistribution of I125-labeled antibody to show deposition in non-target tissues | Chen et al., *FASEB J.* 4(12):3033-9 (1990) |

As noted above, certain targeting polypeptide domains comprise an antibody that binds to the target molecule (e.g., DNA, myosin, cardiac myosin, c-Met, P-selectin, ICAM-1, phosphatidylserine). In some embodiments, the targeting domain is an anti-myosin antibody (e.g. R11D-10 against human cardiac myosin, 2G4-sD7 against cardiac myosin heavy chain, 1B2 and 5C2 against human cardiac myosin heavy chain, 2F4 against human cardiac myosin, monoclonal antibodies against myosin, B7 antibody, B7 scFv, or other antibodies known in the art). In some embodiments, functionally related antibodies that retain the binding characteristics of the original targeting polypeptide domain. The heavy and light chain variable framework regions can be derived from the same or different antibody sequences. CDR regions are readily identified using alignments with known sequences in databases such as Vbase and IMGT.

It is well known in the art that antibody heavy and light chain CDR3 domains play a particularly important role in the binding specificity/affinity of an antibody for an antigen. Accordingly, in certain embodiments, antibodies are generated that include the heavy and/or light chain CDR3s of the particular antibodies described herein. The antibodies can further include the heavy and/or light chain CDR1 and/or CDR2s of the antibodies disclosed herein.

The CDR 1, 2, and/or 3 regions of the engineered antibodies described above can comprise the exact amino acid sequence(s) as those disclosed herein. However, the ordinarily skilled artisan will appreciate that some deviation from the exact CDR sequences may be possible, particularly for CDR1 and CDR2 sequences, which can tolerate more variation than CDR3 sequences without altering epitope specificity (such deviations are, e.g., conservative amino acid substitutions). Accordingly, in another embodiment, the engineered antibody may be composed of one or more CDR1s and CDR2s that are, for example, 80%, 90%, 95%, 98%, 99% or 99.5% identical to the corresponding CDRs of an antibody named herein.

In another embodiment, one or more residues of a CDR may be altered to modify binding to achieve a more favored on-rate of binding, or a more favored off-rate of binding. Using this strategy, an antibody having ultra-high binding affinity (e.g., Kd=10-10 or less) can be achieved. Affinity maturation techniques, well known in the art, can be used to alter the CDR region(s) followed by screening of the resultant binding molecules for the desired change in binding. Accordingly, as CDR(s) are altered, changes in binding affinity as well as immunogenicity can be monitored and scored such that an antibody optimized for the best combined binding and low immunogenicity are achieved.

Modifications can also be made within one or more of the framework or joining regions (i.e., non-CDR residues) of the heavy and/or the light chain variable regions of an antibody, so long as antigen binding affinity subsequent to these modifications is not substantially diminished.

Peptide Linkers and Half-Life Modulator

One skilled in the art would appreciate that bi-specific proteins used in therapeutic applications may not exhibit optimal serum half-lives due to their relatively low molecular weight. In some therapeutic applications, it may therefore be desirable to modulate the half-life of the bi-specific proteins. In some embodiments, to achieve accumulation of the bi-specific protein to the diseased injured or damaged area of an organ, the bi-specific protein is conjugated, operatively associated or fused with a peptide linker. In some embodiments, to achieve accumulation of the bi-specific protein to the diseased injured or damaged area of an organ, the bi-specific protein is conjugated operatively associated or fused with a half-life modulator. Preferably, the peptide linker or the half-life modulator is non-immunogenic in humans.

In some embodiments, the half-life modulators can increase the in vivo half-life of the fusion proteins. For example, the half-life of the bi-specific proteins comprising the half-life modulator is about 1 hour, 2 hour, 3 hours, 4 hours, 5 hours, 6 hours or greater. In some embodiments, the half-life of the bi-specific proteins comprising the half-life modulator is about 24 hours, or greater. In some embodiments, the half-life of the bi-specific proteins comprising the half-life modulator is about a week or greater.

The targeting polypeptide domain and activator domain may be directly joined via a peptide bond. In some embodiments, they may be joined via a half-life modulator. In preferred embodiments, the half-life modulator is a polypeptide. Accordingly, the half-life modulator can have two termini, an N-terminus and a C-terminus. In some embodiments, the half-life modulator is joined at one terminus via a peptide bond to the targeting polypeptide domain and is joined at the other terminus via a peptide bond to the activator domain. In certain embodiments, the linker is joined at the N-terminus to the C-terminus of the targeting polypeptide domain and at the C-terminus to the N-terminus of the activator domain. In other embodiments, the linker is joined at the C-terminus to the targeting polypeptide domain and at the N-terminus to the activator domain. Yet, in other embodiments, the half-life modulator is joined at one of the termini of the bi-specific protein. For example, in some embodiments, the half-life modulator is joined at the C-terminus to the N-terminus of the activator domain. In other embodiments, the half-life modulator is joined at the C-terminus of the targeting domain. In other embodiments, the half-life modulator can be joined at the N-terminus to the C-terminus of the activator domain. Yet in other embodiments, the half-life modulator can be joined at the N-terminus to the C-terminus of the targeting domain.

In some embodiments, the half-life modulator is designed to drive the size of the bi-specific fusion protein beyond about 70 kDa or equivalent radius to minimize renal clearance. In some embodiments, the half-life modulator is designed to extend the half-life of the bi-specific fusion protein through FcRn receptor-mediated recycling or through binding to serum components such as Human Serum Albumin (HSA).

In some embodiments, the peptide linker or the half-life modulator is non-immunogenic in humans. The half-life modulator can be a human serum protein or a derivative thereof that retains at least 50% sequence identity over a region that consists of at least 100 consecutive amino acids. As used herein "sequence identity" means, in the context of comparing a polynucleotide or a polypeptide sequence to a reference sequence, that the polynucleotide or polypeptide sequence is the same or has a specified percentage of nucleotides or residues that are the same at the corresponding locations within the reference sequence when the polynucleotide or polypeptide sequences are optimally aligned.

In some embodiments, the half-life modulator can be modified by glycosylation of one or more glycosylation site present in the half-life modulator. For example, the following amino acids: asparagine, serine, threonine can be added or removed to alter the glycosylation of the half-life modulator. In some embodiments, glycosylation of the half-life modulator in the bi-specific protein can modulate the half-life of the bi-specific protein. In some embodiments, the half-life modulator sequence is modified to reduce glycosylation. Such modification comprising the substitution of Asn (N) by Gln (Q) or Ala (A), and/or the substitution of Ser (S) or Thr (T) by Ala (A).

Human serum albumin (HSA, SEQ ID NO: 54) has a naturally long serum half-life, in part due to its binding to FcRN and recycling. HSA is the most abundant protein in the blood and has a demonstrated safety in humans.

In some embodiments, the half-life modulator is a HSA variant. In some embodiments, the half-life modulator comprises at least 100 consecutive amino acids that are at least 70%, 80%, 85%, 90% or 95% identical to wild type human serum albumin amino acid sequence. In some embodiments, the half-life modulator comprises at least 200 consecutive amino acids that are at least 70%, 80%, 85%, 90% or 95% identical to wild type human serum albumin amino acid sequence. In some embodiments, the half-life modulator comprises at least 300 consecutive amino acids that are at least 70%, 80%, 85%, 90% or 95% identical to wild type human serum albumin amino acid sequence. In some embodiments, the half-life modulator comprises at least 400 consecutive amino acids that are at least 70%, 80%, 85%, 90% or 95% identical to wild type human serum albumin amino acid sequence. In some embodiments, the half-life modulator comprises at least 500 consecutive amino acids that are at least 70%, 80%, 85%, 90% or 95% identical to wild type human serum albumin amino acid sequence.

In some embodiments, the half-life modulator can comprise a human serum albumin sequence or variant thereof. In some embodiments, the human serum albumin sequence can have a 3 aa, a 4aa, a 5aa, a 6aa or more deletion at the C-terminal end of the HSA.

In some embodiments, the HSA variant can have one of more of the following substitutions:
cysteine C58 can be substituted for example, with a serine (C58S),
lysine K420 can be substituted for example, with a glutamic acid (K420E),
asparagine N527 can be substituted for example, with a glutamine (N527Q),
glutamic acid E505 can be substituted for example, with a glycine G (E505G),
valine V547 can be substituted for example, with an alanine (V547A),
Asparagine N527 can be substituted for example, with a Glutamine (N527Q).

In some embodiments, the HSA variant can have amino acids 26-609 and have one of more of the following substitutions:
cysteine C58 can be substituted for example, with a serine (C58S),
lysine K420 can be substituted for example, with a glutamic acid (K420E),
asparagine N527 can be substituted for example, with a glutamine (N527Q),
glutamic acid E505 can be substituted for example, with a glycine G (E505G),
valine V547 can be substituted for example, with an alanine (V547A),
Asparagine N503 and/or N527 can be substituted for example, with an Glutamine (N503Q and/or N527Q).

In some embodiments, the HSA variant (referred herein as mHSA) has the following substitutions: C34S, N503Q (SEQ ID NO: 55). In some embodiments, the HSA variant (referred herein as mHSA7) has the following substitutions C34S, N503Q, E505G and V547A (SEQ ID NO: 56). In some embodiments, the HSA variant has amino acids 26-609 and the following substitutions C58S and N527Q (SEQ ID NO: 124).

In some embodiments, the asparagine at position 503 and/or 527 of HSA, which may be deamidated and decrease half-life, can be removed by the N503Q substitution and/or the N527Q. In some embodiments, the cysteine C34 of HSA may be substituted to serine or alanine (S or A) to remove the free cysteine and minimize alternate disulfide-bond formation.

In some embodiments, the half-life modulator is a modified version of the domain III (mHSA_dIII) of a modified HSA with the N503Q substitution and an additional terminal glycine. Such a modified version retains the HSA property of binding to FcRn and increased serum half-life.

In some embodiments, the half-life modulator comprises at least 100 consecutive amino acids that are at least 70%, 80%, 85%, 90% or 95% identical to a human Fc amino acid sequence (SEQ ID NO: 21 provided in U.S. patent application Ser. No. 13/068,808, which is incorporated herein by reference in its entirety). In some embodiments, the half-life modulator comprises at least 100 consecutive amino acids that are about 70%, about 75%, about 80%, about 85%, about 90% or about 95% identical to a wild-type human Fc amino acid sequence. The Fc domain of an antibody has a natural capability to bind FcRn, resulting in an extended half-life. In some embodiments, the Fc domain of an antibody is engineered not to bind Fc(gamma)R In an exemplary embodiment, the Fc domain is engineered to substitute N297 with Q (N297Q variant). In some embodiments, the half-life modulator is a monomeric variant form of Fc, named scFc. For example, the subset of IgG heavy chain which naturally dimerizes to form Fc is hinge-CH2-CH3. In some embodiments, the Fc domain is engineered to form a single chain by linking the hinge-CH2-CH3 with a flexible linker such as GGGGSGGGGSGGGGSGGGGS to create a hinge-CH2-CH3-linker-hinge-CH2-CH3 chain. In an exemplary embodiment, the single chain Fc (scFc) is engineered to substitute N297 with Q and C220 with S (N297Q, C220S).

In some embodiments, the proteins can comprise the Fc regions of an immunoglobulin molecule (e.g. IgG) as the half-life modulator. Using such a framework results in a constitutively dimeric protein. The primary translation product of the nucleic acid coding for the Fc-fusion protein is a single molecule comprising the signaling and/or the targeting arm linked to single chain of Fc derived from, for example, human IgG1. Following translation, but prior to secretion, this fusion molecule dimerizes via 3 cysteine residues in the Fc region to form dimeric fusions protein. In some embodiments, Fc-fusion proteins can be homodimers having two signaling arms, two targeting arms or two signaling arms and two targeting arms (see FIG. 1A)

In some embodiments, the half-life modulator comprises at least 100 consecutive amino acids that are at least 70%, 80%, 85%, 90% or 95% identical to wild type human alpha-fetoprotein (AFP) amino acid sequence. In some embodiments, the half-life modulator comprises at least 100 consecutive amino acids that are about 70%, 75%, 80%, 85%, 90% or 95% identical to wild type human alpha-fetoprotein (AFP) amino acid sequence. In some embodiments, the N-linked glycosylation site of the AFP is removed by the N251Q substitution.

In some embodiments, the half-life modulator comprises at least 100 consecutive amino acids that are at least 70%, 80%, 85%, 90% or 95% identical wild-type vitamin D-binding protein (VDBP) amino acid sequence. In some embodiments, the half-life modulator comprises at least 100 consecutive amino acids that are about 70%, 75%, 80%, 85%, 90% or 95% identical wild-type vitamin D-binding protein (VDBP) amino acid sequence. In some embodiments, the N-linked glycosylation site of the VDBP can be removed by the N288Q or N288T substitution.

In some embodiments, the half-life modulator comprises at least 100 consecutive amino acids that are at least 70%, 80%, 85%, 90% or 95% identical to wild-type human transthyretin (TTR) amino acid sequence. In some embodiments, the half-life modulator comprises at least 100 consecutive amino acids that are about 70%, 75%, 80%, 85%, 90% or 95% identical to wild type human transthyretin (TTR) amino acid sequence. In some embodiments, the transthyretin is modified to remove the N118 N-glycosylation site. In some embodiments, the half-life modulator is a monomeric form of TTR.

In some embodiments, the half-life modulator comprises at least 100 consecutive amino acids that are at least 70%, 80%, 85%, 90% or 95% identical to a PASylation amino acid sequence. PASylation are proline-, alanine-, and/or serine-rich sequences that mimic PEGylation (see WO/2008/155,134). In some embodiments, the half-life modulator comprises at least 100 consecutive amino acids that are about 70%, 75%, 80%, 85%, 90% or 95% identical to a PASylation amino acid sequence. PASylation are proline-, alanine-, and/or serine-rich sequences that mimic PEGylation (see WO/2008/155,134). Polypeptide stretches of proline, alanine, and/or serine form semi-structured three-dimensional domains with large hydrodynamic radius, thereby reducing clearance of fusion proteins. In some embodiments, the PASylation amino acid sequence is about 200, 300, 400, 500 or 600 amino acids long. For example, the PASylation is a 20 times repeat of the amino acid sequence ASPAAPAPASPAAPAPSAPA (SEQ ID NO: 137).

In some embodiments, the half-life modulator comprises the attachment of polyethylene glycol (PEG) chain or chains to the fusion proteins through chemical attachment either to the N- and/or C-terminus and/or to an amino acid side chain (e.g., PEG-maleimide attachment to cysteines). PEG chains form semi-structured three-dimensional domains with large hydrodynamic radius, thereby reducing clearance of fusion proteins.

In some embodiments, the half-life modulator comprises at least 100 consecutive amino acids that are at least 70%, 80%, 85%, 90% or 95% identical to an albumin-binding domain human antibody (albudAb) amino acid sequence (SEQ ID NO: 138). In some embodiments, the half-life modulator comprises at least 100 consecutive amino acids that are about 70%, 75%, 80%, 85%, 90% or 95% identical to an albumin-binding domain human antibody (albudAb) amino acid sequence. Albumin-binding domain antibodies can increase the fusion protein half-life by binding non-covalently to serum albumin (see WO2008/096158). In some embodiments, the albumin-binding domain human antibody is engineered to remove the C-terminal arginine to remove the Lys-Arg Kex2 protease site.

Representative such half-life modulators include those recited in any one of SEQ ID NOs: 57-59.

In some embodiments, the half-life modulators can be modified to substitute the cysteine residues to serine or alanine residues to reduce the ability to form disulfide bonds.

In some embodiments, the half-life modulators provide a prolonged half-life of the bi-specific fusion protein, as compared to fusion protein without half-life modulator. The effect of a half-life modulator can be evaluated using an assay that determines stability under physiological conditions. For example, bi-specific fusion protein can be incubated at 37° C. in serum (e.g., human serum) for 120 hours, with samples removed at the start of incubation and every 24 hours thereafter. Binding assays as described above are then performed to detect the level of functional bi-specific fusion protein at each time point. This level is then compared to the level of bi-specific fusion protein constructed without half-life modulator (or using a different half-life modulator) to provide a serum stability comparison.

Optional Elements

The half-life modulator may be incorporated or conjugated into a bi-specific fusion protein alone or using a short (e.g., from 2 to 40, 2-50, 2-100 amino acid residues) connector peptide. In some embodiments, the connector polypeptide is present at the N-terminus, at the C-terminus or at both the N-terminus and the C-terminus of the half-life modulator at one or both ends. Suitable short connector polypeptides for use at the N-terminal end of the linker include, for example, dipeptides such as -Gly-Ser- (GS), -Gly-Ala- (GA) and -Ala-Ser-(AS). Suitable short connector polypeptides for use at the C-terminal end of the linker include, for example, dipeptides such as -Leu-Gln- (LQ) and -Thr-Gly- (TG). In some embodiments, the connectors are longer than 2 amino acids. For example, the connectors are 5, 6, 7, 8, 9, 10, 11, 12, 13, 14, 15, 16, 17, 18, 19 or 20 amino acids long or longer. In some embodiments, the connectors are 20 or more 30 or more, 40 or more, 50 or more, 60 or more, 70 or more, 80 or more, 90 or more, 100 or more amino acids long. Preferably, such connectors are flexible (for example glycine-rich) or structured (e.g., alpha-helix rich). In some embodiments, the connector linkers have a sequence recited in SEQ ID NOs: 60-62. In some embodiments, the connector linkers can have a sequence recited in SEQ ID NOs: 60-62 in which the serines are substituted with glutamate. For example, the linker can have a sequence recited in SEQ ID NO: 126. In some embodiments, the connector linkers have a sequence recited in SEQ ID NOs: 28-30 provided in U.S. patent application Ser. No. 13/068,808, which is incorporated herein by reference in its entirety. Such short connector polypeptides and connector recited in SEQ ID NOs: 28-30, if present, may be located at either one or both termini of the half-life modulator.

In some embodiments, the connector polypeptides can be aliphatic linkers. i.e. linkers having aliphatic groups such as alanine, leucine, valine, isoleucine, proline or glycine. For example, the connector can have the following sequences AAALAAA (SEQ ID NO: 127).

In some embodiments, the connectors are based on human proteins such as transthyretin.

It will be apparent that elements in addition to those described above may optionally be included in the bi-specific fusion proteins provided herein. Such elements may be present for a variety of purposes, including to facilitate expression, preparation or purification of the bi-specific fusion protein, or to perform targeting functions.

In some embodiments, the bi-specific fusion proteins have an N-terminal secretion signal that can be cleaved during expression. For example, an N-terminal leader polypeptide may be present. In some embodiments, the N-terminal leader polypeptide has a sequence recited in SEQ ID NO: 105.

A bi-specific fusion protein may also, or alternatively, comprise a polyhistidine (e.g., hexahistidine) tag to facilitate purification. Such a tag comprises at least six histidine consecutive amino acid residues, and may be located at the C- or N-terminus. In certain embodiments, a hexahistidine tag is included at the C-terminus of the bi-specific protein. Additional amino acid residues may also be present at the junction of the polyhistidine to the remainder of the bi-specific protein.

Representative Bi-Specific Proteins

According to some aspects of the invention, the bi-specific proteins have a N-terminal activator (also referred herein as signaling arm), a C-terminal targeting arm and a central peptide linker or half-life modulator. Yet in some aspects of the invention, the bi-specific proteins have an N-terminal activator (also referred herein as signaling arm), and a C-terminal targeting arm. Yet in other aspects of the invention, the bi-specific proteins have a C-terminal activator (also referred herein as signaling arm), and a N-terminal targeting arm. Yet in other aspects of the invention, the bi-specific proteins have a C-terminal activator (also referred herein as signaling arm), an N-terminal targeting arm and a central peptide linker or half-life modulator.

In some aspects of the invention, the bi-specific proteins can further have a linker or connector linking the targeting arm to the half-life modulator and/or the activator domain to the half-life modulator.

Representative bi-specific fusion proteins comprise (from N-terminal to C-terminal):

(a) An optional leader polypeptide;
(b) a targeting polypeptide domain (e.g., comprising or having a sequence recited in SEQ ID NOs: 1-4 and 122);

(c) an optional connector peptide (e.g., comprising or having a sequence recited in SEQ ID NOs: 60-62, 126-127);
(d) a peptide linker or a half-life modulator (e.g., comprising or having a sequence recited in any one of SEQ ID NOs: 54-56 and 124);
(e) an optional connector peptide (e.g., comprising or having a sequence recited in SEQ ID NOs: 60-62, 126-127);
(f) an activator domain (e.g., comprising or having a sequence recited in any one of SEQ ID NOs: 10-30 or 120); and
(g) an optional polyhistidine peptide.

Representative bi-specific fusion proteins comprise (from N-terminal to C-terminal):
(a) an optional leader polypeptide;
(b) an activator domain (e.g., comprising or having a sequence recited in any one of SEQ ID NOs: 10-30 and 120);
(c) an optional connector peptide (e.g., comprising or having a sequence recited in SEQ ID NOs: 60-62, 126-127);
(d) a peptide linker or a half-life modulator (e.g., comprising or having a sequence recited in any one of SEQ ID NOs: 54-56 or 124);
(e) an optional connector peptide (e.g., comprising or having a sequence recited in SEQ ID NOs: 60-62, 126-127);
(f) a targeting polypeptide domain (e.g., comprising or having a sequence recited in SEQ ID NOs: 1-4 and 124); and
(g) an optional polyhistidine peptide.

Representative bi-specific proteins include, but are not limited to,

Targeted, Potency-Reduced, IGF1-Based SGFs:

| | |
|---|---|
| 606 | IGF1(LR3-R37x-3x)_lk40_mHSA_lk40_AnxVC316S_lk8_His6 |
| 683 | IGF1(LR3-R37x-3x)_lk40_Fc_lk40_AnxVmS_lk40_AnxVC316S |
| 711 | IGF1(LR3)_lk15_mHSA_lk15_AnxV |
| 713 | IGF1(LR3)_lk15_mHSA_lk15_AnxV(ni) |
| 716 | IGF1(LR3)_lk15_mHSA7_lk15_AnxV(ni) |
| 727 | IGF1(LR3-R37x-3x)_lk40_mHSA_lk40_AnxV |
| 728 | IGF1(LR3_Y60L)_lk15_mHSA7_lk15_AnxV(ni) |
| 729 | IGF1(LR3)_lk7_mHSA_lk7_AnxV |
| 730 | IGF1(LR3- R37x-3x)_lk15_mHSA7_lk15_AnxV(ni) |
| 731 | IGF1(LR3-Y24L/Y31A)_lk15_mHSA7_lk15_AnxV(ni) |
| 732 | IGF1(LR3-Y24L)_lk15_mHSA7_lk15_AnxV(ni) |
| 733 | IGF1(LR3-Y31A)_lk15_mHSA7_lk15_AnxV(ni) |
| 734 | IGF1(LR3-Y24L/Y31A)_lk7_mHSA7_lk7_AnxV(ni) |
| 737 | IGF1(LR3-Y31A)_lk7_mHSA_lk7_AnxV |
| 739 | IGF1(LR3-Y24L)_lk7_mHSA_lk7_AnxV(ni) |
| 740 | IGF1(LR3-Y31A)_lk7_ mHSA_lk7_AnxV(ni) |
| 741 | IGF1(LR3-Y60L)_lk7_mHSA_lk7_AnxV(ni) |
| 743 | IGF1(LR3-R37X-3X)_lk7_mHSA_lk7_AnxV(ni) |
| 776 | IGF-1(E3R-Y31A)-lk7-HSA(C58S/N527Q)-lk7- AnxV(ni) |

Targeted, Potency-Reduced, Nrg1a-Based SGFs

| | |
|---|---|
| 757 | Nrg1a_lk7_mHSA_lk7_AnxV(ni) |

Representative controls include, but are not limited to:
Non-Targeted, Potency-Reduced, IGF1-Based SGFs

| | |
|---|---|
| 602 | IGF1(LR3-R37x)_lk40_mHSA_lk8_His6 |
| 604 | IGF1(LR3-R37x-3x)_lk2_mHSA_lk8_His6 |
| 703 | IGF1(LR3)_lk15_mHSA |
| 704 | IGF1(LR3)_lk15_mHSA7 |
| 746 | IGF1(LR3-Y31A)_lk7_mHSA |

Non-Targeted, Non-Potency-Reduced, IGF1-Based SGFs

| | |
|---|---|
| 688 | IGF1(LR3-R37x-3x)_lk40_Fc |

Targeted, Non-Potency-Reduced, IGF1-Based SGFs

| | |
|---|---|
| 649 | IGF1(LR3)_lk40_Fc_lk40_AnxVC316S |

Figure 10:
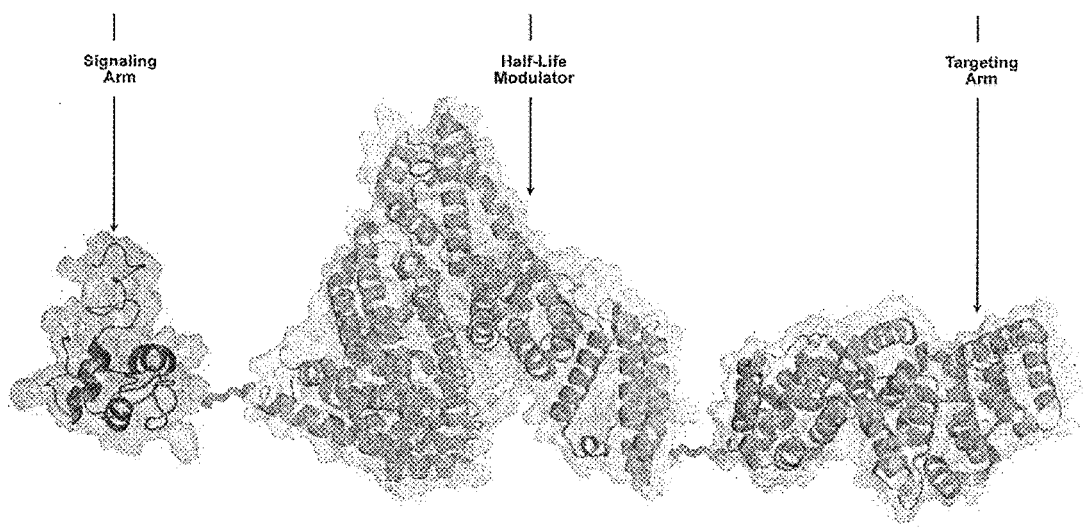
FIG. 10 is a schematic of a targeted engineered growth factor in accordance to some embodiments.

Representative bi-specific proteins include, but are not limited to, the proteins SGF 606 (SEQ ID NO: 70), SGF 683 (SEQ ID NO: 67), SGF 711 (SEQ ID NO: 73), SGF 713 (SEQ ID NO: 74), SGF 716 (SEQ ID NO: 75), SGF 727 (SEQ ID NO: 76), SGF 728 (SEQ ID NO: 77), SGF 729 (SEQ ID NO: 78), SGF 730 (SEQ ID NO: 79), SGF 731 (SEQ ID NO: 80), SGF 732 (SEQ ID NO: 81), SGF 733 (SEQ ID NO: 82), SGF 739 (SEQ ID NO: 83), SGF 740 (SEQ ID NO: 84), SGF 741 (SEQ ID NO: 85), SGF 743 (SEQ ID NO: 86), SGF 734 (SEQ ID NO: 108), SGF 737 (SEQ ID NO: 116), SGF 757 (SEQ ID NO: 110), SGF 776 (SEQ ID NO: 118). Representative bi-specific proteins include, but are not limited to, the proteins SGF illustrated in FIGS. 1A-1B and FIG. 10.

In some embodiments, the bi-specific protein is an engineered protein having from the C-terminus to N-terminus, an activator domain having SEQ ID NO: 120, a connector having SEQ ID NOs: 60-62, 126-127, a linker having SEQ ID NO: 124, a connector having SEQ ID NOs: 60-62, 126-127, and a targeting domain having SEQ ID NO: 122. In some embodiments, the bi-specific protein is IGF1 (E3R/Y31A)_lk7_HSA 26-609 (C58S/N527Q)_lk7_AnxV 2-320 (R63A/K70A/K101A/E138A/D139G/N160A/C316A). In some embodiments, the bi-specific protein has SEQ ID NO: 118.

Representative bi-specific fusion proteins can have a sequence recited in SEQ ID NOs: 67, 70, 73-86, 108, 110, or 116. In some embodiments, the proteins do not have a targeting arm and serve as negative controls. In some embodiments, the non-targeted controls proteins include, but are not limited to, the proteins SGF 604 (SEQ ID NO: 69), SGF 688 (SEQ ID NO: 72), SGF 703 (SEQ ID NO: 68), SGF 704 (SEQ ID NO: 107), SGF 602 (SEQ ID NO: 66), SGF 746 (SEQ ID NO; 109), as illustrated in FIG. 1A-1B, or the representative bi-specific proteins SGF 606, SGF 711, SGF 713, SGF 727, SGF 728, SGF 729, SGF 730, SGF 731, SGF 732, SGF 733, SGF 734, SGF 737, SGF 739, SGF 740, SGF 741, SGF 743, SGF 649 without the targeting arm can be used. In some embodiments, the proteins without the targeting arm can be used as negative control, for example in potency shift assay. In some embodiments, the proteins can comprise the Fc regions of the IgG as the half-life modulator. Using such a framework results in a constitutively dimeric protein.

Preparation of Bi-Specific Proteins

The engineered proteins of the present invention may be synthesized by conventional techniques known in the art, for example, by chemical synthesis such as solid phase peptide synthesis. Such methods are known to those skilled in the art. In general, these methods employ solid or solution phase synthesis methods, well known in the art. Specifically, the methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups and any solid support are removed either sequentially or concurrently to afford the final polypeptide. By simple modification of this general procedure, it is possible to add more than one amino acid at a time to a growing chain, for example, by coupling (under condition that do not racemize chiral centers) a protected tripeptide with a properly protected dipeptide to form, after deprotection, a pentapeptide.

Bi-specific proteins may be synthesized using standard techniques, including liquid- and solid-phase peptide synthesis and recombinant DNA techniques. For solid phase synthesis, the C-terminal amino acid of the sequence is attached to an insoluble support, and the remaining amino acids are added in sequence. For polypeptides longer than about 50 amino acids, shorter regions may be synthesized in this fashion and then condensed to form the longer polypeptide. Methods of forming peptide bonds by activation of a carboxyl terminal end (e.g., by the use of the coupling reagent N, N'-dicyclohexylcarbodiimide) are well known in the art. In some aspects of the invention, the polypeptides can be produced by recombinant DNA techniques by synthesizing DNA encoding the desired polypeptide. Once coding sequences for the desired polypeptides have been synthesized or isolated, they can be cloned into any suitable vector for expression. Numerous cloning vectors are known to those of skill in the art, and the selection of an appropriate cloning vector is a matter of choice. The gene can be placed under the control of a promoter, ribosome binding site (for bacterial expression) and, optionally, an operator (collectively referred to herein as "control" elements), so that the DNA sequence encoding the desired polypeptide is transcribed into RNA in the host cell transformed by a vector containing this expression construction. The coding sequence may or may not contain a signal peptide or leader sequence. Heterologous leader sequences can be added to the coding sequence that causes the secretion of the expressed polypeptide from the host organism. Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

The present invention also encompasses polynucleotides encoding the above-described proteins and protein variants that may be in the form of RNA or in the form of DNA, which DNA includes cDNA and synthetic DNA. The DNA may be double-stranded or single-stranded. The coding sequences that encode the variants of the present invention may vary as a result of the redundancy or degeneracy of the genetic code.

For recombinant DNA techniques, DNA encoding the bi-specific fusion protein is prepared chemically or by isolating and ligating DNA encoding each portion of the fusion protein. The DNA coding for each segment of the bi-specific fusion protein may be isolated from known genes or synthesized de novo. Methods for direct chemical synthesis of DNA are well known in the art, and such syntheses are routinely performed using an automated synthesizer. Chemical synthesis produces a single stranded polynucleotide, which is converted into double stranded DNA by hybridization with a complementary sequence or using DNA polymerase. While chemical synthesis of DNA is generally limited to sequences that are shorter than the bi-specific fusion protein, it will be apparent that the full bi-specific fusion protein may be obtained by ligation of shorter sequences in frame. Alternatively, DNA sequences encoding the bi-specific fusion protein are prepared by cloning. Cloning techniques are well known in the art, and are amply described, for example, by standard references such as Sambrook et al., Molecular Cloning: A Laboratory Manual ($3^{rd}$ ed.), Cold Spring Harbor Laboratory Press (2001). Portions of the DNA may be ligated together in frame to generate the full length coding sequence.

Once the DNA encoding the bi-specific fusion protein is obtained, the DNA may be cloned into a vector for expression in a prokaryotic or eukaryotic host cell. Techniques for incorporating DNA into such vectors are well known to those of ordinary skill in the art. Within such an expression vector, the DNA encoding the bi-specific fusion protein is operably linked to the nucleotide sequences necessary for expression (e.g., a suitable promoter and, if necessary, a terminating signal). A promoter is a nucleotide sequence (typically located 5' to the coding sequence) that directs the transcription of adjacently linked coding sequences. A terminating signal may be a stop codon to end translation and/or a transcription termination signal. Additional regulatory element(s) (e.g., enhancer elements) may also be present within an expression vector. Such a vector is preferably a plasmid or viral vector. Preferably, an expression vector further comprises a selectable marker, which confers resistance to a selection. This allows cells to stably integrate the vector into their chromosomes and grow to form foci, which in turn can be cloned and expanded into cell lines. A variety of selectable markers are known in the art, including, for example, genes that provide resistance to ampicillin, methotrexate, mycophenolic acid, the aminoglycoside G-418, hygromycin and puromycin. Those of ordinary skill in the art are knowledgeable in the numerous expression systems available for expression of proteins including E. coli, other bacterial hosts, yeast, and various higher eukaryotic cells such as the COS, CHO, HEK293, HeLa and myeloma cell lines.

Host cells are transformed or transfected with the vector that comprises the DNA encoding the bi-specific fusion protein using standard methods. Expression in the host cell results in transcription of the DNA into the corresponding mRNA, followed by translation of the mRNA to generate the bi-specific fusion protein.

Once expressed, the bi-specific fusion protein can be purified according to standard procedures, including, for example, ammonium sulfate precipitation or affinity column chromatography. Substantially pure compositions of at least about 90 to 95% homogeneity are preferred, and 98 to 99% or more homogeneity is most preferred for pharmaceutical uses. Once purified, partially or to homogeneity as desired, if to be used therapeutically, the polypeptides should be substantially free of endotoxin.

Pharmaceutical Compositions

The present invention also provides pharmaceutical compositions comprising at least one bi-specific fusion protein as described herein, together with at least one physiologically acceptable carrier. Such compositions may be used for treating patients who are suffering from, or at risk for, tissue damage, in order to prevent tissue damage, or to repair or regenerate damaged tissue. Such patients include, for example, patients who have experienced myocardial infarction, kidney damage, and/or ischemic stroke. If desired, other active ingredients may also be included within the pharmaceutical composition, such as stem cells or other agents that facilitate repair of damaged tissue.

A "patient" is a mammal, preferably a human. The term "treating" (or "treat" or "treatment") means slowing, reducing, or reversing the progression or severity of a symptom, disorder, condition, or disease.

The term "therapeutically effective amount" refers to the amount or dose of bi-specific proteins of this invention which, upon single or multiple dose administration to a patient, provides the desired treatment.

As used herein, the term "physiologically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the bi-specific fusion protein is administered. Physiologically acceptable carriers can be sterile liquids, such as water and oils, including those of petroleum, animal, vegetable or synthetic origin (e.g., peanut oil, soybean oil, mineral oil, or sesame oil). Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water and ethanol. The composition, if desired, can also contain minor amounts of wetting or emulsifying agents, or pH buffering agents.

Pharmaceutical compositions may be formulated for any appropriate manner of administration, including, for example, parenteral, intranasal, topical, oral, or local administration, such as by a transdermal means, for prophylactic and/or therapeutic treatment. These compositions can take any of a variety of well-known forms that suit the mode of administration, such as solutions, suspensions, emulsions, tablets, pills, capsules, powders, aerosols and sustained-release formulations. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical modes of administration and carriers are described in "Remington: The Science and Practice of Pharmacy," A. R. Gennaro, ed. Lippincott Williams & Wilkins, Philadelphia, PA (21st ed., 2005).

Commonly, the pharmaceutical compositions provided herein are administered parenterally (e.g., by intravenous, intramuscular, or subcutaneous injection), or by oral ingestion or topical application.

The term "administering" as used herein is defined as the actual physical introduction of the composition into or onto (as appropriate) the host subject. Any and all methods of introducing the composition into the subject are contemplated according to the present invention; the method is not dependent on any particular means of introduction and is not to be so construed. Means of introduction are well-known to those skilled in the art, and preferably, the composition is administered subcutaneously or intratumorally. One skilled in the art will recognize that, although more than one route can be used for administration, a particular route can provide a more immediate and more effective reaction than another route. Local or systemic delivery can be accomplished by administration comprising application or instillation into body cavities, inhalation or insufflation of an aerosol, or by parenteral introduction, comprising intramuscular, intravenous, intraportal, intrahepatic, peritoneal, subcutaneous, or intradermal administration.

For parenteral administration, the bi-specific fusion protein can either be suspended or dissolved in the carrier. A sterile aqueous carrier is generally preferred, such as water, buffered water, saline or phosphate-buffered saline. In addition, sterile, fixed oils may be employed as a solvent or suspending medium. For this purpose any bland fixed oil may be employed, including synthetic mono- or diglycerides. In addition, fatty acids such as oleic acid find use in the preparation of injectable compositions. Pharmaceutically acceptable auxiliary substances may also be included to approximate physiological conditions, such as pH adjusting and buffering agents, tonicity adjusting agents, dispersing agents, suspending agents, wetting agents, detergents, preservatives, local anesthetics and buffering agents.

In some embodiments, the pharmaceutical composition is formulated for intravenous administration to a patient (e.g., a human). Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a sealed (e.g., hermetically sealed) container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Compositions intended for oral use may be presented as, for example, tablets, troches, lozenges, aqueous or oily suspensions, dispersible powders or granules, emulsion, hard or soft capsules, or syrups or elixirs. Such compositions may further comprise one or more components such as sweetening agents flavoring agents, coloring agents and preserving agents. Tablets contain the active ingredient in admixture with physiologically acceptable excipients that are suitable for the manufacture of tablets. Such excipients include, for example, inert diluents, granulating and disintegrating agents, binding agents and lubricating agents. Formulations for oral use may also be presented as hard gelatin capsules wherein the active ingredient is mixed with an inert solid diluent, or as soft gelatin capsules wherein the active ingredient is mixed with water or an oil medium. Aqueous suspensions comprise the active materials in admixture with one or more excipients suitable for the manufacture of aqueous suspensions. Such excipients include suspending agents and dispersing or wetting agents. Dispersible powders and granules suitable for preparation of an aqueous suspension by the addition of water provide the active ingredient in admixture with a dispersing or wetting agent, suspending agent and one or more preservatives.

Oily suspensions may be formulated by suspending the active ingredients in a vegetable oil (e.g., *arachis* oil, olive oil, sesame oil or coconut oil) or in a mineral oil such as liquid paraffin. Pharmaceutical compositions may also be in the form of oil-in-water emulsions. The oily phase may be a vegetable oil or a mineral oil or mixture thereof. Suitable emulsifying agents include, for example, naturally-occurring gums, naturally-occurring phosphatides and anhydrides.

Pharmaceutical compositions may be sterilized by conventional sterilization techniques, or may be sterile filtered. Sterile aqueous solutions may be packaged for use as is, or lyophilized, the lyophilized preparation being combined with a sterile aqueous carrier prior to administration. The pH of an aqueous pharmaceutical composition typically will be between 3 and 11, more preferably between 5 and 9 or between 6 and 8, and most preferably between 7 and 8, such as 7 to 7.5.

Bi-specific fusion proteins provided herein are generally present within a pharmaceutical composition at a concentration such that administration of a single dose to a patient delivers a therapeutically effective amount. A therapeutically effective amount is an amount that results in a discernible patient benefit, such as detectable repair or regeneration of damaged tissue or diminution of symptoms of tissue damage. Therapeutically effective amounts can be approximated from the amounts sufficient to achieve detectable tissue repair or regeneration in one or more animal models exemplified in Table 3. Nonetheless, it will be apparent that a variety of factors will affect the therapeutically effective amount, including the activity of the bi-specific fusion protein employed; the age, body weight, general health, sex and diet of the patient; the time and route of administration; the rate of excretion; any simultaneous treatment, such as a drug combination; and the type and severity of the tissue damage in the patient undergoing treatment. Optimal dosages may be established using routine testing, and procedures that are well known in the art. Dosages generally range from about 0.5 mg to about 400 mg of bi-specific fusion protein per dose (e.g., 0.5 mg, 1 mg, 2 mg, 5 mg, 10 mg, 50 mg, 100 mg, 200 mg, 300 mg, or 400 mg per dose). In general, compositions providing dosage levels ranging from about 0.1 mg to about 100 mg per kilogram of body weight per day are preferred. In certain embodiments, dosage unit forms contain between from about 10 mg to about 100 mg of bi-specific fusion protein.

Pharmaceutical compositions may be packaged for treating or preventing tissue damage (e.g., for treatment of myocardial infarction or kidney damage). Packaged pharmaceutical preparations include a container holding a therapeutically effective amount of at least one pharmaceutical composition as described herein and instructions (e.g., labeling) indicating that the contained composition is to be used for treating tissue damage (such as myocardial infarction or kidney damage) in a patient. Pharmaceutical compositions may be packaged in multiple single dose units, each containing a fixed amount of bi-specific fusion protein in a sealed package. Alternatively, the container may hold multiple doses of the pharmaceutical composition.

Kits comprising one or more of the bi-specific proteins described herein, as well as instructions for use of such agents to treat tissue damage, are also encompassed.

Methods of Treatment

The pharmaceutical compositions can be administered to a patient (preferably a mammal such as a cow, pig, horse, chicken, cat, dog, or more preferably a human) to treat pathological tissue damage in the patient. Within the context of the present invention, the term "treatment" encompasses both prophylactic and therapeutic administration. In prophylactic applications, a pharmaceutical composition as described herein is administered to a patient susceptible to or otherwise at risk for developing pathological tissue damage, in order to prevent, delay or reduce the severity of tissue damage. In therapeutic applications, treatment is performed in order to reduce the severity of the pathological tissue damage or regenerate tissue after damage. In some embodiments, the pharmaceutical composition can be administered in combination with other therapeutic compositions.

Representative pathological tissue damage includes heart tissue damage (e.g., damage associated with myocardial infarction), kidney tissue damage and tissue damage following a ischemic stroke (e.g. cerebral ischemia, also known as brain ischemia, critical limb ischemia or other ischemia). In some embodiments, the pharmaceutical composition can be used to protect tissue from damage and/or to regenerate tissue and/or blood supply after tissue or organ damage.

Among patients hospitalized with an acute myocardial infarction (AMI), about 20% develop an acute kidney injury (AKI), which is linked to adverse long-term outcomes, including permanent renal impairment and end-stage renal disease. In some embodiments, the pharmaceutical composition can be used to prevent or protect kidney tissue from damage and/or to regenerate tissue and/or blood supply after kidney damage or tissue damage following an acute myocardial infarction (AMI).

In some embodiments, the pharmaceutical composition can be administered to prevent, delay, reduce or treat autoimmune diseases, for example, Systemic Lupus Erythematosus (SLE), also known as Lupus. SLE is an autoimmune disease where many tissues or systems are attacked and become inflamed, for example, joints, skin, liver, kidneys, blood cells, heart, lungs, nervous system, blood vessels. The immune system produces antibodies against self, particular against nuclear proteins and DNA. In some embodiments, the pharmaceutical compositions can be administered to a subject in need thereof to protect tissue from damage and regenerating tissue after damage. In some embodiments, the pharmaceutical composition can be administered in combination with existing immune-suppression or other treatments.

In some embodiments, the pharmaceutical compositions can be administered to a subject in need thereof to prevent, delay, reduce or treat Type I diabetes. In type I diabetes, the body's own immune system destroys the insulin-producing beta cells in the pancreas. In some embodiments, the pharmaceutical compositions can be administered to a subject in need thereof to regenerate beta cells. In some embodiments, the pharmaceutical compositions can be administered in combination with Type I diabetes treatments known in the art.

In some embodiments, the pharmaceutical compositions can be administered to a subject in need thereof to prevent, delay, reduce or treat diabetic nephropathy or podocyte-related disorders. Diabetic nephropathy (also known as Kimmelstiel-Wilson syndrome, or nodular diabetic glomerulo-sclerosis, or intercapillary glomerulonephritis) is one of the three major complications of diabetes, and has been the leading cause for initiation of hemodialysis and is the most common cause of chronic kidney failure and end-stage kidney disease in the Western world. Podocyte-related disease or disorder can be due to a podocyte injury (due to mechanical stress, ischemia, lack of oxygen supply, a toxic substance, an endocrinologic disorder, an infection, a contrast agent, a mechanical trauma, a cytotoxic agent, a medication, an inflammation, radiation, an infection, a dysfunction of the immune system, a genetic disorder, an organ failure, an organ transplantation, or uropathy.) In some embodiments, the pharmaceutical compositions can be administered to a subject in need thereof to treat diabetic nephropathy or podocyte-related disorders. In some embodiments, the pharmaceutical compositions can be administered in combination with diabetic nephropathy treatments known in the art.

In some embodiments, the pharmaceutical compositions can be administered to a subject in need thereof to prevent, delay, reduce or treat tissue or organ degeneration. For example, the pharmaceutical compositions can be used to treat brain, spinal cord or nerve degeneration such as Alzheimer's disease, Parkinson's disease, Multiple sclerosis, or Amyotrophic lateral sclerosis (ALS), also known as Lou Gehrig's disease. In some embodiments, the pharmaceutical compositions can be administered in combination with existing treatments known in the art.

In some embodiments, the pharmaceutical compositions can be administered to a subject in need thereof to prevent, delay, reduce or treat bone and/or cartilage associated disease. In some embodiments, the pharmaceutical compositions can be used to regenerate bone and/or cartilage tissues. The pharmaceutical compositions can be administered in combination with existing treatments known in the art.

Any of a variety of known delivery systems can be used to administer a bi-specific fusion protein including, for example, encapsulation in liposomes, microparticles, microcapsules, recombinant cells capable of expressing the bi-specific fusion protein, receptor-mediated, or a retroviral or other nucleic acid vector. The bi-specific fusion protein may be administered by any convenient route, for example by infusion or bolus injection, by absorption through epithelial or mucocutaneous linings (e.g., oral mucosa, rectal and intestinal mucosa, etc.), and may be administered together with other biologically active agents. Administration can be systemic or local. In addition, it may be desirable to introduce the bi-specific fusion protein into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In some embodiments, it may be desirable to administer the bi-specific fusion protein of the invention locally to the area in need of treatment; this may be achieved by, for example, local infusion during surgery, topical application (e.g., in conjunction with a wound dressing after surgery), by injection, by means of a catheter, by means of a suppository, or by means of an implant, said implant being of a porous, non-porous, or gelatinous material, including membranes, such as sialastic membranes, or fibers. In another embodiment, a vesicle, such as a liposome, can be used to deliver the bi-specific fusion protein. In yet another embodiment, the bi-specific fusion protein is delivered in a controlled release system; for example, such a controlled release system may be placed at or near the therapeutic target (e.g., an organ of the body that has experienced or is at risk for tissue damage). The use of such delivery systems is well known to those of ordinary skill in the art.

In some embodiments, the bi-specific fusion proteins provided herein are effective for treating pathological tissue damage at least in part due to their ability to recruit stem cells to the damaged tissue. In certain cases, sufficient stem cells may reside within the patient (e.g., resident cardiac stem cells). In certain embodiments, however, it may be beneficial to co-administer stem cells (e.g., bone marrow-derived autologous stem cells). Such stem cells may be administered before or after the bi-specific fusion protein, or may be administered simultaneously (either in the same pharmaceutical composition or in separate compositions).

In some embodiments, the bi-specific proteins provided herein are effective in enhancing tissue survival. In some embodiments, the bi-specific proteins can be administered and target a specific tissue or organ (e.g. heart). The bi-specific proteins can then accumulate in the specific tissue or organ (e.g. heart as opposed to another organ) through binding of the targeting domain to the tissue associated target molecule. Once bound to the target molecule, the bi-specific fusion protein can dissociate from the target molecule, move away and re-associate to a target molecule, a growth factor receptor of a different cell of the tissue in a paracrine-like manner (e.g. a damaged cell or an "at risk" cell).

As noted above, the optimal dose depends on certain factors known in the art, but generally ranges from about 0.5 mg to about 400 mg of bi-specific fusion protein per dose (e.g., 10 mg, 50 mg, 100 mg, 200 mg, 300 mg, or 400 mg per dose). A dose of bi-specific fusion protein (within a pharmaceutical composition as described above) can be administered therapeutically to a patient one or more times per hour, day, week, month, or year (e.g., 2, 4, 5, 6, 7, 8, 9, 10, 11, or 12 times per hour, day, week, month, or year). More commonly, a single dose per day or per week comprising an amount of bi-specific fusion protein ranging from about 0.1 mg to about 100 mg per kilogram of body weight is administered.

In other embodiments, a pharmaceutical composition comprising a bi-specific fusion protein may be administered to a patient in a dosage that ranges from about 0.1 mg per week to about 2500 mg per week, about 0.1 mg per week to about 10 mg per week, about 1 mg per week to about 100 mg per week, about 10 mg per week to about 500 mg per week, about 100 mg per week to about 2500 mg per week, about 10 mg per week to about 100 mg per week, or about 100 mg per week to about 1000 mg per week. Alternatively, a pharmaceutical composition comprising a bi-specific fusion protein may be administered at a dose that ranges from about 0.1 mg every other day to about 500 mg every other day, about 1 mg every other day to about 75 mg every other day, about 10 mg every other day to about 50 mg every other day, or about 20 mg every other day to about 40 mg every other day. A pharmaceutical composition comprising a bi-specific fusion protein may alternatively be administered at a dose that ranges from about 0.1 mg three times per week to about 100 mg three times per week, about 1 mg three times per week to about 75 mg three times per week, about 10 mg three times per week to about 50 mg three times per week, or about 20 mg three times per week to about 40 mg three times per week.

In some embodiments of, a pharmaceutical composition comprising a bi-specific fusion protein is administered to a mammal (e.g., a human) continuously for 1, 2, 3, or 4 hours;

1, 2, 3, or 4 times a day; every other day or every third, fourth, fifth, or sixth day; 1, 2, 3, 4, 5, 6, 7, 8, 9, or 10 times a week; biweekly; 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 times a month; bimonthly; 1, 2, 3, 4, 5, 6, 7, 8, 9, or 10 times every six months; 1, 2, 3, 4, 5, 6, 7, 8, 9, 10, 11, 12, 13, 14, 15, 16, 17, 18, 19, or 20 times a year; or biannually. It will be apparent that a pharmaceutical composition comprising a bi-specific fusion protein may, but need not, be administered at different frequencies during a therapeutic regime.

Combination Therapies

In some embodiments, the proteins of the present invention can be administered in combination with one or more additional compounds or therapies. For example, the one or more proteins of the present invention can be co-administered in conjunction with one or more therapeutic compounds. The combination therapy may encompass simultaneous or alternating administration.

The following Examples are offered by way of illustration and not by way of limitation. Unless otherwise specified, all reagents and solvents are of standard commercial grade and are used without further purification. Using routine modifications, the procedures provided in the following Examples may be varied by those of ordinary skill in the art to make and use other bi-specific fusion proteins and pharmaceutical compositions within the scope of the present invention.

Some aspects of the invention relate to a bi-specific protein comprising (a) a targeting domain having a binding specificity to a target molecule associated with the outer surface of a cell of a tissue; and (b) an engineered activator domain having a binding specificity to a receptor associated with the surface of a cell of the tissue, wherein the engineered activator domain has a modified amino acid sequence of an amino acid sequence of a wild-type activator domain, wherein the engineered activator domain decreases activation of the receptor relative to the wild-type activator domain, and wherein the bi-specific protein exhibits a receptor activation at least twice stronger on cells containing the target molecule compared to cells that do not contain the target molecule as measured by phosphorylation of a receptor or a downstream effector molecule.

In some embodiments, the engineered activator domain comprises the wild-type amino acid sequence modified to comprise a deletion, a substitution, an addition, an additional amino acid sequence at an N- and/or C-terminus or a combination thereof. The engineered activator domain can comprise a wild-type activator domain fused to a non-immunogenic protein. The engineered activator domain can comprise a modified amino acid sequence of an amino acid sequence of the wild-type activator domain fused to a non-immunogenic protein.

In some embodiments, the engineered activator domain decreases activation of the receptor relative to the wild-type activator domain by at least 3.5-fold. In some embodiments, the bi-specific protein exhibits a receptor activation at least twice stronger on cells containing the target molecule compared to cells that do not contain the target molecule as measured by phosphorylation of AKT.

In some embodiments, the bi-specific protein can further comprise a half-life modulator wherein the half-life modulator increases the half-life of the bi-specific protein. In some embodiments, the half-life modulator comprises the sequence of Human Serum Albumin, Fc, scFc, Albumin binding domain, PASylation, human alpha-fetoprotein, or variants thereof.

In some embodiments, the engineered activator domain has a binding affinity to a growth factor receptor. In some embodiments, the engineered activator domain and targeting domain are recombinantly fused. In some embodiments, the engineered activator domain and targeting domain are chemically coupled.

In some embodiments, the bi-specific fusion protein promotes tissue regeneration, cell survival, cell differentiation, inhibits apoptosis, induces cell proliferation, promotes cell growth, promotes motility of stem cells, promotes differentiation of stem cells, prevents cell damage, and/or promotes angiogenesis. In some embodiments, the tissue is cardiac tissue, kidney tissue, bone, cartilage, joints, skin, liver tissue, pancreatic tissue, blood cells, lung tissue, brain tissue, and nervous tissue.

In some embodiments, the engineered activator domain comprises a growth factor. In some embodiments, the growth factor comprises IGF-1, NRG, or variants thereof. In some embodiments, the targeting domain comprises Annexin A5 or variants thereof. In some embodiments, the Annexin A5 comprises an amino acid sequence set forth in any one of SEQ ID NOs: 1-4, or 122. In some embodiments, the engineered activator domain comprises IGF-1 (LR3-Y31A). In some embodiments, the engineered activator domain comprises an amino acid sequence set forth in any one of SEQ ID NOs: 18, 19, 23, 24, 28, 29, or 120.

In some embodiments, the half-life modulator is Human Serum Albumin or variants thereof. In some embodiments, the Human Serum Albumin comprises an amino acid sequence set forth in any one of SEQ ID NOs: 54-56, or 124. In some embodiments, the half-life modulator comprises Fc or variant thereof. In some embodiments, the Fc or variant thereof comprises an amino acid sequence set forth in SEQ ID NO: 53.

In some embodiments, the bi-specific protein of further comprises a connector linking the engineered activator domain to the half-life modulator and a connector linking the half-life modulator to the targeting domain. In some embodiments, the linker comprises an amino acid sequence set forth in any one of SEQ ID NOs: 60-62, or 126-127.

In some embodiments, the engineered activator domain is joined via a peptide bond to the amino terminus of the targeting domain or the activator domain is joined via peptide bond to the carboxy terminus of the targeting domain.

In some embodiments, the targeting domain has a binding specificity to phosphatidylserine. In some embodiments, the targeting domain has a binding specificity to a podocyte-associated molecule.

Aspects of the invention relate to a bi-specific protein comprising: (1) an activator domain, wherein the activator domain comprises a growth factor, (2) a targeting domain, wherein the targeting domain comprises a polypeptide that binds to phosphatidylserine at the outer surface of a damaged cell, wherein the bi-specific protein has a half maximal effective concentration lower in the damaged cell ($EC50_{Damaged}$) than a healthy cell ($EC50_{Healthy}$). In some embodiments, the damaged cell is a cell undergoing apoptosis or necrosis. In some embodiments, the activator domain comprises a variant of IGF-1. In some embodiments, the targeting domain comprises human Annexin A5 or variant thereof. In some embodiments, the activator domain comprises a variant of IGF-1 and the targeting domain comprises human annexin A5 or variant thereof. In some embodiments, the IGF-1 variant has an $EC50_{Healthy}/EC50_{Damaged}$ ratio of at least 10:1. In some embodiments, the IGF-1 variant induces survival signaling upon binding to the IGF-1 receptor. In some embodiments, the IGF-1 variant induces the phosphorylation of AKT. In some embodiments, the Annexin A5 has an amino acid sequence set forth in any one of SEQ ID NOs: 1-4, or 122. In some embodiments, the IGF-1 variant and the Annexin A5 or variant thereof are covalently linked by a peptide bond to form a single polypeptide. In some embodiments, the variant of IGF-1 and the Annexin A5 or variant thereof are covalently linked to the peptide linker by a peptide bond to form a single polypeptide. In some embodiments, the IGF-1 variant is linked to the amino terminus of the peptide linker and the annexin A5 or variant thereof is linked to the carboxy terminus of the peptide linker. In some embodiments, the IGF-1 variant is linked to the carboxy terminus of the peptide linker and the annexin A5 or variant thereof is linked to the amino terminus of the peptide linker. In some embodiments, the bi-specific protein further comprises a peptide connector between the IGF-1 variant and peptide linker and a peptide connector between the Annexin A5 or variant thereof and peptide linker.

Aspects of the invention relate to a bi-specific protein comprising: (1) an activator domain, wherein the activator domain comprises a variant of IGF-1; and (2) a targeting domain, wherein the targeting domain comprises annexin A5 or variant thereof, wherein the Annexin A5 or variant thereof binds to phosphatidylserine at the outer surface of a cell within damaged tissue, wherein the bi-specific protein and has a half maximal effective concentration lower in the damaged tissue ($EC50_{Damaged}$) than healthy tissue ($EC50_{Healthy}$). In some embodiments, the damaged tissue is an ischemic tissue. In some embodiments, the IGF-1 variant has an $EC50_{Healthy}/EC50_{Damaged}$ ratio of at least 10:1. In some embodiments, the IGF-1 variant has an amino acid sequence set forth in any one of SEQ ID NOs: 10-30, or 120. In some embodiments, the IGF-1 variant induces survival signaling upon binding to the IGF-1 receptor. In some embodiments, the IGF-1 variant induces the phosphorylation of AKT. In some embodiments, the Annexin A5 has an amino acid sequence set forth in any one of SEQ ID NOs: 1-4, or 122. In some embodiments, the IGF-1 variant and the Annexin A5 or variant thereof are covalently linked by a peptide bond to form a single polypeptide. In some embodiments, the variant of IGF-1 and the Annexin A5 or variant thereof are covalently linked to the peptide linker by a peptide bond to form a single polypeptide. In some embodiments, the IGF-1 variant is linked to the amino terminus of the peptide linker and the annexin A5 or variant thereof is linked to the carboxy terminus of the peptide linker. In some embodiments, the IGF-1 variant is linked to the carboxy terminus of the peptide linker and the annexin A5 or variant thereof is linked to the amino terminus of the peptide linker. In some embodiments, the bi-specific protein further comprises a peptide connector between the IGF-1 variant and peptide linker and a peptide connector between the Annexin A5 or variant thereof and peptide linker.

In some embodiments, the bi-specific protein further comprises a peptide linker. In some embodiments, the peptide linker is a half-life modulator. In some embodiments, the half-life modulator is a human serum albumin or variant thereof. In some embodiments, the half-life modulator is a Fc fragment or variant thereof.

In some embodiments, the human serum albumin or variant thereof has an amino acid sequence set forth in any one of SEQ ID NOs: 54-56, or 124. In some embodiments, the Fc fragment has an amino acid sequence set forth in SEQ ID NO: 53. In some embodiments, the peptide connector has an amino acid sequence set forth in any one of SEQ ID NOs: 60-62, or 126-127.

Aspects of the invention relate to a bi-specific protein comprising: (1) an IGF-1 variant comprising an amino acid sequence set forth in any one of SEQ ID NOs: 18, 19, 23, 24, 28, 29, or 120; and (2) Annexin A5 or variant thereof comprising an amino acid sequence set forth in any one of SEQ ID NOs: 1-4, or 122. In some embodiments, the bi-specific protein further comprises a Human Serum Albumin or variant thereof comprising an amino acid sequence set forth in any one of SEQ ID NOs: 54-56, or 124. In some embodiments, the Human Serum Albumin or variant thereof is linked to a C-terminus of Annexin A5 or variant thereof and to a N-terminus of the IGF-1 variant. In some embodiments, the bi-specific protein further comprises a peptide connector linking a N-terminus of the Human Serum Albumin or variant thereof to the C-terminus of Annexin A5 or variant thereof and a peptide connector linking a C-terminus of the Human Serum Albumin or variant thereof to the N-terminus of the IGF-1 variant. In some embodiments, the peptide connector comprising an amino acid sequence set forth in any one of SEQ ID NOs: 60-62, or 126-127.

Aspects of the invention relate to a pharmaceutical composition comprising the bi-specific protein described herein.

Aspects of the invention relate to an isolated recombinant nucleic acid sequence encoding the bi-specific protein described herein.

Aspects of the invention relate to an engineered protein having SEQ ID NO: 84. Aspects of the invention relate to an isolated recombinant nucleic acid having SEQ ID NO: 102. Aspects of the invention relate to a pharmaceutical composition comprising the bi-specific fusion protein having SEQ ID NO: 84.

Aspects of the invention relate to an engineered protein having SEQ ID NO: 118. Aspects of the invention relate to an isolated recombinant nucleic acid having SEQ ID NO: 119. Aspects of the invention relate to a pharmaceutical composition comprising the bi-specific fusion protein having SEQ ID NO: 118.

Aspects of the invention relate to a method of promoting tissue regeneration or survival in a subject, the method comprising: (a) providing a bi-specific protein having a targeting domain as described herein; and (b) administering in a patient in need thereof a therapeutically effective amount of the bi-specific protein, whereby the targeting domain targets the bi-specific fusion protein to a cell of the tissue and whereby upon exposure of the activator domain to a growth factor receptor at the surface of the cell, the activator domain specifically activates the growth factor receptor of so as to promote tissue regeneration.

Aspects of the invention relate to a method of promoting tissue regeneration or survival in a subject, the method comprising: (a) providing a bi-specific protein having a targeting domain described herein; and (b) administering in a patient in need thereof a therapeutically effective amount of the bi-specific protein, whereby the targeting domain targets the bi-specific fusion protein to a first cell of the tissue and whereby upon exposure of the activator domain to a growth factor receptor at the surface of a second cell, the activator domain specifically activates the growth factor receptor of so as to promote tissue regeneration.

In some embodiments, the targeting domain and the activator domain bind to molecules associated with the surface of the same cell of the tissue. In other embodiments, the targeting domain and the activator domain bind to molecules associated with the surface of different cells of the tissue. In some embodiments, the tissue is cardiac tissue, kidney tissue, bone, cartilage, joints, skin, liver tissue, pancreatic tissue, blood cells, lung tissue, brain tissue, or nervous tissue.

Aspects of the invention relate to a method of promoting tissue regeneration or survival in a subject, the method comprising: (a) providing a bi-specific protein having a targeting domain as described herein; an (b) administering in a patient in need thereof a therapeutically effective amount of the bi-specific protein whereby the Annexin A5 or variant thereof targets the bi-specific fusion protein to a cell of the tissue, wherein the cell expresses phosphatidylserine on the outer leaflet of the plasma membrane, and whereby upon exposure of the IGF-1 variant to a IGF-1 receptor at the surface of the cell, the IGF-1 variant specifically activates the IGF-1 receptor of so as to promote tissue regeneration.

Aspects of the invention relate to a method of promoting tissue regeneration or survival in a subject, the method comprising (a) providing a bi-specific protein having a targeting domain as described herein; and (b) administering in a patient in need thereof a therapeutically effective amount of the bi-specific protein whereby the Annexin A5 or variant thereof targets the bi-specific fusion protein to a first cell of the tissue, wherein the cell expresses phosphatidylserine on the outer leaflet of the plasma membrane, and whereby upon exposure of the IGF-1 variant to a IGF-1 receptor at the surface of a second cell, the IGF-1 variant specifically activates the IGF-1 receptor of so as to promote tissue regeneration.

In some embodiments, the Annexin A5 or variant thereof and the IGF-1 variant bind to different molecules associated with the surface of the same cell of the tissue. In other embodiments, the Annexin A5 or variant thereof and the IGF-1 variant bind to different molecules associated with the surface of different cells of the tissue.

Aspects of the invention relate to a method of promoting tissue regeneration or survival in a subject, the method comprising: (a) providing a bi-specific protein having a targeting domain as described herein; and (b) administering in a patient in need thereof a therapeutically effective amount of the bi-specific protein wherein the bi-specific proteins binds to phosphatidylserine on the outer leaflet of the plasma membrane of a cell of a tissue and to a IGF-1 growth factor receptor at the surface of the cell of the tissue.

Aspects of the invention relate to a method of promoting tissue regeneration or survival in a subject, the method comprising (a) providing a bi-specific protein having a targeting domain as described herein. And (b) administering in a patient in need thereof a therapeutically effective amount of the bi-specific protein wherein the bi-specific proteins binds to phosphatidylserine on the outer leaflet of the plasma membrane of a first cell of a tissue and to a IGF-1 growth factor receptor at the surface of a second cell of the tissue.

In some embodiments, the bi-specific protein binds to molecules associated with the surface of the same cell of the tissue. In other embodiments, the bi-specific protein binds to molecules associated with the surface of different cells of the tissue.

In some embodiments, the bi-specific protein comprises an amino acid sequence of a non-internalizing variant of human Annexin A5 and wherein the bi-specific protein has a prolonged half-life as compared to a bi-specific protein comprising the amino acid sequence of wild-type human Annexin A5.

In some embodiments, the bi-specific protein comprises a targeting domain having an amino acid sequence set forth in SEQ ID NO: 4.

In some embodiments, the bi-specific protein comprising an amino acid sequence set forth in any one of SEQ ID NOs: 67, 70, 73-86, 108, 110, 116, or 118.

EXAMPLES

The following examples should not be construed as limiting the scope of this disclosure.

Example 1. Bi-Specific Fusion Proteins can be Engineered to have Reduced Potency on Healthy Cells In order to enable targeting/selectivity for damaged cells, IGF1 was engineered to have reduced potency on healthy cells as compared to wt IGF-1 (FIGS. 2A-2B). Potency is defined as the concentration needed to achieve the half maximal level of pAKT signaling (pAKT EC50). In some embodiments, the IGF1 engineered variants were engineered using the IGF-1 (LR3) variant which contains a 13 amino acid N-terminal extension and a substitution of Arginine for Glutamate at position 3. The Arginine for Glutamate substitution was added to prevent binding of the fusion protein comprising the IGF-1 variant to IGF binding proteins (IGFBPs) and does not significantly affect potency (see FIGS. 2A-2B, EC50 of wt IGF1 is 1.22±0.74 vs. EC50 of IGF-1 (LR3) is 0.73±0.35).

A potency reduction of 6 fold or more was achieved by:
1. Substituting amino acids. In some embodiments, the tyrosine residues can be substituted. In some embodiments, amino acids 24 and/or 31 can be substituted (e.g., SGFs 740 and 733 which contain the Y31A substitution, SGFs 739 (SEQ ID NO: 83) and 732 (SEQ ID NO: 81) which contain the Y24L substitution, SGFs 728 (SEQ ID NO: 77) and 741 (SEQ ID NO: 85) which contain the Y60L substitution, or SGF 731 which contains both the Y24L and Y31A substitutions).
2. Deleting amino acids. In some embodiments, the amino acid sequences corresponding to sites of proteolysis (e.g. KR, RR) or K and/or R residues can be deleted. In some embodiments, C-terminus amino acids, such as the K68, S69, A70 can be deleted. In some embodiments, the amino acid R37 can be deleted. In some embodiments, the C-terminus amino acids, such as the K68, S69, A70 and the amino acid R37 can be deleted (e.g., SGF 602 which contains a deletion of residue R37, and SGFs 683, 727, 606, 743, and 730 which contain a deletion of residue R37 and deletion of the 3 C-terminal IGF-1 residues (K68, S69, A70)). In some embodiments, up to 3, up to 4, up to 5, up to 6, up to 7, up to 8, up to 9, up to 10 amino acids at the C-terminus can be deleted.
3. Adding (or fusing) a peptide (also referred herein as connector) to a protein domain of the fusion protein (e.g., SGFs 703, 711, 713, 729, 716, 704 which fuse IGF-1 (LR3) to a variant of Human Serum albumin (mHSA) via a 7 or 15 amino acid linker). In some embodiments, the linker can be 2 amino acids long, 3 amino acids long, 4 amino acids long, 5 amino acids long, 6 amino acids long, 7 amino acids long, 8 amino acids long, 9 amino acids long, 10 amino acids long. In some embodiments, the linker can be at least 2 amino acids long, at least 5 amino acids long, at least 10 amino acids long, at least 15 amino acids long, at least 20 amino acids long, at least 25 amino acids long, at least 30 amino acids long, at least 35 amino acids long, at least 40 amino acids long.

The bi-specific proteins were measured in pluripotent stem cell derived cardiomyocytes (iPSC-derived cardiomyocytes from Cellular Dynamics International (CDI)) and signaling was quantified by accumulation of phosphorylated AKT (pAKT).

On day 0, the cardiomyocytes were thawed according to standard protocol and seeded at 1.5e4 cells/well in Plating Media (CDI catalog #CMM-100-110-005).

On day 2, the media was pipetted up and down several times to dislodge dead cells and replaced with 100 μL/well warm Maintenance Media (CDI catalog #CMM-100-120-001). The Maintenance Media was replaced every other day.

On day 14, low serum media was prepared (DMEM no glucose (Invitrogen 11966-025), 1 mM sodium pyruvate, 10 mM galactose, 0.5% serum (supplied by CDI), 0.7 mM CaCl2). Maintenance Media was aspirated and replaced with 100 □L/well low serum media.

On day 15, a lysis solution was prepared [complete M-PER lysis buffer: M-PER lysis buffer (Pierce/ThermoScientific Cat #78501)+150 mM NaCl+protease (Roche Complete) and phosphatase inhibitors (Roche PhosSTOP))] and the bi-specific proteins were prepared in low serum media with 0.7 mM CaCl2. Different serial dilutions (1:7 dilutions) were prepared. The cells were stimulated with diluted solutions of bi-specific proteins by adding 25 μL/well of diluted bi-specific proteins to the existing 100 μL in each well and tapping the plate to mix for 10 seconds. The cells were incubated for 10 minutes at 37° C. The stimulation was stopped by removing the media from wells. The cells were washed with 200 μL/well cold PBS and tapping the plate upside down to remove excess PBS. The cells were lysed in 25 μL/well complete M-PER lysis buffer. The plate was sealed with foil plate seal and placed on orbital shaker 30 minutes at 4° C. The plate was then stored at −80° C. until ready for ELISA.

For the pAKT ELISA, on day 0, 384-well flat white plates (LIA High Binding, Greiner Bio-One, 781074) were coated with anti-Akt capture antibody (clone SKB1, Millipore 05-591). The anti-Akt capture Ab was diluted 1:250 in PBS, 20 μL/well was added, and plates were sealed at room temperature overnight.

On day 1, cell lysate samples were thawed at 4° C. The ELISA plates were washed 3 times with 80 μL/well 0.05% Tween 20/PBS using Plate Washer and the ELISA plates were blocked with 50 μL/well 2% BSA/PBS for 1 hr at room temperature. The recombinant human active Akt standard curve was prepared in MPER buffer in 96 well plate (non-binding surface plate, Corning 3641). The top concentration of rh active Akt1/PKBα (Millipore 14-276) stock (9165 ng/ml) was prepared by making 1:200 dilution (9 serial 1:2 dilutions. After blocking, ELISA plates were washed 3 times with 80 μL/well 0.05% Tween 20/PBS. 20 μL/well samples and standards were added to ELISA plate and incubated for 2 hr at room temperature. The ELISA plates were washed 3 times with 80 μL/well 0.05% Tween 20/PBS. 20 μL/well detection antibody (CST 4060 diluted 1:1000 in 2% BSA/ 0.1% Tween20/PBS) was added and incubated for 1.5 hr at room temperature. The ELISA plates were washed 3 times with 80 μL/well 0.05% Tween 20/PBS. 20 μL/well of the secondary antibody (anti rabbit IgG HRP, CST 7074, diluted 1:1000 in 2% BSA/0.1% Tween 20/PBS) was added and incubated for 30 min at room temperature on shaker (protected from light). The ELISA plates were washed 3 times with 80 μL/well 0.05% Tween 20/PBS. 20 μL/well Super-Signal ELISA Pico Chemiluminescent Substrate (Pierce/ThermoScientific) mixed in equal parts with Enhancer and Peroxide Substrate was added and plate was shaken for 1 min and luminescence was read.

The dose response curves were fit to a three parameter EC50 activation model and the calculated EC50s were compared between wt IGF-1 and the bi-specific proteins (SGFs 649, 711, 683, 713, 729, 716, 727, 606, 743, 730, 740, 733, 739, 732, 728, 741, 731, 757) and the non-targeted control proteins (688, 703, 704, 602, FIGS. 2A-2B). The calculated potency reduction for each of the fusion proteins is taken as the ratio of fit EC50 values between the fusion protein and wt IGF-1 dose response curves ($EC50_{fusion}/EC50_{wt\ IGF1}$).

Figure 3B:
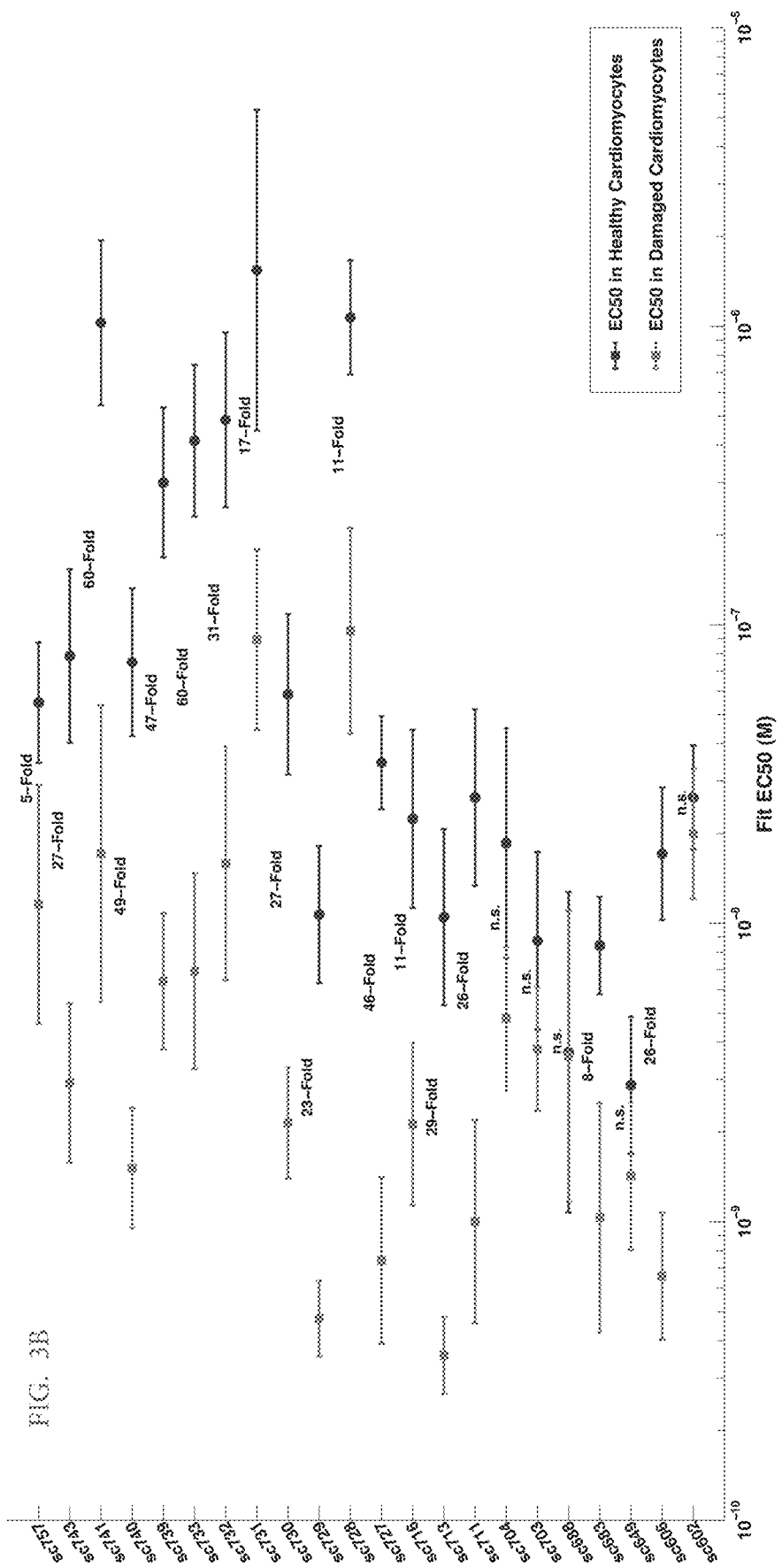
FIG. 3B is a graph depicting the potency shift calculated by EC50 healthy/EC50 damaged for different therapeutic bi-specific proteins compared to non-targeted control proteins on a logarithmic scale according to some embodiments. Fit EC50 values are represented for both the Healthy (filled circles) and Damaged (incubation with 12.5 µg/mL doxorubicin for 24 hours to induce apoptosis; filled triangle) contexts. Error bars represent the 95% confidence interval for the parameters. The calculated Potency Shift for each of the engineered proteins is taken as the ratio of fit EC50 values between the Healthy and Damaged dose response curves (EC50Healthy/EC50Damaged). The Potency Shift is annotated and expressed as the fold increase in Damaged context signaling.
Figure 3C:
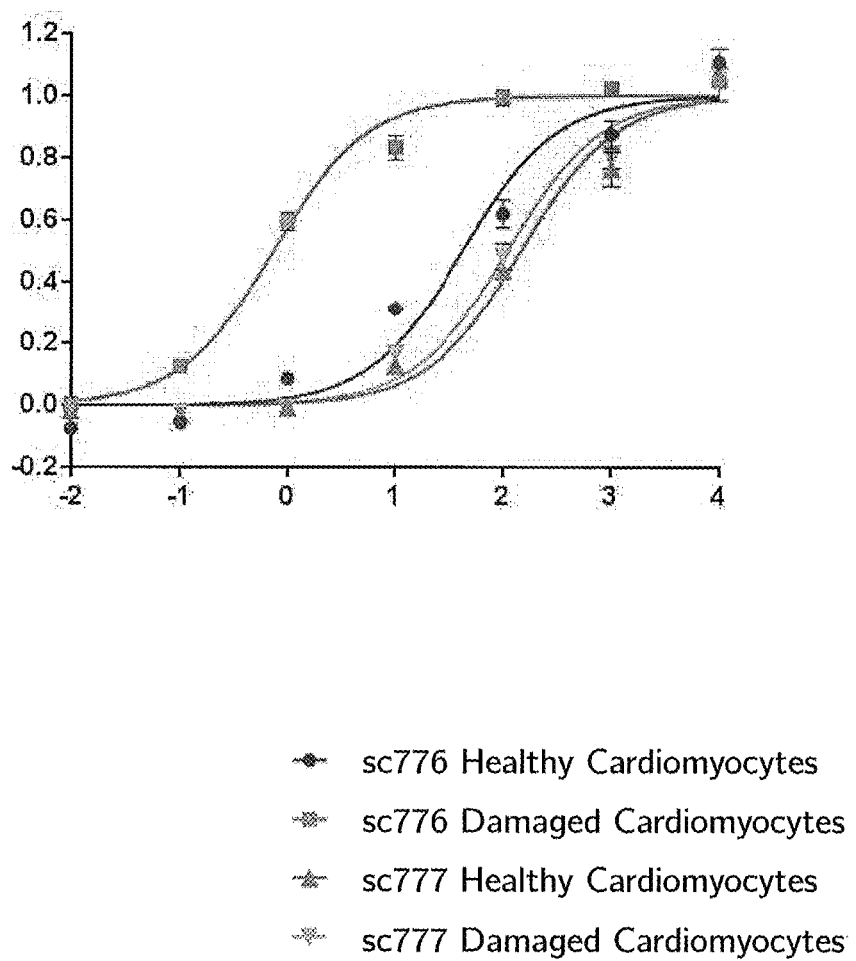
FIG. 3C is a graph depicting pAKT (protein kinase B) dose response in healthy and damaged cardiomyocytes using the therapeutic bi-specific protein 776 (sc776) and the corresponding non-targeted control protein 777 (sc777). As in FIG. 3A, the potencies of candidate Smart Growth Factors are measured at different concentrations (nM) in pluripotent stem cell derived cardiomyocytes and signaling (Y axis) is quantified by the accumulation of phosphorylated Akt. Dose response curves in the healthy and damaged contexts are fit to a three parameter EC50 activation model. Signaling for sc776 is depicted for Healthy (blue, filled circle) and Damaged (red, filled square) contexts, respectively. Signaling responses for sc777 is depicted for the Healthy (purple, filled triangle) and Damaged (green, filled inverse triangle) contexts, respectively.

Example 2: Targeted, Potency Reduced Bi-Specific Fusion Proteins Selectively Signal (i.e, Exhibit a Potency Shift) in Cells Containing Target Molecule Compared to Cells without Target Molecule The ability of phosphatidylserine (PS)-targeted, potency-reduced bi-specific proteins to selectively signal on cells containing the target molecule PS was measured in healthy (which does not display PS at the cell surface) vs. damaged (which displays PS at the cell surface) pluripotent stem cell derived cardiomyocytes (Cellular Dynamics International) and signaling was quantified by accumulation of phosphorylated AKT (FIGS. 3A, 3B and 3C).

Phosphatidylserine(PS)-targeted, potency-reduced bi-specific proteins (having a 6-fold or greater potency reduction compared to wt IGF-1, (e.g. SGFs 743, 741, 740, 739, 733, 732, 731, 730, 729, 728, 727, 716, 713, 711, 606, SEQ ID NOs: 86, 85, 84, 83, 82, 81, 80, 79, 78, 77, 76, 75, 74, 73, and 70, respectively) were compared against non-targeted potency reduced fusion proteins (having 6-fold or greater potency reduction compared to wt IGF-1, e.g. 704, 602, 703, SEQ ID NOs: 107, 66 and 68, respectively), non-targeted non-potency reduced fusion protein (2-fold or lesser reduction compared to wt IGF-1, e.g. SGF 688, SEQ ID NO: 72), and targeted non-potency reduced 2-fold or lesser reduction compared to wt IGF-1 (e.g. SGF 649, SEQ ID NO: 71). See for example FIG. 1B for protein identities and FIGS. 2A-2B for table showing potency reduction vs. wt IGF-1.

On day 0, the cardiomyocytes were thawed according to standard protocol and seeded at 1.5e4 cells/well in Plating Media (CDI catalog #CMM-100-110-005).

On day 2, the media was pipetted up and down several times to dislodge dead cells and replaced with 100 μL/well warm Maintenance Media (CDI catalog #CMM-100-120-001). The Maintenance Media was replaced every other day.

On day 14, low serum media was prepared (DMEM no glucose (Invitrogen 11966-025), 1 mM sodium pyruvate, 10 mM galactose, 0.5% serum (supplied by CDI), 0.7 mM CaCl2). Low serum media was prepared with 12.5 μg/ml doxorubicin. For damaged/treated cells, the Maintenance Media was aspirated and replaced with 100 μL/well low serum media+12.5 μg/mL doxorubicin. For healthy/untreated cells, the Maintenance Media was aspirated and replaced with 100 μL/well low serum media.

On day 15, a lysis solution was prepared [complete M-PER lysis buffer: M-PER lysis buffer (Pierce/ThermoScientific Cat #78501)+150 mM NaCl+protease (Roche Complete) and phosphatase inhibitors (Roche PhosSTOP))] and the bi-specific proteins were prepared in low serum media with 0.7 mM CaCl2. Different serial dilutions (1:7 dilutions) were prepared. The cells were stimulated with diluted solutions of bi-specific proteins by adding 25 µL/well of diluted bi-specific proteins to the existing 100 µL in each well and tapping the plate to mix for 10 seconds. The cells were incubated for 10 minutes at 37° C. The stimulation was stopped by removing the media from wells. The cells were washed with 200 µL/well cold PBS and tapping the plate upside down to remove excess PBS. The cells were lysed in 25 µL/well complete M-PER lysis buffer. The plate was sealed with foil plate seal and placed on orbital shaker 30 minutes at 4° C. The plate was then stored at −80° C. until ready for ELISA.

For the pAKT ELISA, on day 0, 384-well flat white plates (LIA High Binding, Greiner Bio-One, 781074) were coated with anti-Akt capture antibody (clone SKB1, Millipore 05-591). The anti-Akt capture Ab was diluted 1:250 in PBS, 20 µL/well was added, and plates were sealed at room temperature overnight.

On day 1, cell lysate samples were thawed at 4° C. The ELISA plates were washed 3 times with 80 µL/well 0.05% Tween 20/PBS using Plate Washer and the ELISA plates were blocked with 50 µL/well 2% BSA/PBS for 1 hr at room temperature. The recombinant human active Akt standard curve was prepared in MPER buffer in 96 well plates (non-binding surface plate, Corning 3641). The top concentration of rh active Akt1/PKBα (Millipore 14-276) stock (9165 ng/ml) was prepared by making 1:200 dilution (9 serial 1:2 dilutions. After blocking, ELISA plates were washed 3 times with 80 µL/well 0.05% Tween 20/PBS. 20 µL/well samples and standards were added to ELISA plate and incubated for 2 hr at room temperature. The ELISA plates were washed 3 times with 80 µL/well 0.05% Tween 20/PBS. 20 µL/well detection antibody (CST 4060 diluted 1:1000 in 2% BSA/0.1% Tween20/PBS) was added and incubated for 1.5 hr at room temperature. The ELISA plates were washed 3 times with 80 µL/well 0.05% Tween 20/PBS. 20 µL/well of the secondary antibody (anti rabbit IgG HRP, CST 7074, diluted 1:1000 in 2% BSA/0.1% Tween 20/PBS) was added and incubated for 30 min at room temperature on shaker (protected from light). The ELISA plates were washed 3 times with 80 µL/well 0.05% Tween 20/PBS. 20 µL/well SuperSignal ELISA Pico Chemiluminescent Substrate (Pierce/ThermoScientific) mixed in equal parts with Enhancer and Peroxide Substrate was added and plate was shaken for 1 min and luminescence was read.

The dose response curves were compared in healthy and damaged cardiomyocytes (FIG. 3A). The dose response curves were subsequently fit to a three parameter EC50 activation model and the calculated EC50s were compared between the healthy (circles, blue color) and damaged (square, red color) cardiomyocytes.

FIG. 3B shows the potency shift for twenty-two bi-specific proteins on a logarithmic scale. The fit EC50 values are represented for both healthy (filled circles) and damaged (filled triangles) cardiomyocytes. Error bars represent the 95% confidence interval for the parameters. The calculated potency shift for each of the bi-specific proteins is taken as the ratio of fit EC50 values between the healthy and damaged dose response curves (EC50Healthy/EC50Damaged). The potency shift is annotated and expressed as the fold increase in Damaged context signaling.

FIG. 3C is a graph (signaling in function of base 10 log concentration in nM) depicting pAKT (protein kinase B) dose response in healthy and damaged cardiomyocytes using the therapeutic bi-specific protein 776 (sc776) and the corresponding non-targeted control protein 777 (sc777).

As in FIG. 3A, the potencies of Smart Growth Factors sc776 and non-targeted control sc777) are measured in pluripotent stem cell derived cardiomyocytes and signaling is quantified by the accumulation of phosphorylated Akt. Dose response curves in the healthy and damaged contexts are fit to a three parameter EC50 activation model. Signaling for sc776 is depicted for Healthy (blue, filled circle) and Damaged (red, filled square) contexts, respectively. Signaling responses for sc777 is depicted for the Healthy (purple, filled triangle) and Damaged (green, filled inverse triangle) contexts, respectively. The composition of sc776 is IGF1 (E3R/Y31A)_lk7_HSA(C58S/N527Q)_lk7_AnxV(R63A/K70A/K101A/E138A/D139G/N160A/C316A). The non-targeted control sc777 is comprised of IGF1 (E3R/Y31A)_lk7_HSA(C58S/N527Q). As in FIG. 3B, the specificity for signaling in the damaged context is taken as the ratio of fit EC50 values between the Healthy and Damaged dose response curves (EC50Healthy/EC50Damaged). The non-targeted, potency-reduced molecule sc777 does not display a Potency Shift, whereas the targeted, potency-reduced molecule sc776 has a Potency Shift of 57-fold.

These data show that PS-targeted, potency-reduced (≥6-fold potency reduction compared to wt IGF-1) variants of IGF-1 (e.g., SGFs 743, 741, 740, 739, 733, 732, 731, 730, 729, 728, 727, 716, 713, 711, 606, 776) show preferential (10- to 92-fold increased) signaling in damaged cardiomyocytes over healthy cardiomyocytes by the addition of an AnxV-based targeting arm. Also, a PS-targeted, potency-reduced (~4-fold potency reduction compared to wt Nrg1a) variant of Nrg1a (SGF 757) show preferential (5-fold increased) signaling in damaged cardiomyocytes over health cardiomyocytes by the addition of an AnxV-based targeting arm. Control fusion proteins lacking a targeting arm (e.g., SGFs 704, 602, 688, 703) show negligible (≤2-fold) preferential signaling in damaged cardiomyocytes compared to healthy cardiomyocytes, proving the importance of the PS-selective targeting arm in eliciting selective signaling in damaged cells. Moreover, a targeted, non-potency-reduced bi-specific protein (<2-fold potency reduction compared to wt IGF-1) SGF 649 also shows negligible (<2-fold) preferential signaling in damaged cardiomyocytes compared to healthy cardiomyocytes, proving the importance of potency reduction in eliciting selective signaling in damaged cells.

Figure 4:
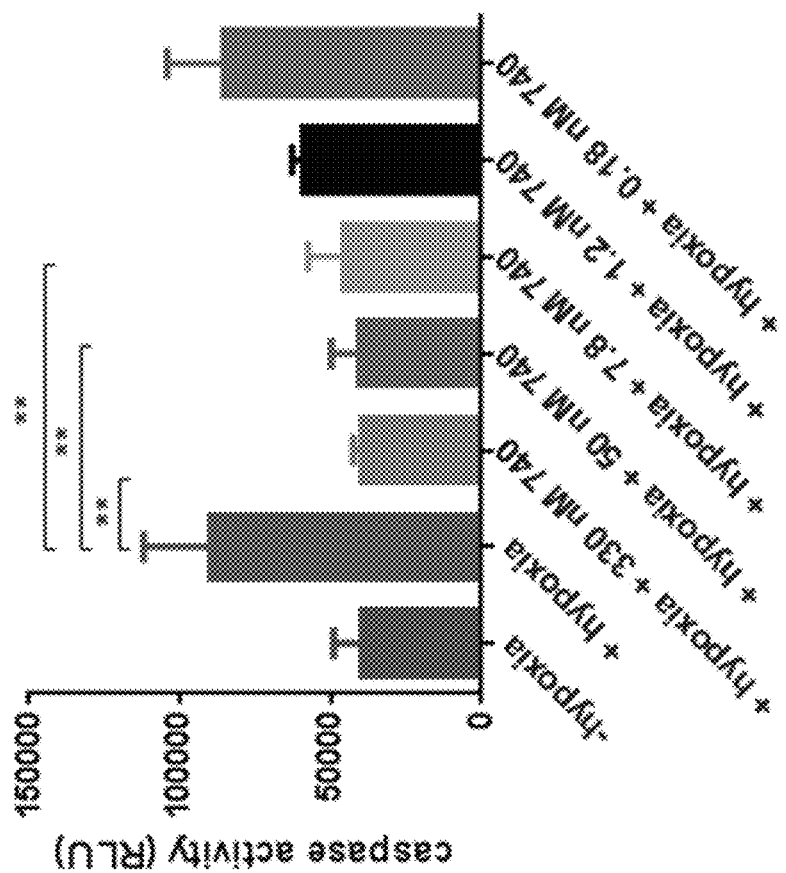
FIG. 4 is a graph depicting reduction of caspase activity induced by hypoxia using therapeutic bi-specific protein SGF 740 in human cardiomyocytes.

Example 3: Reduction of Hypoxia-Induced Apoptosis in Human Cardiomyocytes In Vitro Using Bi-Specific Proteins FIG. 4 shows the reduction of apoptosis using fusions protein SGF 740 in an in vitro human cardiomyocyte hypoxia-induced apoptosis assay.

The bi-specific protein SGF 740 (SEQ ID NO: 84) comprising from the N terminus to the C-terminus: a variant of IGF-1 (LR3, Y31A), a 7 amino acid linker lk7, a variant of HSA (mHSA: C58S, K420E, and N527Q), a 7 amino acid linker lk7, and a non-internalizing variant of annexin A5 (ni-AnxV: R63A, K40A, K101A, E138A, D139G, N160A) was used in vitro to assess its efficacy. Apoptosis was induced by culturing cells at 1% oxygen for 48 hours. Fusion protein SGF 740 was added at the start of the hypoxia period. Caspase activity was measured. Caspases are a family of aspartate-specific, cysteine proteases that serve as the primary mediators of apoptosis. Apoptotic caspases are activated upon the receipt of either an extrinsic or an intrinsic death signal.

On day 0, iCell Cardiomyocytes (Cellular Dynamics, Inc, (CDI) human induced pluripotent stem (iPS) cell-derived cardiomyocytes, catalog #CMC-100-010-001) were thawed according to standard protocol. 96 well plates were coated with 0.1% gelatin 1 h beforehand at 37° C. The cells were plated at 1.5e4 cells/well and cultured in a 37° C./7% CO2 incubator.

On day 2, the media was pipetted up and down 5 times and replaced with 100 μL/well warm maintenance media. At this point cells were moved to a 37° C./5% CO2 incubator. After this switch the cells were left at 37° C./5% CO2 for the rest of the experiment.

On day 4, the media was replaced with fresh maintenance media.

On day 7, the hypoxia assay media (HAM, DMEM no glucose, no glutamine, no phenol red (Life Technologies, A14430-01)+2 mM L-Carnitine, 5 mM Taurine, 5 mM Creatine, 1× Non-essential amino acids (Life Technologies, 11140-50), 10 mM HEPES, 1 mM sodium pyruvate, 1× GlutaMax (Life Technologies, 35050-061), 2.75 mM D-(+) Glucose, 1× Linoleic Acid-Oleic Acid-Albumin (Sigma L9655)) was prepared fresh. The cells were washed twice with 80 μL HAM to replace maintenance media. 100 μL HAM was then added to wells of the plates and the plates were placed in the 37° C./5% CO2 incubator for 2 days.

On day 8, the media was replaced with 100 μL fresh HAM.

On day 9, the hypoxia chamber in the 37° C./5% CO2 incubator was set to 1% O2. The media was replaced with fresh HAM (90 uL). 10× concentrated SGF (bi-specific protein SGF 740) stocks were prepared in HAM (sterile filtered before adding to cells). 10 □L SGF or HAM was added to wells. The hypoxia plate was placed in the hypoxia chamber in the 37° C./5% CO2 incubator at 1% O2 for 48h. Normoxia plate was placed in 37° C./5% CO2 incubator (equilibrated with atmospheric oxygen) for 48h.

On day 11, the samples were analyzed using CaspaseGLO 3/7 assay (Promega) which measures caspase-3/7 activities. The assay uses a proluminescent caspase-3/7 DEVD-aminoluciferin substrate and a thermostable luciferase in a reagent optimized for caspase-3/7 activity, luciferase activity and cell lysis. The addition of the reagent results in cell lysis, followed by caspase cleavage of the substrate. This liberates free aminoluciferin, which is consumed by the luciferase, generating a luminescent signal which is proportional to caspase-3/7 activity.

FIG. 4 shows the caspase activity in control samples [no hypoxia (i.e., normoxia)] and in hypoxia samples treated with different concentrations of bi-specific protein SGF 740: 330 nM bi-specific protein SGF 740, 50 nM bi-specific protein SGF 740, 7.8 nM bi-specific protein SGF 740, 1.2 nM bi-specific protein SGF 740, and 0.18 nM bi-specific protein SGF 740. FIG. 4 shows that bi-specific protein SGF 740 significantly reduces caspase activity and apoptosis induced by hypoxia (p≤0.01) in human cardiomyocytes in vitro.

These results show that bi-specific protein SGF 740 significantly (p⇐0.01) decreases hypoxia-induced apoptosis in human cardiomyocytes in a dose dependent manner. At several concentrations of bi-specific protein SGF 740, hypoxia-induced apoptosis is reduced down to normoxia (i.e., no hypoxia) levels. This result shows that SGFs are effective in treating hypoxia-induced apoptosis in human cardiomyocytes.

Figure 5:
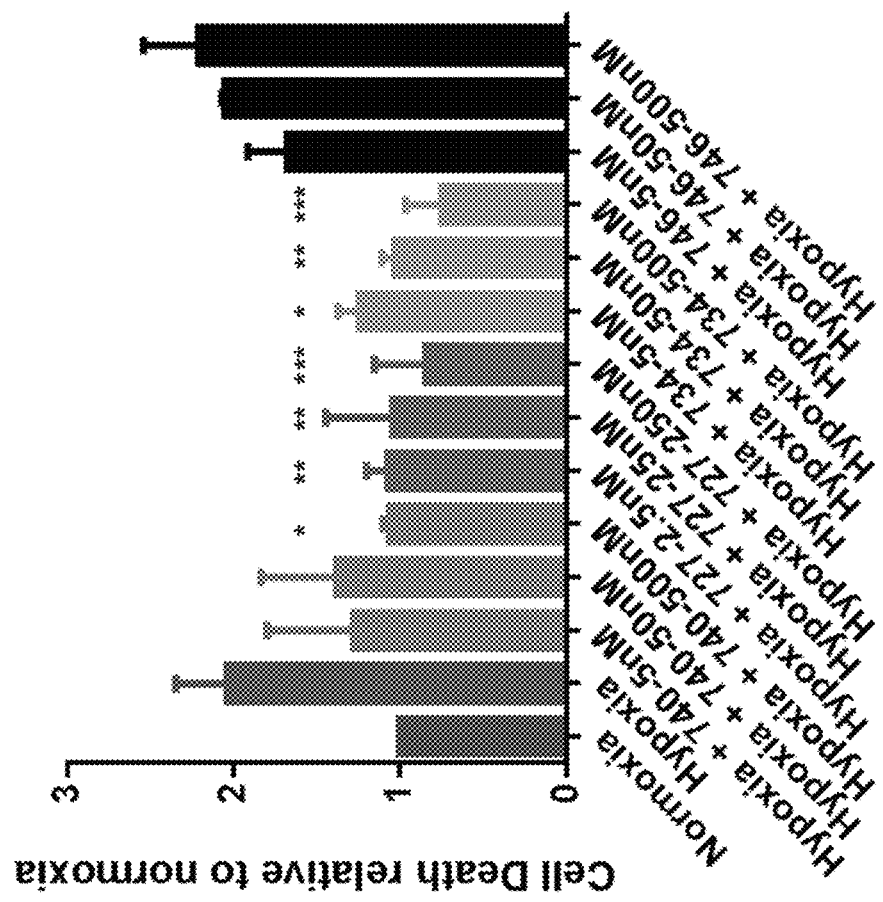
FIG. 5 is a graph depicting reduction of hypoxia-induced cell death using therapeutic bi-specific proteins SGFs 727, 740, 734, and non-targeted control (746) in human kidney proximal tubule epithelial cells.

Example 4: Reduction of Hypoxia-Induced Cell Death in Kidney Proximal Tubule Epithelial Cells In Vitro Using Bi-Specific Proteins The bi-specific proteins SGFs 740, 727, and 734 were used to assess efficacy in a hypoxia induced cell death assay compared to a non-targeted control, SGF 746 (SEQ ID NO: 109) (FIG. 5). The bi-specific protein SGF 740 (SEQ ID NO: 84) comprises from the N terminus to the C-terminus: a variant of IGF-1 (LR3, Y31A), a 7 amino acid linker lk7, a variant of HSA (mHSA: C58S, K420E, and N527Q), a 7 amino acid linker lk7, and a non-internalizing variant of Annexin A5 (ni-AnxV: R63A, K40A, K101A, E138A, D139G, N160A). The bi-specific protein SGF 727 (SEQ ID NO: 76) comprises from the N terminus to the C-terminus: a variant of IGF-1 (LR3-R37X-3X), a 40 amino acid linker lk40, a Human Serum Albumin variant mHSA half-life modulator, a 40 amino acid linker lk40, and Annexin A5. The bi-specific protein SGF 734 (SEQ ID NO: 108) comprises from the N terminus to the C-terminus: a variant of IGF-1 (LR3, Y24L/Y31A), a 7 amino acid linker lk7, a variant of HSA (mHSA7: C58S, K420E, and N527Q, E505G, V547A), a 7 amino acid linker lk7, and a non-internalizing variant of Annexin A5 (AnxV(ni): R63A, K40A, K101A, E138A, D139G, N160A). The non-targeted control SGF 746 comprises from the N terminus to the C-terminus: a variant of IGF-1 (LR3, Y31A), a 7 amino acid linker lk7, and a variant of HSA (mHSA: C58S, K420E, and N527Q).

On day 0, human kidney proximal tubule epithelial cells (ATCC, PCS-400-010) were seeded at 10,000 cells/well in 96 well plates in complete media (Renal Epithelial Cell Basal Medium, Renal Epithelial Cell Growth kit, 10 Units/mL penicillin, 10 □g/mL streptomycin, 10 □g/mL gentamicin, 0.25 □g/mL amphotericin B, ATCC). Sterile water was added to edge wells.

On day 2, wells were washed with PBS and media was switched to low serum media (Renal Epithelial Cell Basal Medium, 0.5% FBS, 5 μg/ml transferrin, 2.4 mM L-glutamine, 1% Penicillin/Streptomycin (10 units/mL Penicillin+ 10 μg/mL Streptomycin)), 100 μL/well. After 5 hours, the cells were treated with the bi-specific proteins SGFs 740, 727, 734, or the non-targeted control protein SGF 746 at different concentrations (5 nM, 50 nM, 500 nM, or 2.5 nM, 25 nM, 250 nM) in 2.5 mM CaCl2 containing media (or low serum media as control). 25 μL of 5× concentration sample was added and cells were incubated in a 37° C./5% CO2 incubator for 1 hour.

After the 1 hour pretreatment with SGF, cells were put into anaerobic pouches (GasPak EZ Anaerobe Pouch System with Indicator, BD 260683) to induce hypoxia and placed in a 37° C./5% CO2 incubator or left under normoxia (i.e., equilibrated with atmospheric oxygen) in the 37° C./5% CO2 incubator (as a control). The cells were incubated for 18 hours.

On day 3, the cells were collected for flow cytometry. The media and floating cells were aspirated and transferred to a V-bottom plate. The cells were washed with 20 μL/well PBS. 30 μL/well trypsin/EDTA was added for primary cells (ATCC PCS-999-003). The plate was returned to the 37° C. incubator for 10 minutes.

The cells were dislodged by tapping the plate. 30 μL/well trypsin neutralization solution was added to collect cells and the cells were transferred to a V-bottom plate. The plate was centrifuged at 700 g at 4° C. for 5 minutes. The supernatant was removed and the cells were resuspended in 100 □L/well. The cells were washed with PBS+0.02% EDTA (0.5 mM EDTA) to remove any bound bi-specific protein. AnxV-FITC staining solution (with propidium iodide (PI)) was prepared; 0.3 μg/mL AnxV-FITC (766.6× dilution from 230 μg/mL stock)+1 μg/mL PI (1000× dilution from 1 mg/mL stock). The plate was centrifuged at 700 g at 4° C. for 5 minutes. The supernatant was removed and the cells were resuspended in 50 µL/well AnxV-FITC staining solution. The plate was incubated for 15 minutes at room temperature. 200 µL/well AnxV binding buffer was added to the cells. Cell death was measured as the percent of propidium iodide positive cells using flow cytometry.

FIG. 5 shows that bi-specific proteins SGFs 740, 727, and 734 significantly reduce cell death induced by hypoxia in human kidney proximal tubule epithelial cells. The non-targeted control protein 746 did not reduce cell death. These data show that targeted bi-specific SGFs are effective in treating hypoxia-induced cell death in human kidney proximal tubule epithelial cells whereas non-targeted proteins are not effective.

Example 5: Comparison of Bi-Specific Proteins Half-Lives after Intravenous Dosing Half-lives of bi-specific proteins in mice were calculated in a single-compartment model (FIG. 6). SGF 727 has the structure IGF-1 (LR3-R37X-3X)-lk40-mHSA-lk40-AnxV (SEQ ID NO: 76), The bi-specific proteins 739-743 have the basic structure of IGF-1 *(LR3)-lk7-mHSA-lk7-AnxV(ni) wherein * denotes a potency reducing deletion or mutation of IGF-1. The bi-specific protein 757 has the structure Nrg1a_lk7_mHSA_lk7_ni-AnxV (SEQ ID NO: 110).
Procedure:

C57BL/6J mice (8-12 weeks old) were weighed and warmed for 5-10 minutes under a heat lamp to allow for vasodilation of lateral tail vein. Animals were placed in a restrainer, their tails were cleaned with alcohol pads and then injected via tail vein with 100 □1 of SGF at 40 nmol/ml formulated in PBS+0.1% MSA. A small volume (5-10 µL) of blood was collected into serum collection tubes after nicking the lateral tail vein at 1, 3, 6, 9, 12, 26.5, 28, 31.5, 33.5, 35.75, and 51 hours post dose. For each subsequent collections, the scab that has formed over the tail was removed and the blood collection. Blood was allowed to clot for 10 minutes after collection, then spun at 10,000×g for 10-15 minutes at 4° C.

Analysis of SGF concentration in blood samples was carried out using an ELISA designed to capture and detect HSA. An assay plate (384-well LIA High Binding, Greiner bio-one, REF 781074) was coated with 20 µL/well cross-adsorbed anti-HSA antibody (Bethyl Labs, A80-229A) diluted 1:50 in Dulbecco's PBS overnight at 4° C. The next day, wells were washed 3× with PBS-T (PBS, 0.05% Tween 20). The plate was then blocked with 80 µL/well protein-free blocking buffer (Pierce, 37572) for 1-2 h at room temperature (RT) while preparing standard curves for each SGF and serum samples (diluted 25×, 100×, 400×, 1600×, 6400× in PBS). Wells were washed with 3× with PBS-T (PBS, 0.05% Tween 20) using plate washer, 20 ul each sample or standard was added to the appropriate plate well and plates were sealed with AluminaSeal and incubated 2h at RT on shaker. Plate was washed 3× with PBS-T (PBS, 0.05% Tween 20) and then 40 µL/well cross-adsorbed goat anti-HSA-HRP detection antibody (Bethyl labs, A80-229P) diluted 1:25 000 in PBS-T was added. Plate was incubated 30 min at RT, on a shaker platform, protected from light then washed 3× with PBS-T (PBS, 0.05% Tween 20) using plate washer. Bound antibodies were detected with Super Signal ELISA Pico chemiluminescent substrate product #37069, Thermo (20 µL/well). Plate luminescence was then analyzed on a Tecan Infinite 200 Pro.

A standard one- or two-compartment PK model was calibrated to experimental drug-serum decay data in mice using custom scripts written for the Simbiology MATLAB software platform (Mathworks, Inc., Natick, MA). Calibration was performed using the built-in nonlinear fitting algorithm (nlinfit) with the exponential error function (exp).
Results:

FIG. 6 lists the calculated half-lives and decay rates for wt IGF-1, wt Nrg and SGFs 727, 739, 740, 741, 743 and 757. The values were determined in MATLAB using a one compartmental model as described above. IGF-1-based SGF half-life was increased between 8.45 and 24.6 fold compared to wt IGF-1. In addition, SGFs had reduced decay rates ranging from 2.1 to 5.66 fold compared to wt IGF-1.

Example 6: Effect of IGF-1-Based Bi-Specific Proteins on Blood Glucose Levels in Mice The clinical application of IGF-1 is limited by risk of hypoglycemia, therefore it is important to understand the effects of these half-life extended SGFs on blood glucose levels. According to some embodiments, an important benefit of the bi-specific proteins is that, due to the presence of a reduced potency IGF-1 signaling arm for efficient targeting, these molecules have the potential to be much safer with respect to hypoglycemia.

Bi-specific proteins containing a signaling arm comprised of insulin-like growth factor-1 (IGF-1), a half-life modulating arm (HLM) and an Annexin A5 (AnxV) targeting arm (TA) designed to bind to phosphatidylserine (PS) exposed on the surface of apoptotic cells were used to assess their effect on blood glucose levels in mice when used at a 160 nmol/kg dose.
Procedure:
Tail Vein Injections and Glucose Monitoring Mice C57BL6/J1 between 24 and 27 g (n=2/dose) were used. They were allowed 3-5 days after arrival for acclimation to the animal housing facility before use. The animals had access to food and water ad libitum since these high doses could potentially result in dangerous hypoglycemia.

On the day of experiment, protein doses were prepared in PBS with 0.1% mouse serum albumin (MSA) as carrier protein. Total injection volume was 100 µl.

The animals were warmed with heat lamp for 5-10 minutes prior to injection to allow for vasodilation and easier identification of tail vein.

The animals were secured in an appropriate restrainer, the tail was cleaned with a sterile alcohol wipe and a dose was injected into the lateral tail vein.

For the first collection, the tail and razor blade were sterilized with an ethanol wipe. A small amount of blood (2-3 µL) was applied to glucose test trips (Abbott, Alpha-Trak2 Glucose Meter, dog setting).

Figure 7A:
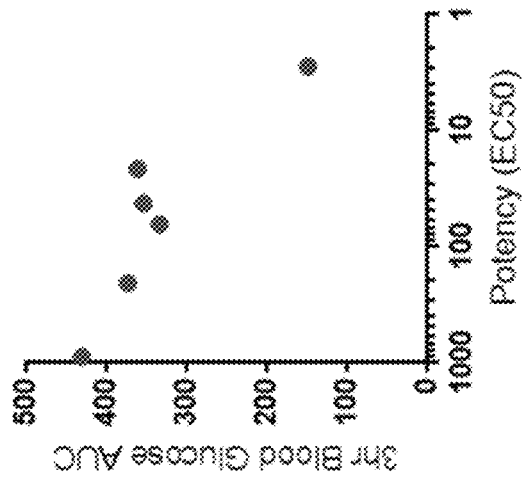
FIGS. 7A and 7B are a set of graphs depicting the effects of different therapeutic bi-specific proteins on blood glucose levels after intravenous dosing.
Figure 7B:
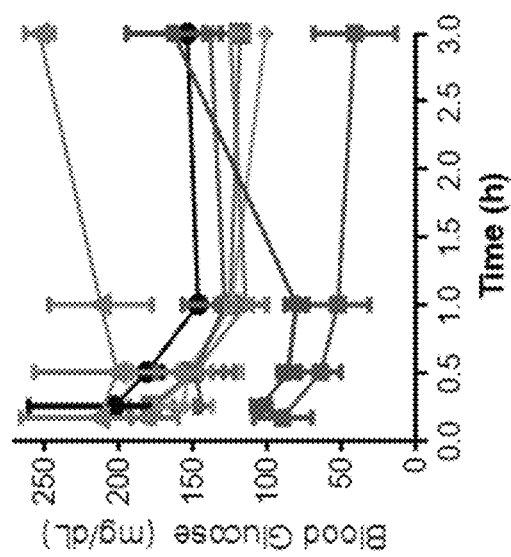

For subsequent collections, the scab that has formed over the tail was removed and the blood collection and glucose measurement were repeated.
Results:

FIG. 7a shows the time-course of blood glucose levels in mice after dosing with targeted reduced potency bi-specific proteins (SGFs 727 (SEQ ID NO: 76), 739 (SEQ ID NO: 83), 740 (SEQ ID NO: 84), 741 (SEQ ID NO: 85) and 743 (SEQ ID NO: 86)) as blood concentration of glucose in mg/dL. Mice were dosed with recombinant Human serum albumin, IGF1 (LR3 variant), or a non-potency-reduced, non-targeted, half-life extended growth factor (protein 688: IGF1 (LR3-R37X-3X)-Fc) as controls. These data show that the targeted, potency-reduced bi-specific proteins (SGFs 727, 739, 740, 741 and 743) have vastly improved safety profiles with respect to hypoglycemia compared to a non-targeted, non-potency-reduced, half-life extended growth factor (protein 688) and IGF1 (LR3). Animals receiving potency-reduced bi-specific molecules do not experience hypoglycemia (defined as <70 mg/dL) whereas animals dosed with IGF1 (LR3) or non-potency-reduced, half-life extended growth factor 688 and at this dose level do experience hypoglycemia. It was noted that the drop in blood glucose caused by IGF1 (LR3) administration is more transient (i.e., recovery seen by 3h) than SGF 688 due to the extremely short (~0.2h) half-life of IGF1 (LR3). FIG. 7b shows the relationship between SGF potency (defined as the concentration required to achieve half maximal pAKT levels, i.e., pAKT EC50) vs. 3 hr blood glucose area under the curve (AUC). This graph demonstrates that greater potency reduction (i.e., increased pAKT EC50) leads to increased 3 hr blood glucose AUC (i.e., less blood glucose reduction).

Patient response to hypoglycemia induced by IGF-1-based SGFs is likely to be highly heterogeneous and these data suggest that, especially for indications that may require chronic treatment, high doses of either wt IGF1 or non-targeted, non-potency-reduced, half-life extended GFs could pose a serious safety risk. These results highlight the importance of considering potency for the generation of targeted molecules. According to some embodiments, targeted molecules with reduced potency on non-target cells and enhanced potency on cells containing target molecules of interest are likely to have much more desirable safety profiles than native or simply half-life extended GFs.

Example 7: Analysis of Signaling Levels of Bi-Specific Proteins in Healthy and Ischemic Rat Tissues To analyze how the bi-specific proteins described herein signal in the heart after ischemic injury, the signaling (phosphorylation of AKT) in healthy and damaged tissue in a rat ischemia/reperfusion (I/R) model of acute myocardial infarction (AMI) was evaluated using 4 test compounds: 1) vehicle (PBS+0.1% mouse serum albumin), 2) wt IGF1 (RnD Systems), 3) a non-targeted, non-potency-reduced control protein (688, IGF1 (LR3-R37x-3x)_lk40_Fc, SEQ ID NO: 72), and 4) a targeted, potency-reduced bi-specific protein (SGF 606, GF1 (LR3-R37x-3x)_lk40_mHSA_lk40_AnxVC316S_lk8_His6, SEQ ID NO: 70), see FIG. 8.

Test compounds were dosed at 16 nmol/kg via intravenous administration at the time of reperfusion, and the tissue was collected for analysis 2 hours post reperfusion. Time and dose were chosen based on the pharmacodynamics of the bi-specific proteins described herein over a period of 6 hours in the hearts of healthy mice. Based on these data, it was reasoned that this dose and time point would allow for the identification of the bi-specific proteins with favorable pharmacodynamic signals in the damaged heart.

Procedure:
Tissue Harvest
Rat I/R surgery with 1 hour of ischemia followed by reperfusion and immediate intravenous (tail vein) injection of vehicle, IGF-1 or SGF dose was performed. After 2 hours of reperfusion, the animal was anesthetized with isoflurane and maintained under deep anesthesia via nose cone during tissue harvest. The thoracic cavity was opened, the right atrium was clipped with dissection scissors and the animal was perfused with 15-20 ml 0.9% NaCl through the apex of the left ventricle to clear the circulatory system and well-perfused tissue of blood. The heart was removed and the heart tissue was transversely sectioned with a razor or microtome blade, cutting into 4 sections: apex, middle, top and basal. The middle section had little right ventricle, consisting mostly of left ventricle, and contained the largest amount of infarct which was often slightly visible by its pallor. The healthy tissue (remote section) was carefully dissected out from the region containing the infarct and border zone (infarct section) and each piece of tissue was placed in separate tubes labeled remote and infarct.

Tissue Homogenization
RIPA Buffer+protease (Roche Complete) and phosphatase inhibitors (Roche PhosSTOP) in ~2:1 ratio μL buffer:mg tissue (ex: for 300 mg tissue, use 600 μL buffer) was added into a tube containing heart tissue samples. The tissue was minced with microscissors to facilitate bead homogenization. 1.6 mm stainless steel beads were added at 1:1 tissue weight: bead weight. The samples were loaded in a Bullet Blender with a speed set up of 8 for 4 minutes, then returned to ice for 1 min. The samples were spun at maximum speed for 1 min then for 15 min at 14,000 rpm 4° C. 1 μL of supernatant was removed and combined with 59 or 119 μL PBS to perform BCA assay. The protein concentration was measured by BCA in duplicate.

PD Assay (pAKT ELISA)
Protocol:
On day 1, 384-well flat white plate (LIA High Binding (Greiner bio-one, REF 781074) were coated with 20 μL/well anti-Akt capture antibody (clone SKB1, Millipore), diluted 1:250 in PBS.

On day 2, the tissue was thawed on ice. The ELISA plates were washed 3 times with 80 μL/well 0.05% PBS-T. The ELISA plates were blocked with 50 μL/well 2% BSA/PBS for 1 hr at room temperature. A recombinant human active Akt standard curve was prepared in 14.44% RIPA in PBS in 96 well plates (non-binding surface (NBS) Corning plate). The rh active Akt1/PKBα (Millipore) was diluted 200× to 9165 ng/mL. After blocking, the ELISA plates were washed 3 times with PBS-T with plate washer. 20 μL/well samples or standards were added from prep plates and incubated for 2 hr at room temperature. The anti-phospho Akt detection antibody was prepared: Non-biotinylated rabbit anti-AKT mAb, Cell Signaling for tissue lysates was diluted 1:1000 in 2% BSA/0.1% Tween20/PBS. The ELISA plates were washed 3 times with 80 μL/well 0.05% Tween 20/PBS. 20 μL/well diluted anti-phospho Akt detection Ab was added and the plates were incubated for 2 hr at room temperature. The secondary detection antibody: Anti-Rabbit-IgG-HRP Ab (CST 7074) dilute d 1:1000 in 2% BSA/0.1% Tween 20/PBS. Wash ELISA plates 3 times with 80 μL/well 0.05% Tween 20/PBS. 20 μL/well diluted secondary detection reagent was added and the plates were incubated for 30 min at room temperature with shaking. The ELISA plates were washed 3 times with 80 μL/well 0.05% Tween 20/PBS. Detection was performed with 20 μl/well Super Signal ELISA Pico chemiluminescent substrate (Thermo). The plates were shaken 1 min and luminescence was read on plate reader.

Figure 8:
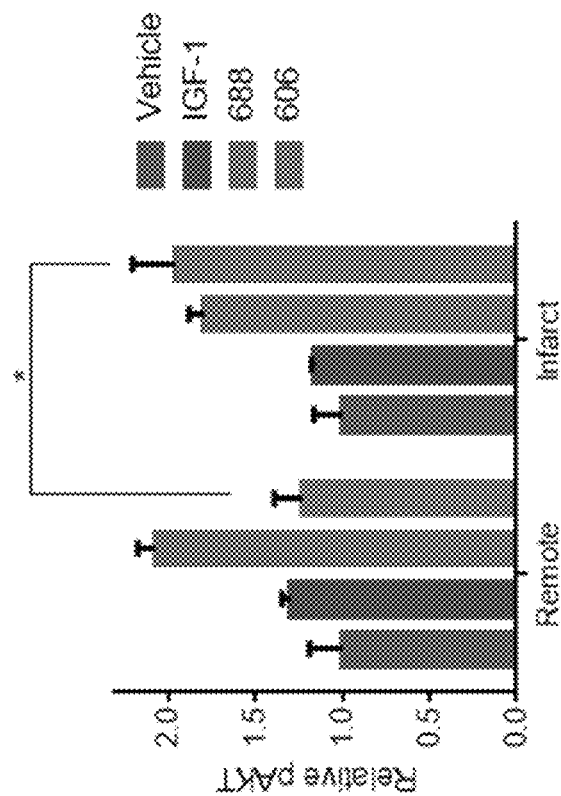
FIG. 8 is a graph depicting relative pAKT levels in damaged (infarct) vs. healthy (remote) rat heart regions. A rat ischemia/reperfusion model was employed to generate ischemic injury by ligation of the left anterior descending coronary artery (LAD) in rats. After 1 hour of ischemia and 2 hours of reperfusion, hearts were excised and microdissected into remote (healthy) and infarcted (damaged) regions informed by anatomical indicators. Tissue homogenates were generated for each region and analyzed for phospho-AKT using a total AKT/pAKT sandwich ELISA. At this timepoint, IGF-1 does not result in increased pAKT in either remote or infarcted tissue whereas a non-targeted, highly potent IGF1 fusion protein (688) increases pAKT non-selectively in both remote and infarcted tissue. Targeted, potency-reduced IGF1 fusion protein, 606, selectively increases pAKT in the infarcted tissue ($p<0.05$), compared to remote tissue.

Results
Data are shown in FIG. 8. In all cases control vehicle-dosed animals serve as the baseline for comparison between trials. For all data shown, pAKT levels in homogenates from remote or infarct heart tissue of SGF-dosed animals have been normalized to vehicle-dosed (PBS-MSA) remote or infarct tissue homogenates, respectively. As such, data for each SGF are displayed as "fold increase" in pAKT level over vehicle-dosed animal for each tissue region.

For each trial, data were analyzed to compare relative pAKT levels in remote tissue or infarct tissue within the same animal by treating the remote and infarcted tissue as paired samples. A two-way ANOVA followed by Sidak's multiple comparison test was performed.

The data show that pAKT levels in tissue from animals dosed with wt IGF-1 were not significantly elevated above vehicle-dosed animals in either remote or infarcted tissue at 2 hours post dosing, suggesting that wt IGF-1 is unable to maintain elevated pAKT levels out to 2 hours post dosing. A half-life extended, non-targeted, non-potency-reduced SGF (688, SEQ ID NO: 72) increased pAKT levels in both remote and infarct tissue compared to vehicle at 2 hours post dosing, indicating that non-targeted, half-life extended GFs can elevate pAKT levels non-selectively (i.e., in both remote and infarct tissue) for at least 2 hours after dosing. In contrast, a targeted, potency-reduced SGF (606) causes selective pAKT elevation only in the infarct tissue at 2 hours post dosing; SGF 606 causes no significant pAKT elevation in remote tissue at this same time point (compared to vehicle). Because there are considerably more apoptotic cells exposing surface phosphatidylserine in the infarcted region that the remote region, these data indicate that targeted, potency-reduced SGFs selectively signal in tissue containing target (e.g., infarct tissue) and, importantly, do not signal in tissue not containing target (e.g. remote tissue). These results show that in vitro selectivity on damaged cardiomyocytes translates to in vivo selectivity in damaged heart tissue. (See FIG. 3, showing that SGF 606 has 22-fold increased selectivity for apoptotic cells vs. non-apoptotic cells, and compare to the data in FIG. 8, showing that the same molecule (SGF 606) selectively signals in infarcted heart tissue).

Example 8: Efficacy of a Potency-Reduced, Targeted HSA-Based SGF 606 in a Rat Ischemia/Reperfusion Model To analyze how the bi-specific proteins described herein prevent tissue damage after ischemic injury, infarct/area-at-risk (AAR) in a rat ischemia/reperfusion (I/R) model of acute myocardial infarction (AMI) was evaluated using 3 test compounds: 1) vehicle (PBS+0.1% mouse serum albumin), 2) wt IGF1 (RnD Systems), 3) a targeted, potency-reduced SGF (606, GF1 (LR3-R37x-3x)_lk40_mHSA_lk40_AnxVC316S_lk8_His6, SEQ ID NO: 70), see FIGS. 9A-C.

Figure 9C:
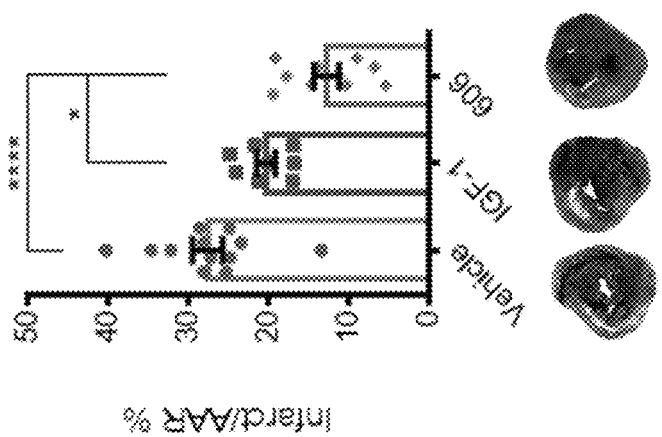
FIGS. 9A, 9B and 9C showed that targeted engineered growth factors according to some embodiments are efficacious in vivo and reduce infarct size in rat ischemia/reperfusion model of acute myocardial infarction (AMI). Targeted, potency reduced IGF1 fusions protein (SGF 606) significantly reduces infract/area-at-risk (AAR) following acute myocardial infarction in rats. Significantly greater infarct/ARR reduction is observed with SGF606 vs. wt IGF1.
Figure 9B:
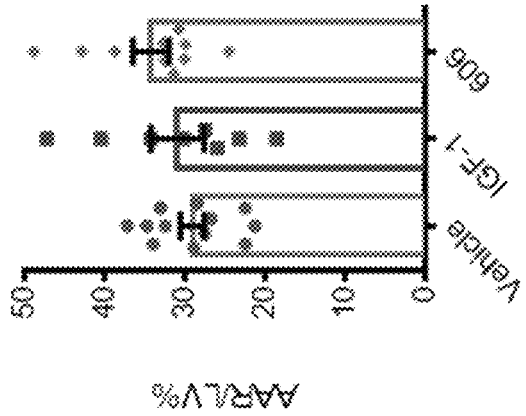
Figure 9A:
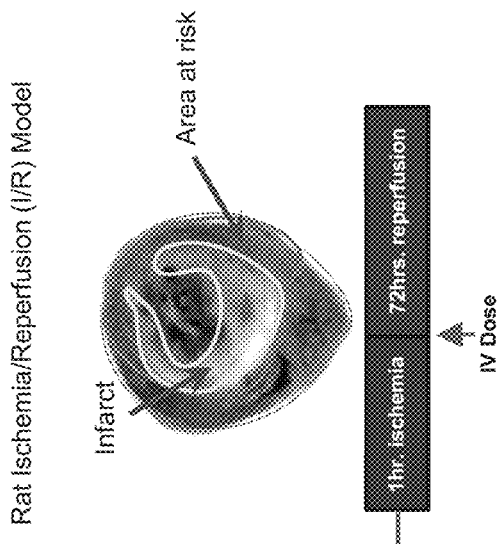

The study design is shown on FIG. 9A. After 72 hours of reperfusion, animals were sacrificed and tissue was harvested for infarct/area-at-risk (AAR) analysis as the primary endpoint.

Procedure:

Surgery

Acute myocardial infarction (AMI) was induced in rats by temporarily ligating the left coronary artery in a surgical ischemia/reperfusion (I/R) protocol as follows: Male CD IGS (200-300 g) rats were ordered to arrive at least 72 hours prior to study to allow for acclimation. All surgical instruments were autoclaved prior to each surgical session. Instrument tips were cleaned by immersion in alcohol, wiped clean with alcohol gauze pad and placed in a glass bead sterilizer between each animal. Animals were anesthetized with ketamine/xylazine cocktail (80-100 mg/kg and 5-10 mg/kg, respectively) and intubated with catheter under visual guidance and placed on a mechanical ventilator (70-85 BPM, tidal volume=10 ml/kg). The animal was placed in right lateral recumbency on a water-circulating heating pad to maintain body temperature during surgery. Electrodes were placed on the limbs of the animals to monitor changes in ECG associated with ischemia. Buprenorphine (0.1 mg/kg) was administered subcutaneously. Standard fluid replacement therapy with normal saline (5 ml SC) was provided.

The surgical site was shaved and cleaned with alcohol and betadine. Once an appropriate surgical plane of anesthesia was confirmed, a skin incision was made over the 4th to 5th intercostal space on the left side of the animal. The underlying muscles were bluntly dissected to reveal the intercostal muscles. Bupivacaine (0.25%, 0.2 ml) was administered subcutaneously along the incision site. Next, a rib spreader was carefully placed to allow for visualization of the heart. The pericardial sac was opened, the left auricle gently retracted and a suture (silk or Prolene, size 6-0 or 7-0) was placed around the left coronary artery (LCA), approximately 1 mm from its origin. The suture was ligated over a piece of sterile polyethylene tubing and maintained for 60 minutes. Proper occlusion was verified by blanching of the myocardium and ischemic changes on the ECG waveform (i.e. ST elevation). If ventricular fibrillation was noted, the heart was gently massaged to restore normal rhythm. After the ischemic period, the tubing was removed and the suture loosened to allow for reperfusion. Immediately after, the tail was warmed and test articles (vehicles, controls or SGFs) suspended in a total volume of 200 µl PBS containing 0.1% serum albumin as a carrier protein was administered via a single intravenous injection through the lateral tail vein. The chest wall was closed with 4-0 vicryl suture (one layer through the chest wall and muscle). The skin wound was closed with wound clips or a suitable skin suture, being careful to minimize dead space. Animals were taken off the ventilator when they began to awaken once anesthetics began to wear off. They were then transferred to a warm recovery unit until they exhibited normal ambulatory and exploratory behavior. Buprenorphine (0.1-0.2 mg/animal) was administered in supplementary soft food following surgery for up to 5 days post-surgery, refreshed as needed. Supplemental oxygen may be supplied to the recovery unit. The animal was then be placed in a clean cage and returned to the animal room. The animals were allowed free access to food and water until they were sacrificed.

Tissue Harvest

At the time of tissue harvest, animals were deeply anesthetized with 5% isoflurane and the thoracic cavity was opened. Animals were perfused with 10-20 mls saline and 1-2 ml of 2% Evans Blue was injected into the left ventricle. The heart was then dried with gauze and briefly frozen for 5 minutes −80° C. The heart was then sliced transversely into approximately 2 mm sections using a rat heart slicer. These sections were then be incubated in 1% TTC at 37° C. for 15-20 minutes and photographed on both sides with a digital camera for image analysis.

Image Analysis

The images were analyzed using computer assisted image analysis.

Results:

Results were analyzed using a One-way ANOVA with Tukey's multiple comparisons test performed in Prism. There was no significant difference in the size of injury produced by the surgical procedure between any of the groups as indicated by comparable size of the area at risk (AAR) with respect to the area of the left ventricle (LV). FIG. 9B and FIG. 9C show that both IGF-1 and SGF 606 were able to significantly reduce infarct size compared to vehicle control dosed animals, as expected. The results show that SGF 606 leads to more significant infarct/AAR reduction than wt IGF1, indicating that a targeted, potency-reduced SGF (e.g. SGF 606), is more efficacious than wt IGF1 at reducing infarct size.

It is understood that the examples and embodiments described herein are for illustrative purposes only and that various modifications of changes in light thereof are to be included within the spirit and purview of this application and scope of the appended claims. All publication, patents and patent applications cited herein are hereby incorporated by reference in their entirety for all purposes.

INCORPORATION BY REFERENCE

All publications, patents and sequence database entries mentioned herein are hereby incorporated by reference in their entirety as if each individual publication or patent was specifically and individually indicated to be incorporated by reference.

The invention claimed is:

1. A bi-specific protein comprising:
   a) a targeting domain having a binding specificity to a target molecule associated with the surface of a cell of a tissue, wherein the targeting domain comprises a variant of human Annexin A5 comprising one or more mutations, wherein the one or more mutations consist of a substitution at the position corresponding to C316 and optionally at one or more positions corresponding to R63, K70, K101, E138, D139, N160, and combinations thereof; and
   b) an activator domain having a binding specificity to a receptor associated with the surface of a cell of the tissue, wherein the activator domain comprises a variant of human insulin-like growth factor IGF-1 having an N-terminal 13-residue extension and a substitution at the position corresponding to E3, and optionally a mutation at one or more positions corresponding to a deletion at position R37, a deletion of amino acids at the position corresponding to K68, S69 and A70, a substitution at one or more position corresponding to Y24, Y31, Y60, and combinations thereof, wherein the variant of IGF-1 decreases activation of the IGF-1 receptor relative to the wild-type IGF-1,
   wherein the bi-specific protein exhibits an activation of the IGF-1 receptor at least twice stronger on cells containing the target molecule compared to cells that do not contain the target molecule as measured by phosphorylation of a receptor or a downstream effector molecule.

2. The bi-specific protein of claim 1, wherein the bi-specific protein promotes tissue regeneration, cell survival, cell differentiation, inhibits apoptosis, induces cell proliferation, promotes cell growth, promotes motility of stem cells, promotes differentiation of stem cells, prevents cell damage, and/or promotes angiogenesis.

3. The bi-specific protein of claim 1, wherein the tissue is a cardiac tissue, kidney tissue, bone, cartilage, skin, liver tissue, pancreatic tissue, blood cells, lung tissue, brain tissue, or nervous tissue.

4. The bi-specific protein of claim 1, wherein the bi-specific protein has a half-maximal effective concentration lower in the damaged tissue (EC50Damaged) than healthy tissue (EC50Healthy).

5. The bi-specific protein of claim 1, wherein the bi-specific protein further comprises a half-life modulator.

6. The bi-specific protein of claim 5, wherein the half-life modulator is a human serum albumin, a Fc fragment or a variant thereof.

7. The bi-specific protein of claim 5, wherein the half-life modulator has at least 80% identity with wild-type human serum albumin.

8. The bi-specific protein of claim 5, wherein the half-life modulator is human serum albumin or variant thereof.

9. The bi-specific protein of claim 5, wherein the half-life modulator has an amino acid sequence set forth in any one of SEQ ID NOs: 54-56, or 124.

10. The bi-specific protein of claim 1, wherein the bi-specific protein comprises an amino acid sequence of a non-internalizing variant of human Annexin A5 and wherein the bi-specific protein has a prolonged half-life as compared to a bi-specific protein comprising the amino acid sequence of wild-type human Annexin A5.

11. The bi-specific protein of claim 1, wherein the bi-specific protein comprises a targeting domain having an amino acid sequence set forth in SEQ ID NO: 4.

12. The bi-specific protein of claim 1, wherein the bi-specific protein comprises a targeting domain having an amino acid sequence set forth in SEQ ID NO: 122.

13. The bi-specific protein of claim 1, wherein the bi-specific protein comprises an activator domain having an amino acid sequence set forth in any one of SEQ ID NOs: 15-20.

14. A bi-specific protein comprising an amino acid sequence set forth in any one of SEQ ID NOs: 74, 75, 77, 79, 80-86.

15. A pharmaceutical composition comprising the bi-specific protein of claim 1 and a physiologically acceptable carrier.

16. A nucleic acid encoding the bi-specific protein of claim 1.

17. A method for of promoting tissue regeneration or tissue survival, the method comprising:
   (a) providing a bi-specific protein having (i) a targeting domain having a binding specificity to a target molecule associated with the surface of a cell of a tissue, wherein the targeting domain comprises a variant of human Annexin A5 comprising one or more mutations, wherein the one or more mutations consist of a substitution at the position corresponding to C316 and optionally at one or more positions corresponding to R63, K70, K101, E138, D139, N160, and combinations thereof; and (ii) an activator domain having a binding specificity to a receptor associated with the surface of a cell of the tissue, wherein the activator domain comprises a variant of human insulin-like growth factor IGF-1 having an N-terminal 13-residue extension and a substitution at the position corresponding to E3, and optionally a mutation at one or more positions corresponding to a deletion at position R37, a deletion of amino acids at the position corresponding to K68, S69 and A70, a substitution at one or more position corresponding to Y24, Y31, Y60, and combinations thereof, wherein the variant of IGF-1 decreases activation of the IGF-1 receptor relative to the wild-type IGF-1; and
   (b) administering to a patient in need thereof a therapeutically effective amount of the bi-specific protein whereby the Annexin A5 variant targets the bi-specific protein to a first cell of the tissue, wherein the cell expresses phosphatidylserine on the outer leaflet of the plasma membrane, and whereby upon exposure of the IGF-1 variant to an IGF-1 receptor at the surface of a second cell, the IGF-1 variant specifically activates the IGF-1 receptor so as to promote tissue regeneration or tissue survival.

18. A method for of protecting tissue from damage, the method comprising:
   (a) providing a bi-specific protein having (i) a targeting domain having a binding specificity to a target molecule associated with the surface of a cell of a tissue, wherein the targeting domain comprises a variant of human Annexin A5 comprising one or more mutations, wherein the one or more mutations consist of a substitution at the position corresponding to C316 and optionally at one or more positions corresponding to R63, K70, K101, E138, D139, N160, and combinations thereof; and (ii) an activator domain having a binding specificity to a receptor associated with the surface of a cell of the tissue, wherein the activator domain comprises a variant of human insulin-like growth factor IGF-1 having an N-terminal 13-residue extension and a substitution at the position corresponding to E3, and optionally a mutation at one or more positions corresponding to a deletion at position R37, a deletion of amino acids at the position corresponding to K68, S69 and A70, a substitution at one or more position corresponding to Y24, Y31, Y60, and combinations thereof, wherein the variant of IGF-1 decreases activation of the IGF-1 receptor relative to the wild-type IGF-1; and
   (b) administering to a patient in need thereof a therapeutically effective amount of the bi-specific protein whereby the Annexin A5 variant targets the bi-specific protein to a first cell of the tissue, wherein the cell expresses phosphatidylserine on the outer leaflet of the plasma membrane, and whereby upon exposure of the IGF-1 variant to an IGF-1 receptor at the surface of a second cell, the IGF-1 variant specifically activates the IGF-1 receptor so as to protect tissue from damage.

19. A method of inhibiting apoptosis, the method comprising:
   (a) providing a bi-specific protein having (i) a targeting domain having a binding specificity to a target molecule associated with the surface of a cell of a tissue, wherein the targeting domain comprises a variant of human Annexin A5 comprising one or more mutations, wherein the one or more mutations consist of a substitution at the position corresponding to C316 and optionally at one or more positions corresponding to R63, K70, K101, E138, D139, N160, and combinations thereof; and (ii) an activator domain having a binding specificity to a receptor associated with the surface of a cell of the tissue, wherein the activator domain comprises a variant of human insulin-like growth factor IGF-1 having an N-terminal 13-residue extension and a substitution at the position corresponding to E3, and optionally a mutation at one or more positions corresponding to a deletion at position R37, a deletion of amino acids at the position corresponding to K68, S69 and A70, a substitution at one or more position corresponding to Y24, Y31, Y60, and combinations thereof, wherein the variant of IGF-1 decreases activation of the IGF-1 receptor relative to the wild-type IGF-1; and
   (b) administering to a patient in need thereof a therapeutically effective amount of the bi-specific protein whereby the Annexin A5 variant targets the bi-specific protein to a first cell of the tissue, wherein the cell expresses phosphatidylserine on the outer leaflet of the plasma membrane, and whereby upon exposure of the IGF-1 variant to an IGF-1 receptor at the surface of a second cell, the IGF-1 variant specifically activates the IGF-1 receptor so as inhibit apoptosis.

\* \* \* \* \*

SEQUENCE LISTING

```
<160> NUMBER OF SEQ ID NOS: 138

<210> SEQ ID NO 1
<211> LENGTH: 319
<212> TYPE: PRT
<213> ORGANISM: Homo sapiens

<400> SEQUENCE: 1

Ala Gln Val Leu Arg Gly Thr Val Thr Asp Phe Pro Gly Phe Asp Glu
1               5                   10                  15

Arg Ala Asp Ala Glu Thr Leu Arg Lys Ala Met Lys Gly Leu Gly Thr
            20                  25                  30

Asp Glu Glu Ser Ile Leu Thr Leu Leu Thr Ser Arg Ser Asn Ala Gln
        35                  40                  45

Arg Gln Glu Ile Ser Ala Ala Phe Lys Thr Leu Phe Gly Arg Asp Leu
    50                  55                  60

Leu Asp Asp Leu Lys Ser Glu Leu Thr Gly Lys Phe Glu Lys Leu Ile
65                  70                  75                  80

Val Ala Leu Met Lys Pro Ser Arg Leu Tyr Asp Ala Tyr Glu Leu Lys
                85                  90                  95

His Ala Leu Lys Gly Ala Gly Thr Asn Glu Lys Val Leu Thr Glu Ile
            100                 105                 110

Ile Ala Ser Arg Thr Pro Glu Glu Leu Arg Ala Ile Lys Gln Val Tyr
        115                 120                 125

Glu Glu Glu Tyr Gly Ser Ser Leu Glu Asp Asp Val Val Gly Asp Thr
    130                 135                 140

Ser Gly Tyr Tyr Gln Arg Met Leu Val Val Leu Leu Gln Ala Asn Arg
145                 150                 155                 160

Asp Pro Asp Ala Gly Ile Asp Glu Ala Gln Val Glu Gln Asp Ala Gln
                165                 170                 175

Ala Leu Phe Gln Ala Gly Glu Leu Lys Trp Gly Thr Asp Glu Glu Lys
            180                 185                 190

Phe Ile Thr Ile Phe Gly Thr Arg Ser Val Ser His Leu Arg Lys Val
        195                 200                 205

Phe Asp Lys Tyr Met Thr Ile Ser Gly Phe Gln Ile Glu Glu Thr Ile
    210                 215                 220

Asp Arg Glu Thr Ser Gly Asn Leu Glu Gln Leu Leu Leu Ala Val Val
225                 230                 235                 240

Lys Ser Ile Arg Ser Ile Pro Ala Tyr Leu Ala Glu Thr Leu Tyr Tyr
                245                 250                 255

Ala Met Lys Gly Ala Gly Thr Asp Asp His Thr Leu Ile Arg Val Met
            260                 265                 270

Val Ser Arg Ser Glu Ile Asp Leu Phe Asn Ile Arg Lys Glu Phe Arg
        275                 280                 285

Lys Asn Phe Ala Thr Ser Leu Tyr Ser Met Ile Lys Gly Asp Thr Ser
    290                 295                 300

Gly Asp Tyr Lys Lys Ala Leu Leu Leu Leu Cys Gly Glu Asp Asp
305                 310                 315
```

```
<210> SEQ ID NO 2
<211> LENGTH: 319
<212> TYPE: PRT
<213> ORGANISM: Artificial Sequence
<220> FEATURE:
<223> OTHER INFORMATION: Synthetic construct

<400> SEQUENCE: 2

Ala Gln Val Leu Arg Gly Thr Val Thr Asp Phe Pro Gly Phe Asp Glu
1               5                   10                  15

Arg Ala Asp Ala Glu Thr Leu Arg Lys Ala Met Lys Gly Leu Gly Thr
            20                  25                  30

Asp Glu Glu Ser Ile Leu Thr Leu Leu Thr Ser Arg Ser Asn Ala Gln
        35                  40                  45

Arg Gln Glu Ile Ser Ala Ala Phe Lys Thr Leu Phe Gly Arg Asp Leu
    50                  55                  60

Leu Asp Asp Leu Lys Ser Glu Leu Thr Gly Lys Phe Glu Lys Leu Ile
65                  70                  75                  80

Val Ala Leu Met Lys Pro Ser Arg Leu Tyr Asp Ala Tyr Glu Leu Lys
                85                  90                  95

His Ala Leu Lys Gly Ala Gly Thr Asn Glu Lys Val Leu Thr Glu Ile
            100                 105                 110

Ile Ala Ser Arg Thr Pro Glu Glu Leu Arg Ala Ile Lys Gln Val Tyr
        115                 120                 125

Glu Glu Glu Tyr Gly Ser Ser Leu Glu Asp Asp Val Val Gly Asp Thr
    130                 135                 140

Ser Gly Tyr Tyr Gln Arg Met Leu Val Val Leu Leu Gln Ala Asn Arg
145                 150                 155                 160

Asp Pro Asp Ala Gly Ile Asp Glu Ala Gln Val Glu Gln Asp Ala Gln
                165                 170                 175

Ala Leu Phe Gln Ala Gly Glu Leu Lys Trp Gly Thr Asp Glu Glu Lys
            180                 185                 190

Phe Ile Thr Ile Phe Gly Thr Arg Ser Val Ser His Leu Arg Lys Val
        195                 200                 205

Phe Asp Lys Tyr Met Thr Ile Ser Gly Phe Gln Ile Glu Glu Thr Ile
    210                 215                 220

Asp Arg Glu Thr Ser Gly Asn Leu Glu Gln Leu Leu Leu Ala Val Val
225                 230                 235                 240

Lys Ser Ile Arg Ser Ile Pro Ala Tyr Leu Ala Glu Thr Leu Tyr Tyr
                245                 250                 255

Ala Met Lys Gly Ala Gly Thr Asp Asp His Thr Leu Ile Arg Val Met
            260                 265                 270

Val Ser Arg Ser Glu Ile Asp Leu Phe Asn Ile Arg Lys Glu Phe Arg
        275                 280                 285

Lys Asn Phe Ala Thr Ser Leu Tyr Ser Met Ile Lys Gly Asp Thr Ser
    290                 295                 300

Gly Asp Tyr Lys Lys Ala Leu Leu Leu Leu Ser Gly Glu Asp Asp
305                 310                 315

<210> SEQ ID NO 3
<211> LENGTH: 333
<212> TYPE: PRT
<213> ORGANISM: Artificial Sequence
<220> FEATURE:
<223> OTHER INFORMATION: Synthetic construct
```

<400> SEQUENCE: 3

```
Ala Gln Val Leu Arg Gly Thr Val Thr Asp Phe Pro Gly Phe Asp Glu
1               5                   10                  15

Arg Ala Asp Ala Glu Thr Leu Arg Lys Ala Met Lys Gly Leu Gly Thr
            20                  25                  30

Asp Glu Glu Ser Ile Leu Thr Leu Leu Thr Ser Arg Ser Asn Ala Gln
        35                  40                  45

Arg Gln Glu Ile Ser Ala Ala Phe Lys Thr Leu Phe Gly Arg Asp Leu
    50                  55                  60

Leu Asp Asp Leu Lys Ser Glu Leu Thr Gly Lys Phe Glu Lys Leu Ile
65                  70                  75                  80

Val Ala Leu Met Lys Pro Ser Arg Leu Tyr Asp Ala Tyr Glu Leu Lys
                85                  90                  95

His Ala Leu Lys Gly Ala Gly Thr Asn Glu Lys Val Leu Thr Glu Ile
            100                 105                 110

Ile Ala Ser Arg Thr Pro Glu Glu Leu Arg Ala Ile Lys Gln Val Tyr
        115                 120                 125

Glu Glu Glu Tyr Gly Ser Ser Leu Glu Asp Asp Val Val Gly Asp Thr
    130                 135                 140

Ser Gly Tyr Tyr Gln Arg Met Leu Val Val Leu Leu Gln Ala Asn Arg
145                 150                 155                 160

Asp Pro Asp Ala Gly Ile Asp Glu Ala Gln Val Glu Gln Asp Ala Gln
                165                 170                 175

Ala Leu Phe Gln Ala Gly Glu Leu Lys Trp Gly Thr Asp Glu Glu Lys
            180                 185                 190

Phe Ile Thr Ile Phe Gly Thr Arg Ser Val Ser His Leu Arg Lys Val
        195                 200                 205

Phe Asp Lys Tyr Met Thr Ile Ser Gly Phe Gln Ile Glu Glu Thr Ile
    210                 215                 220

Asp Arg Glu Thr Ser Gly Asn Leu Glu Gln Leu Leu Leu Ala Val Val
225                 230                 235                 240

Lys Ser Ile Arg Ser Ile Pro Ala Tyr Leu Ala Glu Thr Leu Tyr Tyr
                245                 250                 255

Ala Met Lys Gly Ala Gly Thr Asp Asp His Thr Leu Ile Arg Val Met
            260                 265                 270

Val Ser Arg Ser Glu Ile Asp Leu Phe Asn Ile Arg Lys Glu Phe Arg
        275                 280                 285

Lys Asn Phe Ala Thr Ser Leu Tyr Ser Met Ile Lys Gly Asp Thr Ser
    290                 295                 300

Gly Asp Tyr Lys Lys Ala Leu Leu Leu Leu Ser Gly Glu Asp Asp Gly
305                 310                 315                 320

Ser Gly Gly Ser Gly Ser Gly His His His His His
                325                 330
```

<210> SEQ ID NO 4
<211> LENGTH: 319
<212> TYPE: PRT
<213> ORGANISM: Artificial Sequence
<220> FEATURE:
<223> OTHER INFORMATION: Synthetic construct

<400> SEQUENCE: 4

| | | | | | | | | | | | | | | |
|---|---|---|---|---|---|---|---|---|---|---|---|---|---|---|
|Ala|Gln|Val|Leu|Arg|Gly|Thr|Val|Thr|Asp|Phe|Pro|Gly|Phe|Asp|Glu|
|1| | | |5| | | | |10| | | | |15|
|Arg|Ala|Asp|Ala|Glu|Thr|Leu|Arg|Lys|Ala|Met|Lys|Gly|Leu|Gly|Thr|
| | | |20| | | | |25| | | | |30| | |
|Asp|Glu|Glu|Ser|Ile|Leu|Thr|Leu|Leu|Thr|Ser|Arg|Ser|Asn|Ala|Gln|
| | | |35| | | | |40| | | | |45| | |
|Arg|Gln|Glu|Ile|Ser|Ala|Ala|Phe|Lys|Thr|Leu|Phe|Gly|Ala|Asp|Leu|
| |50| | | | |55| | | | |60| | | | |
|Leu|Asp|Asp|Leu|Ala|Ser|Glu|Leu|Thr|Gly|Lys|Phe|Glu|Lys|Leu|Ile|
|65| | | | |70| | | | |75| | | | |80|
|Val|Ala|Leu|Met|Lys|Pro|Ser|Arg|Leu|Tyr|Asp|Ala|Tyr|Glu|Leu|Lys|
| | | | |85| | | | |90| | | | |95| |
|His|Ala|Leu|Ala|Gly|Ala|Gly|Thr|Asn|Glu|Lys|Val|Leu|Thr|Glu|Ile|
| | | |100| | | | |105| | | | |110| | |
|Ile|Ala|Ser|Arg|Thr|Pro|Glu|Glu|Leu|Arg|Ala|Ile|Lys|Gln|Val|Tyr|
| | | |115| | | | |120| | | | |125| | |
|Glu|Glu|Glu|Tyr|Gly|Ser|Ser|Leu|Ala|Gly|Asp|Val|Val|Gly|Asp|Thr|
| |130| | | | |135| | | | |140| | | | |
|Ser|Gly|Tyr|Tyr|Gln|Arg|Met|Leu|Val|Val|Leu|Leu|Gln|Ala|Ala|Arg|
|145| | | | |150| | | | |155| | | | |160|
|Asp|Pro|Asp|Ala|Gly|Ile|Asp|Glu|Ala|Gln|Val|Glu|Gln|Asp|Ala|Gln|
| | | | |165| | | | |170| | | | |175| |
|Ala|Leu|Phe|Gln|Ala|Gly|Glu|Leu|Lys|Trp|Gly|Thr|Asp|Glu|Glu|Lys|
| | | |180| | | | |185| | | | |190| | |
|Phe|Ile|Thr|Ile|Phe|Gly|Thr|Arg|Ser|Val|Ser|His|Leu|Arg|Lys|Val|
| | | |195| | | | |200| | | | |205| | |
|Phe|Asp|Lys|Tyr|Met|Thr|Ile|Ser|Gly|Phe|Gln|Ile|Glu|Glu|Thr|Ile|
| |210| | | | |215| | | | |220| | | | |
|Asp|Arg|Glu|Thr|Ser|Gly|Asn|Leu|Glu|Gln|Leu|Leu|Leu|Ala|Val|Val|
|225| | | | |230| | | | |235| | | | |240|
|Lys|Ser|Ile|Arg|Ser|Ile|Pro|Ala|Tyr|Leu|Ala|Glu|Thr|Leu|Tyr|Tyr|
| | | | |245| | | | |250| | | | |255| |
|Ala|Met|Lys|Gly|Ala|Gly|Thr|Asp|Asp|His|Thr|Leu|Ile|Arg|Val|Met|
| | | |260| | | | |265| | | | |270| | |
|Val|Ser|Arg|Ser|Glu|Ile|Asp|Leu|Phe|Asn|Ile|Arg|Lys|Glu|Phe|Arg|
| | |275| | | | |280| | | | |285| | | |
|Lys|Asn|Phe|Ala|Thr|Ser|Leu|Tyr|Ser|Met|Ile|Lys|Gly|Asp|Thr|Ser|
| |290| | | | |295| | | | |300| | | | |
|Gly|Asp|Tyr|Lys|Lys|Ala|Leu|Leu|Leu|Leu|Cys|Gly|Glu|Asp|Asp| |
|305| | | | |310| | | | |315| | | | | |

<210> SEQ ID NO 5
<211> LENGTH: 960
<212> TYPE: DNA
<213> ORGANISM: Homo sapiens

<400> SEQUENCE: 5

```
gctcaagtct tgcgtggtac ggtgacagac ttcccaggct tcgatgaaag agcggacgcg      60
gaaacacttc gaaaggcgat gaaagggctc ggtactgacg aagagtccat tttgaccctt     120
cttacgagca ggtcaaacgc tcagaggcaa gaaatctctg cagcctttaa gacactcttt     180
ggacgtgacc ttcttgatga cctcaaatct gagctgacgg gaaagtttga gaaactcatc     240
gtagctttga tgaagcccag ccgattgtat gatgcttacg aactgaaaca cgccctgaaa     300
```

```
ggagcgggaa cgaacgagaa agttttgact gagatcatcg catcgcggac cccggaagag    360
ctcagagcca tcaaacaagt ctacgaggag gagtacggat cgtcattgga agatgacgtg    420 gtggggata cgtcgggtta ctaccaacga atgcttgtcg tgcttttgca ggcaaatcgc     480
gacccggatg cggggatcga cgaggcccaa gtggagcaag atgcgcaagc actcttccag    540
gccggtgaac tcaaatgggg gaccgatgaa gagaagttta tcaccatctt tggcacgagg    600
agtgtaagtc atctgcgtaa agtattcgat aagtatatga caatctcagg gtttcagatt    660
gaggagacaa ttgacaggga aacctccggt aacttggagc agctcttgct tgccgtcgtc    720
aagtccattc gctcgatccc tgcgtatctg gctgaaacac tgtattacgc catgaaaggg    780
gcaggcactg atgaccacac cttgattaga gttatggtgt cgcgatcaga aattgacttg    840
ttcaatatcc ggaaagagtt ccggaagaat tcgcaacga gcctctatag catgatcaaa     900
ggggacactt cggagattta caagaaagcg ttgctccttc tttgcggaga ggatgactaa   960
```

<210> SEQ ID NO 6
<211> LENGTH: 963
<212> TYPE: DNA
<213> ORGANISM: Artificial Sequence
<220> FEATURE:
<223> OTHER INFORMATION: Synthetic construct

<400> SEQUENCE: 6

```
gctcaagtct tgcgtggtac ggtgacagac ttcccaggct tcgatgaaag agcggacgcg     60
gaaacacttc gaaaggcgat gaaagggctc ggtactgacg aagagtccat tttgacccctt   120 cttacgagca ggtcaaacgc tcagaggcaa gaaatctctg cagcctttaa gacactcttt    180
ggacgtgacc ttcttgatga cctcaaatct gagctgacgg gaaagtttga gaaactcatc    240
gtagctttga tgaagcccag ccgattgtat gatgcttacg aactgaaaca cgccctgaaa    300
ggagcgggaa cgaacgagaa agttttgact gagatcatcg catcgcggac cccggaagag    360
ctcagagcca tcaaacaagt ctacgaggag gagtacggat cgtcattgga agatgacgtg    420 gtggggata cgtcgggtta ctaccaacga atgcttgtcg tgcttttgca ggcaaatcgc     480
gacccggatg cggggatcga cgaggcccaa gtggagcaag atgcgcaagc actcttccag    540
gccggtgaac tcaaatgggg gaccgatgaa gagaagttta tcaccatctt tggcacgagg    600
agtgtaagtc atctgcgtaa agtattcgat aagtatatga caatctcagg gtttcagatt    660
gaggagacaa ttgacaggga aacctccggt aacttggagc agctcttgct tgccgtcgtc    720
aagtccattc gctcgatccc tgcgtatctg gctgaaacac tgtattacgc catgaaaggg    780
gcaggcactg atgaccacac cttgattaga gttatggtgt cgcgatcaga aattgacttg    840
ttcaatatcc ggaaagagtt ccggaagaat tcgcaacga gcctctatag catgatcaaa     900
ggggacactt cggagattta caagaaagcg ttgctccttc tttcaggaga ggatgactaa   960
tga                                                                  963
```

<210> SEQ ID NO 7
<211> LENGTH: 1005
<212> TYPE: DNA
<213> ORGANISM: Artificial Sequence
<220> FEATURE:
<223> OTHER INFORMATION: Synthetic construct

<400> SEQUENCE: 7

```
gctcaagtct tgcgtggtac ggtgacagac ttcccaggct tcgatgaaag agcggacgcg     60
gaaacacttc gaaaggcgat gaaagggctc ggtactgacg aagagtccat tttgacccctt   120
```

| | |
|---|---|
| cttacgagca ggtcaaacgc tcagaggcaa gaaatctctg cagcctttaa gacactcttt | 180 |
| ggacgtgacc ttcttgatga cctcaaatct gagctgacgg gaaagtttga gaaactcatc | 240 |
| gtagctttga tgaagcccag ccgattgtat gatgcttacg aactgaaaca cgccctgaaa | 300 |
| ggagcgggaa cgaacgagaa agttttgact gagatcatcg catcgcggac cccggaagag | 360 |
| ctcagagcca tcaaacaagt ctacgaggag gagtacggat cgtcattgga agatgacgtg | 420 |
| gtgggggata cgtcgggtta ctaccaacga atgcttgtcg tgcttttgca ggcaaatcgc | 480 |
| gacccggatg cggggatcga cgaggcccaa gtggagcaag atgcgcaagc actcttccag | 540 |
| gccggtgaac tcaaatgggg gaccgatgaa gagaagttta tcaccatctt tggcacgagg | 600 |
| agtgtaagtc atctgcgtaa agtattcgat aagtatatga caatctcagg gtttcagatt | 660 |
| gaggagacaa ttgacaggga aacctccggt aacttggagc agctcttgct tgccgtcgtc | 720 |
| aagtccattc gctcgatccc tgcgtatctg gctgaaacac tgtattacgc catgaaaggg | 780 |
| gcaggcactg atgaccacac cttgattaga gttatggtgt cgcgatcaga aattgacttg | 840 |
| ttcaatatcc ggaaagagtt ccggaagaat ttcgcaacga gcctctatag catgatcaaa | 900 |
| ggggacactt cgggagatta caagaaagcg ttgctccttc tttcaggaga ggatgacggc | 960 |
| agtggtggct caggtagcgg ccaccatcac catcaccact aatga | 1005 |

<210> SEQ ID NO 8
<211> LENGTH: 963
<212> TYPE: DNA
<213> ORGANISM: Artificial Sequence
<220> FEATURE:
<223> OTHER INFORMATION: Synthetic construct

<400> SEQUENCE: 8

| | |
|---|---|
| gctcaagtct tgcgtggtac ggtgacagac ttcccaggct tcgatgaaag agcggacgcg | 60 |
| gaaacacttc gaaaggcgat gaaagggctc ggtactgacg aagagtccat tttgacccct | 120 |
| cttacgagca ggtcaaacgc tcagaggcaa gaaatctctg cagcctttaa gacactcttt | 180 |
| ggagctgacc ttcttgatga cctcgcatct gagctgacgg gaaagtttga gaaactcatc | 240 |
| gtagctttga tgaagcccag ccgattgtat gatgcttacg aactgaaaca cgccctggct | 300 |
| ggagcgggaa cgaacgagaa agttttgact gagatcatcg catcgcggac cccggaagag | 360 |
| ctcagagcca tcaaacaagt ctacgaggag gagtacggat cgtcattggc aggagacgtg | 420 |
| gtgggggata cgtcgggtta ctaccaacga atgcttgtcg tgcttttgca ggcagctcgc | 480 |
| gacccggatg cggggatcga cgaggcccaa gtggagcaag atgcgcaagc actcttccag | 540 |
| gccggtgaac tcaaatgggg gaccgatgaa gagaagttta tcaccatctt tggcacgagg | 600 |
| agtgtaagtc atctgcgtaa agtattcgat aagtatatga caatctcagg gtttcagatt | 660 |
| gaggagacaa ttgacaggga aacctccggt aacttggagc agctcttgct tgccgtcgtc | 720 |
| aagtccattc gctcgatccc tgcgtatctg gctgaaacac tgtattacgc catgaaaggg | 780 |
| gcaggcactg atgaccacac cttgattaga gttatggtgt cgcgatcaga aattgacttg | 840 |
| ttcaatatcc ggaaagagtt ccggaagaat ttcgcaacga gcctctatag catgatcaaa | 900 |
| ggggacactt cgggagatta caagaaagcg ttgctccttc tttgcggaga ggatgactaa | 960 |
| tga | 963 |

<210> SEQ ID NO 9
<211> LENGTH: 70
<212> TYPE: PRT
<213> ORGANISM: Homo sapiens

```
<400> SEQUENCE: 9

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
    50                  55                  60

Lys Pro Ala Lys Ser Ala
65              70

<210> SEQ ID NO 10
<211> LENGTH: 67
<212> TYPE: PRT
<213> ORGANISM: Artificial Sequence
<220> FEATURE:
<223> OTHER INFORMATION: Synthetic construct

<400> SEQUENCE: 10

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
                20                  25                  30

Arg Arg Ala Pro Gln Thr Gly Ile Val Asp Glu Cys Cys Phe Arg Ser
            35                  40                  45

Cys Asp Leu Arg Arg Leu Glu Met Tyr Cys Ala Pro Leu Lys Pro Ala
    50                  55                  60

Lys Ser Ala
65

<210> SEQ ID NO 11
<211> LENGTH: 83
<212> TYPE: PRT
<213> ORGANISM: Artificial Sequence
<220> FEATURE:
<223> OTHER INFORMATION: Synthetic construct

<400> SEQUENCE: 11

Met Phe Pro Ala Met Pro Leu Ser Ser Leu Phe Val Asn Gly Pro Glu
1               5                   10                  15

Thr Leu Cys Gly Ala Glu Leu Val Asp Ala Leu Gln Phe Val Cys Gly
                20                  25                  30

Asp Arg Gly Phe Tyr Phe Asn Lys Pro Thr Gly Tyr Gly Ser Ser Ser
            35                  40                  45

Arg Arg Ala Pro Gln Thr Gly Ile Val Asp Glu Cys Cys Phe Arg Ser
    50                  55                  60

Cys Asp Leu Arg Arg Leu Glu Met Tyr Cys Ala Pro Leu Lys Pro Ala
65                  70                  75                  80

Lys Ser Ala

<210> SEQ ID NO 12
<211> LENGTH: 70
<212> TYPE: PRT
<213> ORGANISM: Artificial Sequence
<220> FEATURE:
<223> OTHER INFORMATION: Synthetic construct
```

<400> SEQUENCE: 12

Gly Pro Arg Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
50                  55                  60

Lys Pro Ala Lys Ser Ala
65              70

<210> SEQ ID NO 13
<211> LENGTH: 69
<212> TYPE: PRT
<213> ORGANISM: Artificial Sequence
<220> FEATURE:
<223> OTHER INFORMATION: Synthetic construct

<400> SEQUENCE: 13

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Ala Pro Gln Thr Gly Ile Val Asp Glu Cys Cys Phe
            35                  40                  45

Arg Ser Cys Asp Leu Arg Arg Leu Glu Met Tyr Cys Ala Pro Leu Lys
    50                  55                  60

Pro Ala Lys Ser Ala
65

<210> SEQ ID NO 14
<211> LENGTH: 66
<212> TYPE: PRT
<213> ORGANISM: Artificial Sequence
<220> FEATURE:
<223> OTHER INFORMATION: Synthetic construct

<400> SEQUENCE: 14

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Ala Pro Gln Thr Gly Ile Val Asp Glu Cys Cys Phe
            35                  40                  45

Arg Ser Cys Asp Leu Arg Arg Leu Glu Met Tyr Cys Ala Pro Leu Lys
    50                  55                  60

Pro Ala
65

<210> SEQ ID NO 15
<211> LENGTH: 83
<212> TYPE: PRT
<213> ORGANISM: Artificial Sequence
<220> FEATURE:
<223> OTHER INFORMATION: Synthetic construct

<400> SEQUENCE: 15

```
Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Tyr Phe Asn Lys Pro Thr Gly Tyr Gly Ser Ser Ser
        35                  40                  45

Arg Arg Ala Pro Gln Thr Gly Ile Val Asp Glu Cys Cys Phe Arg Ser
    50                  55                  60

Cys Asp Leu Arg Arg Leu Glu Met Tyr Cys Ala Pro Leu Lys Pro Ala
65                  70                  75                  80

Lys Ser Ala
```

<210> SEQ ID NO 16
<211> LENGTH: 79
<212> TYPE: PRT
<213> ORGANISM: Artificial Sequence
<220> FEATURE:
<223> OTHER INFORMATION: Synthetic construct

<400> SEQUENCE: 16

```
Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Tyr Phe Asn Lys Pro Thr Gly Tyr Gly Ser Ser Ser
        35                  40                  45

Arg Ala Pro Gln Thr Gly Ile Val Asp Glu Cys Cys Phe Arg Ser Cys
    50                  55                  60

Asp Leu Arg Arg Leu Glu Met Tyr Cys Ala Pro Leu Lys Pro Ala
65                  70                  75
```

<210> SEQ ID NO 17
<211> LENGTH: 83
<212> TYPE: PRT
<213> ORGANISM: Artificial Sequence
<220> FEATURE:
<223> OTHER INFORMATION: Synthetic construct

<400> SEQUENCE: 17

```
Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Leu Phe Asn Lys Pro Thr Gly Tyr Gly Ser Ser Ser
        35                  40                  45

Arg Arg Ala Pro Gln Thr Gly Ile Val Asp Glu Cys Cys Phe Arg Ser
    50                  55                  60

Cys Asp Leu Arg Arg Leu Glu Met Tyr Cys Ala Pro Leu Lys Pro Ala
65                  70                  75                  80

Lys Ser Ala
```

<210> SEQ ID NO 18
<211> LENGTH: 83
<212> TYPE: PRT
<213> ORGANISM: Artificial Sequence
<220> FEATURE:
<223> OTHER INFORMATION: Synthetic construct

<400> SEQUENCE: 18

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Leu Phe Asn Lys Pro Thr Gly Ala Gly Ser Ser Ser
        35                  40                  45

Arg Arg Ala Pro Gln Thr Gly Ile Val Asp Glu Cys Cys Phe Arg Ser
50                  55                  60

Cys Asp Leu Arg Arg Leu Glu Met Tyr Cys Ala Pro Leu Lys Pro Ala
65                  70                  75                  80

Lys Ser Ala

<210> SEQ ID NO 19
<211> LENGTH: 83
<212> TYPE: PRT
<213> ORGANISM: Artificial Sequence
<220> FEATURE:
<223> OTHER INFORMATION: Synthetic construct

<400> SEQUENCE: 19

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Tyr Phe Asn Lys Pro Thr Gly Ala Gly Ser Ser Ser
        35                  40                  45

Arg Arg Ala Pro Gln Thr Gly Ile Val Asp Glu Cys Cys Phe Arg Ser
50                  55                  60

Cys Asp Leu Arg Arg Leu Glu Met Tyr Cys Ala Pro Leu Lys Pro Ala
65                  70                  75                  80

Lys Ser Ala

<210> SEQ ID NO 20
<211> LENGTH: 83
<212> TYPE: PRT
<213> ORGANISM: Artificial Sequence
<220> FEATURE:
<223> OTHER INFORMATION: Synthetic construct

<400> SEQUENCE: 20

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Tyr Phe Asn Lys Pro Thr Gly Tyr Gly Ser Ser Ser
        35                  40                  45

Arg Arg Ala Pro Gln Thr Gly Ile Val Asp Glu Cys Cys Phe Arg Ser
50                  55                  60

Cys Asp Leu Arg Arg Leu Glu Met Leu Cys Ala Pro Leu Lys Pro Ala
65                  70                  75                  80

Lys Ser Ala

<210> SEQ ID NO 21
<211> LENGTH: 66
<212> TYPE: PRT
<213> ORGANISM: Artificial Sequence

```
<220> FEATURE:
<223> OTHER INFORMATION: Synthetic construct

<400> SEQUENCE: 21

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Ala Pro Gln Thr Gly Ile Val Asp Glu Cys Cys Phe
            35                  40                  45

Arg Ser Cys Asp Leu Arg Arg Leu Glu Met Tyr Cys Ala Pro Leu Lys
    50                  55                  60

Pro Ala
65

<210> SEQ ID NO 22
<211> LENGTH: 70
<212> TYPE: PRT
<213> ORGANISM: Artificial Sequence
<220> FEATURE:
<223> OTHER INFORMATION: Synthetic construct

<400> SEQUENCE: 22

Gly Pro Glu Thr Leu Cys Gly Ala Glu Leu Val Asp Ala Leu Gln Phe
1               5                   10                  15

Val Cys Gly Asp Arg Gly Phe Leu Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
    50                  55                  60

Lys Pro Ala Lys Ser Ala
65                  70

<210> SEQ ID NO 23
<211> LENGTH: 70
<212> TYPE: PRT
<213> ORGANISM: Artificial Sequence
<220> FEATURE:
<223> OTHER INFORMATION: Synthetic construct

<400> SEQUENCE: 23

Gly Pro Glu Thr Leu Cys Gly Ala Glu Leu Val Asp Ala Leu Gln Phe
1               5                   10                  15

Val Cys Gly Asp Arg Gly Phe Leu Phe Asn Lys Pro Thr Gly Ala Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
    50                  55                  60

Lys Pro Ala Lys Ser Ala
65                  70

<210> SEQ ID NO 24
<211> LENGTH: 70
<212> TYPE: PRT
<213> ORGANISM: Artificial Sequence
<220> FEATURE:
<223> OTHER INFORMATION: Synthetic construct
```

```
<400> SEQUENCE: 24

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Ala Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70

<210> SEQ ID NO 25
<211> LENGTH: 70
<212> TYPE: PRT
<213> ORGANISM: Artificial Sequence
<220> FEATURE:
<223> OTHER INFORMATION: Synthetic construct

<400> SEQUENCE: 25

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Leu Cys Ala Pro Leu
    50                  55                  60

Lys Pro Ala Lys Ser Ala
65                  70

<210> SEQ ID NO 26
<211> LENGTH: 63
<212> TYPE: PRT
<213> ORGANISM: Artificial Sequence
<220> FEATURE:
<223> OTHER INFORMATION: Synthetic construct

<400> SEQUENCE: 26

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Ala Pro Gln Thr Gly Ile Val Asp Glu Cys Cys Phe Arg Ser Cys
        35                  40                  45

Asp Leu Arg Arg Leu Glu Met Tyr Cys Ala Pro Leu Lys Pro Ala
    50                  55                  60

<210> SEQ ID NO 27
<211> LENGTH: 67
<212> TYPE: PRT
<213> ORGANISM: Artificial Sequence
<220> FEATURE:
<223> OTHER INFORMATION: Synthetic construct

<400> SEQUENCE: 27

Thr Leu Cys Gly Ala Glu Leu Val Asp Ala Leu Gln Phe Val Cys Gly
1               5                   10                  15

Asp Arg Gly Phe Leu Phe Asn Lys Pro Thr Gly Tyr Gly Ser Ser Ser
            20                  25                  30
```

Arg Arg Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Lys Ser Ala
 65

<210> SEQ ID NO 28
<211> LENGTH: 67
<212> TYPE: PRT
<213> ORGANISM: Artificial Sequence
<220> FEATURE:
<223> OTHER INFORMATION: Synthetic construct

<400> SEQUENCE: 28

Thr Leu Cys Gly Ala Glu Leu Val Asp Ala Leu Gln Phe Val Cys Gly
 1               5                  10                  15

Asp Arg Gly Phe Leu Phe Asn Lys Pro Thr Gly Ala Gly Ser Ser Ser
                20                  25                  30

Arg Arg Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Lys Ser Ala
 65

<210> SEQ ID NO 29
<211> LENGTH: 67
<212> TYPE: PRT
<213> ORGANISM: Artificial Sequence
<220> FEATURE:
<223> OTHER INFORMATION: Synthetic construct

<400> SEQUENCE: 29

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Ala Gly Ser Ser Ser
                20                  25                  30

Arg Arg Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Lys Ser Ala
 65

<210> SEQ ID NO 30
<211> LENGTH: 67
<212> TYPE: PRT
<213> ORGANISM: Artificial Sequence
<220> FEATURE:
<223> OTHER INFORMATION: Synthetic construct

<400> SEQUENCE: 30

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
                20                  25                  30

Arg Arg Ala Pro Gln Thr Gly Ile Val Asp Glu Cys Cys Phe Arg Ser
        35                  40                  45

Cys Asp Leu Arg Arg Leu Glu Met Leu Cys Ala Pro Leu Lys Pro Ala
    50                  55                  60

Lys Ser Ala
65

<210> SEQ ID NO 31
<211> LENGTH: 210
<212> TYPE: DNA
<213> ORGANISM: Homo sapiens

<400> SEQUENCE: 31
ggcccagaaa cactttgtgg agccgaactg gtggatgctc tccaattcgt ttgcggcgac      60
cgcggattct actttaacaa gcccaccggt tacgggtctt caagccggag ggccccgcag     120
actggcatcg tcgacgagtg ctgttttaga agctgcgatc tgcgacggtt ggagatgtat     180
tgtgcacctc tgaagcccgc gaaaagtgct                                      210

<210> SEQ ID NO 32
<211> LENGTH: 201
<212> TYPE: DNA
<213> ORGANISM: Artificial Sequence
<220> FEATURE:
<223> OTHER INFORMATION: Synthetic construct

<400> SEQUENCE: 32
acactttgtg gagccgaact ggtggatgct ctccaattcg tttgcggcga ccgcggattc      60
tactttaaca agcccaccgg ttacgggtct tcaagccgga gggccccgca gactggcatc     120
gtcgacgagt gctgttttag aagctgcgat ctgcgacggt tggagatgta ttgtgcacct     180
ctgaagcccg cgaaaagtgc t                                               201

<210> SEQ ID NO 33
<211> LENGTH: 249
<212> TYPE: DNA
<213> ORGANISM: Artificial Sequence
<220> FEATURE:
<223> OTHER INFORMATION: Synthetic construct

<400> SEQUENCE: 33
atgttcccag ccatgccctt gtccagcctg tttgttaacg cccagaaaac actttgtgga      60
gccgaactgg tggatgctct ccaattcgtt gcggcgacc gcggattcta ctttaacaag     120
cccaccggtt acgggtcttc aagccggagg gccccgcaga ctggcatcgt cgacgagtgc     180
tgttttagaa gctgcgatct gcgacggttg agatgtatt gtgcacctct gaagcccgcg     240
aaaagtgct                                                             249

<210> SEQ ID NO 34
<211> LENGTH: 210
<212> TYPE: DNA
<213> ORGANISM: Artificial Sequence
<220> FEATURE:
<223> OTHER INFORMATION: Synthetic construct

<400> SEQUENCE: 34
ggcccaagaa cactttgtgg agccgaactg gtggatgctc tccaattcgt ttgcggcgac      60
cgcggattct actttaacaa gcccaccggt tacgggtctt caagccggag ggccccgcag     120
actggcatcg tcgacgagtg ctgttttaga agctgcgatc tgcgacggtt ggagatgtat     180
tgtgcacctc tgaagcccgc gaaaagtgct                                      210

<210> SEQ ID NO 35
<211> LENGTH: 207
<212> TYPE: DNA
<213> ORGANISM: Artificial Sequence
<220> FEATURE:
<223> OTHER INFORMATION: Synthetic construct

<400> SEQUENCE: 35

```
ggcccagaaa cactttgtgg agccgaactg gtggatgctc tccaattcgt ttgcggcgac    60
cgcggattct actttaacaa gcccaccggt tacgggtctt caagccgggc cccgcagact   120
ggcatcgtcg acgagtgctg ttttagaagc tgcgatctgc gacggttgga gatgtattgt   180
gcacctctga agcccgcgaa aagtgct                                       207
```

<210> SEQ ID NO 36
<211> LENGTH: 201
<212> TYPE: DNA
<213> ORGANISM: Artificial Sequence
<220> FEATURE:
<223> OTHER INFORMATION: Synthetic construct

<400> SEQUENCE: 36

```
ggcccagaaa cactttgtgg agccgaactg gtggatgctc tccaattcgt ttgcggcgac    60
cgcggattct actttaacaa gcccaccggt tacgggtctt caagccggag ggccccgcag   120
actggcatcg tcgacgagtg ctgttttaga agctgcgatc tgcgacggtt ggagatgtat   180
tgtgcacctc tgaagcccgc g                                             201
```

<210> SEQ ID NO 37
<211> LENGTH: 249
<212> TYPE: DNA
<213> ORGANISM: Artificial Sequence
<220> FEATURE:
<223> OTHER INFORMATION: Synthetic construct

<400> SEQUENCE: 37

```
atgttcccag ccatgccctt gtccagcctg tttgttaacg gcccaagaac actttgtgga    60
gccgaactgg tggatgctct ccaattcgtt tgcggcgacc gcggattcta ctttaacaag   120
cccaccggtt acgggtcttc aagccggagg gccccgcaga ctggcatcgt cgacgagtgc   180
tgttttagaa gctgcgatct gcgacggttg gagatgtatt gtgcacctct gaagcccgcg   240
aaaagtgct                                                           249
```

<210> SEQ ID NO 38
<211> LENGTH: 237
<212> TYPE: DNA
<213> ORGANISM: Artificial Sequence
<220> FEATURE:
<223> OTHER INFORMATION: Synthetic construct

<400> SEQUENCE: 38

```
atgttcccag ccatgccctt gtccagcctg tttgttaacg gcccaagaac actttgtgga    60
gccgaactgg tggatgctct ccaattcgtt tgcggcgacc gcggattcta ctttaacaag   120
cccaccggtt acgggtcttc aagccgggcc ccgcagactg catcgtcga cgagtgctgt    180
tttagaagct gcgatctgcg acggttggag atgtattgtg cacctctgaa gcccgcg     237
```

<210> SEQ ID NO 39
<211> LENGTH: 249
<212> TYPE: DNA
<213> ORGANISM: Artificial Sequence
<220> FEATURE:
<223> OTHER INFORMATION: Syntehtic construct

<400> SEQUENCE: 39

```
atgttcccag ccatgccctt gtccagcctg tttgttaacg gcccaagaac actttgtgga      60
gccgaactgg tggatgctct ccaattcgtt tgcggcgacc gcggattcct ctttaacaag     120
cccaccggtt acgggtcttc aagccggagg gccccgcaga ctggcatcgt cgacgagtgc     180
tgttttagaa gctgcgatct gcgacggttg gagatgtatt gtgcacctct gaagcccgcg     240
aaaagtgct                                                             249
```

<210> SEQ ID NO 40
<211> LENGTH: 249
<212> TYPE: DNA
<213> ORGANISM: Artificial Sequence
<220> FEATURE:
<223> OTHER INFORMATION: Synthetic construct

<400> SEQUENCE: 40

```
atgttcccag ccatgccctt gtccagcctg tttgttaacg gcccaagaac actttgtgga      60
gccgaactgg tggatgctct ccaattcgtt tgcggcgacc gcggattcct ctttaacaag     120
cccaccggtg ccgggtcttc aagccggagg gccccgcaga ctggcatcgt cgacgagtgc     180
tgttttagaa gctgcgatct gcgacggttg gagatgtatt gtgcacctct gaagcccgcg     240
aaaagtgct                                                             249
```

<210> SEQ ID NO 41
<211> LENGTH: 249
<212> TYPE: DNA
<213> ORGANISM: Artificial Sequence
<220> FEATURE:
<223> OTHER INFORMATION: Synthetic construct

<400> SEQUENCE: 41

```
atgttcccag ccatgccctt gtccagcctg tttgttaacg gcccaagaac actttgtgga      60
gccgaactgg tggatgctct ccaattcgtt tgcggcgacc gcggattcta ctttaacaag     120
cccaccggtg ccgggtcttc aagccggagg gccccgcaga ctggcatcgt cgacgagtgc     180
tgttttagaa gctgcgatct gcgacggttg gagatgtatt gtgcacctct gaagcccgcg     240
aaaagtgct                                                             249
```

<210> SEQ ID NO 42
<211> LENGTH: 249
<212> TYPE: DNA
<213> ORGANISM: Artificial Sequence
<220> FEATURE:
<223> OTHER INFORMATION: Synthetic construct

<400> SEQUENCE: 42

```
atgttcccag ccatgccctt gtccagcctg tttgttaacg gcccaagaac actttgtgga      60
gccgaactgg tggatgctct ccaattcgtt tgcggcgacc gcggattcta ctttaacaag     120
cccaccggtt acgggtcttc aagccggagg gccccgcaga ctggcatcgt cgacgagtgc     180
tgttttagaa gctgcgatct gcgacggttg gagatgttgt gtgcacctct gaagcccgcg     240
aaaagtgct                                                             249
```

```
<210> SEQ ID NO 43
<211> LENGTH: 198
<212> TYPE: DNA
<213> ORGANISM: Artificial Sequence
<220> FEATURE:
<223> OTHER INFORMATION: Synthetic construct

<400> SEQUENCE: 43
ggcccagaaa cactttgtgg agccgaactg gtggatgctc tccaattcgt ttgcggcgac      60
cgcggattct actttaacaa gcccaccggt tacgggtctt caagccgggc cccgcagact     120
ggcatcgtcg acgagtgctg ttttagaagc tgcgatctgc gacggttgga gatgtattgt     180
gcacctctga agcccgcg                                                   198

<210> SEQ ID NO 44
<211> LENGTH: 210
<212> TYPE: DNA
<213> ORGANISM: Artificial Sequence
<220> FEATURE:
<223> OTHER INFORMATION: Synthetic construct

<400> SEQUENCE: 44
ggcccagaaa cactttgtgg agccgaactg gtggatgctc tccaattcgt ttgcggcgac      60
cgcggattcc tctttaacaa gcccaccggt tacgggtctt caagccggag ggccccgcag     120
actggcatcg tcgacgagtg ctgttttaga agctgcgatc tgcgacggtt ggagatgtat     180
tgtgcacctc tgaagcccgc gaaaagtgct                                      210

<210> SEQ ID NO 45
<211> LENGTH: 210
<212> TYPE: DNA
<213> ORGANISM: Artificial Sequence
<220> FEATURE:
<223> OTHER INFORMATION: Synthetic construct

<400> SEQUENCE: 45
ggcccagaaa cactttgtgg agccgaactg gtggatgctc tccaattcgt ttgcggcgac      60
cgcggattcc tctttaacaa gcccaccggt gccgggtctt caagccggag ggccccgcag     120
actggcatcg tcgacgagtg ctgttttaga agctgcgatc tgcgacggtt ggagatgtat     180
tgtgcacctc tgaagcccgc gaaaagtgct                                      210

<210> SEQ ID NO 46
<211> LENGTH: 210
<212> TYPE: DNA
<213> ORGANISM: Artificial Sequence
<220> FEATURE:
<223> OTHER INFORMATION: Syntehtic construct

<400> SEQUENCE: 46
ggcccagaaa cactttgtgg agccgaactg gtggatgctc tccaattcgt ttgcggcgac      60
cgcggattct actttaacaa gcccaccggt gccgggtctt caagccggag ggccccgcag     120
actggcatcg tcgacgagtg ctgttttaga agctgcgatc tgcgacggtt ggagatgtat     180
tgtgcacctc tgaagcccgc gaaaagtgct                                      210

<210> SEQ ID NO 47
<211> LENGTH: 210
<212> TYPE: DNA
<213> ORGANISM: Artificial Sequence
<220> FEATURE:
<223> OTHER INFORMATION: Synthetic construct
```

<400> SEQUENCE: 47

```
ggcccagaaa cactttgtgg agccgaactg gtggatgctc tccaattcgt ttgcggcgac    60
cgcggattct actttaacaa gcccaccggt tacgggtctt caagccggag ggccccgcag   120
actggcatcg tcgacgagtg ctgttttaga agctgcgatc tgcgacggtt ggagatgttg   180
tgtgcacctc tgaagcccgc gaaaagtgct                                    210
```

<210> SEQ ID NO 48
<211> LENGTH: 189
<212> TYPE: DNA
<213> ORGANISM: Artificial Sequence
<220> FEATURE:
<223> OTHER INFORMATION: Synthetic construct

<400> SEQUENCE: 48

```
acactttgtg gagccgaact ggtggatgct ctccaattcg tttgcggcga ccgcggattc    60
tactttaaca gcccaccgg ttacgggtct tcaagccggg ccccgcagac tggcatcgtc   120
gacgagtgct gttttagaag ctgcgatctg cgacggttgg agatgtattg tgcacctctg   180
aagcccgcg                                                           189
```

<210> SEQ ID NO 49
<211> LENGTH: 201
<212> TYPE: DNA
<213> ORGANISM: Artificial Sequence
<220> FEATURE:
<223> OTHER INFORMATION: Synthetic construct

<400> SEQUENCE: 49

```
acactttgtg gagccgaact ggtggatgct ctccaattcg tttgcggcga ccgcggattc    60
ctctttaaca gcccaccgg ttacgggtct tcaagccgga gggccccgca gactggcatc   120
gtcgacgagt gctgttttag aagctgcgat ctgcgacggt tggagatgta ttgtgcacct   180
ctgaagcccg cgaaaagtgc t                                             201
```

<210> SEQ ID NO 50
<211> LENGTH: 201
<212> TYPE: DNA
<213> ORGANISM: Artificial Sequence
<220> FEATURE:
<223> OTHER INFORMATION: Synthetic construct

<400> SEQUENCE: 50

```
acactttgtg gagccgaact ggtggatgct ctccaattcg tttgcggcga ccgcggattc    60
ctctttaaca gcccaccgg tgccgggtct tcaagccgga gggccccgca gactggcatc   120
gtcgacgagt gctgttttag aagctgcgat ctgcgacggt tggagatgta ttgtgcacct   180
ctgaagcccg cgaaaagtgc t                                             201
```

<210> SEQ ID NO 51
<211> LENGTH: 201
<212> TYPE: DNA
<213> ORGANISM: Artificial Sequence
<220> FEATURE:
<223> OTHER INFORMATION: Synthetic construct

<400> SEQUENCE: 51

```
acactttgtg gagccgaact ggtggatgct ctccaattcg tttgcggcga ccgcggattc    60
tactttaaca gcccaccgg tgccgggtct tcaagccgga gggccccgca gactggcatc   120
```

```
gtcgacgagt gctgttttag aagctgcgat ctgcgacggt tggagatgta ttgtgcacct    180
ctgaagcccg cgaaaagtgc t                                              201

<210> SEQ ID NO 52
<211> LENGTH: 201
<212> TYPE: DNA
<213> ORGANISM: Artificial Sequence
<220> FEATURE:
<223> OTHER INFORMATION: Synthetic construct

<400> SEQUENCE: 52
acactttgtg gagccgaact ggtggatgct ctccaattcg tttgcggcga ccgcggattc    60
tactttaaca agcccaccgg ttacgggtct tcaagccgga gggccccgca gactggcatc    120
gtcgacgagt gctgttttag aagctgcgat ctgcgacggt tggagatgtt gtgtgcacct    180
ctgaagcccg cgaaaagtgc t                                              201

<210> SEQ ID NO 53
<211> LENGTH: 226
<212> TYPE: PRT
<213> ORGANISM: Artificial Sequence
<220> FEATURE:
<223> OTHER INFORMATION: Synthetic construct

<400> SEQUENCE: 53

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Gln Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225
```

```
<210> SEQ ID NO 54
<211> LENGTH: 585
<212> TYPE: PRT
<213> ORGANISM: Homor sapiens

<400> SEQUENCE: 54
```

| Asp | Ala | His | Lys | Ser | Glu | Val | Ala | His | Arg | Phe | Lys | Asp | Leu | Gly | Glu |
|---|---|---|---|---|---|---|---|---|---|---|---|---|---|---|---|
| 1 | | | | 5 | | | | | 10 | | | | | 15 | |

| Glu | Asn | Phe | Lys | Ala | Leu | Val | Leu | Ile | Ala | Phe | Ala | Gln | Tyr | Leu | Gln |
|---|---|---|---|---|---|---|---|---|---|---|---|---|---|---|---|
| | | | 20 | | | | | 25 | | | | | 30 | | |

| Gln | Cys | Pro | Phe | Glu | Asp | His | Val | Lys | Leu | Val | Asn | Glu | Val | Thr | Glu |
|---|---|---|---|---|---|---|---|---|---|---|---|---|---|---|---|
| | | 35 | | | | | 40 | | | | | 45 | | | |

| Phe | Ala | Lys | Thr | Cys | Val | Ala | Asp | Glu | Ser | Ala | Glu | Asn | Cys | Asp | Lys |
|---|---|---|---|---|---|---|---|---|---|---|---|---|---|---|---|
| | 50 | | | | | 55 | | | | | 60 | | | | |

| Ser | Leu | His | Thr | Leu | Phe | Gly | Asp | Lys | Leu | Cys | Thr | Val | Ala | Thr | Leu |
|---|---|---|---|---|---|---|---|---|---|---|---|---|---|---|---|
| 65 | | | | | 70 | | | | | 75 | | | | | 80 |

| Arg | Glu | Thr | Tyr | Gly | Glu | Met | Ala | Asp | Cys | Cys | Ala | Lys | Gln | Glu | Pro |
|---|---|---|---|---|---|---|---|---|---|---|---|---|---|---|---|
| | | | | 85 | | | | | 90 | | | | | 95 | |

| Glu | Arg | Asn | Glu | Cys | Phe | Leu | Gln | His | Lys | Asp | Asp | Asn | Pro | Asn | Leu |
|---|---|---|---|---|---|---|---|---|---|---|---|---|---|---|---|
| | | | 100 | | | | | 105 | | | | | 110 | | |

| Pro | Arg | Leu | Val | Arg | Pro | Glu | Val | Asp | Val | Met | Cys | Thr | Ala | Phe | His |
|---|---|---|---|---|---|---|---|---|---|---|---|---|---|---|---|
| | | | 115 | | | | | 120 | | | | | 125 | | |

| Asp | Asn | Glu | Glu | Thr | Phe | Leu | Lys | Lys | Tyr | Leu | Tyr | Glu | Ile | Ala | Arg |
|---|---|---|---|---|---|---|---|---|---|---|---|---|---|---|---|
| | 130 | | | | | 135 | | | | | 140 | | | | |

| Arg | His | Pro | Tyr | Phe | Tyr | Ala | Pro | Glu | Leu | Leu | Phe | Phe | Ala | Lys | Arg |
|---|---|---|---|---|---|---|---|---|---|---|---|---|---|---|---|
| 145 | | | | | 150 | | | | | 155 | | | | | 160 |

| Tyr | Lys | Ala | Ala | Phe | Thr | Glu | Cys | Cys | Gln | Ala | Ala | Asp | Lys | Ala | Ala |
|---|---|---|---|---|---|---|---|---|---|---|---|---|---|---|---|
| | | | | 165 | | | | | 170 | | | | | 175 | |

| Cys | Leu | Leu | Pro | Lys | Leu | Asp | Glu | Leu | Arg | Asp | Glu | Gly | Lys | Ala | Ser |
|---|---|---|---|---|---|---|---|---|---|---|---|---|---|---|---|
| | | | 180 | | | | | 185 | | | | | 190 | | |

| Ser | Ala | Lys | Gln | Arg | Leu | Lys | Cys | Ala | Ser | Leu | Gln | Lys | Phe | Gly | Glu |
|---|---|---|---|---|---|---|---|---|---|---|---|---|---|---|---|
| | | 195 | | | | | 200 | | | | | 205 | | | |

| Arg | Ala | Phe | Lys | Ala | Trp | Ala | Val | Ala | Arg | Leu | Ser | Gln | Arg | Phe | Pro |
|---|---|---|---|---|---|---|---|---|---|---|---|---|---|---|---|
| | 210 | | | | | 215 | | | | | 220 | | | | |

| Lys | Ala | Glu | Phe | Ala | Glu | Val | Ser | Lys | Leu | Val | Thr | Asp | Leu | Thr | Lys |
|---|---|---|---|---|---|---|---|---|---|---|---|---|---|---|---|
| 225 | | | | | 230 | | | | | 235 | | | | | 240 |

| Val | His | Thr | Glu | Cys | Cys | His | Gly | Asp | Leu | Leu | Glu | Cys | Ala | Asp | Asp |
|---|---|---|---|---|---|---|---|---|---|---|---|---|---|---|---|
| | | | | 245 | | | | | 250 | | | | | 255 | |

| Arg | Ala | Asp | Leu | Ala | Lys | Tyr | Ile | Cys | Glu | Asn | Gln | Asp | Ser | Ile | Ser |
|---|---|---|---|---|---|---|---|---|---|---|---|---|---|---|---|
| | | | 260 | | | | | 265 | | | | | 270 | | |

| Ser | Lys | Leu | Lys | Glu | Cys | Cys | Glu | Lys | Pro | Leu | Leu | Glu | Lys | Ser | His |
|---|---|---|---|---|---|---|---|---|---|---|---|---|---|---|---|
| | | 275 | | | | | 280 | | | | | 285 | | | |

| Cys | Ile | Ala | Glu | Val | Glu | Asn | Asp | Glu | Met | Pro | Ala | Asp | Leu | Pro | Ser |
|---|---|---|---|---|---|---|---|---|---|---|---|---|---|---|---|
| | 290 | | | | | 295 | | | | | 300 | | | | |

| Leu | Ala | Ala | Asp | Phe | Val | Glu | Ser | Lys | Asp | Val | Cys | Lys | Asn | Tyr | Ala |
|---|---|---|---|---|---|---|---|---|---|---|---|---|---|---|---|
| 305 | | | | | 310 | | | | | 315 | | | | | 320 |

| Glu | Ala | Lys | Asp | Val | Phe | Leu | Gly | Met | Phe | Leu | Tyr | Glu | Tyr | Ala | Arg |
|---|---|---|---|---|---|---|---|---|---|---|---|---|---|---|---|
| | | | | 325 | | | | | 330 | | | | | 335 | |

| Arg | His | Pro | Asp | Tyr | Ser | Val | Val | Leu | Leu | Leu | Arg | Leu | Ala | Lys | Thr |
|---|---|---|---|---|---|---|---|---|---|---|---|---|---|---|---|
| | | | 340 | | | | | 345 | | | | | 350 | | |

| Tyr | Glu | Thr | Thr | Leu | Glu | Lys | Cys | Cys | Ala | Ala | Ala | Asp | Pro | His | Glu |
|---|---|---|---|---|---|---|---|---|---|---|---|---|---|---|---|
| | | 355 | | | | | 360 | | | | | 365 | | | |

| Cys | Tyr | Ala | Lys | Val | Phe | Asp | Glu | Phe | Lys | Pro | Leu | Val | Glu | Glu | Pro |
|---|---|---|---|---|---|---|---|---|---|---|---|---|---|---|---|
| | 370 | | | | | 375 | | | | | 380 | | | | |

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
        420                 425                 430

Val Gly Ser Lys Cys Cys Lys His Pro Glu Ala Lys Arg Met Pro Cys
    435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Gly Lys Lys Leu Val
                565                 570                 575

Ala Ala Ser Gln Ala Ala Leu Gly Leu
            580                 585

<210> SEQ ID NO 55
<211> LENGTH: 585
<212> TYPE: PRT
<213> ORGANISM: Artificial Sequence
<220> FEATURE:
<223> OTHER INFORMATION: Synthetic construct

<400> SEQUENCE: 55

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

```
Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Gln Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560
```

Ala Asp Asp Lys Glu Thr Cys Phe Ala Glu Gly Lys Lys Leu Val
              565                 570                 575

Ala Ala Ser Gln Ala Ala Leu Gly Leu
        580                 585

<210> SEQ ID NO 56
<211> LENGTH: 585
<212> TYPE: PRT
<213> ORGANISM: Artificial Sequence
<220> FEATURE:
<223> OTHER INFORMATION: Synthetic construct

<400> SEQUENCE: 56

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Gln Ala Gly Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Ala Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 57
<211> LENGTH: 1755
<212> TYPE: DNA
<213> ORGANISM: Homo sapiens

<400> SEQUENCE: 57
gacgctcaca agtctgaagt ggcacatagg ttcaaagatc tgggcgaaga gaactttaag      60
gccctcgtcc tgatcgcttt cgcacagtac ctccagcagt gtcccttttga agatcacgtg    120 aaactggtca atgaggtgac cgaatttgcc aagacatgcg tggctgatga gagtgcagaa    180
aactgtgaca atcactgca tactctcttt ggagataagc tgtgcaccgt cgccacactc    240
agagagactt atggggaaat ggctgactgt tgcgcaaaac aggagcctga acggaatgag    300
tgtttcctcc agcacaagga tgacaaccca aatctgcccc gcctcgtgcg acctgaggtc    360
gatgtgatgt gcaccgcctt tcatgacaac gaagagacat cctgaagaa atacctgtat    420 gaaattgctc gtaggcaccc atactttat gccccccgagc tcctgttctt tgcaaagaga    480
tacaaagctg ccttcactga atgttgccag gcagctgata aggccgcatg tctcctgcct    540
aaactggacg agctccggga tgaaggtaag gcttccagcg ccaaacagcg cctgaagtgc    600
gcttctctcc agaagtttgg cgagcgagca ttcaaagcct gggctgtggc ccgtctcagt    660
cagaggtttc caaaggcaga atttgctgag gtgtcaaaac tggtgaccga cctcacaaag    720

```
gtccatactg agtgttgcca cggagatctg ctggaatgtg ccgacgatag agcagacctc    780
gctaaatata tctgcgagaa tcaggattcc attagctcta agctgaaaga atgttgcgag    840
aagcccctcc tggaaaagag tcattgtatc gccgaggtgg aaaacgacga gatgccagca    900
gatctgccat cactcgctgc cgactttgtg aatccaaag atgtctgcaa gaattacgca     960
gaggctaaag acgtgttcct ggggatgttt ctgtatgagt acgcccggcg tcaccccgat   1020
tatagcgtcg tgctcctgct ccgactggca aagacctacg aaacaactct ggagaaatgt   1080
tgcgctgccg cagaccctca tgaatgttat gctaaggtgt tcgatgagtt taagccactc   1140
gtcgaagagc cccagaacct gattaaacag aattgcgaac tgttcgagca gctcggtgaa   1200
tacaagtttc agaacgccct gctcgtgcgt tataccaaaa aggtccctca ggtgtctaca   1260
ccaactctgg tggaggtcag taggaatctg ggcaaagtgg gatcaaagtg ttgcaaacac   1320
cccgaggcaa agagaatgcc ttgtgctgaa gattacctct ccgtcgtgct gaaccagctc   1380
tgcgtgctgc atgaaaagac cccagtcagc gaccgggtga caaaatgttg caccgaatct   1440
ctggtcaatc gccgacccctg tttcagtgcc ctcgaagtgg acgaaactta tgtgcctaag   1500
gagtttaatg ctgaaacatt caccttttcac gccgatatct gcactctgtc cgagaaagaa   1560
aggcagatta agaaacagac agcactggtc gagctcgtga agcataaacc aaaggctacc   1620
aaggagcagc tgaaagccgt catggacgat ttcgcagctt ttgtggaaaa gtgttgcaaa   1680
gccgacgata aggagacttg tttcgcagaa gaggggaaaa agctcgtggc tgccagccag   1740
gcagctctgg gtctg                                                    1755
```

<210> SEQ ID NO 58
<211> LENGTH: 1755
<212> TYPE: DNA
<213> ORGANISM: Artificial Sequence
<220> FEATURE:
<223> OTHER INFORMATION: Synthetic construct

<400> SEQUENCE: 58

```
gacgctcaca agtctgaagt ggcacatagg ttcaaagatc tgggcgaaga gaactttaag     60
gccctcgtcc tgatcgcttt cgcacagtac ctccagcagt ctcccttga agatcacgtg    120 aaactggtca atgaggtgac cgaatttgcc aagacatgcg tggctgatga gagtgcagaa    180
aactgtgaca aatcactgca tactctcttt ggagataagc tgtgcaccgt cgccacactc    240
agagagactt atggggaaat ggctgactgt tgcgcaaaac aggagcctga acggaatgag    300
tgtttcctcc agcacaagga tgacaaccca aatctgcccc gctcgtgcg acctgaggtc     360 gatgtgatgt gcaccgcctt tcatgacaac gaagagacat tcctgaagaa atacctgtat    420
gaaattgctc gtaggcaccc atactttat gcccccgagc tcctgttctt tgcaaagaga     480
tacaaagctg ccttcactga atgttgccag gcagctgata aggccgcatg tctcctgcct    540
aaactggacg agtccgggga tgaagtaag gcttccagcg ccaaacagcg cctgaagtgc     600
gcttctctcc agaagttgg cgagcgagca ttcaaagcct gggctgtggc ccgtctcagt    660
cagaggtttc caaaggcaga attgctgagt tgtcaaaac tggtgaccga cctcacaaag    720
gtccatactg agtgttgcca cggagatctg ctggaatgtg ccgacgatag agcagacctc    780
gctaaatata tctgcgagaa tcaggattcc attagctcta agctgaaaga atgttgcgag    840
aagcccctcc tggaaaagag tcattgtatc gccgaggtgg aaaacgacga gatgccagca    900
gatctgccat cactcgctgc cgactttgtg aatccaaag atgtctgcaa gaattacgca     960
```

| | |
|---|---|
| gaggctaaag acgtgttcct ggggatgttt ctgtatgagt acgcccggcg tcaccccgat | 1020 |
| tatagcgtcg tgctcctgct ccgactggca aagacctacg aaacaactct ggagaaatgt | 1080 |
| tgcgctgccg cagaccctca tgaatgttat gctaaggtgt tcgatgagtt taagccactc | 1140 |
| gtcgaagagc cccagaacct gattaaacag aattgcgaac tgttcgagca gctcggtgaa | 1200 |
| tacaagtttc agaacgccct gctcgtgcgt tataccaaaa aggtccctca ggtgtctaca | 1260 |
| ccaactctgg tggaggtcag taggaatctg ggcaaagtgg gatcaaagtg ttgcaaacac | 1320 |
| cccgaggcaa agagaatgcc ttgtgctgaa gattacctct ccgtcgtgct gaaccagctc | 1380 |
| tgcgtgctgc atgaaaagac cccagtcagc gaccgggtga caaaatgttg caccgaatct | 1440 |
| ctggtcaatc gccgaccctg tttcagtgcc ctcgaagtgg acgaaactta tgtgcctaag | 1500 |
| gagtttcagg ctgaaacatt caccttttcac gccgatatct gcactctgtc cgagaaagaa | 1560 |
| aggcagatta agaaacagac agcactggtc gagctcgtga agcataaacc aaaggctacc | 1620 |
| aaggagcagc tgaaagccgt catggacgat ttcgcagctt ttgtggaaaa gtgttgcaaa | 1680 |
| gccgacgata aggagacttg tttcgcagaa gagggaaaaa agctcgtggc tgccagccag | 1740 |
| gcagctctgg gtctg | 1755 |

<210> SEQ ID NO 59
<211> LENGTH: 1755
<212> TYPE: DNA
<213> ORGANISM: Artificial Sequence
<220> FEATURE:
<223> OTHER INFORMATION: Synthetic construct

<400> SEQUENCE: 59

| | |
|---|---|
| gacgctcaca agtctgaagt ggcacatagg ttcaaagatc tgggcgaaga gaactttaag | 60 |
| gccctcgtcc tgatcgcttt cgcacagtac ctccagcagt ctcccttttga agatcacgtg | 120 |
| aaactggtca atgaggtgac cgaatttgcc aagacatgcg tggctgatga gagtgcagaa | 180 |
| aactgtgaca aatcactgca tactctcttt ggagataagc tgtgcaccgt cgccacactc | 240 |
| agagagactt atggggaaat ggctgactgt tgcgcaaaac aggagcctga acggaatgag | 300 |
| tgtttcctcc agcacaagga tgacaaccca aatctgcccc gctcgtgcg acctgaggtc | 360 |
| gatgtgatgt gcaccgcctt tcatgacaac gaagagacat tcctgaagaa atacctgtat | 420 |
| gaaattgctc gtaggcaccc atactttttat gcccccgagc tcctgttctt tgcaaagaga | 480 |
| tacaaagctg ccttcactga atgttgccag gcagctgata aggccgcatg tctcctgcct | 540 |
| aaactggacg agctccggga tgaaggtaag gcttccagcg ccaaacagcg cctgaagtgc | 600 |
| gcttctctcc agaagtttgg cgagcgagca ttcaaagcct gggctgtggc ccgtctcagt | 660 |
| cagaggtttc caaaggcaga atttgctgag gtgtcaaaac tggtgaccga cctcacaaag | 720 |
| gtccatactg agtgttgcca cggagatctg ctggaatgtg ccgacgatag agcagacctc | 780 |
| gctaaatata tctgcgagaa tcaggattcc attagctcta agctgaaaga atgttgcgag | 840 |
| aagcccctcc tggaaaagag tcattgtatc gccgaggtgg aaaacgacga gatgccagca | 900 |
| gatctgccat cactcgctgc cgactttgtg gaatccaaag atgtctgcaa gaattacgca | 960 |
| gaggctaaag acgtgttcct ggggatgttt ctgtatgagt acgcccggcg tcaccccgat | 1020 |
| tatagcgtcg tgctcctgct ccgactggca aagacctacg aaacaactct ggagaaatgt | 1080 |
| tgcgctgccg cagaccctca tgaatgttat gctaaggtgt tcgatgagtt taagccactc | 1140 |
| gtcgaagagc cccagaacct gattaaacag aattgcgaac tgttcgagca gctcggtgaa | 1200 |
| tacaagtttc agaacgccct gctcgtgcgt tataccaaaa aggtccctca ggtgtctaca | 1260 |

-continued

```
ccaactctgg tggaggtcag taggaatctg ggcaaagtgg gatcaaagtg ttgcaaacac    1320
cccgaggcaa agagaatgcc ttgtgctgaa gattacctct ccgtcgtgct gaaccagctc    1380
tgcgtgctgc atgaaaagac cccagtcagc gaccgggtga caaaatgttg caccgaatct    1440
ctggtcaatc gccgaccctg tttcagtgcc ctcgaagtgg acgaaactta tgtgcctaag    1500
gagtttcagg ctggaacatt caccttttcac gccgatatct gcactctgtc cgagaaagaa    1560
aggcagatta gaaacagac agcactggtc gagctcgtga agcataaacc aaaggctacc    1620
aaggagcagc tgaaagccgc catggacgat ttcgcagctt ttgtggaaaa gtgttgcaaa    1680
gccgacgata aggagacttg tttcgcagaa gaggggaaaa agctcgtggc tgccagccag    1740
gcagctctgg gtctg                                                     1755
```

<210> SEQ ID NO 60
<211> LENGTH: 7
<212> TYPE: PRT
<213> ORGANISM: Artificial Sequence
<220> FEATURE:
<223> OTHER INFORMATION: Synthetic construct

<400> SEQUENCE: 60

Gly Ser Gly Gly Gly Ser Gly
1               5

<210> SEQ ID NO 61
<211> LENGTH: 15
<212> TYPE: PRT
<213> ORGANISM: Artificial Sequence
<220> FEATURE:
<223> OTHER INFORMATION: Synthetic construct

<400> SEQUENCE: 61

Gly Ser Gly Gly Ser Gly Gly Gly Ser Gly Gly Ser Gly Gly Gly
1               5                   10                  15

<210> SEQ ID NO 62
<211> LENGTH: 40
<212> TYPE: PRT
<213> ORGANISM: Artificial Sequence
<220> FEATURE:
<223> OTHER INFORMATION: Synthetic construct

<400> SEQUENCE: 62

Gly Ser Gly Gly Ser Gly Gly Gly Ser Gly Gly Gly Ser Gly Gly Gly
1               5                   10                  15

Ser Gly Gly Gly Ser Gly Gly Gly Ser Gly Gly Gly Ser Gly Gly Gly
                20                  25                  30

Ser Gly Gly Gly Ser Gly Gly Gly
        35                  40

<210> SEQ ID NO 63
<211> LENGTH: 21
<212> TYPE: DNA
<213> ORGANISM: Artificial Sequence
<220> FEATURE:
<223> OTHER INFORMATION: Synthetic construct

<400> SEQUENCE: 63
gggagcggtg gtgggagtgg c                                               21

<210> SEQ ID NO 64
<211> LENGTH: 45

<212> TYPE: DNA
<213> ORGANISM: Artificial Sequence
<220> FEATURE:
<223> OTHER INFORMATION: Synthetic construct

<400> SEQUENCE: 64
gggtctggcg gttcagggggg aggaagtgga ggctcaggag gtggt        45

<210> SEQ ID NO 65
<211> LENGTH: 120
<212> TYPE: DNA
<213> ORGANISM: Artificial Sequence
<220> FEATURE:
<223> OTHER INFORMATION: Synthetic construct

<400> SEQUENCE: 65
ggttccggag gttctggcgg tggatctggg ggcggtagcg gaggcggcag tggtggtggc     60 agcggggggag ggtcaggtgg gggtagtggc ggtggttctg gaggtggttc aggaggagga   120

<210> SEQ ID NO 66
<211> LENGTH: 721
<212> TYPE: PRT
<213> ORGANISM: Artificial Sequence
<220> FEATURE:
<223> OTHER INFORMATION: Synthetic construct

<400> SEQUENCE: 66

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Tyr Phe Asn Lys Pro Thr Gly Tyr Gly Ser Ser Ser
        35                  40                  45

Arg Ala Pro Gln Thr Gly Ile Val Asp Glu Cys Cys Phe Arg Ser Cys
    50                  55                  60

Asp Leu Arg Arg Leu Glu Met Tyr Cys Ala Pro Leu Lys Pro Ala Lys
65                  70                  75                  80

Ser Ala Gly Ser Gly Gly Ser Gly Gly Gly Ser Gly Gly Gly Ser Gly
                85                  90                  95

Gly Gly Ser Gly Gly Gly Ser Gly Gly Gly Ser Gly Gly Gly Ser Gly
            100                 105                 110

Gly Gly Ser Gly Gly Gly Ser Gly Gly Gly Asp Ala His Lys Ser Glu
        115                 120                 125

Val Ala His Arg Phe Lys Asp Leu Gly Glu Glu Asn Phe Lys Ala Leu
    130                 135                 140

Val Leu Ile Ala Phe Ala Gln Tyr Leu Gln Gln Ser Pro Phe Glu Asp
145                 150                 155                 160

His Val Lys Leu Val Asn Glu Val Thr Glu Phe Ala Lys Thr Cys Val
                165                 170                 175

Ala Asp Glu Ser Ala Glu Asn Cys Asp Lys Ser Leu His Thr Leu Phe
            180                 185                 190

Gly Asp Lys Leu Cys Thr Val Ala Thr Leu Arg Glu Thr Tyr Gly Glu
        195                 200                 205

Met Ala Asp Cys Cys Ala Lys Gln Glu Pro Glu Arg Asn Glu Cys Phe
    210                 215                 220

Leu Gln His Lys Asp Asp Asn Pro Asn Leu Pro Arg Leu Val Arg Pro
225                 230                 235                 240

Glu Val Asp Val Met Cys Thr Ala Phe His Asp Asn Glu Glu Thr Phe

-continued

```
                245                 250                 255
Leu Lys Lys Tyr Leu Tyr Glu Ile Ala Arg Arg His Pro Tyr Phe Tyr
            260                 265                 270
Ala Pro Glu Leu Leu Phe Phe Ala Lys Arg Tyr Lys Ala Ala Phe Thr
            275                 280                 285
Glu Cys Cys Gln Ala Ala Asp Lys Ala Ala Cys Leu Leu Pro Lys Leu
            290                 295                 300
Asp Glu Leu Arg Asp Glu Gly Lys Ala Ser Ser Ala Lys Gln Arg Leu
305                 310                 315                 320
Lys Cys Ala Ser Leu Gln Lys Phe Gly Glu Arg Ala Phe Lys Ala Trp
                325                 330                 335
Ala Val Ala Arg Leu Ser Gln Arg Phe Pro Lys Ala Glu Phe Ala Glu
                340                 345                 350
Val Ser Lys Leu Val Thr Asp Leu Thr Lys Val His Thr Glu Cys Cys
                355                 360                 365
His Gly Asp Leu Leu Glu Cys Ala Asp Asp Arg Ala Asp Leu Ala Lys
            370                 375                 380
Tyr Ile Cys Glu Asn Gln Asp Ser Ile Ser Ser Lys Leu Lys Glu Cys
385                 390                 395                 400
Cys Glu Lys Pro Leu Leu Glu Lys Ser His Cys Ile Ala Glu Val Glu
                405                 410                 415
Asn Asp Glu Met Pro Ala Asp Leu Pro Ser Leu Ala Ala Asp Phe Val
                420                 425                 430
Glu Ser Lys Asp Val Cys Lys Asn Tyr Ala Glu Ala Lys Asp Val Phe
            435                 440                 445
Leu Gly Met Phe Leu Tyr Glu Tyr Ala Arg Arg His Pro Asp Tyr Ser
            450                 455                 460
Val Val Leu Leu Leu Arg Leu Ala Lys Thr Tyr Glu Thr Thr Leu Glu
465                 470                 475                 480
Lys Cys Cys Ala Ala Ala Asp Pro His Glu Cys Tyr Ala Lys Val Phe
                485                 490                 495
Asp Glu Phe Lys Pro Leu Val Glu Glu Pro Gln Asn Leu Ile Lys Gln
            500                 505                 510
Asn Cys Glu Leu Phe Glu Gln Leu Gly Glu Tyr Lys Phe Gln Asn Ala
            515                 520                 525
Leu Leu Val Arg Tyr Thr Lys Lys Val Pro Gln Val Ser Thr Pro Thr
            530                 535                 540
Leu Val Glu Val Ser Arg Asn Leu Gly Lys Val Gly Ser Lys Cys Cys
545                 550                 555                 560
Lys His Pro Glu Ala Lys Arg Met Pro Cys Ala Glu Asp Tyr Leu Ser
                565                 570                 575
Val Val Leu Asn Gln Leu Cys Val Leu His Glu Lys Thr Pro Val Ser
                580                 585                 590
Asp Arg Val Thr Lys Cys Cys Thr Glu Ser Leu Val Asn Arg Arg Pro
                595                 600                 605
Cys Phe Ser Ala Leu Glu Val Asp Glu Thr Tyr Val Pro Lys Glu Phe
            610                 615                 620
Gln Ala Glu Thr Phe Thr Phe His Ala Asp Ile Cys Thr Leu Ser Glu
625                 630                 635                 640
Lys Glu Arg Gln Ile Lys Lys Gln Thr Ala Leu Val Glu Leu Val Lys
                645                 650                 655
His Lys Pro Lys Ala Thr Lys Glu Gln Leu Lys Ala Val Met Asp Asp
                660                 665                 670
```

```
Phe Ala Ala Phe Val Glu Lys Cys Cys Lys Ala Asp Asp Lys Glu Thr
            675                 680                 685

Cys Phe Ala Glu Glu Gly Lys Lys Leu Val Ala Ala Ser Gln Ala Ala
            690                 695                 700

Leu Gly Leu Gly Ser Gly Gly Ser Gly Ser Gly His His His His
705                 710                 715                 720

His

<210> SEQ ID NO 67
<211> LENGTH: 1063
<212> TYPE: PRT
<213> ORGANISM: Artificial Sequence
<220> FEATURE:
<223> OTHER INFORMATION: Synthetic construct

<400> SEQUENCE: 67

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
                20                  25                  30

Asp Arg Gly Phe Tyr Phe Asn Lys Pro Thr Gly Tyr Gly Ser Ser Ser
            35                  40                  45

Arg Ala Pro Gln Thr Gly Ile Val Asp Glu Cys Cys Phe Arg Ser Cys
50                  55                  60

Asp Leu Arg Arg Leu Glu Met Tyr Cys Ala Pro Leu Lys Pro Ala Gly
65                  70                  75                  80

Ser Gly Gly Ser Gly Gly Ser Gly Gly Ser Gly Gly Ser Gly Gly Ser
                85                  90                  95

Gly Gly Gly Ser Gly Gly Gly Ser Gly Gly Gly Ser Gly Gly Gly Ser
                100                 105                 110

Gly Gly Gly Ser Gly Gly Gly Asp Lys Thr His Thr Cys Pro Pro Cys
            115                 120                 125

Pro Ala Pro Glu Leu Leu Gly Gly Pro Ser Val Phe Leu Phe Pro Pro
            130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Gln Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300
```

```
Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
            325                 330                 335

Gln Lys Ser Leu Ser Leu Ser Pro Gly Gly Ser Gly Gly Ser Gly Gly
            340                 345                 350

Gly Ser Gly Gly Gly Ser Gly Gly Ser Gly Gly Gly Ser Gly Gly
        355                 360                 365

Gly Ser Gly Gly Gly Ser Gly Gly Ser Gly Gly Gly Ser Gly Gly
        370                 375                 380

Gly Ala Gln Val Leu Arg Gly Thr Val Thr Asp Phe Pro Gly Phe Asp
385                 390                 395                 400

Glu Arg Ala Asp Ala Glu Thr Leu Arg Lys Ala Met Lys Gly Leu Gly
                405                 410                 415

Thr Asp Glu Glu Ser Ile Leu Thr Leu Leu Thr Ser Arg Ser Asn Ala
                420                 425                 430

Gln Arg Gln Glu Ile Ser Ala Ala Phe Lys Thr Leu Phe Gly Arg Asp
            435                 440                 445

Leu Leu Asp Asp Leu Lys Ser Glu Leu Thr Gly Lys Phe Glu Lys Leu
450                 455                 460

Ile Val Ala Leu Met Lys Pro Ser Arg Leu Tyr Asp Ala Tyr Glu Leu
465                 470                 475                 480

Lys His Ala Leu Lys Gly Ala Gly Thr Asn Glu Lys Val Leu Thr Glu
                485                 490                 495

Ile Ile Ala Ser Arg Thr Pro Glu Glu Leu Arg Ala Ile Lys Gln Val
                500                 505                 510

Tyr Glu Glu Glu Tyr Gly Ser Ser Leu Glu Asp Asp Val Val Gly Asp
            515                 520                 525

Thr Ser Gly Tyr Tyr Gln Arg Met Leu Val Val Leu Leu Gln Ala Asn
530                 535                 540

Arg Asp Pro Asp Ala Gly Ile Asp Glu Ala Gln Val Glu Gln Asp Ala
545                 550                 555                 560

Gln Ala Leu Phe Gln Ala Gly Glu Leu Lys Trp Gly Thr Asp Glu Glu
                565                 570                 575

Lys Phe Ile Thr Ile Phe Gly Thr Arg Ser Val Ser His Leu Arg Lys
                580                 585                 590

Val Phe Asp Lys Tyr Met Thr Ile Ser Gly Phe Gln Ile Glu Glu Thr
            595                 600                 605

Ile Asp Arg Glu Thr Ser Gly Asn Leu Glu Gln Leu Leu Leu Ala Val
610                 615                 620

Val Lys Ser Ile Arg Ser Ile Pro Ala Tyr Leu Ala Glu Thr Leu Tyr
625                 630                 635                 640

Tyr Ala Met Lys Gly Ala Gly Thr Asp Asp His Thr Leu Ile Arg Val
                645                 650                 655

Met Val Ser Arg Ser Glu Ile Asp Leu Phe Asn Ile Arg Lys Glu Phe
                660                 665                 670

Arg Lys Asn Phe Ala Thr Ser Leu Tyr Ser Met Ile Lys Gly Asp Thr
            675                 680                 685

Ser Gly Asp Tyr Lys Lys Ala Leu Leu Leu Leu Ser Gly Glu Asp Asp
            690                 695                 700

Gly Ser Gly Gly Ser Gly Gly Ser Gly Gly Gly Ser Gly Gly Gly
705                 710                 715                 720

Ser Gly Gly Gly Ser Gly Gly Gly Ser Gly Gly Gly Ser Gly Gly Gly
```

```
            725                 730                 735
Ser Gly Gly Gly Ser Gly Ser Gly Ala Gln Val Leu Arg Gly Thr Val
            740                 745                 750

Thr Asp Phe Pro Gly Phe Asp Glu Arg Ala Asp Ala Glu Thr Leu Arg
            755                 760                 765

Lys Ala Met Lys Gly Leu Gly Thr Asp Glu Glu Ser Ile Leu Thr Leu
            770                 775                 780

Leu Thr Ser Arg Ser Asn Ala Gln Arg Gln Glu Ile Ser Ala Ala Phe
785                 790                 795                 800

Lys Thr Leu Phe Gly Arg Asp Leu Leu Asp Asp Leu Lys Ser Glu Leu
            805                 810                 815

Thr Gly Lys Phe Glu Lys Leu Ile Val Ala Leu Met Lys Pro Ser Arg
            820                 825                 830

Leu Tyr Asp Ala Tyr Glu Leu Lys His Ala Leu Lys Gly Ala Gly Thr
            835                 840                 845

Asn Glu Lys Val Leu Thr Glu Ile Ile Ala Ser Arg Thr Pro Glu Glu
            850                 855                 860

Leu Arg Ala Ile Lys Gln Val Tyr Glu Glu Glu Tyr Gly Ser Ser Leu
865                 870                 875                 880

Glu Asp Asp Val Val Gly Asp Thr Ser Gly Tyr Tyr Gln Arg Met Leu
            885                 890                 895

Val Val Leu Leu Gln Ala Asn Arg Asp Pro Asp Ala Gly Ile Asp Glu
            900                 905                 910

Ala Gln Val Glu Gln Asp Ala Gln Ala Leu Phe Gln Ala Gly Glu Leu
            915                 920                 925

Lys Trp Gly Thr Asp Glu Glu Lys Phe Ile Thr Ile Phe Gly Thr Arg
            930                 935                 940

Ser Val Ser His Leu Arg Lys Val Phe Asp Lys Tyr Met Thr Ile Ser
945                 950                 955                 960

Gly Phe Gln Ile Glu Glu Thr Ile Asp Arg Glu Thr Ser Gly Asn Leu
            965                 970                 975

Glu Gln Leu Leu Leu Ala Val Val Lys Ser Ile Arg Ser Ile Pro Ala
            980                 985                 990

Tyr Leu Ala Glu Thr Leu Tyr Tyr Ala Met Lys Gly Ala Gly Thr Asp
            995                 1000                1005

Asp His Thr Leu Ile Arg Val Met Val Ser Arg Ser Glu Ile Asp
            1010                1015                1020

Leu Phe Asn Ile Arg Lys Glu Phe Arg Lys Asn Phe Ala Thr Ser
            1025                1030                1035

Leu Tyr Ser Met Ile Lys Gly Asp Thr Ser Gly Asp Tyr Lys Lys
            1040                1045                1050

Ala Leu Leu Leu Leu Ser Gly Glu Asp Asp
            1055                1060

<210> SEQ ID NO 68
<211> LENGTH: 683
<212> TYPE: PRT
<213> ORGANISM: Artificial Sequence
<220> FEATURE:
<223> OTHER INFORMATION: Synthetic construct

<400> SEQUENCE: 68

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
```

-continued

```
                20                  25                  30
Asp Arg Gly Phe Tyr Phe Asn Lys Pro Thr Gly Tyr Gly Ser Ser Ser
            35                  40                  45

Arg Arg Ala Pro Gln Thr Gly Ile Val Asp Glu Cys Cys Phe Arg Ser
 50                  55                  60

Cys Asp Leu Arg Arg Leu Glu Met Tyr Cys Ala Pro Leu Lys Pro Ala
 65                  70                  75                  80

Lys Ser Ala Gly Ser Gly Ser Gly Gly Ser Gly Gly Ser Gly
                85                  90                  95

Gly Gly Asp Ala His Lys Ser Glu Val Ala His Arg Phe Lys Asp Leu
            100                 105                 110

Gly Glu Glu Asn Phe Lys Ala Leu Val Leu Ile Ala Phe Ala Gln Tyr
            115                 120                 125

Leu Gln Gln Ser Pro Phe Glu Asp His Val Lys Leu Val Asn Glu Val
            130                 135                 140

Thr Glu Phe Ala Lys Thr Cys Val Ala Asp Glu Ser Ala Glu Asn Cys
145                 150                 155                 160

Asp Lys Ser Leu His Thr Leu Phe Gly Asp Lys Leu Cys Thr Val Ala
                165                 170                 175

Thr Leu Arg Glu Thr Tyr Gly Glu Met Ala Asp Cys Cys Ala Lys Gln
                180                 185                 190

Glu Pro Glu Arg Asn Glu Cys Phe Leu Gln His Lys Asp Asp Asn Pro
            195                 200                 205

Asn Leu Pro Arg Leu Val Arg Pro Glu Val Asp Val Met Cys Thr Ala
            210                 215                 220

Phe His Asp Asn Glu Glu Thr Phe Leu Lys Lys Tyr Leu Tyr Glu Ile
225                 230                 235                 240

Ala Arg Arg His Pro Tyr Phe Tyr Ala Pro Glu Leu Leu Phe Phe Ala
                245                 250                 255

Lys Arg Tyr Lys Ala Ala Phe Thr Glu Cys Cys Gln Ala Ala Asp Lys
            260                 265                 270

Ala Ala Cys Leu Leu Pro Lys Leu Asp Glu Leu Arg Asp Glu Gly Lys
            275                 280                 285

Ala Ser Ser Ala Lys Gln Arg Leu Lys Cys Ala Ser Leu Gln Lys Phe
            290                 295                 300

Gly Glu Arg Ala Phe Lys Ala Trp Ala Val Ala Arg Leu Ser Gln Arg
305                 310                 315                 320

Phe Pro Lys Ala Glu Phe Ala Glu Val Ser Lys Leu Val Thr Asp Leu
                325                 330                 335

Thr Lys Val His Thr Glu Cys Cys His Gly Asp Leu Leu Glu Cys Ala
                340                 345                 350

Asp Asp Arg Ala Asp Leu Ala Lys Tyr Ile Cys Glu Asn Gln Asp Ser
            355                 360                 365

Ile Ser Ser Lys Leu Lys Glu Cys Cys Glu Lys Pro Leu Leu Glu Lys
            370                 375                 380

Ser His Cys Ile Ala Glu Val Glu Asn Asp Glu Met Pro Ala Asp Leu
385                 390                 395                 400

Pro Ser Leu Ala Ala Asp Phe Val Glu Ser Lys Asp Val Cys Lys Asn
                405                 410                 415

Tyr Ala Glu Ala Lys Asp Val Phe Leu Gly Met Phe Leu Tyr Glu Tyr
            420                 425                 430

Ala Arg Arg His Pro Asp Tyr Ser Val Val Leu Leu Leu Arg Leu Ala
            435                 440                 445
```

```
Lys Thr Tyr Glu Thr Thr Leu Glu Lys Cys Cys Ala Ala Ala Asp Pro
    450                 455                 460

His Glu Cys Tyr Ala Lys Val Phe Asp Glu Phe Lys Pro Leu Val Glu
465                 470                 475                 480

Glu Pro Gln Asn Leu Ile Lys Gln Asn Cys Glu Leu Phe Glu Gln Leu
                485                 490                 495

Gly Glu Tyr Lys Phe Gln Asn Ala Leu Leu Val Arg Tyr Thr Lys Lys
            500                 505                 510

Val Pro Gln Val Ser Thr Pro Thr Leu Val Glu Val Ser Arg Asn Leu
        515                 520                 525

Gly Lys Val Gly Ser Lys Cys Cys Lys His Pro Glu Ala Lys Arg Met
    530                 535                 540

Pro Cys Ala Glu Asp Tyr Leu Ser Val Val Leu Asn Gln Leu Cys Val
545                 550                 555                 560

Leu His Glu Lys Thr Pro Val Ser Asp Arg Val Thr Lys Cys Cys Thr
                565                 570                 575

Glu Ser Leu Val Asn Arg Arg Pro Cys Phe Ser Ala Leu Glu Val Asp
            580                 585                 590

Glu Thr Tyr Val Pro Lys Glu Phe Gln Ala Glu Thr Phe Thr Phe His
        595                 600                 605

Ala Asp Ile Cys Thr Leu Ser Glu Lys Glu Arg Gln Ile Lys Lys Gln
    610                 615                 620

Thr Ala Leu Val Glu Leu Val Lys His Lys Pro Lys Ala Thr Lys Glu
625                 630                 635                 640

Gln Leu Lys Ala Val Met Asp Asp Phe Ala Ala Phe Val Glu Lys Cys
                645                 650                 655

Cys Lys Ala Asp Asp Lys Glu Thr Cys Phe Ala Glu Glu Gly Lys Lys
            660                 665                 670

Leu Val Ala Ala Ser Gln Ala Ala Leu Gly Leu
        675                 680

<210> SEQ ID NO 69
<211> LENGTH: 680
<212> TYPE: PRT
<213> ORGANISM: Artificial Sequence
<220> FEATURE:
<223> OTHER INFORMATION: Synthetic construct

<400> SEQUENCE: 69

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Tyr Phe Asn Lys Pro Thr Gly Tyr Gly Ser Ser Ser
        35                  40                  45

Arg Ala Pro Gln Thr Gly Ile Val Asp Glu Cys Cys Phe Arg Ser Cys
    50                  55                  60

Asp Leu Arg Arg Leu Glu Met Tyr Cys Ala Pro Leu Lys Pro Ala Gly
65                  70                  75                  80

Gly Asp Ala His Lys Ser Glu Val Ala His Arg Phe Lys Asp Leu Gly
                85                  90                  95

Glu Glu Asn Phe Lys Ala Leu Val Leu Ile Ala Phe Ala Gln Tyr Leu
            100                 105                 110

Gln Gln Ser Pro Phe Glu Asp His Val Lys Leu Val Asn Glu Val Thr
        115                 120                 125
```

```
Glu Phe Ala Lys Thr Cys Val Ala Asp Glu Ser Ala Glu Asn Cys Asp
    130                 135                 140
Lys Ser Leu His Thr Leu Phe Gly Asp Lys Leu Cys Thr Val Ala Thr
145                 150                 155                 160
Leu Arg Glu Thr Tyr Gly Glu Met Ala Asp Cys Cys Ala Lys Gln Glu
                165                 170                 175
Pro Glu Arg Asn Glu Cys Phe Leu Gln His Lys Asp Asp Asn Pro Asn
                180                 185                 190
Leu Pro Arg Leu Val Arg Pro Glu Val Asp Val Met Cys Thr Ala Phe
                195                 200                 205
His Asp Asn Glu Glu Thr Phe Leu Lys Lys Tyr Leu Tyr Glu Ile Ala
210                 215                 220
Arg Arg His Pro Tyr Phe Tyr Ala Pro Glu Leu Leu Phe Phe Ala Lys
225                 230                 235                 240
Arg Tyr Lys Ala Ala Phe Thr Glu Cys Cys Gln Ala Ala Asp Lys Ala
                245                 250                 255
Ala Cys Leu Leu Pro Lys Leu Asp Glu Leu Arg Asp Glu Gly Lys Ala
                260                 265                 270
Ser Ser Ala Lys Gln Arg Leu Lys Cys Ala Ser Leu Gln Lys Phe Gly
                275                 280                 285
Glu Arg Ala Phe Lys Ala Trp Ala Val Ala Arg Leu Ser Gln Arg Phe
290                 295                 300
Pro Lys Ala Glu Phe Ala Glu Val Ser Lys Leu Val Thr Asp Leu Thr
305                 310                 315                 320
Lys Val His Thr Glu Cys Cys His Gly Asp Leu Leu Glu Cys Ala Asp
                325                 330                 335
Asp Arg Ala Asp Leu Ala Lys Tyr Ile Cys Glu Asn Gln Asp Ser Ile
                340                 345                 350
Ser Ser Lys Leu Lys Glu Cys Cys Glu Lys Pro Leu Leu Glu Lys Ser
                355                 360                 365
His Cys Ile Ala Glu Val Glu Asn Asp Glu Met Pro Ala Asp Leu Pro
370                 375                 380
Ser Leu Ala Ala Asp Phe Val Glu Ser Lys Asp Val Cys Lys Asn Tyr
385                 390                 395                 400
Ala Glu Ala Lys Asp Val Phe Leu Gly Met Phe Leu Tyr Glu Tyr Ala
                405                 410                 415
Arg Arg His Pro Asp Tyr Ser Val Val Leu Leu Leu Arg Leu Ala Lys
                420                 425                 430
Thr Tyr Glu Thr Thr Leu Glu Lys Cys Cys Ala Ala Ala Asp Pro His
                435                 440                 445
Glu Cys Tyr Ala Lys Val Phe Asp Glu Phe Lys Pro Leu Val Glu Glu
450                 455                 460
Pro Gln Asn Leu Ile Lys Gln Asn Cys Glu Leu Phe Glu Gln Leu Gly
465                 470                 475                 480
Glu Tyr Lys Phe Gln Asn Ala Leu Leu Val Arg Tyr Thr Lys Lys Val
                485                 490                 495
Pro Gln Val Ser Thr Pro Thr Leu Val Glu Val Ser Arg Asn Leu Gly
                500                 505                 510
Lys Val Gly Ser Lys Cys Cys Lys His Pro Glu Ala Lys Arg Met Pro
                515                 520                 525
Cys Ala Glu Asp Tyr Leu Ser Val Val Leu Asn Gln Leu Cys Val Leu
530                 535                 540
```

His Glu Lys Thr Pro Val Ser Asp Arg Val Thr Lys Cys Cys Thr Glu
545                 550                 555                 560

Ser Leu Val Asn Arg Arg Pro Cys Phe Ser Ala Leu Glu Val Asp Glu
            565                 570                 575

Thr Tyr Val Pro Lys Glu Phe Gln Ala Glu Thr Phe Thr Phe His Ala
        580                 585                 590

Asp Ile Cys Thr Leu Ser Glu Lys Glu Arg Gln Ile Lys Lys Gln Thr
    595                 600                 605

Ala Leu Val Glu Leu Val Lys His Lys Pro Lys Ala Thr Lys Glu Gln
610                 615                 620

Leu Lys Ala Val Met Asp Asp Phe Ala Ala Phe Val Glu Lys Cys Cys
625                 630                 635                 640

Lys Ala Asp Asp Lys Glu Thr Cys Phe Ala Glu Glu Gly Lys Lys Leu
            645                 650                 655

Val Ala Ala Ser Gln Ala Ala Leu Gly Leu Gly Ser Gly Gly Ser Gly
                660                 665                 670

Ser Gly His His His His His His
        675                 680

<210> SEQ ID NO 70
<211> LENGTH: 1077
<212> TYPE: PRT
<213> ORGANISM: Artificial Sequence
<220> FEATURE:
<223> OTHER INFORMATION: Synthetic construct

<400> SEQUENCE: 70

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Tyr Phe Asn Lys Pro Thr Gly Tyr Gly Ser Ser Ser
        35                  40                  45

Arg Ala Pro Gln Thr Gly Ile Val Asp Glu Cys Cys Phe Arg Ser Cys
50                  55                  60

Asp Leu Arg Arg Leu Glu Met Tyr Cys Ala Pro Leu Lys Pro Ala Gly
65                  70                  75                  80

Ser Gly Gly Ser Gly Gly Gly Ser Gly Gly Ser Gly Gly Gly Ser
            85                  90                  95

Gly Gly Gly Ser Gly Gly Gly Ser Gly Gly Gly Ser Gly Gly Gly Ser
            100                 105                 110

Gly Gly Gly Ser Gly Gly Gly Asp Ala His Lys Ser Glu Val Ala His
            115                 120                 125

Arg Phe Lys Asp Leu Gly Glu Glu Asn Phe Lys Ala Leu Val Leu Ile
130                 135                 140

Ala Phe Ala Gln Tyr Leu Gln Gln Ser Pro Phe Glu Asp His Val Lys
145                 150                 155                 160

Leu Val Asn Glu Val Thr Glu Phe Ala Lys Thr Cys Val Ala Asp Glu
            165                 170                 175

Ser Ala Glu Asn Cys Asp Lys Ser Leu His Thr Leu Phe Gly Asp Lys
        180                 185                 190

Leu Cys Thr Val Ala Thr Leu Arg Glu Thr Tyr Gly Glu Met Ala Asp
    195                 200                 205

Cys Cys Ala Lys Gln Glu Pro Glu Arg Asn Glu Cys Phe Leu Gln His
210                 215                 220

```
Lys Asp Asp Asn Pro Asn Leu Pro Arg Leu Val Arg Pro Glu Val Asp
225                 230                 235                 240

Val Met Cys Thr Ala Phe His Asp Asn Glu Glu Thr Phe Leu Lys Lys
            245                 250                 255

Tyr Leu Tyr Glu Ile Ala Arg Arg His Pro Tyr Phe Tyr Ala Pro Glu
        260                 265                 270

Leu Leu Phe Phe Ala Lys Arg Tyr Lys Ala Ala Phe Thr Glu Cys Cys
    275                 280                 285

Gln Ala Ala Asp Lys Ala Ala Cys Leu Leu Pro Lys Leu Asp Glu Leu
290                 295                 300

Arg Asp Glu Gly Lys Ala Ser Ser Ala Lys Gln Arg Leu Lys Cys Ala
305                 310                 315                 320

Ser Leu Gln Lys Phe Gly Glu Arg Ala Phe Lys Ala Trp Ala Val Ala
            325                 330                 335

Arg Leu Ser Gln Arg Phe Pro Lys Ala Glu Phe Ala Glu Val Ser Lys
            340                 345                 350

Leu Val Thr Asp Leu Thr Lys Val His Thr Glu Cys Cys His Gly Asp
        355                 360                 365

Leu Leu Glu Cys Ala Asp Asp Arg Ala Asp Leu Ala Lys Tyr Ile Cys
    370                 375                 380

Glu Asn Gln Asp Ser Ile Ser Ser Lys Leu Lys Glu Cys Cys Glu Lys
385                 390                 395                 400

Pro Leu Leu Glu Lys Ser His Cys Ile Ala Glu Val Glu Asn Asp Glu
                405                 410                 415

Met Pro Ala Asp Leu Pro Ser Leu Ala Ala Asp Phe Val Glu Ser Lys
            420                 425                 430

Asp Val Cys Lys Asn Tyr Ala Glu Ala Lys Asp Val Phe Leu Gly Met
            435                 440                 445

Phe Leu Tyr Glu Tyr Ala Arg Arg His Pro Asp Tyr Ser Val Val Leu
    450                 455                 460

Leu Leu Arg Leu Ala Lys Thr Tyr Glu Thr Thr Leu Glu Lys Cys Cys
465                 470                 475                 480

Ala Ala Ala Asp Pro His Glu Cys Tyr Ala Lys Val Phe Asp Glu Phe
            485                 490                 495

Lys Pro Leu Val Glu Glu Pro Gln Asn Leu Ile Lys Gln Asn Cys Glu
            500                 505                 510

Leu Phe Glu Gln Leu Gly Glu Tyr Lys Phe Gln Asn Ala Leu Leu Val
        515                 520                 525

Arg Tyr Thr Lys Lys Val Pro Gln Val Ser Thr Pro Thr Leu Val Glu
530                 535                 540

Val Ser Arg Asn Leu Gly Lys Val Gly Ser Lys Cys Cys Lys His Pro
545                 550                 555                 560

Glu Ala Lys Arg Met Pro Cys Ala Glu Asp Tyr Leu Ser Val Val Leu
                565                 570                 575

Asn Gln Leu Cys Val Leu His Glu Lys Thr Pro Val Ser Asp Arg Val
            580                 585                 590

Thr Lys Cys Cys Thr Glu Ser Leu Val Asn Arg Arg Pro Cys Phe Ser
            595                 600                 605

Ala Leu Glu Val Asp Glu Thr Tyr Val Pro Lys Glu Phe Gln Ala Glu
        610                 615                 620

Thr Phe Thr Phe His Ala Asp Ile Cys Thr Leu Ser Glu Lys Glu Arg
625                 630                 635                 640

Gln Ile Lys Lys Gln Thr Ala Leu Val Glu Leu Val Lys His Lys Pro
```

-continued

```
                645                 650                 655
Lys Ala Thr Lys Glu Gln Leu Lys Ala Val Met Asp Asp Phe Ala Ala
            660                 665                 670

Phe Val Glu Lys Cys Cys Lys Ala Asp Asp Lys Glu Thr Cys Phe Ala
            675                 680                 685

Glu Glu Gly Lys Lys Leu Val Ala Ala Ser Gln Ala Ala Leu Gly Leu
            690                 695                 700

Gly Ser Gly Gly Ser Gly Gly Gly Ser Gly Gly Gly Ser Gly Gly Gly
705                 710                 715                 720

Ser Gly Gly Gly Ser Gly Gly Gly Ser Gly Gly Gly Ser Gly Gly Gly
            725                 730                 735

Ser Gly Gly Gly Ser Gly Gly Gly Ala Gln Val Leu Arg Gly Thr Val
            740                 745                 750

Thr Asp Phe Pro Gly Phe Asp Glu Arg Ala Asp Ala Glu Thr Leu Arg
            755                 760                 765

Lys Ala Met Lys Gly Leu Gly Thr Asp Glu Glu Ser Ile Leu Thr Leu
            770                 775                 780

Leu Thr Ser Arg Ser Asn Ala Gln Arg Gln Glu Ile Ser Ala Ala Phe
785                 790                 795                 800

Lys Thr Leu Phe Gly Arg Asp Leu Leu Asp Asp Leu Lys Ser Glu Leu
                805                 810                 815

Thr Gly Lys Phe Glu Lys Leu Ile Val Ala Leu Met Lys Pro Ser Arg
                820                 825                 830

Leu Tyr Asp Ala Tyr Glu Leu Lys His Ala Leu Lys Gly Ala Gly Thr
                835                 840                 845

Asn Glu Lys Val Leu Thr Glu Ile Ile Ala Ser Arg Thr Pro Glu Glu
850                 855                 860

Leu Arg Ala Ile Lys Gln Val Tyr Glu Glu Tyr Gly Ser Ser Leu
865                 870                 875                 880

Glu Asp Asp Val Val Gly Asp Thr Ser Gly Tyr Tyr Gln Arg Met Leu
                885                 890                 895

Val Val Leu Leu Gln Ala Asn Arg Asp Pro Asp Ala Gly Ile Asp Glu
                900                 905                 910

Ala Gln Val Glu Gln Asp Ala Gln Ala Leu Phe Gln Ala Gly Glu Leu
                915                 920                 925

Lys Trp Gly Thr Asp Glu Glu Lys Phe Ile Thr Ile Phe Gly Thr Arg
                930                 935                 940

Ser Val Ser His Leu Arg Lys Val Phe Asp Lys Tyr Met Thr Ile Ser
945                 950                 955                 960

Gly Phe Gln Ile Glu Glu Thr Ile Asp Arg Glu Thr Ser Gly Asn Leu
                965                 970                 975

Glu Gln Leu Leu Leu Ala Val Val Lys Ser Ile Arg Ser Ile Pro Ala
                980                 985                 990

Tyr Leu Ala Glu Thr Leu Tyr Tyr Ala Met Lys Gly Ala Gly Thr Asp
                995                1000                1005

Asp His Thr Leu Ile Arg Val Met Val Ser Arg Ser Glu Ile Asp
            1010                1015                1020

Leu Phe Asn Ile Arg Lys Glu Phe Arg Lys Asn Phe Ala Thr Ser
            1025                1030                1035

Leu Tyr Ser Met Ile Lys Gly Asp Thr Ser Gly Asp Tyr Lys Lys
            1040                1045                1050

Ala Leu Leu Leu Leu Ser Gly Glu Asp Asp Gly Ser Gly Gly Ser
            1055                1060                1065
```

Gly Ser Gly His His His His His His
    1070            1075

<210> SEQ ID NO 71
<211> LENGTH: 708
<212> TYPE: PRT
<213> ORGANISM: Artificial Sequence
<220> FEATURE:
<223> OTHER INFORMATION: Synthetic construct

<400> SEQUENCE: 71

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Tyr Phe Asn Lys Pro Thr Gly Tyr Gly Ser Ser Ser
        35                  40                  45

Arg Arg Ala Pro Gln Thr Gly Ile Val Asp Glu Cys Cys Phe Arg Ser
    50                  55                  60

Cys Asp Leu Arg Arg Leu Glu Met Tyr Cys Ala Pro Leu Lys Pro Ala
65                  70                  75                  80

Lys Ser Ala Gly Ser Gly Gly Ser Gly Gly Ser Gly Gly Gly Gly Ser
                85                  90                  95

Gly Gly Gly Ser Gly Gly Gly Ser Gly Gly Gly Ser Gly Gly Gly Ser
            100                 105                 110

Gly Gly Gly Ser Gly Gly Gly Ser Gly Gly Gly Asp Lys Thr His Thr
        115                 120                 125

Cys Pro Pro Cys Pro Ala Pro Glu Leu Leu Gly Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Gln Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Gly Ser Gly
            340                 345                 350

Gly Ser Gly Gly Gly Ser Gly Gly Gly Ser Gly Gly
        355                 360                 365

Gly Ser Gly Gly Gly Ser Gly Gly Gly Ser Gly Gly
        370                 375                 380

Gly Ser Gly Gly Gly Ala Gln Val Leu Arg Gly Thr Val Thr Asp Phe
385                 390                 395                 400

Pro Gly Phe Asp Glu Arg Ala Asp Ala Glu Thr Leu Arg Lys Ala Met
                405                 410                 415

Lys Gly Leu Gly Thr Asp Glu Glu Ser Ile Leu Thr Leu Leu Thr Ser
            420                 425                 430

Arg Ser Asn Ala Gln Arg Gln Glu Ile Ser Ala Ala Phe Lys Thr Leu
        435                 440                 445

Phe Gly Arg Asp Leu Leu Asp Asp Leu Lys Ser Glu Leu Thr Gly Lys
    450                 455                 460

Phe Glu Lys Leu Ile Val Ala Leu Met Lys Pro Ser Arg Leu Tyr Asp
465                 470                 475                 480

Ala Tyr Glu Leu Lys His Ala Leu Lys Gly Ala Gly Thr Asn Glu Lys
                485                 490                 495

Val Leu Thr Glu Ile Ile Ala Ser Arg Thr Pro Glu Glu Leu Arg Ala
            500                 505                 510

Ile Lys Gln Val Tyr Glu Glu Tyr Gly Ser Ser Leu Glu Asp Asp
        515                 520                 525

Val Val Gly Asp Thr Ser Gly Tyr Tyr Gln Arg Met Leu Val Val Leu
    530                 535                 540

Leu Gln Ala Asn Arg Asp Pro Asp Ala Gly Ile Asp Glu Ala Gln Val
545                 550                 555                 560

Glu Gln Asp Ala Gln Ala Leu Phe Gln Ala Gly Glu Leu Lys Trp Gly
                565                 570                 575

Thr Asp Glu Glu Lys Phe Ile Thr Ile Phe Gly Thr Arg Ser Val Ser
            580                 585                 590

His Leu Arg Lys Val Phe Asp Lys Tyr Met Thr Ile Ser Gly Phe Gln
        595                 600                 605

Ile Glu Glu Thr Ile Asp Arg Glu Thr Ser Gly Asn Leu Glu Gln Leu
    610                 615                 620

Leu Leu Ala Val Val Lys Ser Ile Arg Ser Ile Pro Ala Tyr Leu Ala
625                 630                 635                 640

Glu Thr Leu Tyr Tyr Ala Met Lys Gly Ala Gly Thr Asp Asp His Thr
                645                 650                 655

Leu Ile Arg Val Met Val Ser Arg Ser Glu Ile Asp Leu Phe Asn Ile
            660                 665                 670

Arg Lys Glu Phe Arg Lys Asn Phe Ala Thr Ser Leu Tyr Ser Met Ile
        675                 680                 685

Lys Gly Asp Thr Ser Gly Asp Tyr Lys Lys Ala Leu Leu Leu Leu Ser
    690                 695                 700

Gly Glu Asp Asp
705

<210> SEQ ID NO 72
<211> LENGTH: 345
<212> TYPE: PRT
<213> ORGANISM: Artificial Sequence
<220> FEATURE:
<223> OTHER INFORMATION: Synthetic construct

<400> SEQUENCE: 72

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Tyr Phe Asn Lys Pro Thr Gly Tyr Gly Ser Ser Ser
            35                  40                  45

Arg Ala Pro Gln Thr Gly Ile Val Asp Glu Cys Cys Phe Arg Ser Cys
50                  55                  60

Asp Leu Arg Arg Leu Glu Met Tyr Cys Ala Pro Leu Lys Pro Ala Gly
65                  70                  75                  80

Ser Gly Gly Ser Gly Gly Ser Gly Gly Ser Gly Gly Ser
                85                  90                  95

Gly Gly Gly Ser Gly Gly Gly Ser Gly Gly Gly Ser Gly Gly Gly Ser
                100                 105                 110

Gly Gly Gly Ser Gly Gly Gly Asp Lys Thr His Thr Cys Pro Pro Cys
                115                 120                 125

Pro Ala Pro Glu Leu Leu Gly Gly Pro Ser Val Phe Leu Phe Pro Pro
            130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
                180                 185                 190

Glu Gln Tyr Gln Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
            245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
            290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly
            340                 345

<210> SEQ ID NO 73
<211> LENGTH: 1017
<212> TYPE: PRT
<213> ORGANISM: Artificial Sequence
<220> FEATURE:
<223> OTHER INFORMATION: Synthetic construct

<400> SEQUENCE: 73

Met Phe Pro Ala Met Pro Leu Ser Ser Leu Phe Val Asn Gly Pro Arg
1               5                   10                  15

```
Thr Leu Cys Gly Ala Glu Leu Val Asp Ala Leu Gln Phe Val Cys Gly
         20                  25                  30

Asp Arg Gly Phe Tyr Phe Asn Lys Pro Thr Gly Tyr Gly Ser Ser Ser
     35                  40                  45

Arg Arg Ala Pro Gln Thr Gly Ile Val Asp Glu Cys Cys Phe Arg Ser
 50                  55                  60

Cys Asp Leu Arg Arg Leu Glu Met Tyr Cys Ala Pro Leu Lys Pro Ala
 65                  70                  75                  80

Lys Ser Ala Gly Ser Gly Ser Gly Gly Ser Gly Gly Ser Gly
                 85                  90                  95

Gly Gly Asp Ala His Lys Ser Glu Val Ala His Arg Phe Lys Asp Leu
             100                 105                 110

Gly Glu Glu Asn Phe Lys Ala Leu Val Leu Ile Ala Phe Ala Gln Tyr
             115                 120                 125

Leu Gln Gln Ser Pro Phe Glu Asp His Val Lys Leu Val Asn Glu Val
130                 135                 140

Thr Glu Phe Ala Lys Thr Cys Val Ala Asp Glu Ser Ala Glu Asn Cys
145                 150                 155                 160

Asp Lys Ser Leu His Thr Leu Phe Gly Asp Lys Leu Cys Thr Val Ala
                 165                 170                 175

Thr Leu Arg Glu Thr Tyr Gly Glu Met Ala Asp Cys Cys Ala Lys Gln
             180                 185                 190

Glu Pro Glu Arg Asn Glu Cys Phe Leu Gln His Lys Asp Asp Asn Pro
             195                 200                 205

Asn Leu Pro Arg Leu Val Arg Pro Glu Val Asp Val Met Cys Thr Ala
         210                 215                 220

Phe His Asp Asn Glu Glu Thr Phe Leu Lys Lys Tyr Leu Tyr Glu Ile
225                 230                 235                 240

Ala Arg Arg His Pro Tyr Phe Tyr Ala Pro Glu Leu Leu Phe Phe Ala
                 245                 250                 255

Lys Arg Tyr Lys Ala Ala Phe Thr Glu Cys Cys Gln Ala Ala Asp Lys
             260                 265                 270

Ala Ala Cys Leu Leu Pro Lys Leu Asp Glu Leu Arg Asp Glu Gly Lys
             275                 280                 285

Ala Ser Ser Ala Lys Gln Arg Leu Lys Cys Ala Ser Leu Gln Lys Phe
         290                 295                 300

Gly Glu Arg Ala Phe Lys Ala Trp Ala Val Ala Arg Leu Ser Gln Arg
305                 310                 315                 320

Phe Pro Lys Ala Glu Phe Ala Glu Val Ser Lys Leu Val Thr Asp Leu
                 325                 330                 335

Thr Lys Val His Thr Glu Cys Cys His Gly Asp Leu Leu Glu Cys Ala
             340                 345                 350

Asp Asp Arg Ala Asp Leu Ala Lys Tyr Ile Cys Glu Asn Gln Asp Ser
             355                 360                 365

Ile Ser Ser Lys Leu Lys Glu Cys Cys Glu Lys Pro Leu Leu Glu Lys
         370                 375                 380

Ser His Cys Ile Ala Glu Val Glu Asn Asp Glu Met Pro Ala Asp Leu
385                 390                 395                 400

Pro Ser Leu Ala Ala Asp Phe Val Glu Ser Lys Asp Val Cys Lys Asn
                 405                 410                 415

Tyr Ala Glu Ala Lys Asp Val Phe Leu Gly Met Phe Leu Tyr Glu Tyr
             420                 425                 430
```

-continued

```
Ala Arg Arg His Pro Asp Tyr Ser Val Val Leu Leu Arg Leu Ala
        435                 440                 445
Lys Thr Tyr Glu Thr Thr Leu Glu Lys Cys Cys Ala Ala Ala Asp Pro
450                 455                 460
His Glu Cys Tyr Ala Lys Val Phe Asp Glu Phe Lys Pro Leu Val Glu
465                 470                 475                 480
Glu Pro Gln Asn Leu Ile Lys Gln Asn Cys Glu Leu Phe Glu Gln Leu
                485                 490                 495
Gly Glu Tyr Lys Phe Gln Asn Ala Leu Leu Val Arg Tyr Thr Lys Lys
            500                 505                 510
Val Pro Gln Val Ser Thr Pro Thr Leu Val Glu Val Ser Arg Asn Leu
        515                 520                 525
Gly Lys Val Gly Ser Lys Cys Cys Lys His Pro Glu Ala Lys Arg Met
530                 535                 540
Pro Cys Ala Glu Asp Tyr Leu Ser Val Val Leu Asn Gln Leu Cys Val
545                 550                 555                 560
Leu His Glu Lys Thr Pro Val Ser Asp Arg Val Thr Lys Cys Cys Thr
                565                 570                 575
Glu Ser Leu Val Asn Arg Arg Pro Cys Phe Ser Ala Leu Glu Val Asp
            580                 585                 590
Glu Thr Tyr Val Pro Lys Glu Phe Gln Ala Glu Thr Phe Thr Phe His
        595                 600                 605
Ala Asp Ile Cys Thr Leu Ser Glu Lys Glu Arg Gln Ile Lys Lys Gln
610                 615                 620
Thr Ala Leu Val Glu Leu Val Lys His Lys Pro Lys Ala Thr Lys Glu
625                 630                 635                 640
Gln Leu Lys Ala Val Met Asp Asp Phe Ala Ala Phe Val Glu Lys Cys
                645                 650                 655
Cys Lys Ala Asp Asp Lys Glu Thr Cys Phe Ala Glu Glu Gly Lys Lys
            660                 665                 670
Leu Val Ala Ala Ser Gln Ala Ala Leu Gly Leu Gly Ser Gly Gly Ser
        675                 680                 685
Gly Gly Gly Ser Gly Gly Ser Gly Gly Gly Ala Gln Val Leu Arg Gly
690                 695                 700
Thr Val Thr Asp Phe Pro Gly Phe Asp Glu Arg Ala Asp Ala Glu Thr
705                 710                 715                 720
Leu Arg Lys Ala Met Lys Gly Leu Gly Thr Asp Glu Glu Ser Ile Leu
                725                 730                 735
Thr Leu Leu Thr Ser Arg Ser Asn Ala Gln Arg Gln Glu Ile Ser Ala
            740                 745                 750
Ala Phe Lys Thr Leu Phe Gly Arg Asp Leu Leu Asp Asp Leu Lys Ser
        755                 760                 765
Glu Leu Thr Gly Lys Phe Glu Lys Leu Ile Val Ala Leu Met Lys Pro
770                 775                 780
Ser Arg Leu Tyr Asp Ala Tyr Glu Leu Lys His Ala Leu Lys Gly Ala
785                 790                 795                 800
Gly Thr Asn Glu Lys Val Leu Thr Glu Ile Ile Ala Ser Arg Thr Pro
                805                 810                 815
Glu Glu Leu Arg Ala Ile Lys Gln Val Tyr Glu Glu Tyr Gly Ser
            820                 825                 830
Ser Leu Glu Asp Asp Val Val Gly Asp Thr Ser Gly Tyr Tyr Gln Arg
        835                 840                 845
Met Leu Val Val Leu Leu Gln Ala Asn Arg Asp Pro Asp Ala Gly Ile
```

```
                    850                 855                 860
Asp Glu Ala Gln Val Glu Gln Asp Ala Gln Ala Leu Phe Gln Ala Gly
865                 870                 875                 880

Glu Leu Lys Trp Gly Thr Asp Glu Glu Lys Phe Ile Thr Ile Phe Gly
                885                 890                 895

Thr Arg Ser Val Ser His Leu Arg Lys Val Phe Asp Lys Tyr Met Thr
            900                 905                 910

Ile Ser Gly Phe Gln Ile Glu Gly Thr Ile Asp Arg Glu Thr Ser Gly
        915                 920                 925

Asn Leu Glu Gln Leu Leu Ala Val Val Lys Ser Ile Arg Ser Ile
    930                 935                 940

Pro Ala Tyr Leu Ala Glu Thr Leu Tyr Tyr Ala Met Lys Gly Ala Gly
945                 950                 955                 960

Thr Asp Asp His Thr Leu Ile Arg Val Met Val Ser Arg Ser Glu Ile
                965                 970                 975

Asp Leu Phe Asn Ile Arg Lys Glu Phe Arg Lys Asn Phe Ala Thr Ser
            980                 985                 990

Leu Tyr Ser Met Ile Lys Gly Asp  Thr Ser Gly Asp Tyr  Lys Lys Ala
        995                1000                1005

Leu Leu  Leu Leu Cys Gly Glu  Asp Asp
    1010                1015
```

<210> SEQ ID NO 74
<211> LENGTH: 1017
<212> TYPE: PRT
<213> ORGANISM: Artificial Sequence
<220> FEATURE:
<223> OTHER INFORMATION: Synthetic construct

<400> SEQUENCE: 74

```
Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Tyr Phe Asn Lys Pro Thr Gly Tyr Gly Ser Ser Ser
        35                  40                  45

Arg Arg Ala Pro Gln Thr Gly Ile Val Asp Glu Cys Cys Phe Arg Ser
    50                  55                  60

Cys Asp Leu Arg Arg Leu Glu Met Tyr Cys Ala Pro Leu Lys Pro Ala
65                  70                  75                  80

Lys Ser Ala Gly Ser Gly Gly Ser Gly Gly Ser Gly Gly Ser Gly
            85                  90                  95

Gly Gly Asp Ala His Lys Ser Glu Val Ala His Arg Phe Lys Asp Leu
        100                 105                 110

Gly Glu Glu Asn Phe Lys Ala Leu Val Leu Ile Ala Phe Ala Gln Tyr
    115                 120                 125

Leu Gln Gln Ser Pro Phe Glu Asp His Val Lys Leu Val Asn Glu Val
130                 135                 140

Thr Glu Phe Ala Lys Thr Cys Val Ala Asp Glu Ser Ala Glu Asn Cys
145                 150                 155                 160

Asp Lys Ser Leu His Thr Leu Phe Gly Asp Lys Leu Cys Thr Val Ala
                165                 170                 175

Thr Leu Arg Glu Thr Tyr Gly Glu Met Ala Asp Cys Cys Ala Lys Gln
            180                 185                 190

Glu Pro Glu Arg Asn Glu Cys Phe Leu Gln His Lys Asp Asp Asn Pro
```

-continued

```
            195                 200                 205
Asn Leu Pro Arg Leu Val Arg Pro Glu Val Asp Val Met Cys Thr Ala
    210                 215                 220

Phe His Asp Asn Glu Glu Thr Phe Leu Lys Lys Tyr Leu Tyr Glu Ile
225                 230                 235                 240

Ala Arg Arg His Pro Tyr Phe Tyr Ala Pro Glu Leu Leu Phe Phe Ala
                245                 250                 255

Lys Arg Tyr Lys Ala Ala Phe Thr Glu Cys Cys Gln Ala Ala Asp Lys
            260                 265                 270

Ala Ala Cys Leu Leu Pro Lys Leu Asp Glu Leu Arg Asp Glu Gly Lys
        275                 280                 285

Ala Ser Ser Ala Lys Gln Arg Leu Lys Cys Ala Ser Leu Gln Lys Phe
    290                 295                 300

Gly Glu Arg Ala Phe Lys Ala Trp Ala Val Ala Arg Leu Ser Gln Arg
305                 310                 315                 320

Phe Pro Lys Ala Glu Phe Ala Glu Val Ser Lys Leu Val Thr Asp Leu
                325                 330                 335

Thr Lys Val His Thr Glu Cys Cys His Gly Asp Leu Leu Glu Cys Ala
            340                 345                 350

Asp Asp Arg Ala Asp Leu Ala Lys Tyr Ile Cys Glu Asn Gln Asp Ser
        355                 360                 365

Ile Ser Ser Lys Leu Lys Glu Cys Cys Glu Lys Pro Leu Leu Glu Lys
    370                 375                 380

Ser His Cys Ile Ala Glu Val Glu Asn Asp Glu Met Pro Ala Asp Leu
385                 390                 395                 400

Pro Ser Leu Ala Ala Asp Phe Val Glu Ser Lys Asp Val Cys Lys Asn
                405                 410                 415

Tyr Ala Glu Ala Lys Asp Val Phe Leu Gly Met Phe Leu Tyr Glu Tyr
            420                 425                 430

Ala Arg Arg His Pro Asp Tyr Ser Val Val Leu Leu Leu Arg Leu Ala
        435                 440                 445

Lys Thr Tyr Glu Thr Thr Leu Glu Lys Cys Cys Ala Ala Ala Asp Pro
    450                 455                 460

His Glu Cys Tyr Ala Lys Val Phe Asp Glu Phe Lys Pro Leu Val Glu
465                 470                 475                 480

Glu Pro Gln Asn Leu Ile Lys Gln Asn Cys Glu Leu Phe Glu Gln Leu
                485                 490                 495

Gly Glu Tyr Lys Phe Gln Asn Ala Leu Leu Val Arg Tyr Thr Lys Lys
            500                 505                 510

Val Pro Gln Val Ser Thr Pro Thr Leu Val Glu Val Ser Arg Asn Leu
        515                 520                 525

Gly Lys Val Gly Ser Lys Cys Cys Lys His Pro Glu Ala Lys Arg Met
    530                 535                 540

Pro Cys Ala Glu Asp Tyr Leu Ser Val Val Leu Asn Gln Leu Cys Val
545                 550                 555                 560

Leu His Glu Lys Thr Pro Val Ser Asp Arg Val Thr Lys Cys Cys Thr
                565                 570                 575

Glu Ser Leu Val Asn Arg Arg Pro Cys Phe Ser Ala Leu Glu Val Asp
            580                 585                 590

Glu Thr Tyr Val Pro Lys Glu Phe Gln Ala Glu Thr Phe Thr Phe His
        595                 600                 605

Ala Asp Ile Cys Thr Leu Ser Glu Lys Glu Arg Gln Ile Lys Lys Gln
    610                 615                 620
```

Thr Ala Leu Val Glu Leu Val Lys His Lys Pro Lys Ala Thr Lys Glu
625                 630                 635                 640

Gln Leu Lys Ala Val Met Asp Asp Phe Ala Ala Phe Val Glu Lys Cys
            645                 650                 655

Cys Lys Ala Asp Asp Lys Glu Thr Cys Phe Ala Glu Glu Gly Lys Lys
            660                 665                 670

Leu Val Ala Ala Ser Gln Ala Ala Leu Gly Leu Gly Ser Gly Gly Ser
            675                 680                 685

Gly Gly Gly Ser Gly Gly Ser Gly Gly Gly Ala Gln Val Leu Arg Gly
            690                 695                 700

Thr Val Thr Asp Phe Pro Gly Phe Asp Glu Arg Ala Asp Ala Glu Thr
705                 710                 715                 720

Leu Arg Lys Ala Met Lys Gly Leu Gly Thr Asp Glu Glu Ser Ile Leu
            725                 730                 735

Thr Leu Leu Thr Ser Arg Ser Asn Ala Gln Arg Gln Glu Ile Ser Ala
            740                 745                 750

Ala Phe Lys Thr Leu Phe Gly Ala Asp Leu Leu Asp Asp Leu Ala Ser
            755                 760                 765

Glu Leu Thr Gly Lys Phe Glu Lys Leu Ile Val Ala Leu Met Lys Pro
770                 775                 780

Ser Arg Leu Tyr Asp Ala Tyr Glu Leu Lys His Ala Leu Ala Gly Ala
785                 790                 795                 800

Gly Thr Asn Glu Lys Val Leu Thr Glu Ile Ile Ala Ser Arg Thr Pro
            805                 810                 815

Glu Glu Leu Arg Ala Ile Lys Gln Val Tyr Glu Glu Tyr Gly Ser
            820                 825                 830

Ser Leu Ala Gly Asp Val Val Gly Asp Thr Ser Gly Tyr Tyr Gln Arg
            835                 840                 845

Met Leu Val Val Leu Leu Gln Ala Ala Arg Asp Pro Asp Ala Gly Ile
850                 855                 860

Asp Glu Ala Gln Val Glu Gln Asp Ala Gln Ala Leu Phe Gln Ala Gly
865                 870                 875                 880

Glu Leu Lys Trp Gly Thr Asp Glu Glu Lys Phe Ile Thr Ile Phe Gly
            885                 890                 895

Thr Arg Ser Val Ser His Leu Arg Lys Val Phe Asp Lys Tyr Met Thr
            900                 905                 910

Ile Ser Gly Phe Gln Ile Glu Glu Thr Ile Asp Arg Glu Thr Ser Gly
            915                 920                 925

Asn Leu Glu Gln Leu Leu Leu Ala Val Val Lys Ser Ile Arg Ser Ile
930                 935                 940

Pro Ala Tyr Leu Ala Glu Thr Leu Tyr Tyr Ala Met Lys Gly Ala Gly
945                 950                 955                 960

Thr Asp Asp His Thr Leu Ile Arg Val Met Val Ser Arg Ser Glu Ile
            965                 970                 975

Asp Leu Phe Asn Ile Arg Lys Glu Phe Arg Lys Asn Phe Ala Thr Ser
            980                 985                 990

Leu Tyr Ser Met Ile Lys Gly Asp Thr Ser Gly Asp Tyr Lys Lys Ala
            995                 1000                1005

Leu Leu Leu Leu Cys Gly Glu Asp Asp
    1010            1015

<210> SEQ ID NO 75
<211> LENGTH: 1017

<212> TYPE: PRT
<213> ORGANISM: Artificial Sequence
<220> FEATURE:
<223> OTHER INFORMATION: Synthetic construct

<400> SEQUENCE: 75

```
Met Phe Pro Ala Met Pro Leu Ser Ser Leu Phe Val Asn Gly Pro Arg
1               5                   10                  15
Thr Leu Cys Gly Ala Glu Leu Val Asp Ala Leu Gln Phe Val Cys Gly
            20                  25                  30
Asp Arg Gly Phe Tyr Phe Asn Lys Pro Thr Gly Tyr Gly Ser Ser Ser
        35                  40                  45
Arg Arg Ala Pro Gln Thr Gly Ile Val Asp Glu Cys Cys Phe Arg Ser
50                  55                  60
Cys Asp Leu Arg Arg Leu Glu Met Tyr Cys Ala Pro Leu Lys Pro Ala
65                  70                  75                  80
Lys Ser Ala Gly Ser Gly Gly Ser Gly Gly Ser Gly Gly Ser Gly
            85                  90                  95
Gly Gly Asp Ala His Lys Ser Glu Val Ala His Arg Phe Lys Asp Leu
            100                 105                 110
Gly Glu Glu Asn Phe Lys Ala Leu Val Leu Ile Ala Phe Ala Gln Tyr
            115                 120                 125
Leu Gln Gln Ser Pro Phe Glu Asp His Val Lys Leu Val Asn Glu Val
130                 135                 140
Thr Glu Phe Ala Lys Thr Cys Val Ala Asp Glu Ser Ala Glu Asn Cys
145                 150                 155                 160
Asp Lys Ser Leu His Thr Leu Phe Gly Asp Lys Leu Cys Thr Val Ala
            165                 170                 175
Thr Leu Arg Glu Thr Tyr Gly Glu Met Ala Asp Cys Cys Ala Lys Gln
            180                 185                 190
Glu Pro Glu Arg Asn Glu Cys Phe Leu Gln His Lys Asp Asp Asn Pro
            195                 200                 205
Asn Leu Pro Arg Leu Val Arg Pro Glu Val Asp Val Met Cys Thr Ala
210                 215                 220
Phe His Asp Asn Glu Glu Thr Phe Leu Lys Lys Tyr Leu Tyr Glu Ile
225                 230                 235                 240
Ala Arg Arg His Pro Tyr Phe Tyr Ala Pro Glu Leu Leu Phe Phe Ala
            245                 250                 255
Lys Arg Tyr Lys Ala Ala Phe Thr Glu Cys Cys Gln Ala Ala Asp Lys
            260                 265                 270
Ala Ala Cys Leu Leu Pro Lys Leu Asp Glu Leu Arg Asp Glu Gly Lys
            275                 280                 285
Ala Ser Ser Ala Lys Gln Arg Leu Lys Cys Ala Ser Leu Gln Lys Phe
290                 295                 300
Gly Glu Arg Ala Phe Lys Ala Trp Ala Val Ala Arg Leu Ser Gln Arg
305                 310                 315                 320
Phe Pro Lys Ala Glu Phe Ala Glu Val Ser Lys Leu Val Thr Asp Leu
            325                 330                 335
Thr Lys Val His Thr Glu Cys Cys His Gly Asp Leu Leu Glu Cys Ala
            340                 345                 350
Asp Asp Arg Ala Asp Leu Ala Lys Tyr Ile Cys Glu Asn Gln Asp Ser
            355                 360                 365
Ile Ser Ser Lys Leu Lys Glu Cys Cys Glu Lys Pro Leu Leu Glu Lys
            370                 375                 380
```

```
Ser His Cys Ile Ala Glu Val Glu Asn Asp Glu Met Pro Ala Asp Leu
385                 390                 395                 400

Pro Ser Leu Ala Ala Asp Phe Val Glu Ser Lys Asp Val Cys Lys Asn
            405                 410                 415

Tyr Ala Glu Ala Lys Asp Val Phe Leu Gly Met Phe Leu Tyr Glu Tyr
        420                 425                 430

Ala Arg Arg His Pro Asp Tyr Ser Val Val Leu Leu Leu Arg Leu Ala
    435                 440                 445

Lys Thr Tyr Glu Thr Thr Leu Glu Lys Cys Cys Ala Ala Ala Asp Pro
    450                 455                 460

His Glu Cys Tyr Ala Lys Val Phe Asp Glu Phe Lys Pro Leu Val Glu
465                 470                 475                 480

Glu Pro Gln Asn Leu Ile Lys Gln Asn Cys Glu Leu Phe Glu Gln Leu
            485                 490                 495

Gly Glu Tyr Lys Phe Gln Asn Ala Leu Leu Val Arg Tyr Thr Lys Lys
        500                 505                 510

Val Pro Gln Val Ser Thr Pro Thr Leu Val Glu Val Ser Arg Asn Leu
        515                 520                 525

Gly Lys Val Gly Ser Lys Cys Cys Lys His Pro Glu Ala Lys Arg Met
530                 535                 540

Pro Cys Ala Glu Asp Tyr Leu Ser Val Val Leu Asn Gln Leu Cys Val
545                 550                 555                 560

Leu His Glu Lys Thr Pro Val Ser Asp Arg Val Thr Lys Cys Cys Thr
            565                 570                 575

Glu Ser Leu Val Asn Arg Arg Pro Cys Phe Ser Ala Leu Glu Val Asp
        580                 585                 590

Glu Thr Tyr Val Pro Lys Glu Phe Gln Ala Gly Thr Phe Thr Phe His
        595                 600                 605

Ala Asp Ile Cys Thr Leu Ser Glu Lys Glu Arg Gln Ile Lys Lys Gln
        610                 615                 620

Thr Ala Leu Val Glu Leu Val Lys His Lys Pro Lys Ala Thr Lys Glu
625                 630                 635                 640

Gln Leu Lys Ala Ala Met Asp Asp Phe Ala Ala Phe Val Glu Lys Cys
            645                 650                 655

Cys Lys Ala Asp Asp Lys Glu Thr Cys Phe Ala Glu Glu Gly Lys Lys
        660                 665                 670

Leu Val Ala Ala Ser Gln Ala Ala Leu Gly Leu Gly Ser Gly Gly Ser
        675                 680                 685

Gly Gly Gly Ser Gly Gly Ser Gly Gly Gly Ala Gln Val Leu Arg Gly
690                 695                 700

Thr Val Thr Asp Phe Pro Gly Phe Asp Glu Arg Ala Asp Ala Glu Thr
705                 710                 715                 720

Leu Arg Lys Ala Met Lys Gly Leu Gly Thr Asp Glu Glu Ser Ile Leu
            725                 730                 735

Thr Leu Leu Thr Ser Arg Ser Asn Ala Gln Arg Gln Glu Ile Ser Ala
        740                 745                 750

Ala Phe Lys Thr Leu Phe Gly Ala Asp Leu Leu Asp Asp Leu Ala Ser
        755                 760                 765

Glu Leu Thr Gly Lys Phe Glu Lys Leu Ile Val Ala Leu Met Lys Pro
        770                 775                 780

Ser Arg Leu Tyr Asp Ala Tyr Glu Leu Lys His Ala Leu Ala Gly Ala
785                 790                 795                 800

Gly Thr Asn Glu Lys Val Leu Thr Glu Ile Ile Ala Ser Arg Thr Pro
```

-continued

```
                805                 810                 815
Glu Glu Leu Arg Ala Ile Lys Gln Val Tyr Glu Glu Tyr Gly Ser
            820                 825                 830

Ser Leu Ala Gly Asp Val Val Gly Asp Thr Ser Gly Tyr Tyr Gln Arg
            835                 840                 845

Met Leu Val Val Leu Leu Gln Ala Ala Arg Asp Pro Asp Ala Gly Ile
    850                 855                 860

Asp Glu Ala Gln Val Glu Gln Asp Ala Gln Ala Leu Phe Gln Ala Gly
865                 870                 875                 880

Glu Leu Lys Trp Gly Thr Asp Glu Glu Lys Phe Ile Thr Ile Phe Gly
                885                 890                 895

Thr Arg Ser Val Ser His Leu Arg Lys Val Phe Asp Lys Tyr Met Thr
            900                 905                 910

Ile Ser Gly Phe Gln Ile Glu Glu Thr Ile Asp Arg Glu Thr Ser Gly
            915                 920                 925

Asn Leu Glu Gln Leu Leu Leu Ala Val Val Lys Ser Ile Arg Ser Ile
    930                 935                 940

Pro Ala Tyr Leu Ala Glu Thr Leu Tyr Tyr Ala Met Lys Gly Ala Gly
945                 950                 955                 960

Thr Asp Asp His Thr Leu Ile Arg Val Met Val Ser Arg Ser Glu Ile
                965                 970                 975

Asp Leu Phe Asn Ile Arg Lys Glu Phe Arg Lys Asn Phe Ala Thr Ser
            980                 985                 990

Leu Tyr Ser Met Ile Lys Gly Asp  Thr Ser Gly Asp Tyr  Lys Lys Ala
            995                 1000                1005

Leu Leu  Leu Leu Cys Gly Glu  Asp Asp
    1010                1015

<210> SEQ ID NO 76
<211> LENGTH: 1063
<212> TYPE: PRT
<213> ORGANISM: Artificial Sequence
<220> FEATURE:
<223> OTHER INFORMATION: Synthetic construct

<400> SEQUENCE: 76

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Tyr Phe Asn Lys Pro Thr Gly Tyr Gly Ser Ser Ser
        35                  40                  45

Arg Ala Pro Gln Thr Gly Ile Val Asp Glu Cys Cys Phe Arg Ser Cys
    50                  55                  60

Asp Leu Arg Arg Leu Glu Met Tyr Cys Ala Pro Leu Lys Pro Ala Gly
65                  70                  75                  80

Ser Gly Gly Ser Gly Gly Gly Ser Gly Gly Gly Ser Gly Gly Gly Ser
                85                  90                  95

Gly Gly Gly Ser Gly Gly Gly Ser Gly Gly Gly Ser Gly Gly Gly Ser
            100                 105                 110

Gly Gly Gly Ser Gly Gly Gly Asp Ala His Lys Ser Glu Val Ala His
        115                 120                 125

Arg Phe Lys Asp Leu Gly Glu Glu Asn Phe Lys Ala Leu Val Leu Ile
    130                 135                 140

Ala Phe Ala Gln Tyr Leu Gln Gln Ser Pro Phe Glu Asp His Val Lys
```

```
            145                 150                 155                 160
Leu Val Asn Glu Val Thr Glu Phe Ala Lys Thr Cys Val Ala Asp Glu
                165                 170                 175

Ser Ala Glu Asn Cys Asp Lys Ser Leu His Thr Leu Phe Gly Asp Lys
                180                 185                 190

Leu Cys Thr Val Ala Thr Leu Arg Glu Thr Tyr Gly Glu Met Ala Asp
                195                 200                 205

Cys Cys Ala Lys Gln Glu Pro Glu Arg Asn Glu Cys Phe Leu Gln His
    210                 215                 220

Lys Asp Asp Asn Pro Asn Leu Pro Arg Leu Val Arg Pro Glu Val Asp
225                 230                 235                 240

Val Met Cys Thr Ala Phe His Asp Asn Glu Glu Thr Phe Leu Lys Lys
                245                 250                 255

Tyr Leu Tyr Glu Ile Ala Arg Arg His Pro Tyr Phe Tyr Ala Pro Glu
                260                 265                 270

Leu Leu Phe Phe Ala Lys Arg Tyr Lys Ala Ala Phe Thr Glu Cys Cys
                275                 280                 285

Gln Ala Ala Asp Lys Ala Ala Cys Leu Leu Pro Lys Leu Asp Glu Leu
    290                 295                 300

Arg Asp Glu Gly Lys Ala Ser Ser Ala Lys Gln Arg Leu Lys Cys Ala
305                 310                 315                 320

Ser Leu Gln Lys Phe Gly Glu Arg Ala Phe Lys Ala Trp Ala Val Ala
                325                 330                 335

Arg Leu Ser Gln Arg Phe Pro Lys Ala Glu Phe Ala Glu Val Ser Lys
                340                 345                 350

Leu Val Thr Asp Leu Thr Lys Val His Thr Glu Cys Cys His Gly Asp
                355                 360                 365

Leu Leu Glu Cys Ala Asp Asp Arg Ala Asp Leu Ala Lys Tyr Ile Cys
                370                 375                 380

Glu Asn Gln Asp Ser Ile Ser Ser Lys Leu Lys Glu Cys Cys Glu Lys
385                 390                 395                 400

Pro Leu Leu Glu Lys Ser His Cys Ile Ala Glu Val Glu Asn Asp Glu
                405                 410                 415

Met Pro Ala Asp Leu Pro Ser Leu Ala Ala Asp Phe Val Glu Ser Lys
                420                 425                 430

Asp Val Cys Lys Asn Tyr Ala Glu Ala Lys Asp Val Phe Leu Gly Met
                435                 440                 445

Phe Leu Tyr Glu Tyr Ala Arg Arg His Pro Asp Tyr Ser Val Val Leu
                450                 455                 460

Leu Leu Arg Leu Ala Lys Thr Tyr Glu Thr Thr Leu Glu Lys Cys Cys
465                 470                 475                 480

Ala Ala Ala Asp Pro His Glu Cys Tyr Ala Lys Val Phe Asp Glu Phe
                485                 490                 495

Lys Pro Leu Val Glu Glu Pro Gln Asn Leu Ile Lys Gln Asn Cys Glu
                500                 505                 510

Leu Phe Glu Gln Leu Gly Glu Tyr Lys Phe Gln Asn Ala Leu Leu Val
                515                 520                 525

Arg Tyr Thr Lys Lys Val Pro Gln Val Ser Thr Pro Thr Leu Val Glu
                530                 535                 540

Val Ser Arg Asn Leu Gly Lys Val Gly Ser Lys Cys Cys Lys His Pro
545                 550                 555                 560

Glu Ala Lys Arg Met Pro Cys Ala Glu Asp Tyr Leu Ser Val Val Leu
                565                 570                 575
```

-continued

Asn Gln Leu Cys Val Leu His Glu Lys Thr Pro Val Ser Asp Arg Val
            580                 585                 590

Thr Lys Cys Cys Thr Glu Ser Leu Val Asn Arg Arg Pro Cys Phe Ser
        595                 600                 605

Ala Leu Glu Val Asp Glu Thr Tyr Val Pro Lys Glu Phe Gln Ala Glu
    610                 615                 620

Thr Phe Thr Phe His Ala Asp Ile Cys Thr Leu Ser Glu Lys Glu Arg
625                 630                 635                 640

Gln Ile Lys Lys Gln Thr Ala Leu Val Glu Leu Val Lys His Lys Pro
                645                 650                 655

Lys Ala Thr Lys Glu Gln Leu Lys Ala Val Met Asp Asp Phe Ala Ala
            660                 665                 670

Phe Val Glu Lys Cys Cys Lys Ala Asp Asp Lys Glu Thr Cys Phe Ala
        675                 680                 685

Glu Glu Gly Lys Lys Leu Val Ala Ala Ser Gln Ala Ala Leu Gly Leu
    690                 695                 700

Gly Ser Gly Gly Ser Gly Gly Gly Ser Gly Gly Gly Ser Gly Gly Gly
705                 710                 715                 720

Ser Gly Gly Gly Ser Gly Gly Gly Ser Gly Gly Gly Ser Gly Gly Gly
                725                 730                 735

Ser Gly Gly Gly Ser Gly Gly Gly Ala Gln Val Leu Arg Gly Thr Val
            740                 745                 750

Thr Asp Phe Pro Gly Phe Asp Glu Arg Ala Asp Ala Glu Thr Leu Arg
        755                 760                 765

Lys Ala Met Lys Gly Leu Gly Thr Asp Glu Glu Ser Ile Leu Thr Leu
    770                 775                 780

Leu Thr Ser Arg Ser Asn Ala Gln Arg Gln Glu Ile Ser Ala Ala Phe
785                 790                 795                 800

Lys Thr Leu Phe Gly Arg Asp Leu Leu Asp Asp Leu Lys Ser Glu Leu
                805                 810                 815

Thr Gly Lys Phe Glu Lys Leu Ile Val Ala Leu Met Lys Pro Ser Arg
            820                 825                 830

Leu Tyr Asp Ala Tyr Glu Leu Lys His Ala Leu Lys Gly Ala Gly Thr
        835                 840                 845

Asn Glu Lys Val Leu Thr Glu Ile Ile Ala Ser Arg Thr Pro Glu Glu
    850                 855                 860

Leu Arg Ala Ile Lys Gln Val Tyr Glu Glu Tyr Gly Ser Ser Leu
865                 870                 875                 880

Glu Asp Asp Val Val Gly Asp Thr Ser Gly Tyr Tyr Gln Arg Met Leu
                885                 890                 895

Val Val Leu Leu Gln Ala Asn Arg Asp Pro Asp Ala Gly Ile Asp Glu
            900                 905                 910

Ala Gln Val Glu Gln Asp Ala Gln Ala Leu Phe Gln Ala Gly Glu Leu
        915                 920                 925

Lys Trp Gly Thr Asp Glu Glu Lys Phe Ile Thr Ile Phe Gly Thr Arg
    930                 935                 940

Ser Val Ser His Leu Arg Lys Val Phe Asp Lys Tyr Met Thr Ile Ser
945                 950                 955                 960

Gly Phe Gln Ile Glu Glu Thr Ile Asp Arg Glu Thr Ser Gly Asn Leu
                965                 970                 975

Glu Gln Leu Leu Leu Ala Val Val Lys Ser Ile Arg Ser Ile Pro Ala
            980                 985                 990

-continued

Tyr Leu Ala Glu Thr Leu Tyr Tyr Ala Met Lys Gly Ala Gly Thr Asp
            995                 1000                1005

Asp His Thr Leu Ile Arg Val Met Val Ser Arg Ser Glu Ile Asp
    1010                1015                1020

Leu Phe Asn Ile Arg Lys Glu Phe Arg Lys Asn Phe Ala Thr Ser
    1025                1030                1035

Leu Tyr Ser Met Ile Lys Gly Asp Thr Ser Gly Asp Tyr Lys Lys
    1040                1045                1050

Ala Leu Leu Leu Leu Cys Gly Glu Asp Asp
    1055                1060

<210> SEQ ID NO 77
<211> LENGTH: 1017
<212> TYPE: PRT
<213> ORGANISM: Artificial Sequence
<220> FEATURE:
<223> OTHER INFORMATION: Synthetic construct

<400> SEQUENCE: 77

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Tyr Phe Asn Lys Pro Thr Gly Tyr Gly Ser Ser Ser
        35                  40                  45

Arg Arg Ala Pro Gln Thr Gly Ile Val Asp Glu Cys Cys Phe Arg Ser
    50                  55                  60

Cys Asp Leu Arg Arg Leu Glu Met Leu Cys Ala Pro Leu Lys Pro Ala
65                  70                  75                  80

Lys Ser Ala Gly Ser Gly Gly Ser Gly Gly Ser Gly Gly Ser Gly
                85                  90                  95

Gly Gly Asp Ala His Lys Ser Glu Val Ala His Arg Phe Lys Asp Leu
            100                 105                 110

Gly Glu Glu Asn Phe Lys Ala Leu Val Leu Ile Ala Phe Ala Gln Tyr
        115                 120                 125

Leu Gln Gln Ser Pro Phe Glu Asp His Val Lys Leu Val Asn Glu Val
    130                 135                 140

Thr Glu Phe Ala Lys Thr Cys Val Ala Asp Glu Ser Ala Glu Asn Cys
145                 150                 155                 160

Asp Lys Ser Leu His Thr Leu Phe Gly Asp Lys Leu Cys Thr Val Ala
                165                 170                 175

Thr Leu Arg Glu Thr Tyr Gly Glu Met Ala Asp Cys Cys Ala Lys Gln
            180                 185                 190

Glu Pro Glu Arg Asn Glu Cys Phe Leu Gln His Lys Asp Asp Asn Pro
        195                 200                 205

Asn Leu Pro Arg Leu Val Arg Pro Glu Val Asp Val Met Cys Thr Ala
    210                 215                 220

Phe His Asp Asn Glu Glu Thr Phe Leu Lys Lys Tyr Leu Tyr Glu Ile
225                 230                 235                 240

Ala Arg Arg His Pro Tyr Phe Tyr Ala Pro Glu Leu Leu Phe Phe Ala
                245                 250                 255

Lys Arg Tyr Lys Ala Ala Phe Thr Glu Cys Cys Gln Ala Ala Asp Lys
            260                 265                 270

Ala Ala Cys Leu Leu Pro Lys Leu Asp Glu Leu Arg Asp Glu Gly Lys
        275                 280                 285

```
Ala Ser Ser Ala Lys Gln Arg Leu Lys Cys Ala Ser Leu Gln Lys Phe
    290                 295                 300
Gly Glu Arg Ala Phe Lys Ala Trp Ala Val Ala Arg Leu Ser Gln Arg
305                 310                 315                 320
Phe Pro Lys Ala Glu Phe Ala Glu Val Ser Lys Leu Val Thr Asp Leu
                325                 330                 335
Thr Lys Val His Thr Glu Cys Cys His Gly Asp Leu Leu Glu Cys Ala
            340                 345                 350
Asp Asp Arg Ala Asp Leu Ala Lys Tyr Ile Cys Glu Asn Gln Asp Ser
        355                 360                 365
Ile Ser Ser Lys Leu Lys Glu Cys Cys Glu Lys Pro Leu Leu Glu Lys
370                 375                 380
Ser His Cys Ile Ala Glu Val Glu Asn Asp Glu Met Pro Ala Asp Leu
385                 390                 395                 400
Pro Ser Leu Ala Ala Asp Phe Val Glu Ser Lys Asp Val Cys Lys Asn
                405                 410                 415
Tyr Ala Glu Ala Lys Asp Val Phe Leu Gly Met Phe Leu Tyr Glu Tyr
            420                 425                 430
Ala Arg Arg His Pro Asp Tyr Ser Val Val Leu Leu Leu Arg Leu Ala
        435                 440                 445
Lys Thr Tyr Glu Thr Thr Leu Glu Lys Cys Cys Ala Ala Ala Asp Pro
450                 455                 460
His Glu Cys Tyr Ala Lys Val Phe Asp Glu Phe Lys Pro Leu Val Glu
465                 470                 475                 480
Glu Pro Gln Asn Leu Ile Lys Gln Asn Cys Glu Leu Phe Glu Gln Leu
                485                 490                 495
Gly Glu Tyr Lys Phe Gln Asn Ala Leu Leu Val Arg Tyr Thr Lys Lys
            500                 505                 510
Val Pro Gln Val Ser Thr Pro Thr Leu Val Glu Val Ser Arg Asn Leu
        515                 520                 525
Gly Lys Val Gly Ser Lys Cys Cys Lys His Pro Glu Ala Lys Arg Met
530                 535                 540
Pro Cys Ala Glu Asp Tyr Leu Ser Val Val Leu Asn Gln Leu Cys Val
545                 550                 555                 560
Leu His Glu Lys Thr Pro Val Ser Asp Arg Val Thr Lys Cys Cys Thr
                565                 570                 575
Glu Ser Leu Val Asn Arg Arg Pro Cys Phe Ser Ala Leu Glu Val Asp
            580                 585                 590
Glu Thr Tyr Val Pro Lys Glu Phe Gln Ala Gly Thr Phe Thr Phe His
        595                 600                 605
Ala Asp Ile Cys Thr Leu Ser Glu Lys Glu Arg Gln Ile Lys Lys Gln
610                 615                 620
Thr Ala Leu Val Glu Leu Val Lys His Lys Pro Lys Ala Thr Lys Glu
625                 630                 635                 640
Gln Leu Lys Ala Ala Met Asp Asp Phe Ala Ala Phe Val Glu Lys Cys
                645                 650                 655
Cys Lys Ala Asp Asp Lys Glu Thr Cys Phe Ala Glu Glu Gly Lys Lys
            660                 665                 670
Leu Val Ala Ala Ser Gln Ala Leu Gly Leu Gly Ser Gly Gly Ser
        675                 680                 685
Gly Gly Gly Ser Gly Gly Ser Gly Gly Gly Ala Gln Val Leu Arg Gly
690                 695                 700
Thr Val Thr Asp Phe Pro Gly Phe Asp Glu Arg Ala Asp Ala Glu Thr
```

```
              705                 710                 715                 720
Leu Arg Lys Ala Met Lys Gly Leu Gly Thr Asp Glu Glu Ser Ile Leu
                725                 730                 735

Thr Leu Leu Thr Ser Arg Ser Asn Ala Gln Arg Gln Glu Ile Ser Ala
                740                 745                 750

Ala Phe Lys Thr Leu Phe Gly Ala Asp Leu Leu Asp Leu Ala Ser
                755                 760                 765

Glu Leu Thr Gly Lys Phe Glu Lys Leu Ile Val Ala Leu Met Lys Pro
            770                 775                 780

Ser Arg Leu Tyr Asp Ala Tyr Glu Leu Lys His Ala Leu Ala Gly Ala
785                 790                 795                 800

Gly Thr Asn Glu Lys Val Leu Thr Glu Ile Ala Ser Arg Thr Pro
                805                 810                 815

Glu Glu Leu Arg Ala Ile Lys Gln Val Tyr Glu Glu Tyr Gly Ser
                820                 825                 830

Ser Leu Ala Gly Asp Val Val Gly Asp Thr Ser Gly Tyr Tyr Gln Arg
                835                 840                 845

Met Leu Val Val Leu Leu Gln Ala Ala Arg Asp Pro Asp Ala Gly Ile
    850                 855                 860

Asp Glu Ala Gln Val Glu Gln Asp Ala Gln Ala Leu Phe Gln Ala Gly
865                 870                 875                 880

Glu Leu Lys Trp Gly Thr Asp Glu Glu Lys Phe Ile Thr Ile Phe Gly
                885                 890                 895

Thr Arg Ser Val Ser His Leu Arg Lys Val Phe Asp Lys Tyr Met Thr
                900                 905                 910

Ile Ser Gly Phe Gln Ile Glu Glu Thr Ile Asp Arg Glu Thr Ser Gly
            915                 920                 925

Asn Leu Glu Gln Leu Leu Leu Ala Val Val Lys Ser Ile Arg Ser Ile
            930                 935                 940

Pro Ala Tyr Leu Ala Glu Thr Leu Tyr Tyr Ala Met Lys Gly Ala Gly
945                 950                 955                 960

Thr Asp Asp His Thr Leu Ile Arg Val Met Val Ser Arg Ser Glu Ile
                965                 970                 975

Asp Leu Phe Asn Ile Arg Lys Glu Phe Arg Lys Asn Phe Ala Thr Ser
                980                 985                 990

Leu Tyr Ser Met Ile Lys Gly Asp  Thr Ser Gly Asp Tyr  Lys Lys Ala
            995                 1000                1005

Leu Leu  Leu Leu Cys Gly Glu  Asp Asp
    1010                1015

<210> SEQ ID NO 78
<211> LENGTH: 1001
<212> TYPE: PRT
<213> ORGANISM: Artificial Sequence
<220> FEATURE:
<223> OTHER INFORMATION: Synthetic construct

<400> SEQUENCE: 78

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
                20                  25                  30

Asp Arg Gly Phe Tyr Phe Asn Lys Pro Thr Gly Tyr Gly Ser Ser Ser
            35                  40                  45

Arg Arg Ala Pro Gln Thr Gly Ile Val Asp Glu Cys Cys Phe Arg Ser
```

```
            50                  55                  60
Cys Asp Leu Arg Arg Leu Glu Met Tyr Cys Ala Pro Leu Lys Pro Ala
 65                      70                  75                  80

Lys Ser Ala Gly Ser Gly Gly Ser Gly Asp Ala His Lys Ser Glu
                 85                  90                  95

Val Ala His Arg Phe Lys Asp Leu Gly Glu Glu Asn Phe Lys Ala Leu
                    100                 105                 110

Val Leu Ile Ala Phe Ala Gln Tyr Leu Gln Gln Ser Pro Phe Glu Asp
                115                 120                 125

His Val Lys Leu Val Asn Glu Val Thr Glu Phe Ala Lys Thr Cys Val
            130                 135                 140

Ala Asp Glu Ser Ala Glu Asn Cys Asp Lys Ser Leu His Thr Leu Phe
145                 150                 155                 160

Gly Asp Lys Leu Cys Thr Val Ala Thr Leu Arg Glu Thr Tyr Gly Glu
                165                 170                 175

Met Ala Asp Cys Cys Ala Lys Gln Glu Pro Glu Arg Asn Glu Cys Phe
            180                 185                 190

Leu Gln His Lys Asp Asp Asn Pro Asn Leu Pro Arg Leu Val Arg Pro
        195                 200                 205

Glu Val Asp Val Met Cys Thr Ala Phe His Asp Asn Glu Glu Thr Phe
210                 215                 220

Leu Lys Lys Tyr Leu Tyr Glu Ile Ala Arg Arg His Pro Tyr Phe Tyr
225                 230                 235                 240

Ala Pro Glu Leu Leu Phe Phe Ala Lys Arg Tyr Lys Ala Ala Phe Thr
                245                 250                 255

Glu Cys Cys Gln Ala Ala Asp Lys Ala Ala Cys Leu Leu Pro Lys Leu
            260                 265                 270

Asp Glu Leu Arg Asp Glu Gly Lys Ala Ser Ser Ala Lys Gln Arg Leu
        275                 280                 285

Lys Cys Ala Ser Leu Gln Lys Phe Gly Glu Arg Ala Phe Lys Ala Trp
290                 295                 300

Ala Val Ala Arg Leu Ser Gln Arg Phe Pro Lys Ala Glu Phe Ala Glu
305                 310                 315                 320

Val Ser Lys Leu Val Thr Asp Leu Thr Lys Val His Thr Glu Cys Cys
                325                 330                 335

His Gly Asp Leu Leu Glu Cys Ala Asp Asp Arg Ala Asp Leu Ala Lys
            340                 345                 350

Tyr Ile Cys Glu Asn Gln Asp Ser Ile Ser Ser Lys Leu Lys Glu Cys
                355                 360                 365

Cys Glu Lys Pro Leu Leu Glu Lys Ser His Cys Ile Ala Glu Val Glu
        370                 375                 380

Asn Asp Glu Met Pro Ala Asp Leu Pro Ser Leu Ala Ala Asp Phe Val
385                 390                 395                 400

Glu Ser Lys Asp Val Cys Lys Asn Tyr Ala Glu Ala Lys Asp Val Phe
                405                 410                 415

Leu Gly Met Phe Leu Tyr Glu Tyr Ala Arg Arg His Pro Asp Tyr Ser
                420                 425                 430

Val Val Leu Leu Leu Arg Leu Ala Lys Thr Tyr Glu Thr Thr Leu Glu
            435                 440                 445

Lys Cys Cys Ala Ala Ala Asp Pro His Glu Cys Tyr Ala Lys Val Phe
        450                 455                 460

Asp Glu Phe Lys Pro Leu Val Glu Glu Pro Gln Asn Leu Ile Lys Gln
465                 470                 475                 480
```

```
Asn Cys Glu Leu Phe Glu Gln Leu Gly Glu Tyr Lys Phe Gln Asn Ala
            485                 490                 495

Leu Leu Val Arg Tyr Thr Lys Lys Val Pro Gln Val Ser Thr Pro Thr
        500                 505                 510

Leu Val Glu Val Ser Arg Asn Leu Gly Lys Val Gly Ser Lys Cys Cys
        515                 520                 525

Lys His Pro Glu Ala Lys Arg Met Pro Cys Ala Glu Asp Tyr Leu Ser
        530                 535                 540

Val Val Leu Asn Gln Leu Cys Val Leu His Glu Lys Thr Pro Val Ser
545                 550                 555                 560

Asp Arg Val Thr Lys Cys Cys Thr Glu Ser Leu Val Asn Arg Arg Pro
            565                 570                 575

Cys Phe Ser Ala Leu Glu Val Asp Glu Thr Tyr Val Pro Lys Glu Phe
            580                 585                 590

Gln Ala Glu Thr Phe Thr Phe His Ala Asp Ile Cys Thr Leu Ser Glu
            595                 600                 605

Lys Glu Arg Gln Ile Lys Lys Gln Thr Ala Leu Val Glu Leu Val Lys
        610                 615                 620

His Lys Pro Lys Ala Thr Lys Glu Gln Leu Lys Ala Val Met Asp Asp
625                 630                 635                 640

Phe Ala Ala Phe Val Glu Lys Cys Cys Lys Ala Asp Asp Lys Glu Thr
            645                 650                 655

Cys Phe Ala Glu Glu Gly Lys Lys Leu Val Ala Ala Ser Gln Ala Ala
            660                 665                 670

Leu Gly Leu Gly Ser Gly Gly Ser Gly Ala Gln Val Leu Arg Gly
        675                 680                 685

Thr Val Thr Asp Phe Pro Gly Phe Asp Glu Arg Ala Asp Ala Glu Thr
        690                 695                 700

Leu Arg Lys Ala Met Lys Gly Leu Gly Thr Asp Glu Glu Ser Ile Leu
705                 710                 715                 720

Thr Leu Leu Thr Ser Arg Ser Asn Ala Gln Arg Gln Glu Ile Ser Ala
            725                 730                 735

Ala Phe Lys Thr Leu Phe Gly Arg Asp Leu Leu Asp Asp Leu Lys Ser
            740                 745                 750

Glu Leu Thr Gly Lys Phe Glu Lys Leu Ile Val Ala Leu Met Lys Pro
        755                 760                 765

Ser Arg Leu Tyr Asp Ala Tyr Glu Leu Lys His Ala Leu Lys Gly Ala
        770                 775                 780

Gly Thr Asn Glu Lys Val Leu Thr Glu Ile Ile Ala Ser Arg Thr Pro
785                 790                 795                 800

Glu Glu Leu Arg Ala Ile Lys Gln Val Tyr Glu Glu Glu Tyr Gly Ser
            805                 810                 815

Ser Leu Glu Asp Asp Val Val Gly Asp Thr Ser Gly Tyr Tyr Gln Arg
            820                 825                 830

Met Leu Val Val Leu Leu Gln Ala Asn Arg Asp Pro Asp Ala Gly Ile
            835                 840                 845

Asp Glu Ala Gln Val Glu Gln Asp Ala Gln Ala Leu Phe Gln Ala Gly
        850                 855                 860

Glu Leu Lys Trp Gly Thr Asp Glu Glu Lys Phe Ile Thr Ile Phe Gly
865                 870                 875                 880

Thr Arg Ser Val Ser His Leu Arg Lys Val Phe Asp Lys Tyr Met Thr
            885                 890                 895
```

-continued

```
Ile Ser Gly Phe Gln Ile Glu Glu Thr Ile Asp Arg Glu Thr Ser Gly
            900                 905                 910

Asn Leu Glu Gln Leu Leu Leu Ala Val Val Lys Ser Ile Arg Ser Ile
        915                 920                 925

Pro Ala Tyr Leu Ala Glu Thr Leu Tyr Ala Met Lys Gly Ala Gly
        930                 935                 940

Thr Asp Asp His Thr Leu Ile Arg Val Met Val Ser Arg Ser Glu Ile
945                 950                 955                 960

Asp Leu Phe Asn Ile Arg Lys Glu Phe Arg Lys Asn Phe Ala Thr Ser
                965                 970                 975

Leu Tyr Ser Met Ile Lys Gly Asp Thr Ser Gly Asp Tyr Lys Lys Ala
            980                 985                 990

Leu Leu Leu Leu Cys Gly Glu Asp  Asp
        995                 1000
```

<210> SEQ ID NO 79
<211> LENGTH: 1013
<212> TYPE: PRT
<213> ORGANISM: Artificial Sequence
<220> FEATURE:
<223> OTHER INFORMATION: Synthetic construct

<400> SEQUENCE: 79

```
Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Tyr Phe Asn Lys Pro Thr Gly Tyr Gly Ser Ser Ser
        35                  40                  45

Arg Ala Pro Gln Thr Gly Ile Val Asp Glu Cys Cys Phe Arg Ser Cys
50                  55                  60

Asp Leu Arg Arg Leu Glu Met Tyr Cys Ala Pro Leu Lys Pro Ala Gly
65                  70                  75                  80

Ser Gly Gly Ser Gly Gly Gly Ser Gly Gly Ser Gly Gly Gly Asp Ala
            85                  90                  95

His Lys Ser Glu Val Ala His Arg Phe Lys Asp Leu Gly Glu Glu Asn
            100                 105                 110

Phe Lys Ala Leu Val Leu Ile Ala Phe Ala Gln Tyr Leu Gln Gln Ser
        115                 120                 125

Pro Phe Glu Asp His Val Lys Leu Val Asn Glu Val Thr Glu Phe Ala
    130                 135                 140

Lys Thr Cys Val Ala Asp Glu Ser Ala Glu Asn Cys Asp Lys Ser Leu
145                 150                 155                 160

His Thr Leu Phe Gly Asp Lys Leu Cys Thr Val Ala Thr Leu Arg Glu
                165                 170                 175

Thr Tyr Gly Glu Met Ala Asp Cys Cys Ala Lys Gln Glu Pro Glu Arg
            180                 185                 190

Asn Glu Cys Phe Leu Gln His Lys Asp Asp Asn Pro Asn Leu Pro Arg
        195                 200                 205

Leu Val Arg Pro Glu Val Asp Val Met Cys Thr Ala Phe His Asp Asn
    210                 215                 220

Glu Glu Thr Phe Leu Lys Lys Tyr Leu Tyr Glu Ile Ala Arg Arg His
225                 230                 235                 240

Pro Tyr Phe Tyr Ala Pro Glu Leu Leu Phe Phe Ala Lys Arg Tyr Lys
                245                 250                 255
```

```
Ala Ala Phe Thr Glu Cys Cys Gln Ala Ala Asp Lys Ala Ala Cys Leu
            260                 265                 270

Leu Pro Lys Leu Asp Glu Leu Arg Asp Glu Gly Lys Ala Ser Ser Ala
        275                 280                 285

Lys Gln Arg Leu Lys Cys Ala Ser Leu Gln Lys Phe Gly Glu Arg Ala
    290                 295                 300

Phe Lys Ala Trp Ala Val Ala Arg Leu Ser Gln Arg Phe Pro Lys Ala
305                 310                 315                 320

Glu Phe Ala Glu Val Ser Lys Leu Val Thr Asp Leu Thr Lys Val His
                325                 330                 335

Thr Glu Cys Cys His Gly Asp Leu Leu Glu Cys Ala Asp Asp Arg Ala
            340                 345                 350

Asp Leu Ala Lys Tyr Ile Cys Glu Asn Gln Asp Ser Ile Ser Ser Lys
        355                 360                 365

Leu Lys Glu Cys Cys Glu Lys Pro Leu Leu Glu Lys Ser His Cys Ile
    370                 375                 380

Ala Glu Val Glu Asn Asp Glu Met Pro Ala Asp Leu Pro Ser Leu Ala
385                 390                 395                 400

Ala Asp Phe Val Glu Ser Lys Asp Val Cys Lys Asn Tyr Ala Glu Ala
                405                 410                 415

Lys Asp Val Phe Leu Gly Met Phe Leu Tyr Glu Tyr Ala Arg Arg His
            420                 425                 430

Pro Asp Tyr Ser Val Val Leu Leu Arg Leu Ala Lys Thr Tyr Glu
        435                 440                 445

Thr Thr Leu Glu Lys Cys Cys Ala Ala Ala Asp Pro His Glu Cys Tyr
    450                 455                 460

Ala Lys Val Phe Asp Glu Phe Lys Pro Leu Val Glu Glu Pro Gln Asn
465                 470                 475                 480

Leu Ile Lys Gln Asn Cys Glu Leu Phe Glu Gln Leu Gly Glu Tyr Lys
                485                 490                 495

Phe Gln Asn Ala Leu Leu Val Arg Tyr Thr Lys Lys Val Pro Gln Val
            500                 505                 510

Ser Thr Pro Thr Leu Val Glu Val Ser Arg Asn Leu Gly Lys Val Gly
        515                 520                 525

Ser Lys Cys Cys Lys His Pro Glu Ala Lys Arg Met Pro Cys Ala Glu
    530                 535                 540

Asp Tyr Leu Ser Val Val Leu Asn Gln Leu Cys Val Leu His Glu Lys
545                 550                 555                 560

Thr Pro Val Ser Asp Arg Val Thr Lys Cys Cys Thr Glu Ser Leu Val
                565                 570                 575

Asn Arg Arg Pro Cys Phe Ser Ala Leu Glu Val Asp Glu Thr Tyr Val
            580                 585                 590

Pro Lys Glu Phe Gln Ala Gly Thr Phe Thr Phe His Ala Asp Ile Cys
        595                 600                 605

Thr Leu Ser Glu Lys Glu Arg Gln Ile Lys Lys Gln Thr Ala Leu Val
    610                 615                 620

Glu Leu Val Lys His Lys Pro Lys Ala Thr Lys Glu Gln Leu Lys Ala
625                 630                 635                 640

Ala Met Asp Asp Phe Ala Ala Phe Val Glu Lys Cys Cys Lys Ala Asp
                645                 650                 655

Asp Lys Glu Thr Cys Phe Ala Glu Glu Gly Lys Lys Leu Val Ala Ala
            660                 665                 670

Ser Gln Ala Ala Leu Gly Leu Gly Ser Gly Gly Ser Gly Gly Gly Ser
```

```
                675                 680                 685
Gly Gly Ser Gly Gly Gly Ala Gln Val Leu Arg Gly Thr Val Thr Asp
            690                 695                 700

Phe Pro Gly Phe Asp Glu Arg Ala Asp Ala Glu Thr Leu Arg Lys Ala
705                 710                 715                 720

Met Lys Gly Leu Gly Thr Asp Glu Glu Ser Ile Leu Thr Leu Leu Thr
                725                 730                 735

Ser Arg Ser Asn Ala Gln Arg Gln Glu Ile Ser Ala Ala Phe Lys Thr
            740                 745                 750

Leu Phe Gly Ala Asp Leu Leu Asp Asp Leu Ala Ser Glu Leu Thr Gly
        755                 760                 765

Lys Phe Glu Lys Leu Ile Val Ala Leu Met Lys Pro Ser Arg Leu Tyr
770                 775                 780

Asp Ala Tyr Glu Leu Lys His Ala Leu Ala Gly Ala Gly Thr Asn Glu
785                 790                 795                 800

Lys Val Leu Thr Glu Ile Ile Ala Ser Arg Thr Pro Glu Glu Leu Arg
                805                 810                 815

Ala Ile Lys Gln Val Tyr Glu Glu Tyr Gly Ser Ser Leu Ala Gly
            820                 825                 830

Asp Val Val Gly Asp Thr Ser Gly Tyr Tyr Gln Arg Met Leu Val Val
        835                 840                 845

Leu Leu Gln Ala Ala Arg Asp Pro Asp Ala Gly Ile Asp Glu Ala Gln
850                 855                 860

Val Glu Gln Asp Ala Gln Ala Leu Phe Gln Ala Gly Glu Leu Lys Trp
865                 870                 875                 880

Gly Thr Asp Glu Glu Lys Phe Ile Thr Ile Phe Gly Thr Arg Ser Val
                885                 890                 895

Ser His Leu Arg Lys Val Phe Asp Lys Tyr Met Thr Ile Ser Gly Phe
            900                 905                 910

Gln Ile Glu Glu Thr Ile Asp Arg Glu Thr Ser Gly Asn Leu Glu Gln
        915                 920                 925

Leu Leu Leu Ala Val Val Lys Ser Ile Arg Ser Ile Pro Ala Tyr Leu
930                 935                 940

Ala Glu Thr Leu Tyr Tyr Ala Met Lys Gly Ala Gly Thr Asp Asp His
945                 950                 955                 960

Thr Leu Ile Arg Val Met Val Ser Arg Ser Glu Ile Asp Leu Phe Asn
                965                 970                 975

Ile Arg Lys Glu Phe Arg Lys Asn Phe Ala Thr Ser Leu Tyr Ser Met
            980                 985                 990

Ile Lys Gly Asp Thr Ser Gly Asp  Tyr Lys Lys Ala Leu  Leu Leu Leu
        995                 1000                 1005

Cys Gly  Glu Asp Asp
    1010

<210> SEQ ID NO 80
<211> LENGTH: 1017
<212> TYPE: PRT
<213> ORGANISM: Artificial Sequence
<220> FEATURE:
<223> OTHER INFORMATION: Synthetic construct

<400> SEQUENCE: 80

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
```

```
                  20                  25                  30
Asp Arg Gly Phe Leu Phe Asn Lys Pro Thr Gly Ala Gly Ser Ser Ser
            35                  40                  45

Arg Arg Ala Pro Gln Thr Gly Ile Val Asp Glu Cys Cys Phe Arg Ser
    50                  55                  60

Cys Asp Leu Arg Arg Leu Glu Met Tyr Cys Ala Pro Leu Lys Pro Ala
65                  70                  75                  80

Lys Ser Ala Gly Ser Gly Ser Gly Gly Ser Gly Gly Ser Gly
                85                  90                  95

Gly Gly Asp Ala His Lys Ser Glu Val Ala His Arg Phe Lys Asp Leu
            100                 105                 110

Gly Glu Glu Asn Phe Lys Ala Leu Val Leu Ile Ala Phe Ala Gln Tyr
            115                 120                 125

Leu Gln Gln Ser Pro Phe Glu Asp His Val Lys Leu Val Asn Glu Val
            130                 135                 140

Thr Glu Phe Ala Lys Thr Cys Val Ala Asp Glu Ser Ala Glu Asn Cys
145                 150                 155                 160

Asp Lys Ser Leu His Thr Leu Phe Gly Asp Lys Leu Cys Thr Val Ala
            165                 170                 175

Thr Leu Arg Glu Thr Tyr Gly Glu Met Ala Asp Cys Cys Ala Lys Gln
            180                 185                 190

Glu Pro Glu Arg Asn Glu Cys Phe Leu Gln His Lys Asp Asp Asn Pro
            195                 200                 205

Asn Leu Pro Arg Leu Val Arg Pro Glu Val Asp Val Met Cys Thr Ala
            210                 215                 220

Phe His Asp Asn Glu Glu Thr Phe Leu Lys Lys Tyr Leu Tyr Glu Ile
225                 230                 235                 240

Ala Arg Arg His Pro Tyr Phe Tyr Ala Pro Glu Leu Leu Phe Phe Ala
            245                 250                 255

Lys Arg Tyr Lys Ala Ala Phe Thr Glu Cys Cys Gln Ala Ala Asp Lys
            260                 265                 270

Ala Ala Cys Leu Leu Pro Lys Leu Asp Glu Leu Arg Asp Glu Gly Lys
            275                 280                 285

Ala Ser Ser Ala Lys Gln Arg Leu Lys Cys Ala Ser Leu Gln Lys Phe
            290                 295                 300

Gly Glu Arg Ala Phe Lys Ala Trp Ala Val Ala Arg Leu Ser Gln Arg
305                 310                 315                 320

Phe Pro Lys Ala Glu Phe Ala Glu Val Ser Lys Leu Val Thr Asp Leu
            325                 330                 335

Thr Lys Val His Thr Glu Cys Cys His Gly Asp Leu Leu Glu Cys Ala
            340                 345                 350

Asp Asp Arg Ala Asp Leu Ala Lys Tyr Ile Cys Glu Asn Gln Asp Ser
            355                 360                 365

Ile Ser Ser Lys Leu Lys Glu Cys Cys Glu Lys Pro Leu Leu Glu Lys
            370                 375                 380

Ser His Cys Ile Ala Glu Val Glu Asn Asp Glu Met Pro Ala Asp Leu
385                 390                 395                 400

Pro Ser Leu Ala Ala Asp Phe Val Glu Ser Lys Asp Val Cys Lys Asn
            405                 410                 415

Tyr Ala Glu Ala Lys Asp Val Phe Leu Gly Met Phe Leu Tyr Glu Tyr
            420                 425                 430

Ala Arg Arg His Pro Asp Tyr Ser Val Val Leu Leu Leu Arg Leu Ala
            435                 440                 445
```

```
Lys Thr Tyr Glu Thr Thr Leu Glu Lys Cys Cys Ala Ala Asp Pro
    450                 455                 460

His Glu Cys Tyr Ala Lys Val Phe Asp Glu Phe Lys Pro Leu Val Glu
465                 470                 475                 480

Glu Pro Gln Asn Leu Ile Lys Gln Asn Cys Glu Leu Phe Glu Gln Leu
                485                 490                 495

Gly Glu Tyr Lys Phe Gln Asn Ala Leu Leu Val Arg Tyr Thr Lys Lys
            500                 505                 510

Val Pro Gln Val Ser Thr Pro Thr Leu Val Glu Val Ser Arg Asn Leu
        515                 520                 525

Gly Lys Val Gly Ser Lys Cys Cys Lys His Pro Glu Ala Lys Arg Met
    530                 535                 540

Pro Cys Ala Glu Asp Tyr Leu Ser Val Val Leu Asn Gln Leu Cys Val
545                 550                 555                 560

Leu His Glu Lys Thr Pro Val Ser Asp Arg Val Thr Lys Cys Cys Thr
                565                 570                 575

Glu Ser Leu Val Asn Arg Arg Pro Cys Phe Ser Ala Leu Glu Val Asp
            580                 585                 590

Glu Thr Tyr Val Pro Lys Glu Phe Gln Ala Gly Thr Phe Thr Phe His
        595                 600                 605

Ala Asp Ile Cys Thr Leu Ser Glu Lys Glu Arg Gln Ile Lys Lys Gln
    610                 615                 620

Thr Ala Leu Val Glu Leu Val Lys His Lys Pro Lys Ala Thr Lys Glu
625                 630                 635                 640

Gln Leu Lys Ala Ala Met Asp Asp Phe Ala Ala Phe Val Glu Lys Cys
                645                 650                 655

Cys Lys Ala Asp Asp Lys Glu Thr Cys Phe Ala Glu Glu Gly Lys Lys
            660                 665                 670

Leu Val Ala Ala Ser Gln Ala Ala Leu Gly Leu Gly Ser Gly Gly Ser
        675                 680                 685

Gly Gly Gly Ser Gly Gly Ser Gly Gly Gly Ala Gln Val Leu Arg Gly
    690                 695                 700

Thr Val Thr Asp Phe Pro Gly Phe Asp Glu Arg Ala Asp Ala Glu Thr
705                 710                 715                 720

Leu Arg Lys Ala Met Lys Gly Leu Gly Thr Asp Glu Glu Ser Ile Leu
                725                 730                 735

Thr Leu Leu Thr Ser Arg Ser Asn Ala Gln Arg Gln Glu Ile Ser Ala
            740                 745                 750

Ala Phe Lys Thr Leu Phe Gly Ala Asp Leu Leu Asp Leu Ala Ser
        755                 760                 765

Glu Leu Thr Gly Lys Phe Glu Lys Leu Ile Val Ala Leu Met Lys Pro
    770                 775                 780

Ser Arg Leu Tyr Asp Ala Tyr Glu Leu Lys His Ala Leu Ala Gly Ala
785                 790                 795                 800

Gly Thr Asn Glu Lys Val Leu Thr Glu Ile Ile Ala Ser Arg Thr Pro
                805                 810                 815

Glu Glu Leu Arg Ala Ile Lys Gln Val Tyr Glu Glu Glu Tyr Gly Ser
            820                 825                 830

Ser Leu Ala Gly Asp Val Val Gly Asp Thr Ser Gly Tyr Tyr Gln Arg
        835                 840                 845

Met Leu Val Val Leu Leu Gln Ala Ala Arg Asp Pro Asp Ala Gly Ile
    850                 855                 860
```

```
Asp Glu Ala Gln Val Glu Gln Asp Ala Gln Ala Leu Phe Gln Ala Gly
865                 870                 875                 880

Glu Leu Lys Trp Gly Thr Asp Glu Glu Lys Phe Ile Thr Ile Phe Gly
            885                 890                 895

Thr Arg Ser Val Ser His Leu Arg Lys Val Phe Asp Lys Tyr Met Thr
        900                 905                 910

Ile Ser Gly Phe Gln Ile Glu Thr Ile Asp Arg Glu Thr Ser Gly
    915                 920                 925

Asn Leu Glu Gln Leu Leu Ala Val Val Lys Ser Ile Arg Ser Ile
    930                 935                 940

Pro Ala Tyr Leu Ala Glu Thr Leu Tyr Tyr Ala Met Lys Gly Ala Gly
945                 950                 955                 960

Thr Asp Asp His Thr Leu Ile Arg Val Met Val Ser Arg Ser Glu Ile
            965                 970                 975

Asp Leu Phe Asn Ile Arg Lys Glu Phe Arg Lys Asn Phe Ala Thr Ser
        980                 985                 990

Leu Tyr Ser Met Ile Lys Gly Asp  Thr Ser Gly Asp Tyr  Lys Lys Ala
        995                 1000                1005

Leu Leu  Leu Leu Cys Gly Glu  Asp Asp
    1010            1015

<210> SEQ ID NO 81
<211> LENGTH: 1017
<212> TYPE: PRT
<213> ORGANISM: Artificial Sequence
<220> FEATURE:
<223> OTHER INFORMATION: Synthetic construct

<400> SEQUENCE: 81

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Leu Phe Asn Lys Pro Thr Gly Tyr Gly Ser Ser Ser
        35                  40                  45

Arg Arg Ala Pro Gln Thr Gly Ile Val Asp Glu Cys Cys Phe Arg Ser
50                  55                  60

Cys Asp Leu Arg Arg Leu Glu Met Tyr Cys Ala Pro Leu Lys Pro Ala
65                  70                  75                  80

Lys Ser Ala Gly Ser Gly Gly Ser Gly Gly Ser Gly Gly Ser Gly
            85                  90                  95

Gly Gly Asp Ala His Lys Ser Glu Val Ala His Arg Phe Lys Asp Leu
            100                 105                 110

Gly Glu Glu Asn Phe Lys Ala Leu Val Leu Ile Ala Phe Ala Gln Tyr
        115                 120                 125

Leu Gln Gln Ser Pro Phe Glu Asp His Val Lys Leu Val Asn Glu Val
    130                 135                 140

Thr Glu Phe Ala Lys Thr Cys Val Ala Asp Glu Ser Ala Glu Asn Cys
145                 150                 155                 160

Asp Lys Ser Leu His Thr Leu Phe Gly Asp Lys Leu Cys Thr Val Ala
                165                 170                 175

Thr Leu Arg Glu Thr Tyr Gly Glu Met Ala Asp Cys Cys Ala Lys Gln
            180                 185                 190

Glu Pro Glu Arg Asn Glu Cys Phe Leu Gln His Lys Asp Asp Asn Pro
        195                 200                 205
```

-continued

```
Asn Leu Pro Arg Leu Val Arg Pro Glu Val Asp Val Met Cys Thr Ala
    210                 215                 220
Phe His Asp Asn Glu Glu Thr Phe Leu Lys Lys Tyr Leu Tyr Glu Ile
225                 230                 235                 240
Ala Arg Arg His Pro Tyr Phe Tyr Ala Pro Glu Leu Leu Phe Phe Ala
                245                 250                 255
Lys Arg Tyr Lys Ala Ala Phe Thr Glu Cys Cys Gln Ala Ala Asp Lys
            260                 265                 270
Ala Ala Cys Leu Leu Pro Lys Leu Asp Glu Leu Arg Asp Glu Gly Lys
        275                 280                 285
Ala Ser Ser Ala Lys Gln Arg Leu Lys Cys Ala Ser Leu Gln Lys Phe
    290                 295                 300
Gly Glu Arg Ala Phe Lys Ala Trp Ala Val Ala Arg Leu Ser Gln Arg
305                 310                 315                 320
Phe Pro Lys Ala Glu Phe Ala Glu Val Ser Lys Leu Val Thr Asp Leu
                325                 330                 335
Thr Lys Val His Thr Glu Cys Cys His Gly Asp Leu Leu Glu Cys Ala
            340                 345                 350
Asp Asp Arg Ala Asp Leu Ala Lys Tyr Ile Cys Glu Asn Gln Asp Ser
        355                 360                 365
Ile Ser Ser Lys Leu Lys Glu Cys Cys Glu Lys Pro Leu Leu Glu Lys
    370                 375                 380
Ser His Cys Ile Ala Glu Val Glu Asn Asp Glu Met Pro Ala Asp Leu
385                 390                 395                 400
Pro Ser Leu Ala Ala Asp Phe Val Glu Ser Lys Asp Val Cys Lys Asn
                405                 410                 415
Tyr Ala Glu Ala Lys Asp Val Phe Leu Gly Met Phe Leu Tyr Glu Tyr
            420                 425                 430
Ala Arg Arg His Pro Asp Tyr Ser Val Val Leu Leu Leu Arg Leu Ala
        435                 440                 445
Lys Thr Tyr Glu Thr Thr Leu Glu Lys Cys Cys Ala Ala Ala Asp Pro
    450                 455                 460
His Glu Cys Tyr Ala Lys Val Phe Asp Glu Phe Lys Pro Leu Val Glu
465                 470                 475                 480
Glu Pro Gln Asn Leu Ile Lys Gln Asn Cys Glu Leu Phe Glu Gln Leu
                485                 490                 495
Gly Glu Tyr Lys Phe Gln Asn Ala Leu Leu Val Arg Tyr Thr Lys Lys
            500                 505                 510
Val Pro Gln Val Ser Thr Pro Thr Leu Val Glu Val Ser Arg Asn Leu
        515                 520                 525
Gly Lys Val Gly Ser Lys Cys Cys Lys His Pro Glu Ala Lys Arg Met
    530                 535                 540
Pro Cys Ala Glu Asp Tyr Leu Ser Val Val Leu Asn Gln Leu Cys Val
545                 550                 555                 560
Leu His Glu Lys Thr Pro Val Ser Asp Arg Val Thr Lys Cys Cys Thr
                565                 570                 575
Glu Ser Leu Val Asn Arg Arg Pro Cys Phe Ser Ala Leu Glu Val Asp
            580                 585                 590
Glu Thr Tyr Val Pro Lys Glu Phe Gln Ala Gly Thr Phe Thr Phe His
        595                 600                 605
Ala Asp Ile Cys Thr Leu Ser Glu Lys Glu Arg Gln Ile Lys Lys Gln
    610                 615                 620
Thr Ala Leu Val Glu Leu Val Lys His Lys Pro Lys Ala Thr Lys Glu
```

```
            625                 630                 635                 640
    Gln Leu Lys Ala Ala Met Asp Asp Phe Ala Ala Phe Val Glu Lys Cys
                        645                 650                 655

Cys Lys Ala Asp Asp Lys Glu Thr Cys Phe Ala Glu Glu Gly Lys Lys
                        660                 665                 670

Leu Val Ala Ala Ser Gln Ala Leu Gly Leu Gly Ser Gly Gly Ser
                        675                 680                 685

Gly Gly Gly Ser Gly Gly Ser Gly Gly Gly Ala Gln Val Leu Arg Gly
                690                 695                 700

Thr Val Thr Asp Phe Pro Gly Phe Asp Glu Arg Ala Asp Ala Glu Thr
    705                 710                 715                 720

Leu Arg Lys Ala Met Lys Gly Leu Gly Thr Asp Glu Ser Ile Leu
                        725                 730                 735

Thr Leu Leu Thr Ser Arg Ser Asn Ala Gln Arg Gln Glu Ile Ser Ala
                        740                 745                 750

Ala Phe Lys Thr Leu Phe Gly Ala Asp Leu Leu Asp Leu Ala Ser
                        755                 760                 765

Glu Leu Thr Gly Lys Phe Glu Lys Leu Ile Val Ala Leu Met Lys Pro
                        770                 775                 780

Ser Arg Leu Tyr Asp Ala Tyr Glu Leu Lys His Ala Leu Ala Gly Ala
    785                 790                 795                 800

Gly Thr Asn Glu Lys Val Leu Thr Glu Ile Ile Ala Ser Arg Thr Pro
                        805                 810                 815

Glu Glu Leu Arg Ala Ile Lys Gln Val Tyr Glu Glu Glu Tyr Gly Ser
                        820                 825                 830

Ser Leu Ala Gly Asp Val Val Gly Asp Thr Ser Gly Tyr Tyr Gln Arg
                        835                 840                 845

Met Leu Val Val Leu Gln Ala Ala Arg Asp Pro Asp Ala Gly Ile
                        850                 855                 860

Asp Glu Ala Gln Val Glu Gln Asp Ala Gln Ala Leu Phe Gln Ala Gly
    865                 870                 875                 880

Glu Leu Lys Trp Gly Thr Asp Glu Glu Lys Phe Ile Thr Ile Phe Gly
                        885                 890                 895

Thr Arg Ser Val Ser His Leu Arg Lys Val Phe Asp Lys Tyr Met Thr
                        900                 905                 910

Ile Ser Gly Phe Gln Ile Glu Glu Thr Ile Asp Arg Glu Thr Ser Gly
                        915                 920                 925

Asn Leu Glu Gln Leu Leu Leu Ala Val Val Lys Ser Ile Arg Ser Ile
                        930                 935                 940

Pro Ala Tyr Leu Ala Glu Thr Leu Tyr Tyr Ala Met Lys Gly Ala Gly
    945                 950                 955                 960

Thr Asp Asp His Thr Leu Ile Arg Val Met Val Ser Arg Ser Glu Ile
                        965                 970                 975

Asp Leu Phe Asn Ile Arg Lys Glu Phe Arg Lys Asn Phe Ala Thr Ser
                        980                 985                 990

Leu Tyr Ser Met Ile Lys Gly Asp  Thr Ser Gly Asp Tyr  Lys Lys Ala
                    995                 1000                1005

Leu Leu  Leu Leu Cys Gly Glu  Asp Asp
        1010                1015

<210> SEQ ID NO 82
<211> LENGTH: 1017
<212> TYPE: PRT
<213> ORGANISM: Artificial Sequence
```

<220> FEATURE:
<223> OTHER INFORMATION: Synthetic construct

<400> SEQUENCE: 82

```
Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Tyr Phe Asn Lys Pro Thr Gly Ala Gly Ser Ser Ser
        35                  40                  45

Arg Arg Ala Pro Gln Thr Gly Ile Val Asp Glu Cys Cys Phe Arg Ser
    50                  55                  60

Cys Asp Leu Arg Arg Leu Glu Met Tyr Cys Ala Pro Leu Lys Pro Ala
65                  70                  75                  80

Lys Ser Ala Gly Ser Gly Gly Ser Gly Gly Ser Gly Gly Ser Gly Gly
                85                  90                  95

Gly Gly Asp Ala His Lys Ser Glu Val Ala His Arg Phe Lys Asp Leu
            100                 105                 110

Gly Glu Glu Asn Phe Lys Ala Leu Val Leu Ile Ala Phe Ala Gln Tyr
            115                 120                 125

Leu Gln Gln Ser Pro Phe Glu Asp His Val Lys Leu Val Asn Glu Val
    130                 135                 140

Thr Glu Phe Ala Lys Thr Cys Val Ala Asp Glu Ser Ala Glu Asn Cys
145                 150                 155                 160

Asp Lys Ser Leu His Thr Leu Phe Gly Asp Lys Leu Cys Thr Val Ala
                165                 170                 175

Thr Leu Arg Glu Thr Tyr Gly Glu Met Ala Asp Cys Cys Ala Lys Gln
            180                 185                 190

Glu Pro Glu Arg Asn Glu Cys Phe Leu Gln His Lys Asp Asp Asn Pro
            195                 200                 205

Asn Leu Pro Arg Leu Val Arg Pro Glu Val Asp Val Met Cys Thr Ala
    210                 215                 220

Phe His Asp Asn Glu Glu Thr Phe Leu Lys Lys Tyr Leu Tyr Glu Ile
225                 230                 235                 240

Ala Arg Arg His Pro Tyr Phe Tyr Ala Pro Glu Leu Leu Phe Phe Ala
                245                 250                 255

Lys Arg Tyr Lys Ala Ala Phe Thr Glu Cys Cys Gln Ala Ala Asp Lys
            260                 265                 270

Ala Ala Cys Leu Leu Pro Lys Leu Asp Glu Leu Arg Asp Glu Gly Lys
            275                 280                 285

Ala Ser Ser Ala Lys Gln Arg Leu Lys Cys Ala Ser Leu Gln Lys Phe
    290                 295                 300

Gly Glu Arg Ala Phe Lys Ala Trp Ala Val Ala Arg Leu Ser Gln Arg
305                 310                 315                 320

Phe Pro Lys Ala Glu Phe Ala Glu Val Ser Lys Leu Val Thr Asp Leu
                325                 330                 335

Thr Lys Val His Thr Glu Cys Cys His Gly Asp Leu Leu Glu Cys Ala
            340                 345                 350

Asp Asp Arg Ala Asp Leu Ala Lys Tyr Ile Cys Glu Asn Gln Asp Ser
            355                 360                 365

Ile Ser Ser Lys Leu Lys Glu Cys Cys Glu Lys Pro Leu Leu Glu Lys
    370                 375                 380

Ser His Cys Ile Ala Glu Val Glu Asn Asp Glu Met Pro Ala Asp Leu
385                 390                 395                 400
```

-continued

```
Pro Ser Leu Ala Ala Asp Phe Val Glu Ser Lys Asp Val Cys Lys Asn
            405                 410                 415

Tyr Ala Glu Ala Lys Asp Val Phe Leu Gly Met Phe Leu Tyr Glu Tyr
        420                 425                 430

Ala Arg Arg His Pro Asp Tyr Ser Val Val Leu Leu Leu Arg Leu Ala
        435                 440                 445

Lys Thr Tyr Glu Thr Thr Leu Glu Lys Cys Cys Ala Ala Ala Asp Pro
    450                 455                 460

His Glu Cys Tyr Ala Lys Val Phe Asp Glu Phe Lys Pro Leu Val Glu
465                 470                 475                 480

Glu Pro Gln Asn Leu Ile Lys Gln Asn Cys Glu Leu Phe Glu Gln Leu
                485                 490                 495

Gly Glu Tyr Lys Phe Gln Asn Ala Leu Leu Val Arg Tyr Thr Lys Lys
            500                 505                 510

Val Pro Gln Val Ser Thr Pro Thr Leu Val Glu Val Ser Arg Asn Leu
        515                 520                 525

Gly Lys Val Gly Ser Lys Cys Cys Lys His Pro Glu Ala Lys Arg Met
    530                 535                 540

Pro Cys Ala Glu Asp Tyr Leu Ser Val Val Leu Asn Gln Leu Cys Val
545                 550                 555                 560

Leu His Glu Lys Thr Pro Val Ser Asp Arg Val Thr Lys Cys Cys Thr
                565                 570                 575

Glu Ser Leu Val Asn Arg Arg Pro Cys Phe Ser Ala Leu Glu Val Asp
            580                 585                 590

Glu Thr Tyr Val Pro Lys Glu Phe Gln Ala Gly Thr Phe Thr Phe His
        595                 600                 605

Ala Asp Ile Cys Thr Leu Ser Glu Lys Glu Arg Gln Ile Lys Lys Gln
        610                 615                 620

Thr Ala Leu Val Glu Leu Val Lys His Lys Pro Lys Ala Thr Lys Glu
625                 630                 635                 640

Gln Leu Lys Ala Ala Met Asp Asp Phe Ala Ala Phe Val Glu Lys Cys
                645                 650                 655

Cys Lys Ala Asp Asp Lys Glu Thr Cys Phe Ala Glu Glu Gly Lys Lys
            660                 665                 670

Leu Val Ala Ala Ser Gln Ala Ala Leu Gly Leu Gly Ser Gly Gly Ser
        675                 680                 685

Gly Gly Gly Ser Gly Gly Ser Gly Gly Gly Ala Gln Val Leu Arg Gly
    690                 695                 700

Thr Val Thr Asp Phe Pro Gly Phe Asp Glu Arg Ala Asp Ala Glu Thr
705                 710                 715                 720

Leu Arg Lys Ala Met Lys Gly Leu Gly Thr Asp Glu Glu Ser Ile Leu
                725                 730                 735

Thr Leu Leu Thr Ser Arg Ser Asn Ala Gln Arg Gln Glu Ile Ser Ala
            740                 745                 750

Ala Phe Lys Thr Leu Phe Gly Ala Asp Leu Leu Asp Leu Ala Ser
        755                 760                 765

Glu Leu Thr Gly Lys Phe Glu Lys Leu Ile Val Ala Leu Met Lys Pro
    770                 775                 780

Ser Arg Leu Tyr Asp Ala Tyr Glu Leu Lys His Ala Leu Ala Gly Ala
785                 790                 795                 800

Gly Thr Asn Glu Lys Val Leu Thr Glu Ile Ile Ala Ser Arg Thr Pro
                805                 810                 815
```

```
Glu Glu Leu Arg Ala Ile Lys Gln Val Tyr Glu Glu Tyr Gly Ser
            820                 825                 830

Ser Leu Ala Gly Asp Val Val Gly Asp Thr Ser Gly Tyr Tyr Gln Arg
        835                 840                 845

Met Leu Val Val Leu Leu Gln Ala Ala Arg Asp Pro Asp Ala Gly Ile
    850                 855                 860

Asp Glu Ala Gln Val Glu Gln Asp Ala Gln Ala Leu Phe Gln Ala Gly
865                 870                 875                 880

Glu Leu Lys Trp Gly Thr Asp Glu Glu Lys Phe Ile Thr Ile Phe Gly
                885                 890                 895

Thr Arg Ser Val Ser His Leu Arg Lys Val Phe Asp Lys Tyr Met Thr
        900                 905                 910

Ile Ser Gly Phe Gln Ile Glu Glu Thr Ile Asp Arg Glu Thr Ser Gly
        915                 920                 925

Asn Leu Glu Gln Leu Leu Ala Val Val Lys Ser Ile Arg Ser Ile
    930                 935                 940

Pro Ala Tyr Leu Ala Glu Thr Leu Tyr Tyr Ala Met Lys Gly Ala Gly
945                 950                 955                 960

Thr Asp Asp His Thr Leu Ile Arg Val Met Val Ser Arg Ser Glu Ile
                965                 970                 975

Asp Leu Phe Asn Ile Arg Lys Glu Phe Arg Lys Asn Phe Ala Thr Ser
                980                 985                 990

Leu Tyr Ser Met Ile Lys Gly Asp  Thr Ser Gly Asp Tyr  Lys Lys Ala
        995                 1000                1005

Leu Leu  Leu Leu Cys Gly Glu  Asp Asp
    1010                1015

<210> SEQ ID NO 83
<211> LENGTH: 1001
<212> TYPE: PRT
<213> ORGANISM: Artificial Sequence
<220> FEATURE:
<223> OTHER INFORMATION: Synthetic construct

<400> SEQUENCE: 83

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Leu Phe Asn Lys Pro Thr Gly Tyr Gly Ser Ser Ser
        35                  40                  45

Arg Arg Ala Pro Gln Thr Gly Ile Val Asp Glu Cys Cys Phe Arg Ser
    50                  55                  60

Cys Asp Leu Arg Arg Leu Glu Met Tyr Cys Ala Pro Leu Lys Pro Ala
65                  70                  75                  80

Lys Ser Ala Gly Ser Gly Gly Ser Gly Asp Ala His Lys Ser Glu
                85                  90                  95

Val Ala His Arg Phe Lys Asp Leu Gly Glu Glu Asn Phe Lys Ala Leu
            100                 105                 110

Val Leu Ile Ala Phe Ala Gln Tyr Leu Gln Gln Ser Pro Phe Glu Asp
        115                 120                 125

His Val Lys Leu Val Asn Glu Val Thr Glu Phe Ala Lys Thr Cys Val
    130                 135                 140

Ala Asp Glu Ser Ala Glu Asn Cys Asp Lys Ser Leu His Thr Leu Phe
145                 150                 155                 160
```

Gly Asp Lys Leu Cys Thr Val Ala Thr Leu Arg Glu Thr Tyr Gly Glu
            165                 170                 175

Met Ala Asp Cys Cys Ala Lys Gln Glu Pro Glu Arg Asn Glu Cys Phe
            180                 185                 190

Leu Gln His Lys Asp Asp Asn Pro Asn Leu Pro Arg Leu Val Arg Pro
            195                 200                 205

Glu Val Asp Val Met Cys Thr Ala Phe His Asp Asn Glu Glu Thr Phe
210                 215                 220

Leu Lys Lys Tyr Leu Tyr Glu Ile Ala Arg Arg His Pro Tyr Phe Tyr
225                 230                 235                 240

Ala Pro Glu Leu Leu Phe Phe Ala Lys Arg Tyr Lys Ala Ala Phe Thr
            245                 250                 255

Glu Cys Cys Gln Ala Ala Asp Lys Ala Ala Cys Leu Leu Pro Lys Leu
            260                 265                 270

Asp Glu Leu Arg Asp Glu Gly Lys Ala Ser Ser Ala Lys Gln Arg Leu
            275                 280                 285

Lys Cys Ala Ser Leu Gln Lys Phe Gly Glu Arg Ala Phe Lys Ala Trp
            290                 295                 300

Ala Val Ala Arg Leu Ser Gln Arg Phe Pro Lys Ala Glu Phe Ala Glu
305                 310                 315                 320

Val Ser Lys Leu Val Thr Asp Leu Thr Lys Val His Thr Glu Cys Cys
            325                 330                 335

His Gly Asp Leu Leu Glu Cys Ala Asp Asp Arg Ala Asp Leu Ala Lys
            340                 345                 350

Tyr Ile Cys Glu Asn Gln Asp Ser Ile Ser Ser Lys Leu Lys Glu Cys
            355                 360                 365

Cys Glu Lys Pro Leu Leu Glu Lys Ser His Cys Ile Ala Glu Val Glu
            370                 375                 380

Asn Asp Glu Met Pro Ala Asp Leu Pro Ser Leu Ala Ala Asp Phe Val
385                 390                 395                 400

Glu Ser Lys Asp Val Cys Lys Asn Tyr Ala Glu Ala Lys Asp Val Phe
            405                 410                 415

Leu Gly Met Phe Leu Tyr Glu Tyr Ala Arg Arg His Pro Asp Tyr Ser
            420                 425                 430

Val Val Leu Leu Leu Arg Leu Ala Lys Thr Tyr Glu Thr Thr Leu Glu
            435                 440                 445

Lys Cys Cys Ala Ala Ala Asp Pro His Glu Cys Tyr Ala Lys Val Phe
            450                 455                 460

Asp Glu Phe Lys Pro Leu Val Glu Glu Pro Gln Asn Leu Ile Lys Gln
465                 470                 475                 480

Asn Cys Glu Leu Phe Glu Gln Leu Gly Glu Tyr Lys Phe Gln Asn Ala
            485                 490                 495

Leu Leu Val Arg Tyr Thr Lys Lys Val Pro Gln Val Ser Thr Pro Thr
            500                 505                 510

Leu Val Glu Val Ser Arg Asn Leu Gly Lys Val Gly Ser Lys Cys Cys
            515                 520                 525

Lys His Pro Glu Ala Lys Arg Met Pro Cys Ala Glu Asp Tyr Leu Ser
            530                 535                 540

Val Val Leu Asn Gln Leu Cys Val Leu His Glu Lys Thr Pro Val Ser
545                 550                 555                 560

Asp Arg Val Thr Lys Cys Cys Thr Glu Ser Leu Val Asn Arg Arg Pro
            565                 570                 575

Cys Phe Ser Ala Leu Glu Val Asp Glu Thr Tyr Val Pro Lys Glu Phe

-continued

```
                580                 585                 590
Gln Ala Glu Thr Phe Thr Phe His Ala Asp Ile Cys Thr Leu Ser Glu
            595                 600                 605
Lys Glu Arg Gln Ile Lys Lys Gln Thr Ala Leu Val Glu Leu Val Lys
            610                 615                 620
His Lys Pro Lys Ala Thr Lys Glu Gln Leu Lys Ala Val Met Asp Asp
625                 630                 635                 640
Phe Ala Ala Phe Val Glu Lys Cys Cys Lys Ala Asp Asp Lys Glu Thr
                645                 650                 655
Cys Phe Ala Glu Glu Gly Lys Lys Leu Val Ala Ala Ser Gln Ala Ala
            660                 665                 670
Leu Gly Leu Gly Ser Gly Gly Ser Gly Ala Gln Val Leu Arg Gly
            675                 680                 685
Thr Val Thr Asp Phe Pro Gly Phe Asp Glu Arg Ala Asp Ala Glu Thr
            690                 695                 700
Leu Arg Lys Ala Met Lys Gly Leu Gly Thr Asp Glu Glu Ser Ile Leu
705                 710                 715                 720
Thr Leu Leu Thr Ser Arg Ser Asn Ala Gln Arg Gln Glu Ile Ser Ala
                725                 730                 735
Ala Phe Lys Thr Leu Phe Gly Ala Asp Leu Leu Asp Asp Leu Ala Ser
            740                 745                 750
Glu Leu Thr Gly Lys Phe Glu Lys Leu Ile Val Ala Leu Met Lys Pro
            755                 760                 765
Ser Arg Leu Tyr Asp Ala Tyr Glu Leu Lys His Ala Leu Ala Gly Ala
            770                 775                 780
Gly Thr Asn Glu Lys Val Leu Thr Glu Ile Ile Ala Ser Arg Thr Pro
785                 790                 795                 800
Glu Glu Leu Arg Ala Ile Lys Gln Val Tyr Glu Glu Tyr Gly Ser
                805                 810                 815
Ser Leu Ala Gly Asp Val Val Gly Asp Thr Ser Gly Tyr Tyr Gln Arg
            820                 825                 830
Met Leu Val Val Leu Leu Gln Ala Ala Arg Asp Pro Asp Ala Gly Ile
            835                 840                 845
Asp Glu Ala Gln Val Glu Gln Asp Ala Gln Ala Leu Phe Gln Ala Gly
            850                 855                 860
Glu Leu Lys Trp Gly Thr Asp Glu Glu Lys Phe Ile Thr Ile Phe Gly
865                 870                 875                 880
Thr Arg Ser Val Ser His Leu Arg Lys Val Phe Asp Lys Tyr Met Thr
                885                 890                 895
Ile Ser Gly Phe Gln Ile Glu Glu Thr Ile Asp Arg Glu Thr Ser Gly
            900                 905                 910
Asn Leu Glu Gln Leu Leu Leu Ala Val Val Lys Ser Ile Arg Ser Ile
            915                 920                 925
Pro Ala Tyr Leu Ala Glu Thr Leu Tyr Tyr Ala Met Lys Gly Ala Gly
            930                 935                 940
Thr Asp Asp His Thr Leu Ile Arg Val Met Val Ser Arg Ser Glu Ile
945                 950                 955                 960
Asp Leu Phe Asn Ile Arg Lys Glu Phe Arg Lys Asn Phe Ala Thr Ser
                965                 970                 975
Leu Tyr Ser Met Ile Lys Gly Asp Thr Ser Gly Asp Tyr Lys Lys Ala
            980                 985                 990
Leu Leu Leu Leu Cys Gly Glu Asp  Asp
            995                 1000
```

-continued

```
<210> SEQ ID NO 84
<211> LENGTH: 1001
<212> TYPE: PRT
<213> ORGANISM: Artificial Sequence
<220> FEATURE:
<223> OTHER INFORMATION: Synthetic construct

<400> SEQUENCE: 84

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
                20                  25                  30

Asp Arg Gly Phe Tyr Phe Asn Lys Pro Thr Gly Ala Gly Ser Ser Ser
            35                  40                  45

Arg Arg Ala Pro Gln Thr Gly Ile Val Asp Glu Cys Cys Phe Arg Ser
    50                  55                  60

Cys Asp Leu Arg Arg Leu Glu Met Tyr Cys Ala Pro Leu Lys Pro Ala
65                  70                  75                  80

Lys Ser Ala Gly Ser Gly Gly Ser Gly Asp Ala His Lys Ser Glu
                85                  90                  95

Val Ala His Arg Phe Lys Asp Leu Gly Glu Glu Asn Phe Lys Ala Leu
                100                 105                 110

Val Leu Ile Ala Phe Ala Gln Tyr Leu Gln Gln Ser Pro Phe Glu Asp
            115                 120                 125

His Val Lys Leu Val Asn Glu Val Thr Glu Phe Ala Lys Thr Cys Val
    130                 135                 140

Ala Asp Glu Ser Ala Glu Asn Cys Asp Lys Ser Leu His Thr Leu Phe
145                 150                 155                 160

Gly Asp Lys Leu Cys Thr Val Ala Thr Leu Arg Glu Thr Tyr Gly Glu
                165                 170                 175

Met Ala Asp Cys Cys Ala Lys Gln Glu Pro Glu Arg Asn Glu Cys Phe
            180                 185                 190

Leu Gln His Lys Asp Asp Asn Pro Asn Leu Pro Arg Leu Val Arg Pro
    195                 200                 205

Glu Val Asp Val Met Cys Thr Ala Phe His Asp Asn Glu Glu Thr Phe
210                 215                 220

Leu Lys Lys Tyr Leu Tyr Glu Ile Ala Arg Arg His Pro Tyr Phe Tyr
225                 230                 235                 240

Ala Pro Glu Leu Leu Phe Phe Ala Lys Arg Tyr Lys Ala Ala Phe Thr
                245                 250                 255

Glu Cys Cys Gln Ala Ala Asp Lys Ala Ala Cys Leu Leu Pro Lys Leu
            260                 265                 270

Asp Glu Leu Arg Asp Glu Gly Lys Ala Ser Ser Ala Lys Gln Arg Leu
    275                 280                 285

Lys Cys Ala Ser Leu Gln Lys Phe Gly Glu Arg Ala Phe Lys Ala Trp
290                 295                 300

Ala Val Ala Arg Leu Ser Gln Arg Phe Pro Lys Ala Glu Phe Ala Glu
305                 310                 315                 320

Val Ser Lys Leu Val Thr Asp Leu Thr Lys Val His Thr Glu Cys Cys
                325                 330                 335

His Gly Asp Leu Leu Glu Cys Ala Asp Asp Arg Ala Asp Leu Ala Lys
            340                 345                 350

Tyr Ile Cys Glu Asn Gln Asp Ser Ile Ser Ser Lys Leu Lys Glu Cys
    355                 360                 365
```

```
Cys Glu Lys Pro Leu Leu Glu Lys Ser His Cys Ile Ala Glu Val Glu
    370                 375                 380

Asn Asp Glu Met Pro Ala Asp Leu Pro Ser Leu Ala Ala Asp Phe Val
385                 390                 395                 400

Glu Ser Lys Asp Val Cys Lys Asn Tyr Ala Glu Ala Lys Asp Val Phe
                405                 410                 415

Leu Gly Met Phe Leu Tyr Glu Tyr Ala Arg Arg His Pro Asp Tyr Ser
            420                 425                 430

Val Val Leu Leu Leu Arg Leu Ala Lys Thr Tyr Glu Thr Thr Leu Glu
        435                 440                 445

Lys Cys Cys Ala Ala Ala Asp Pro His Glu Cys Tyr Ala Lys Val Phe
450                 455                 460

Asp Glu Phe Lys Pro Leu Val Glu Glu Pro Gln Asn Leu Ile Lys Gln
465                 470                 475                 480

Asn Cys Glu Leu Phe Glu Gln Leu Gly Glu Tyr Lys Phe Gln Asn Ala
                485                 490                 495

Leu Leu Val Arg Tyr Thr Lys Lys Val Pro Gln Val Ser Thr Pro Thr
                500                 505                 510

Leu Val Glu Val Ser Arg Asn Leu Gly Lys Val Gly Ser Lys Cys Cys
            515                 520                 525

Lys His Pro Glu Ala Lys Arg Met Pro Cys Ala Glu Asp Tyr Leu Ser
        530                 535                 540

Val Val Leu Asn Gln Leu Cys Val Leu His Glu Lys Thr Pro Val Ser
545                 550                 555                 560

Asp Arg Val Thr Lys Cys Cys Thr Glu Ser Leu Val Asn Arg Arg Pro
                565                 570                 575

Cys Phe Ser Ala Leu Glu Val Asp Glu Thr Tyr Val Pro Lys Glu Phe
            580                 585                 590

Gln Ala Glu Thr Phe Thr Phe His Ala Asp Ile Cys Thr Leu Ser Glu
        595                 600                 605

Lys Glu Arg Gln Ile Lys Lys Gln Thr Ala Leu Val Glu Leu Val Lys
610                 615                 620

His Lys Pro Lys Ala Thr Lys Glu Gln Leu Lys Ala Val Met Asp Asp
625                 630                 635                 640

Phe Ala Ala Phe Val Glu Lys Cys Cys Lys Ala Asp Asp Lys Glu Thr
                645                 650                 655

Cys Phe Ala Glu Glu Gly Lys Lys Leu Val Ala Ala Ser Gln Ala Ala
            660                 665                 670

Leu Gly Leu Gly Ser Gly Gly Ser Gly Ala Gln Val Leu Arg Gly
        675                 680                 685

Thr Val Thr Asp Phe Pro Gly Phe Asp Glu Arg Ala Asp Ala Glu Thr
        690                 695                 700

Leu Arg Lys Ala Met Lys Gly Leu Gly Thr Asp Glu Glu Ser Ile Leu
705                 710                 715                 720

Thr Leu Leu Thr Ser Arg Ser Asn Ala Gln Arg Gln Glu Ile Ser Ala
                725                 730                 735

Ala Phe Lys Thr Leu Phe Gly Ala Asp Leu Leu Asp Asp Leu Ala Ser
            740                 745                 750

Glu Leu Thr Gly Lys Phe Glu Lys Leu Ile Val Ala Leu Met Lys Pro
        755                 760                 765

Ser Arg Leu Tyr Asp Ala Tyr Glu Leu Lys His Ala Leu Ala Gly Ala
        770                 775                 780
```

```
Gly Thr Asn Glu Lys Val Leu Thr Glu Ile Ile Ala Ser Arg Thr Pro
785                 790                 795                 800

Glu Glu Leu Arg Ala Ile Lys Gln Val Tyr Glu Glu Tyr Gly Ser
            805                 810                 815

Ser Leu Ala Gly Asp Val Val Gly Asp Thr Ser Gly Tyr Tyr Gln Arg
            820                 825                 830

Met Leu Val Val Leu Leu Gln Ala Ala Arg Asp Pro Asp Ala Gly Ile
            835                 840                 845

Asp Glu Ala Gln Val Glu Gln Asp Ala Gln Ala Leu Phe Gln Ala Gly
            850                 855                 860

Glu Leu Lys Trp Gly Thr Asp Glu Glu Lys Phe Ile Thr Ile Phe Gly
865                 870                 875                 880

Thr Arg Ser Val Ser His Leu Arg Lys Val Phe Asp Lys Tyr Met Thr
            885                 890                 895

Ile Ser Gly Phe Gln Ile Glu Glu Thr Ile Asp Arg Glu Thr Ser Gly
            900                 905                 910

Asn Leu Glu Gln Leu Leu Leu Ala Val Val Lys Ser Ile Arg Ser Ile
            915                 920                 925

Pro Ala Tyr Leu Ala Glu Thr Leu Tyr Tyr Ala Met Lys Gly Ala Gly
            930                 935                 940

Thr Asp Asp His Thr Leu Ile Arg Val Met Val Ser Arg Ser Glu Ile
945                 950                 955                 960

Asp Leu Phe Asn Ile Arg Lys Glu Phe Arg Lys Asn Phe Ala Thr Ser
            965                 970                 975

Leu Tyr Ser Met Ile Lys Gly Asp Thr Ser Gly Asp Tyr Lys Lys Ala
            980                 985                 990

Leu Leu Leu Leu Cys Gly Glu Asp  Asp
            995                 1000

<210> SEQ ID NO 85
<211> LENGTH: 1001
<212> TYPE: PRT
<213> ORGANISM: Artificial Sequence
<220> FEATURE:
<223> OTHER INFORMATION: Synthetic construct

<400> SEQUENCE: 85

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Tyr Phe Asn Lys Pro Thr Gly Tyr Gly Ser Ser Ser
            35                  40                  45

Arg Arg Ala Pro Gln Thr Gly Ile Val Asp Glu Cys Cys Phe Arg Ser
50                  55                  60

Cys Asp Leu Arg Arg Leu Glu Met Leu Cys Ala Pro Leu Lys Pro Ala
65                  70                  75                  80

Lys Ser Ala Gly Ser Gly Gly Ser Gly Asp Ala His Lys Ser Glu
            85                  90                  95

Val Ala His Arg Phe Lys Asp Leu Gly Glu Glu Asn Phe Lys Ala Leu
            100                 105                 110

Val Leu Ile Ala Phe Ala Gln Tyr Leu Gln Gln Ser Pro Phe Glu Asp
            115                 120                 125

His Val Lys Leu Val Asn Glu Val Thr Glu Phe Ala Lys Thr Cys Val
            130                 135                 140
```

```
Ala Asp Glu Ser Ala Glu Asn Cys Asp Lys Ser Leu His Thr Leu Phe
145                 150                 155                 160

Gly Asp Lys Leu Cys Thr Val Ala Thr Leu Arg Glu Thr Tyr Gly Glu
            165                 170                 175

Met Ala Asp Cys Cys Ala Lys Gln Glu Pro Glu Arg Asn Glu Cys Phe
        180                 185                 190

Leu Gln His Lys Asp Asp Asn Pro Asn Leu Pro Arg Leu Val Arg Pro
    195                 200                 205

Glu Val Asp Val Met Cys Thr Ala Phe His Asp Asn Glu Glu Thr Phe
210                 215                 220

Leu Lys Lys Tyr Leu Tyr Glu Ile Ala Arg Arg His Pro Tyr Phe Tyr
225                 230                 235                 240

Ala Pro Glu Leu Leu Phe Phe Ala Lys Arg Tyr Lys Ala Ala Phe Thr
            245                 250                 255

Glu Cys Cys Gln Ala Ala Asp Lys Ala Ala Cys Leu Leu Pro Lys Leu
        260                 265                 270

Asp Glu Leu Arg Asp Glu Gly Lys Ala Ser Ser Ala Lys Gln Arg Leu
    275                 280                 285

Lys Cys Ala Ser Leu Gln Lys Phe Gly Glu Arg Ala Phe Lys Ala Trp
290                 295                 300

Ala Val Ala Arg Leu Ser Gln Arg Phe Pro Lys Ala Glu Phe Ala Glu
305                 310                 315                 320

Val Ser Lys Leu Val Thr Asp Leu Thr Lys Val His Thr Glu Cys Cys
            325                 330                 335

His Gly Asp Leu Leu Glu Cys Ala Asp Asp Arg Ala Asp Leu Ala Lys
        340                 345                 350

Tyr Ile Cys Glu Asn Gln Asp Ser Ile Ser Ser Lys Leu Lys Glu Cys
    355                 360                 365

Cys Glu Lys Pro Leu Leu Glu Lys Ser His Cys Ile Ala Glu Val Glu
370                 375                 380

Asn Asp Glu Met Pro Ala Asp Leu Pro Ser Leu Ala Ala Asp Phe Val
385                 390                 395                 400

Glu Ser Lys Asp Val Cys Lys Asn Tyr Ala Glu Ala Lys Asp Val Phe
            405                 410                 415

Leu Gly Met Phe Leu Tyr Glu Tyr Ala Arg Arg His Pro Asp Tyr Ser
        420                 425                 430

Val Val Leu Leu Leu Arg Leu Ala Lys Thr Tyr Glu Thr Thr Leu Glu
    435                 440                 445

Lys Cys Cys Ala Ala Ala Asp Pro His Glu Cys Tyr Ala Lys Val Phe
450                 455                 460

Asp Glu Phe Lys Pro Leu Val Glu Glu Pro Gln Asn Leu Ile Lys Gln
465                 470                 475                 480

Asn Cys Glu Leu Phe Glu Gln Leu Gly Glu Tyr Lys Phe Gln Asn Ala
            485                 490                 495

Leu Leu Val Arg Tyr Thr Lys Lys Val Pro Gln Val Ser Thr Pro Thr
        500                 505                 510

Leu Val Glu Val Ser Arg Asn Leu Gly Lys Val Gly Ser Lys Cys Cys
    515                 520                 525

Lys His Pro Glu Ala Lys Arg Met Pro Cys Ala Glu Asp Tyr Leu Ser
530                 535                 540

Val Val Leu Asn Gln Leu Cys Val Leu His Glu Lys Thr Pro Val Ser
545                 550                 555                 560

Asp Arg Val Thr Lys Cys Cys Thr Glu Ser Leu Val Asn Arg Arg Pro
```

-continued

```
                565                 570                 575
        Cys Phe Ser Ala Leu Glu Val Asp Glu Thr Tyr Val Pro Lys Glu Phe
                        580                 585                 590
        Gln Ala Glu Thr Phe Thr Phe His Ala Asp Ile Cys Thr Leu Ser Glu
                        595                 600                 605
        Lys Glu Arg Gln Ile Lys Lys Gln Thr Ala Leu Val Glu Leu Val Lys
                        610                 615                 620
        His Lys Pro Lys Ala Thr Lys Glu Gln Leu Lys Ala Val Met Asp Asp
        625                 630                 635                 640
        Phe Ala Ala Phe Val Glu Lys Cys Cys Lys Ala Asp Asp Lys Glu Thr
                        645                 650                 655
        Cys Phe Ala Glu Glu Gly Lys Lys Leu Val Ala Ala Ser Gln Ala Ala
                        660                 665                 670
        Leu Gly Leu Gly Ser Gly Gly Ser Gly Ala Gln Val Leu Arg Gly
                        675                 680                 685
        Thr Val Thr Asp Phe Pro Gly Phe Asp Glu Arg Ala Asp Ala Glu Thr
                        690                 695                 700
        Leu Arg Lys Ala Met Lys Gly Leu Gly Thr Asp Glu Glu Ser Ile Leu
        705                 710                 715                 720
        Thr Leu Leu Thr Ser Arg Ser Asn Ala Gln Arg Gln Glu Ile Ser Ala
                        725                 730                 735
        Ala Phe Lys Thr Leu Phe Gly Ala Asp Leu Leu Asp Asp Leu Ala Ser
                        740                 745                 750
        Glu Leu Thr Gly Lys Phe Glu Lys Leu Ile Val Ala Leu Met Lys Pro
                        755                 760                 765
        Ser Arg Leu Tyr Asp Ala Tyr Glu Leu Lys His Ala Leu Ala Gly Ala
                        770                 775                 780
        Gly Thr Asn Glu Lys Val Leu Thr Glu Ile Ile Ala Ser Arg Thr Pro
        785                 790                 795                 800
        Glu Glu Leu Arg Ala Ile Lys Gln Val Tyr Glu Glu Glu Tyr Gly Ser
                        805                 810                 815
        Ser Leu Ala Gly Asp Val Val Gly Asp Thr Ser Gly Tyr Tyr Gln Arg
                        820                 825                 830
        Met Leu Val Val Leu Leu Gln Ala Ala Arg Asp Pro Asp Ala Gly Ile
                        835                 840                 845
        Asp Glu Ala Gln Val Glu Gln Asp Ala Gln Ala Leu Phe Gln Ala Gly
                        850                 855                 860
        Glu Leu Lys Trp Gly Thr Asp Glu Glu Lys Phe Ile Thr Ile Phe Gly
        865                 870                 875                 880
        Thr Arg Ser Val Ser His Leu Arg Lys Val Phe Asp Lys Tyr Met Thr
                        885                 890                 895
        Ile Ser Gly Phe Gln Ile Glu Glu Thr Ile Asp Arg Glu Thr Ser Gly
                        900                 905                 910
        Asn Leu Glu Gln Leu Leu Leu Ala Val Val Lys Ser Ile Arg Ser Ile
                        915                 920                 925
        Pro Ala Tyr Leu Ala Glu Thr Leu Tyr Tyr Ala Met Lys Gly Ala Gly
                        930                 935                 940
        Thr Asp Asp His Thr Leu Ile Arg Val Met Val Ser Arg Ser Glu Ile
        945                 950                 955                 960
        Asp Leu Phe Asn Ile Arg Lys Glu Phe Arg Lys Asn Phe Ala Thr Ser
                        965                 970                 975
        Leu Tyr Ser Met Ile Lys Gly Asp Thr Ser Gly Asp Tyr Lys Lys Ala
                        980                 985                 990
```

Leu Leu Leu Leu Cys Gly Glu Asp Asp
         995                    1000

<210> SEQ ID NO 86
<211> LENGTH: 997
<212> TYPE: PRT
<213> ORGANISM: Artificial Sequence
<220> FEATURE:
<223> OTHER INFORMATION: Synthetic construct

<400> SEQUENCE: 86

Met Phe Pro Ala Met Pro Leu Ser Ser Leu Phe Val Asn Gly Pro Arg
1                 5                    10                 15

Thr Leu Cys Gly Ala Glu Leu Val Asp Ala Leu Gln Phe Val Cys Gly
           20                    25                 30

Asp Arg Gly Phe Tyr Phe Asn Lys Pro Thr Gly Tyr Gly Ser Ser Ser
        35                    40                 45

Arg Ala Pro Gln Thr Gly Ile Val Asp Glu Cys Cys Phe Arg Ser Cys
    50                    55                 60

Asp Leu Arg Arg Leu Glu Met Tyr Cys Ala Pro Leu Lys Pro Ala Gly
65                      70                 75               80

Ser Gly Gly Gly Ser Gly Asp Ala His Lys Ser Glu Val Ala His Arg
                 85                    90                 95

Phe Lys Asp Leu Gly Glu Glu Asn Phe Lys Ala Leu Val Leu Ile Ala
           100                   105              110

Phe Ala Gln Tyr Leu Gln Gln Ser Pro Phe Glu Asp His Val Lys Leu
        115                   120              125

Val Asn Glu Val Thr Glu Phe Ala Lys Thr Cys Val Ala Asp Glu Ser
    130                   135              140

Ala Glu Asn Cys Asp Lys Ser Leu His Thr Leu Phe Gly Asp Lys Leu
145                   150               155              160

Cys Thr Val Ala Thr Leu Arg Glu Thr Tyr Gly Glu Met Ala Asp Cys
           165                   170              175

Cys Ala Lys Gln Glu Pro Glu Arg Asn Glu Cys Phe Leu Gln His Lys
        180                   185              190

Asp Asp Asn Pro Asn Leu Pro Arg Leu Val Arg Pro Glu Val Asp Val
    195                   200              205

Met Cys Thr Ala Phe His Asp Asn Glu Glu Thr Phe Leu Lys Lys Tyr
    210                   215              220

Leu Tyr Glu Ile Ala Arg Arg His Pro Tyr Phe Tyr Ala Pro Glu Leu
225                   230               235              240

Leu Phe Phe Ala Lys Arg Tyr Lys Ala Ala Phe Thr Glu Cys Cys Gln
           245                   250              255

Ala Ala Asp Lys Ala Ala Cys Leu Leu Pro Lys Leu Asp Glu Leu Arg
        260                   265              270

Asp Glu Gly Lys Ala Ser Ser Ala Lys Gln Arg Leu Lys Cys Ala Ser
    275                   280              285

Leu Gln Lys Phe Gly Glu Arg Ala Phe Lys Ala Trp Ala Val Ala Arg
    290                   295              300

Leu Ser Gln Arg Phe Pro Lys Ala Glu Phe Ala Glu Val Ser Lys Leu
305                   310               315              320

Val Thr Asp Leu Thr Lys Val His Thr Glu Cys Cys His Gly Asp Leu
           325                   330              335

Leu Glu Cys Ala Asp Asp Arg Ala Asp Leu Ala Lys Tyr Ile Cys Glu
        340                   345              350

```
Asn Gln Asp Ser Ile Ser Ser Lys Leu Lys Glu Cys Cys Glu Lys Pro
        355                 360                 365
Leu Leu Glu Lys Ser His Cys Ile Ala Glu Val Glu Asn Asp Glu Met
    370                 375                 380
Pro Ala Asp Leu Pro Ser Leu Ala Ala Asp Phe Val Glu Ser Lys Asp
385                 390                 395                 400
Val Cys Lys Asn Tyr Ala Glu Ala Lys Asp Val Phe Leu Gly Met Phe
                405                 410                 415
Leu Tyr Glu Tyr Ala Arg Arg His Pro Asp Tyr Ser Val Val Leu Leu
            420                 425                 430
Leu Arg Leu Ala Lys Thr Tyr Glu Thr Thr Leu Glu Lys Cys Cys Ala
        435                 440                 445
Ala Ala Asp Pro His Glu Cys Tyr Ala Lys Val Phe Asp Glu Phe Lys
    450                 455                 460
Pro Leu Val Glu Glu Pro Gln Asn Leu Ile Lys Gln Asn Cys Glu Leu
465                 470                 475                 480
Phe Glu Gln Leu Gly Glu Tyr Lys Phe Gln Asn Ala Leu Leu Val Arg
                485                 490                 495
Tyr Thr Lys Lys Val Pro Gln Val Ser Thr Pro Thr Leu Val Glu Val
            500                 505                 510
Ser Arg Asn Leu Gly Lys Val Gly Ser Lys Cys Cys Lys His Pro Glu
        515                 520                 525
Ala Lys Arg Met Pro Cys Ala Glu Asp Tyr Leu Ser Val Val Leu Asn
    530                 535                 540
Gln Leu Cys Val Leu His Glu Lys Thr Pro Val Ser Asp Arg Val Thr
545                 550                 555                 560
Lys Cys Cys Thr Glu Ser Leu Val Asn Arg Arg Pro Cys Phe Ser Ala
                565                 570                 575
Leu Glu Val Asp Glu Thr Tyr Val Pro Lys Glu Phe Gln Ala Glu Thr
            580                 585                 590
Phe Thr Phe His Ala Asp Ile Cys Thr Leu Ser Glu Lys Glu Arg Gln
        595                 600                 605
Ile Lys Lys Gln Thr Ala Leu Val Glu Leu Val Lys His Lys Pro Lys
    610                 615                 620
Ala Thr Lys Glu Gln Leu Lys Ala Val Met Asp Asp Phe Ala Ala Phe
625                 630                 635                 640
Val Glu Lys Cys Cys Lys Ala Asp Asp Lys Glu Thr Cys Phe Ala Glu
                645                 650                 655
Glu Gly Lys Lys Leu Val Ala Ala Ser Gln Ala Ala Leu Gly Leu Gly
            660                 665                 670
Ser Gly Gly Ser Gly Ala Gln Val Leu Arg Gly Thr Val Thr Asp
        675                 680                 685
Phe Pro Gly Phe Asp Glu Arg Ala Asp Ala Glu Thr Leu Arg Lys Ala
    690                 695                 700
Met Lys Gly Leu Gly Thr Asp Glu Glu Ser Ile Leu Thr Leu Leu Thr
705                 710                 715                 720
Ser Arg Ser Asn Ala Gln Arg Gln Glu Ile Ser Ala Ala Phe Lys Thr
                725                 730                 735
Leu Phe Gly Ala Asp Leu Leu Asp Asp Leu Ala Ser Glu Leu Thr Gly
            740                 745                 750
Lys Phe Glu Lys Leu Ile Val Ala Leu Met Lys Pro Ser Arg Leu Tyr
        755                 760                 765
```

```
Asp Ala Tyr Glu Leu Lys His Ala Leu Ala Gly Ala Gly Thr Asn Glu
    770                 775                 780

Lys Val Leu Thr Glu Ile Ile Ala Ser Arg Thr Pro Glu Glu Leu Arg
785                 790                 795                 800

Ala Ile Lys Gln Val Tyr Glu Glu Tyr Gly Ser Ser Leu Ala Gly
                805                 810                 815

Asp Val Val Gly Asp Thr Ser Gly Tyr Tyr Gln Arg Met Leu Val Val
            820                 825                 830

Leu Leu Gln Ala Ala Arg Asp Pro Asp Ala Gly Ile Asp Glu Ala Gln
                835                 840                 845

Val Glu Gln Asp Ala Gln Ala Leu Phe Gln Ala Gly Glu Leu Lys Trp
850                 855                 860

Gly Thr Asp Glu Glu Lys Phe Ile Thr Ile Phe Gly Thr Arg Ser Val
865                 870                 875                 880

Ser His Leu Arg Lys Val Phe Asp Lys Tyr Met Thr Ile Ser Gly Phe
                885                 890                 895

Gln Ile Glu Glu Thr Ile Asp Arg Glu Thr Ser Gly Asn Leu Glu Gln
                900                 905                 910

Leu Leu Leu Ala Val Val Lys Ser Ile Arg Ser Ile Pro Ala Tyr Leu
            915                 920                 925

Ala Glu Thr Leu Tyr Tyr Ala Met Lys Gly Ala Gly Thr Asp Asp His
    930                 935                 940

Thr Leu Ile Arg Val Met Val Ser Arg Ser Glu Ile Asp Leu Phe Asn
945                 950                 955                 960

Ile Arg Lys Glu Phe Arg Lys Asn Phe Ala Thr Ser Leu Tyr Ser Met
                965                 970                 975

Ile Lys Gly Asp Thr Ser Gly Asp Tyr Lys Lys Ala Leu Leu Leu Leu
            980                 985                 990

Cys Gly Glu Asp Asp
        995
```

<210> SEQ ID NO 87
<211> LENGTH: 2046
<212> TYPE: DNA
<213> ORGANISM: Artificial Sequence
<220> FEATURE:
<223> OTHER INFORMATION: Synthetic construct

<400> SEQUENCE: 87

```
atgttcccag ccatgccctt gtccagcctg tttgttaacg cccaagaac actttgtgga     60
gccgaactgg tggatgctct ccaattcgtt gcggcgacc gcggattcta ctttaacaag    120
cccaccggtt acgggtcttc aagccgggcc ccgcagactg catcgtcga cgagtgctgt    180
tttagaagct gcgatctgcg acggttggag atgtattgtg cacctctgaa gcccgcggga    240
ggagacgctc acaagtctga gtggcacat aggttcaaag atctgggcga agagaacttt    300
aaggccctcg tcctgatcgc tttcgcacag tacctccagc agtctcccttt tgaagatcac    360
gtgaaactgg tcaatgaggt gaccgaattt gccaagacat gcgtggctga tgagagtgca    420
gaaaactgtg acaaatcact gcatactctc tttggagata agctgtgcac cgtcgccaca    480
ctcagagaga cttatgggga atggctgac tgttgcgcaa acaggagcc tgaacggaat    540
gagtgtttcc tccagcacaa ggatgacaac ccaaatctgc cccgcctcgt gcgacctgag    600
gtcgatgtga tgtgcaccgc cttcatgac aacgaagaga cattcctgaa gaaatacctg    660
tatgaaattg ctcgtaggca cccatacttt atgcccccg agctcctgtt ctttgcaaag    720
```

| | |
|---|---|
| agatacaaag ctgccttcac tgaatgttgc caggcagctg ataaggccgc atgtctcctg | 780 |
| cctaaactgg acgagctccg ggatgaaggt aaggcttcca gcgccaaaca gcgcctgaag | 840 |
| tgcgcttctc tccagaagtt tggcgagcga gcattcaaag cctgggctgt ggcccgtctc | 900 |
| agtcagaggt ttccaaaggc agaatttgct gaggtgtcaa aactggtgac cgacctcaca | 960 |
| aaggtccata ctgagtgttg ccacggagat ctgctggaat gtgccgacga tagagcagac | 1020 |
| ctcgctaaat atatctgcga gaatcaggat tccattagct ctaagctgaa gaatgttgc | 1080 |
| gagaagcccc tcctggaaaa gagtcattgt atcgccgagg tggaaaacga cgagatgcca | 1140 |
| gcagatctgc catcactcgc tgccgacttt gtggaatcca agatgtctg caagaattac | 1200 |
| gcagaggcta agacgtgtt cctggggatg tttctgtatg agtacgcccg gcgtcacccc | 1260 |
| gattatagcg tcgtgctcct gctccgactg gcaaagacct acgaaacaac tctggagaaa | 1320 |
| tgttgcgctg ccgcagaccc tcatgaatgt tatgctaagg tgttcgatga gtttaagcca | 1380 |
| ctcgtcgaag agccccagaa cctgattaaa cagaattgcg aactgttcga gcagctcggt | 1440 |
| gaatacaagt ttcagaacgc cctgctcgtg cgttatacca aaaaggtccc tcaggtgtct | 1500 |
| acaccaactc tggtggaggt cagtaggaat ctgggcaaag tgggatcaaa gtgttgcaaa | 1560 |
| caccccgagg caaagagaat gccttgtgct gaagattacc tctccgtcgt gctgaaccag | 1620 |
| ctctgcgtgc tgcatgaaaa gaccccagtc agcgaccggg tgacaaaatg ttgcaccgaa | 1680 |
| tctctggtca atcgccgacc ctgtttcagt gccctcgaag tggacgaaac ttatgtgcct | 1740 |
| aaggagtttc aggctgaaac attcacccttt cacgccgata tctgcactct gtccgagaaa | 1800 |
| gaaaggcaga ttaagaaaca gacagcactg gtcgagctcg tgaagcataa accaaaggct | 1860 |
| accaaggagc agctgaaagc cgtcatggac gatttcgcag cttttgtgga aaagtgttgc | 1920 |
| aaagccgacg ataaggagac ttgtttcgca gaagagggga aaaagctcgt ggctgccagc | 1980 |
| caggcagctc tgggtctggg cagtggtggc tcaggtagcg gccaccatca ccatcaccac | 2040 |
| taatga | 2046 |

<210> SEQ ID NO 88
<211> LENGTH: 3237
<212> TYPE: DNA
<213> ORGANISM: Artificial Sequence
<220> FEATURE:
<223> OTHER INFORMATION: Synthetic construct

<400> SEQUENCE: 88

| | |
|---|---|
| atgttcccag ccatgccctt gtccagcctg tttgttaacg gcccaagaac actttgtgga | 60 |
| gccgaactgg tggatgctct ccaattcgtt tgcggcgacc gcggattcta ctttaacaag | 120 |
| cccaccggtt acgggtcttc aagccgggcc ccgcagactg gcatcgtcga cgagtgctgt | 180 |
| tttagaagct gcgatctgcg acggttggag atgtattgtg cacctctgaa gcccgcgggt | 240 |
| tccggagggtt ctggcggtgg atctgggggc ggtagcggag gcggcagtgg tggtggcagc | 300 |
| gggggagggt caggtggggg tagtggcggt ggttctggag gtggttcagg aggaggagac | 360 |
| gctcacaagt ctgaagtggc acataggttc aaagatctgg gcgaagagaa ctttaaggcc | 420 |
| ctcgtcctga tcgctttcgc acagtacctc agcagtctc cctttgaaga tcacgtgaaa | 480 |
| ctggtcaatg aggtgaccga atttgccaag acatgcgtgg ctgatgagag tgcagaaaac | 540 |
| tgtgacaaat cactgcatac tctctttgga gataagctgt gcaccgtcgc cacactcaga | 600 |
| gagacttatg gggaaatggc tgactgttgc gcaaaacagg agcctgaacg gaatgagtgt | 660 |
| ttcctccagc acaaggatga caacccaaat ctgccccgcc tcgtgcgacc tgaggtcgat | 720 |

```
gtgatgtgca ccgcctttca tgacaacgaa gagacattcc tgaagaaata cctgtatgaa    780
attgctcgta ggcacccata cttttatgcc cccgagctcc tgttctttgc aaagagatac    840
aaagctgcct tcactgaatg ttgccaggca gctgataagg ccgcatgtct cctgcctaaa    900
ctggacgagc tccgggatga aggtaaggct tccagcgcca acagcgcct  gaagtgcgct    960 tctctccaga gtttggcga  gcgagcattc aaagcctggg ctgtggcccg tctcagtcag   1020
aggtttccaa aggcagaatt tgctgaggtg tcaaaactgg tgaccgacct cacaaaggtc   1080
catactgagt gttgccacgg agatctgctg gaatgtgccg acgatagagc agacctcgct   1140
aaatatatct gcgagaatca ggattccatt agctctaagc tgaaagaatg ttgcgagaag   1200
cccctcctgg aaaagagtca ttgtatcgcc gaggtggaaa acgacgagat gccagcagat   1260
ctgccatcac tcgctgccga ctttgtggaa tccaaagatg tctgcaagaa ttacgcagag   1320
gctaaagacg tgttcctggg gatgtttctg tatgagtacg cccggcgtca ccccgattat   1380
agcgtcgtgc tcctgctccg actggcaaag acctacgaaa caactctgga gaaatgttgc   1440
gctgccgcag accctcatga atgttatgct aaggtgttcg atgagtttaa gccactcgtc   1500
gaaagagccc agaacctgat taaacagaat tgcgaactgt tcgagcagct cggtgaatac   1560
aagtttcaga acgccctgct cgtgcgttat accaaaaagg tccctcaggt gtctacacca   1620
actctggtgg aggtcagtag gaatctgggc aaagtgggat caaagtgttg caaacacccc   1680
gaggcaaaga gaatgccttg tgctgaagat tacctctccg tcgtgctgaa ccagctctgc   1740
gtgctgcatg aaaagacccc agtcagcgac cgggtgacaa aatgttgcac cgaatctctg   1800
gtcaatcgcc gaccctgttt cagtgccctc gaagtggacg aaacttatgt gcctaaggag   1860
tttcaggctg aaacattcac cttttcacgcc gatatctgca ctctgtccga aaagaaagg   1920 cagattaaga acagacagc  actggtcgag ctcgtgaagc ataaaccaaa ggctaccaag   1980
gagcagctga aagccgtcat ggacgatttc gcagcttttg tggaaaagtg ttgcaaagcc   2040
gacgataagg agacttgttt cgcagaagag gggaaaaagc tcgtggctgc cagccaggca   2100
gctctgggtc tggggtctgg tggatcaggg ggaggttcag gcggggggcag tggcggggga   2160 tctggaggtg gcagtggggg cggttccgga ggtggatcag gaggaggaag tggcggcggt   2220
agcggtggtg gtgctcaagt cttgcgtggt acggtgacag acttcccagg cttcgatgaa   2280
agagcggacg cggaaacact tcgaaaggcg atgaaagggc tcggtactga cgaagagtcc   2340
attttgaccc ttcttacgag caggtcaaac gctcagaggc aagaaatctc tgcagccttt   2400
aagacactct ttgacgtgga ccttcttgat gacctcaaat ctgagctgac gggaaagttt   2460
gagaaactca tcgtagcttt gatgaagccc agccgattgt atgatgctta cgaactgaaa   2520
cacgccctga aggagcggg  aacgaacgag aaagttttga ctgagatcat cgcatcgcgg   2580
accccggaag agctcagagc catcaaacaa gtctacgagg aggagtacgg atcgtcattg   2640
gaagatgacg tggtgggga  tacgtcgggt tactaccaac gaatgcttgt cgtgcttttg   2700
caggcaaatc gcgacccgga tgcggggatc gacgaggccc aagtggagca agatgcgcaa   2760
gcactcttcc aggccggtga actcaaatgg gggaccgatg aagagaagtt tatcaccatc   2820
tttggcacga ggagtgtaag tcatctgcgt aaagtattcg ataagtatat gacaatctca   2880
gggtttcaga ttgaggagac aattgacagg gaaacctccg gtaacttgga gcagctcttg   2940
cttgccgtcg tcaagtccat tcgctcgatc cctgcgtatc tggctgaaac actgtattac   3000
gccatgaaag gggcaggcac tgatgaccac accttgatta gagttatggt gtcgcgatca   3060
```

| | |
|---|---:|
| gaaattgact tgttcaatat ccggaaagag ttccggaaga atttcgcaac gagcctctat | 3120 |
| agcatgatca aagggacac ttcgggagat acaagaaag cgttgctcct tctttcagga | 3180 |
| gaggatgacg gcagtggtgg ctcaggtagc ggccaccatc accatcacca ctaatga | 3237 |

<210> SEQ ID NO 89
<211> LENGTH: 2130
<212> TYPE: DNA
<213> ORGANISM: Artificial Sequence
<220> FEATURE:
<223> OTHER INFORMATION: Synthetic construct

<400> SEQUENCE: 89

| | |
|---|---:|
| atgttcccag ccatgccctt gtccagcctg tttgttaacg gcccaagaac actttgtgga | 60 |
| gccgaactgg tggatgctct ccaattcgtt tgcggcgacc gcggattcta ctttaacaag | 120 |
| cccaccggtt acgggtcttc aagccggagg gccccgcaga ctggcatcgt cgacgagtgc | 180 |
| tgttttagaa gctgcgatct gcgacggttg gagatgtatt gtgcacctct gaagcccgcg | 240 |
| aaaagtgctg gttccggagg ttctggcggt ggatctgggg gcgtagcgg aggcggcagt | 300 |
| ggtggtggca gcgggggagg gtcaggtggg ggtagtggcg gtggttctgg aggtggttca | 360 |
| ggaggaggag ataagaccca tacatgccct ccgtgccccg caccggaact cttgggtggc | 420 |
| ccatcagtct ttctgttccc gccaaagccc aaagacacac tgatgatttc gcgcacgccc | 480 |
| gaagtcactt gcgtcgtggt ggatgtgtcg catgaggacc cggaggtcaa gttcaactgg | 540 |
| tacgtcgatg gtgtagaagt ccacaacgcc aagaccaagc ctcgggagga gcagtatcag | 600 |
| tccacctacc gggtagtgag cgtgcttaca gtgctccatc aggactggct gaacggcaaa | 660 |
| gaatacaaat gcaaagtcag caacaaagcg ctgccagcgc ccatcgagaa acaattagc | 720 |
| aaagcgaaag gcagcccag agaacctcaa gtgtatacat gccgccgtc gcgggaggaa | 780 |
| atgacaaaga atcaggtatc cctgacgtgt cttgtgaaag cttttaccc atccgacatt | 840 |
| gcggtagagt gggagtcgaa tgggcaaccc gagaacaact ataagacgac tccccagtc | 900 |
| ttggattcag acggctcttt tttcttgtac tcgaaactca cagtcgacaa gtccagatgg | 960 |
| cagcagggga cgtgttcag ctgcagcgtg atgcacgagg cccttcacaa ccactatacg | 1020 |
| cagaaatcat taagcttatc gcctgggggg tctggtggat caggggaggg ttcaggcggg | 1080 |
| ggcagtggcg ggggatctgg aggtggcagt ggggggcggtt ccggaggtgg atcaggagga | 1140 |
| ggaagtggcg gcggtagcgg tggtggtgct caagtcttgc gtggtacggt gacagacttc | 1200 |
| ccaggcttcg atgaaagagc ggacgcggaa acacttcgaa aggcgatgaa agggctcggt | 1260 |
| actgacgaag agtccatttt gacccttctt acgagcaggt caaacgctca gaggcaagaa | 1320 |
| atctctgcag cctttaagac actctttgga cgtgaccttc ttgatgacct caaatctgag | 1380 |
| ctgacgggaa agtttgagaa actcatcgta gctttgatga gcccagccg attgtatgat | 1440 |
| gcttacgaac tgaaacacgc cctgaaagga gcgggaacga acgagaaagt tttgactgag | 1500 |
| atcatcgcat cgcggacccc ggaagagctc agagccatca acaagtcta cgaggaggag | 1560 |
| tacggatcgt cattggaaga tgacgtggtg ggggatacgt cgggttacta ccaacgaatg | 1620 |
| cttgtcgtgc ttttgcaggc aaatcgcgac ccggatgcgg ggatcgacga ggcccaagtg | 1680 |
| gagcaagatg cgcaagcact cttccaggcc ggtgaactca atggggac cgatgaagag | 1740 |
| aagtttatca ccatctttgg cacgaggagt gtaagtcatc tgcgtaaagt attcgataag | 1800 |
| tatatgacaa tctcagggtt tcagattgag gagacaattg acaggaaac ctccggtaac | 1860 |
| ttggagcagc tcttgcttgc cgtcgtcaag tccattcgct cgatccctgc gtatctggct | 1920 |

| | |
|---|---:|
| gaaacactgt attacgccat gaaaggggca ggcactgatg accacacctt gattagagtt | 1980 |
| atggtgtcgc gatcagaaat tgacttgttc aatatccgga aagagttccg gaagaatttc | 2040 |
| gcaacgagcc tctatagcat gatcaaaggg gacacttcgg gagattacaa gaaagcgttg | 2100 |
| ctccttcttt caggagagga tgactaatga | 2130 |

<210> SEQ ID NO 90
<211> LENGTH: 1038
<212> TYPE: DNA
<213> ORGANISM: Artificial Sequence
<220> FEATURE:
<223> OTHER INFORMATION: Synthetic construct

<400> SEQUENCE: 90

| | |
|---|---:|
| atgttcccag ccatgccctt gtccagcctg tttgttaacg cccaagaac actttgtgga | 60 |
| gccgaactgg tggatgctct ccaattcgtt tgcggcgacc gcggattcta ctttaacaag | 120 |
| cccaccggtt acgggtcttc aagccggggcc ccgcagactg catcgtcga cgagtgctgt | 180 |
| tttagaagct gcgatctgcg acggttggag atgtattgtg cacctctgaa gcccgcggggt | 240 |
| tccggaggtt ctggcggtgg atctgggggc ggtagcggag cggcagtgg tggtggcagc | 300 |
| gggggagggt caggtggggg tagtggcggt ggttctggag gtggttcagg aggaggagat | 360 |
| aagacccata catgccctcc gtgccccgca ccggaactct gggtggccc atcagtcttt | 420 |
| ctgttcccgc caaagcccaa agacacactg atgatttcgc gcacgcccga agtcacttgc | 480 |
| gtcgtggtgg atgtgtcgca tgaggacccg gaggtcaagt tcaactggta cgtcgatggt | 540 |
| gtagaagtcc acaacgccaa gaccaagcct cgggaggagc agtatcagtc cacctaccgg | 600 |
| gtagtgagcg tgcttacagt gctccatcag gactggctga acggcaaaga atacaaatgc | 660 |
| aaagtcagca acaaagcgct gccagcgccc atcgagaaaa caattagcaa agcgaagggg | 720 |
| cagcccagag aacctcaagt gtatacattg ccgccgtcgc gggaggaaat gacaaagaat | 780 |
| caggtatccc tgacgtgtct tgtgaaaggc ttttacccat ccgacattgc ggtagagtgg | 840 |
| gagtcgaatg gcaacccga gaacaactat aagacgactc ccccagtctt ggattcagac | 900 |
| ggatccttt tcttgtactc gaaactcaca gtcgacaagt ccagatggca gcaggggaac | 960 |
| gtgttcagct gcagcgtgat gcacgaggcc cttcacaacc actatacgca gaaatcatta | 1020 |
| agcttatcgc ctgggtaa | 1038 |

<210> SEQ ID NO 91
<211> LENGTH: 3053
<212> TYPE: DNA
<213> ORGANISM: Artificial Sequence
<220> FEATURE:
<223> OTHER INFORMATION: Synthetic construct

<400> SEQUENCE: 91

| | |
|---|---:|
| tgttcccagc catgcccttg tccagcctgt tgttaacgg cccaagaaca ctttgtggag | 60 |
| ccgaactggt ggatgctctc caattcgttt gcggcgaccg cggattctac tttaacaagc | 120 |
| caccggtta cgggtcttca agccggaggg cccgcagac tggcatcgtc gacgagtgct | 180 |
| gttttagaag ctgcgatctg cgacggttgg agatgtattg tgcacctctg aagcccgcga | 240 |
| aaagtgctgg ttccggaggg agcggtggtg ggagtggcgg atctggtgga ggagacgctc | 300 |
| acaagtctga agtggcacat aggttcaaag atctgggcga agagaacttt aaggccctcg | 360 |
| tcctgatcgc tttcgcacag tacctccagc agtctcccct tgaagatcac gtgaaactgg | 420 |

```
tcaatgaggt gaccgaattt gccaagacat gcgtggctga tgagagtgca gaaaactgtg   480
acaaatcact gcatactctc tttggagata agctgtgcac cgtcgccaca ctcagagaga   540
cttatgggga atggctgac tgttgcgcaa acaggagcc tgaacggaat gagtgtttcc     600
tccagcacaa ggatgacaac ccaaatctgc ccgcctcgt gcgacctgag gtcgatgtga    660
tgtgcaccgc ctttcatgac aacgaagaga cattcctgaa gaaatacctg tatgaaattg   720
ctcgtaggca cccatacttt tatgcccccg agctcctgtt ctttgcaaag agatacaaag   780
ctgccttcac tgaatgttgc caggcagctg ataaggccgc atgtctcctg cctaaactgg   840
acgagctccg ggatgaaggt aaggcttcca gcgccaaaca gcgcctgaag tgcgcttctc   900
tccagaagtt tggcgagcga gcattcaaag cctgggctgt ggcccgtctc agtcagaggt   960
ttccaaaggc agaatttgct gaggtgtcaa aactggtgac cgacctcaca aaggtccata  1020
ctgagtgttg ccacggagat ctgctggaat gtgccgacga tagagcagac ctcgctaaat  1080
atatctgcga gaatcaggat tccattagct ctaagctgaa agaatgttgc gagaagcccc  1140
tcctggaaaa gagtcattgt atcgccgagg tggaaaacga cgagatgcca gcagatctgc  1200
catcactcgc tgccgacttt gtggaatcca aagatgtctg caagaattac gcagaggcta  1260
aagacgtgtt cctggggatg tttctgtatg agtacgcccg cgtcacccc gattatagcg    1320 tcgtgctcct gctccgactg gcaaagacct acgaaacaac tctggagaaa tgttgcgctg  1380
ccgcagaccc tcatgaatgt tatgctaagg tgttcgatga gtttaagcca ctcgtcgaag  1440
agccccagaa cctgattaaa cagaattgcg aactgttcga gcagctcggt gaatacaagt  1500 tcagaacgc cctgctcgtg cgttatacca aaaaggtccc tcaggtgtct acaccaactc    1560
tggtggaggt cagtaggaat ctgggcaaag tgggatcaaa gtgttgcaaa cacccccgagg 1620 caaagagaat gccttgtgct gaagattacc tctccgtcgt gctgaaccag ctctgcgtgc  1680
tgcatgaaaa gaccccagtc agcgaccggg tgacaaaatg ttgcaccgaa tctctggtca  1740
atcgccgacc ctgtttcagt gccctcgaag tggacgaaac ttatgtgcct aaggagtttc  1800
aggctgaaac attcacctttt cacgccgata tctgcactct gtccgagaaa gaaaggcaga  1860
ttaagaaaca gacagcactg gtcgagctcg tgaagcataa accaaaggct accaaggagc  1920
agctgaaagc cgtcatggac gatttcgcag cttttgtgga aaagtgttgc aaagccgacg  1980
ataaggagac ttgtttcgca gaagagggga aaaagctcgt ggctgccagc caggcagctc  2040
tgggtctggg gtctggcggt tcaggggag gaagtggagg ctcaggaggt ggtgctcaag   2100
tcttgcgtgg tacggtgaca gacttcccag gcttcgatga agagcggac gcggaaacac   2160 ttcgaaaggc gatgaaaggg ctcggtactg acgaagagtc cattttgacc cttcttacga  2220
gcaggtcaaa cgctcagagg caagaaatct ctgcagcctt taagacactc tttggacgtg  2280
accttcttga tgacctcaaa tctgagctga cgggaaagtt tgagaaactc atcgtagctt  2340
tgatgaagcc cagccgattg tatgatgctt acgaactgaa acacgccctg aaaggagcgg   2400
gaacgaacga gaaagtttg actgagatca tcgcatcgcg gacccggaa gagctcagag    2460 ccatcaaaca agtctacgag gaggagtacg gatcgtcatt ggaagatgac gtggtggggg  2520
atacgtcggg ttactaccaa cgaatgcttg tcgtgctttt gcaggcaaat cgcgacccgg   2580
atgcggggat cgacgaggcc caagtggagc aagatgcgca agcactcttc caggccggtg  2640
aactcaaatg ggggaccgat gaagagaagt ttatcaccat ctttggcacg aggagtgtaa   2700
gtcatctgcg taaagtattc gataagtata tgacaatctc agggtttcag attgaggaga  2760
caattgacag ggaaaccctcc ggtaacttgg agcagctctt gcttgccgtc gtcaagtcca   2820
```

-continued

| | |
|---|---|
| ttcgctcgat ccctgcgtat ctggctgaaa cactgtatta cgccatgaaa ggggcaggca | 2880 |
| ctgatgacca caccttgatt agagttatgg tgtcgcgatc agaaattgac ttgttcaata | 2940 |
| tccggaaaga gttccggaag aatttcgcaa cgagcctcta tagcatgatc aaaggggaca | 3000 |
| cttcgggaga ttacaagaaa gcgttgctcc ttctttgcgg agaggatgac taa | 3053 |

<210> SEQ ID NO 92
<211> LENGTH: 3057
<212> TYPE: DNA
<213> ORGANISM: Artificial Sequence
<220> FEATURE:
<223> OTHER INFORMATION: Synthetic construct

<400> SEQUENCE: 92

| | |
|---|---|
| atgttcccag ccatgccctt gtccagcctg tttgttaacg cccaagaac actttgtgga | 60 |
| gccgaactgg tggatgctct ccaattcgtt tgcggcgacc gcggattcta ctttaacaag | 120 |
| cccaccggtt acgggtcttc aagccggagg ccccgcaga ctggcatcgt cgacgagtgc | 180 |
| tgttttagaa gctgcgatct gcgacggttg agatgtatt gtgcacctct gaagcccgcg | 240 |
| aaaagtgctg gttccggagg gagcggtggt gggagtggcg gatctggtgg aggagacgct | 300 |
| cacaagtctg aagtggcaca taggttcaaa gatctgggcg aagagaactt taaggccctc | 360 |
| gtcctgatcg ctttcgcaca gtacctccag cagtctccct ttgaagatca cgtgaaactg | 420 |
| gtcaatgagg tgaccgaatt tgccaagaca tgcgtggctg atgagagtgc agaaaactgt | 480 |
| gacaaatcac tgcatactct ctttggagat aagctgtgca ccgtcgccac actcagagag | 540 |
| acttatgggg aaatggctga ctgttgcgca aaacaggagc ctgaacggaa tgagtgtttc | 600 |
| ctccagcaca aggatgacaa cccaaatctg ccccgcctcg tgcgacctga ggtcgatgtg | 660 |
| atgtgcaccg cctttcatga caacgaagag acattcctga gaaatacct gtatgaaatt | 720 |
| gctcgtaggc acccatactt ttatgccccc gagctcctgt tctttgcaaa gagatacaaa | 780 |
| gctgccttca ctgaatgttg ccaggcagct gataaggccg catgtctcct gcctaaactg | 840 |
| gacgagctcc gggatgaagg taaggcttcc agcgccaaac agcgcctgaa gtgcgcttct | 900 |
| ctccagaagt ttggcgagcg agcattcaaa gcctgggctg tggcccgtct cagtcagagg | 960 |
| tttccaaagg cagaatttgc tgaggtgtca aaactggtga ccgacctcac aaaggtccat | 1020 |
| actgagtgtt gccacggaga tctgctggaa tgtgccgacg atagagcaga cctcgctaaa | 1080 |
| tatatctgcg agaatcagga ttccattagc tctaagctga agaatgttg cgagaagccc | 1140 |
| ctcctggaaa agagtcattg tatcgccgag gtggaaaacg acgagatgcc agcagatctg | 1200 |
| ccatcactcg ctgccgactt tgtggaatcc aaagatgtct gcaagaatta cgcagaggct | 1260 |
| aaagacgtgt tcctggggat gtttctgtat gagtacgccc ggcgtcaccc cgattatagc | 1320 |
| gtcgtgctcc tgctccgact ggcaaagacc tacgaaacaa ctctggagaa atgttgcgct | 1380 |
| gccgcagacc ctcatgaatg ttatgctaag gtgttcgatg agtttaagcc actcgtcgaa | 1440 |
| gagccccaga acctgattaa acagaattgc gaactgttcg agcagctcgg tgaatacaag | 1500 |
| tttcagaacg ccctgctcgt gcgttatacc aaaaaggtcc ctcaggtgtc tacaccaact | 1560 |
| ctggtggagg tcagtaggaa tctgggcaaa gtgggatcaa agtgttgcaa acaccccgag | 1620 |
| gcaaagagaa tgccttgtgc tgaagattac ctctccgtcg tgctgaacca gctctgcgtg | 1680 |
| ctgcatgaaa agacccccagt cagcgaccgg gtgacaaaat gttgcaccga atctctggtc | 1740 |
| aatcgccgac cctgtttcag tgccctcgaa gtggacgaaa cttatgtgcc taaggagttt | 1800 |

| | |
|---|---|
| caggctgaaa cattcacctt tcacgccgat atctgcactc tgtccgagaa agaaaggcag | 1860 |
| attaagaaac agacagcact ggtcgagctc gtgaagcata aaccaaaggc taccaaggag | 1920 |
| cagctgaaag ccgtcatgga cgatttcgca gcttttgtgg aaaagtgttg caaagccgac | 1980 |
| gataaggaga cttgtttcgc agaagagggg aaaaagctcg tggctgccag ccaggcagct | 2040 |
| ctgggtctgg ggtctggcgg ttcaggggga ggaagtggag gctcaggagg tggtgctcaa | 2100 |
| gtcttgcgtg gtacggtgac agacttccca ggcttcgatg aaagagcgga cgcggaaaca | 2160 |
| cttcgaaagg cgatgaaagg gctcggtact gacgaagagt ccattttgac ccttcttacg | 2220 |
| agcaggtcaa acgctcagag gcaagaaatc tctgcagcct ttaagacact ctttggagct | 2280 |
| gaccttcttg atgacctcgc atctgagctg acgggaaagt ttgagaaact catcgtagct | 2340 |
| ttgatgaagc ccagccgatt gtatgatgct tacgaactga acacgccct ggctggagcg | 2400 |
| ggaacgaacg agaaagtttt gactgagatc atcgcatcgc ggaccccgga gagctcaga | 2460 |
| gccatcaaac aagtctacga ggaggagtac ggatcgtcat ggcaggaga cgtggtgggg | 2520 |
| gatacgtcgg gttactacca acgaatgctt gtcgtgcttt tgcaggcagc tcgcgacccg | 2580 |
| gatgcgggga tcgacgaggc ccaagtggag caagatgcgc aagcactctt ccaggccggt | 2640 |
| gaactcaaat gggggaccga tgaagagaag tttatcacca tctttggcac gaggagtgta | 2700 |
| agtcatctgc gtaaagtatt cgataagtat atgacaatct cagggtttca gattgaggag | 2760 |
| acaattgaca gggaaacctc cggtaacttg gagcagctct tgcttgccgt cgtcaagtcc | 2820 |
| attcgctcga tccctgcgta tctggctgaa acactgtatt acgccatgaa aggggcaggc | 2880 |
| actgatgacc acaccttgat tagagttatg tgtcgcgat cagaaattga cttgttcaat | 2940 |
| atccggaaag agttccggaa gaatttcgca acgagcctct atagcatgat caaaggggac | 3000 |
| acttcgggag attacaagaa agcgttgctc cttctttgcg gagaggatga ctaatga | 3057 |

<210> SEQ ID NO 93
<211> LENGTH: 3057
<212> TYPE: DNA
<213> ORGANISM: Artificial Sequence
<220> FEATURE:
<223> OTHER INFORMATION: Synthetic construct

<400> SEQUENCE: 93

| | |
|---|---|
| atgttcccag ccatgccctt gtccagcctg tttgttaacg cccaagaac actttgtgga | 60 |
| gccgaactgg tggatgctct ccaattcgtt tgcggcgacc gcggattcta ctttaacaag | 120 |
| cccaccggtt acgggtcttc aagccggagg gccccgcaga ctggcatcgt cgacgagtgc | 180 |
| tgttttagaa gctgcgatct cgacggttg gagatgtatt gtgcacctct gaagcccgcg | 240 |
| aaaagtgctg gttccggagg gagcggtggt gggagtggcg gatctggtgg aggagacgct | 300 |
| cacaagtctg aagtggcaca taggttcaaa gatctgggcg aagagaactt taaggccctc | 360 |
| gtcctgatcg ctttcgcaca gtacctccag cagtctccct ttgaagatca cgtgaaactg | 420 |
| gtcaatgagg tgaccgaatt tgccaagaca tgcgtggctg atgagagtgc agaaaactgt | 480 |
| gacaaatcac tgcatactct ctttggagat aagctgtgca ccgtcgccac actcagagag | 540 |
| acttatgggg aaatggctga ctgttgcgca aaacaggagc tgaacggaa tgagtgtttc | 600 |
| ctccagcaca aggatgacaa cccaaatctg ccccgcctcg tgcgacctga ggtcgatgtg | 660 |
| atgtgcaccg cctttcatga caacgaagag acattcctga gaaataccct gtatgaaatt | 720 |
| gctcgtaggc acccatactt ttatgccccc gagctcctgt tctttgcaaa agatacaaa | 780 |
| gctgccttca ctgaatgttg ccaggcagct gataaggccg catgtctcct gcctaaactg | 840 |

-continued

```
gacgagctcc gggatgaagg taaggcttcc agcgccaaac agcgcctgaa gtgcgcttct    900
ctccagaagt ttggcgagcg agcattcaaa gcctgggctg tggcccgtct cagtcagagg    960
tttccaaagg cagaatttgc tgaggtgtca aaactggtga ccgacctcac aaaggtccat   1020
actgagtgtt gccacggaga tctgctggaa tgtgccgacg atagagcaga cctcgctaaa   1080
tatatctgcg agaatcagga ttccattagc tctaagctga agaatgttg cgagaagccc    1140 ctcctggaaa agagtcattg tatcgccgag gtggaaaacg acgagatgcc agcagatctg   1200
ccatcactcg ctgccgactt tgtggaatcc aaagatgtct gcaagaatta cgcagaggct   1260
aaagacgtgt tcctggggat gtttctgtat gagtacgccc ggcgtcaccc cgattatagc   1320
gtcgtgctcc tgctccgact ggcaaagacc tacgaaacaa ctctggagaa atgttgcgct   1380
gccgcagacc tcatgaatg ttatgctaag gtgttcgatg agtttaagcc actcgtcgaa    1440
gagccccaga acctgattaa acagaattgc gaactgttcg agcagctcgg tgaatacaag   1500
tttcagaacg ccctgctcgt gcgttatacc aaaaaggtcc ctcaggtgtc tacaccaact   1560
ctggtggagg tcagtaggaa tctgggcaaa gtgggatcaa agtgttgcaa acaccccgag   1620
gcaaagagaa tgccttgtgc tgaagattac ctctccgtcg tgctgaacca gctctgcgtg   1680
ctgcatgaaa agaccccagt cagcgaccgg gtgacaaaat gttgcaccga atctctggtc   1740
aatcgccgac cctgtttcag tgccctcgaa gtggacgaaa cttatgtgcc taaggagttt   1800
caggctggaa cattcaccttt tcacgccgat atctgcactc tgtccgagaa agaaaggcag   1860
attaagaaac agacagcact ggtcgagctc gtgaagcata aaccaaaggc taccaaggag   1920
cagctgaaag ccgccatgga cgatttcgca gcttttgtgg aaaagtgttg caaagccgac   1980
gataaggaga cttgtttcgc agaagagggg aaaaagctcg tggctgccag ccaggcagct   2040
ctgggtctgg ggtctggcgg ttcaggggga ggaagtggag gctcaggagg tggtgctcaa   2100
gtcttgcgtg gtacggtgac agacttccca ggcttcgatg aaagagcgga cgcggaaaca   2160
cttcgaaagg cgatgaaagg gctcggtact gacgaagagt ccattttgac ccttcttacg   2220
agcaggtcaa acgctcagag gcaagaaatc tctgcagcct ttaagacact ctttggagct   2280
gaccttcttg atgacctcgc atctgagctg acgggaaagt ttgagaaact catcgtagct   2340
ttgatgaagc ccagccgatt gtatgatgct tacgaactga acacgccct ggctggagcg    2400 ggaacgaacg agaaagtttt gactgagatc atcgcatcgc ggaccccgga agagctcaga   2460
gccatcaaac aagtctacga ggaggagtac ggatcgtcat ggcaggaga cgtggtgggg    2520 gatacgtcgg gttactacca acgaatgctt gtcgtgcttt gcaggcagc tcgcgacccg    2580 gatgcgggga tcgacgaggc ccaagtggag caagatgcgc aagcactctt ccaggccggt   2640
gaactcaaat gggggaccga tgaagagaag tttatcacca tctttggcac gaggagtgta   2700
agtcatctgc gtaaagtatt cgataagtat atgacaatct cagggtttca gattgaggag   2760
acaattgaca gggaaacctc cggtaacttg agcagctctc tgcttgccgt cgtcaagtcc   2820
attcgctcga tccctgcgta tctggctgaa acactgtatt acgccatgaa aggggcaggc   2880
actgatgacc acaccttgat tagagttatg gtgtcgcgat cagaaattga cttgttcaat   2940
atccggaaag agttccggaa gaatttcgca acgagcctct atagcatgat caaagggac    3000 acttcgggag attacaagaa agcgttgctc cttctttgcg gagaggatga ctaatga      3057
```

<210> SEQ ID NO 94
<211> LENGTH: 3195
<212> TYPE: DNA

<213> ORGANISM: Artificial Sequence
<220> FEATURE:
<223> OTHER INFORMATION: Synthetic construct

<400> SEQUENCE: 94

```
atgttcccag ccatgccctt gtccagcctg tttgttaacg cccaagaac actttgtgga      60
gccgaactgg tggatgctct ccaattcgtt tgcggcgacc gcggattcta ctttaacaag     120
cccaccggtt acgggtcttc aagccgggcc ccgcagactg gcatcgtcga cgagtgctgt     180
tttagaagct gcgatctgcg acggttggag atgtattgtg cacctctgaa gcccgcgggt     240
tccggaggtt ctggcggtgg atctgggggc ggtagcggag gcggcagtgg tggtggcagc     300
ggggggagggt caggtggggg tagtggcggt ggttctggag gtggttcagg aggaggagac     360
gctcacaagt ctgaagtggc acataggttc aaagatctgg gcgaagagaa ctttaaggcc     420
ctcgtcctga tcgctttcgc acagtacctc cagcagtctc cctttgaaga tcacgtgaaa     480
ctggtcaatg aggtgaccga atttgccaag acatgcgtgg ctgatgagag tgcagaaaac     540
tgtgacaaat cactgcatac tctctttgga gataagctgt gcaccgtcgc cacactcaga     600
gagacttatg ggaaatggc tgactgttgc gcaaaacagg agcctgaacg aatgagtgt     660
ttcctccagc acaaggatga caacccaaat ctgccccgcc tcgtgcgacc tgaggtcgat     720
gtgatgtgca ccgcctttca tgacaacgaa gagacattcc tgaagaaata cctgtatgaa     780
attgctcgta ggcacccata cttttatgcc cccgagctcc tgttctttgc aaagagatac     840
aaagctgcct tcactgaatg ttgccaggca gctgataagg ccgcatgtct cctgcctaaa     900
ctggacgagc tccgggatga aggtaaggct tccagcgcca acagcgcct gaagtgcgct     960
tctctccaga gtttggcga gcgagcattc aaagcctggg ctgtggcccg tctcagtcag    1020
aggtttccaa aggcagaatt tgctgagtg tcaaaactgg tgaccgacct cacaaaggtc    1080
catactgagt gttgccacgg agatctgctg gaatgtgccg acgatagagc agacctcgct    1140
aaatatatct gcgagaatca ggattccatt agctctaagc tgaaagaatg ttgcgagaag    1200
cccctcctgg aaaagagtca ttgtatcgcc gaggtggaaa acgacgagat gccagcagat    1260
ctgccatcac tcgctgccga cttttgtggaa tccaaagatg tctgcaagaa ttacgcagag    1320
gctaaagacg tgttcctggg gatgtttctg tatgagtacg cccggcgtca ccccgattat    1380
agcgtcgtgc tcctgctccg actggcaaag acctacgaaa caactctgga gaaatgttgc    1440
gctgccgcag accctcatga atgttatgct aaggtgttcg atgagtttaa gccactcgtc    1500
gaagagcccc agaacctgat taaacagaat tgcgaactgt tcgagcagct cggtgaatac    1560
aagtttcaga acgccctgct cgtgcgttat accaaaaagg tccctcaggt gtctacacca    1620
actctggtgg aggtcagtag gaatctgggc aaagtgggat caaagtgttg caaacacccc    1680
gaggcaaaga gaatgccttg tgctgaagat tacctctccg tcgtgctgaa ccagctctgc    1740
gtgctgcatg aaaagacccc agtcagcgac cgggtgacaa atgttgcac cgaatctctg    1800
gtcaatcgcc gaccctgttt cagtgccctc gaagtggacg aaacttatgt gcctaaggag    1860
tttcaggctg aaacattcac ctttcacgcc gatatctgca ctctgtccga gaagaaagg    1920
cagattaaga acagacagc actggtcgag ctcgtgaagc ataaaccaaa ggctaccaag    1980
gagcagctga agccgtcat ggacgatttc gcagcttttg tggaaaagtg ttgcaaagcc    2040
gacgataagg agacttgttt cgcagaagag gggaaaaagc tcgtggctgc cagccaggca    2100
gctctgggtc tgggctctgg tggatcaggg ggaggttcag gcggggcag tggcggggga    2160
tctggaggtg gcagtggggg cggttccgga ggtggatcag gaggaggaag tggcggcggt    2220
```

```
agcggtggtg gtgctcaagt cttgcgtggt acggtgacag acttcccagg cttcgatgaa    2280
agagcggacg cggaaacact tcgaaaggcg atgaaagggc tcggtactga cgaagagtcc    2340
attttgaccc ttcttacgag caggtcaaac gctcagaggc aagaaatctc tgcagccttt    2400
aagacactct tggacgtga ccttcttgat gacctcaaat ctgagctgac gggaaagttt    2460
gagaaactca tcgtagcttt gatgaagccc agccgattgt atgatgctta cgaactgaaa    2520
cacgccctga aggagcggg aacgaacgag aaagttttga ctgagatcat cgcatcgcgg    2580
accccggaag agctcagagc catcaaacaa gtctacgagg aggagtacgg atcgtcattg    2640
gaagatgacg tggtggggga tacgtcgggt tactaccaac gaatgcttgt cgtgcttttg    2700
caggcaaatc gcgacccgga tgcggggatc gacgaggccc aagtggagca agatgcgcaa    2760
gcactcttcc aggccggtga actcaaatgg gggaccgatg aagagaagtt tatcaccatc    2820
tttggcacga ggagtgtaag tcatctgcgt aaagtattcg ataagtatat gacaatctca    2880
gggtttcaga ttgaggagac aattgacagg gaaacctccg gtaacttgga gcagctcttg    2940
cttgccgtcg tcaagtccat tcgctcgatc cctgcgtatc tggctgaaac actgtattac    3000
gccatgaaag gggcaggcac tgatgaccac accttgatta gagttatggt gtcgcgatca    3060
gaaattgact tgttcaatat ccggaaagag ttccggaaga atttcgcaac gagcctctat    3120
agcatgatca aggggacac ttcgggagat acaagaaag cgttgctcct tctttgcgga    3180
gaggatgact gataa                                                    3195

<210> SEQ ID NO 95
<211> LENGTH: 3057
<212> TYPE: DNA
<213> ORGANISM: Artificial Sequence
<220> FEATURE:
<223> OTHER INFORMATION: Synthetic construct

<400> SEQUENCE: 95
atgttcccag ccatgccctt gtccagcctg tttgttaacg gcccaagaac actttgtgga      60
gccgaactgg tggatgctct ccaattcgtt tgcggcgacc gcggattcta ctttaacaag     120
cccaccggtt acgggtcttc aagccggagg gccccgcaga ctggcatcgt cgacgagtgc     180
tgttttagaa gctgcgatct gcgacggttg gagatgttgt gtgcacctct gaagcccgcg     240
aaaagtgctg gttccggagg gagcggtggt gggagtggcg gatctggtgg aggagacgct     300
cacaagtctg aagtggcaca taggttcaaa gatctgggcg aagagaactt taaggccctc     360
gtcctgatcg ctttcgcaca gtacctccag cagtctccct tgaagatca cgtgaaactg     420 gtcaatgagg tgaccgaatt tgccaagaca tgcgtggctg atgagagtgc agaaaactgt     480
gacaaatcac tgcatactct ctttggagat aagctgtgca ccgtcgccac actcagagag     540
acttatgggg aaatggctga ctgttgcgca aaacaggagc ctgaacggaa tgagtgtttc     600
ctccagcaca aggatgacaa cccaaatctg ccccgcctcg tgcgacctga ggtcgatgtg     660
atgtgcaccg cctttcatga caacgaagag acattcctga gaaataccct gtatgaaatt     720
gctcgtaggc acccatactt ttatgccccc gagctcctgt tctttgcaaa gagatacaaa     780
gctgccttca ctgaatgttg ccaggcagct gataaggccg catgtctcct gcctaaactg     840
gacgagctcc gggatgaagg taaggcttcc agcgccaaac agcgcctgaa gtgcgcttct     900
ctccagaagt tggcgagcg agcattcaaa gcctgggctg tggcccgtct cagtcagagg     960
tttccaaagg cagaatttgc tgaggtgtca aaactggtga ccgacctcac aaaggtccat    1020
```

```
actgagtgtt gccacggaga tctgctggaa tgtgccgacg atagagcaga cctcgctaaa    1080
tatatctgcg agaatcagga ttccattagc tctaagctga agaatgttg cgagaagccc     1140 ctcctggaaa agagtcattg tatcgccgag gtggaaaacg acgagatgcc agcagatctg    1200
ccatcactcg ctgccgactt tgtggaatcc aaagatgtct gcaagaatta cgcagaggct    1260
aaagacgtgt tcctggggat gtttctgtat gagtacgccc ggcgtcaccc cgattatagc    1320
gtcgtgctcc tgctccgact ggcaaagacc tacgaaacaa ctctggagaa atgttgcgct    1380
gccgcagacc ctcatgaatg ttatgctaag gtgttcgatg agtttaagcc actcgtcgaa    1440
gagccccaga acctgattaa acagaattgc gaactgttcg agcagctcgg tgaatacaag    1500
tttcagaacg ccctgctcgt gcgttatacc aaaaaggtcc ctcaggtgtc tacaccaact    1560
ctggtggagg tcagtaggaa tctgggcaaa gtgggatcaa agtgttgcaa acaccccgag    1620
gcaaagagaa tgccttgtgc tgaagattac ctctccgtcg tgctgaacca gctctgcgtg    1680
ctgcatgaaa agaccccagt cagcgaccgg gtgacaaaat gttgcaccga atctctggtc    1740
aatcgccgac cctgtttcag tgccctcgaa gtggacgaaa cttatgtgcc taaggagttt    1800
caggctggaa cattcacctt tcacgccgat atctgcactc tgtccgagaa agaaaggcag    1860
attaagaaac agacagcact ggtcgagctc gtgaagcata aaccaaaggc taccaaggag    1920
cagctgaaag ccgccatgga cgatttcgca gcttttgtgg aaaagtgttg caaagccgac    1980
gataaggaga cttgtttcgc agaagagggg aaaaagctcg tggctgccag ccaggcagct    2040
ctgggtctgg ggtctggcgg ttcaggggga ggaagtggag gctcaggagg tggtgctcaa    2100
gtcttgcgtg gtacggtgac agacttccca ggcttcgatg aaagagcgga cgcggaaaca    2160
cttcgaaagg cgatgaaagg gctcggtact gacgaagagt ccatttttgac ccttcttacg    2220 agcaggtcaa acgctcagag gcaagaaatc tctgcagcct ttaagacact ctttggagct    2280
gaccttcttg atgacctcgc atctgagctg acgggaaagt ttgagaaact catcgtagct    2340
ttgatgaagc ccagccgatt gtatgatgct tacgaactga acacgccct ggctggagcg     2400 ggaacgaacg agaaagtttt gactgagatc atcgcatcgc ggaccccgga agagctcaga    2460
gccatcaaac aagtctacga ggaggagtac ggatcgtcat ggcaggaga cgtggtgggg     2520 gatacgtcgg gttactacca acgaatgctt gtcgtgcttt tgcaggcagc tcgcgacccg    2580
gatgcgggga tcgacgaggc ccaagtggag caagatgcgc aagcactctt ccaggccggt    2640
gaactcaaat gggggaccga tgaagagaag tttatcacca tctttggcac gaggagtgta    2700
agtcatctgc gtaaagtatt cgataagtat atgacaatct cagggtttca gattgaggag    2760
acaattgaca gggaaacctc cggtaacttg gagcagctct tgcttgccgt cgtcaagtcc    2820
attcgctcga tccctgcgta tctggctgaa acactgtatt acgccatgaa aggggcaggc    2880
actgatgacc acaccttgat tagagttatg gtgtcgcgat cagaaattga cttgttcaat    2940
atccggaaag agttccggaa gaatttcgca acgagcctct atagcatgat caaaggggac    3000
acttcgggag attacaagaa agcgttgctc cttctttgcg gagaggatga ctaatga      3057
```

<210> SEQ ID NO 96
<211> LENGTH: 3009
<212> TYPE: DNA
<213> ORGANISM: Artificial Sequence
<220> FEATURE:
<223> OTHER INFORMATION: Synthetic construct

<400> SEQUENCE: 96

```
atgttcccag ccatgccctt gtccagcctg tttgttaacg gcccaagaac actttgtgga      60
```

-continued

```
gccgaactgg tggatgctct ccaattcgtt tgcggcgacc gcggattcta ctttaacaag    120
cccaccggtt acgggtcttc aagccggagg gccccgcaga ctggcatcgt cgacgagtgc    180
tgttttagaa gctgcgatct gcgacggttg gagatgtatt gtgcacctct gaagcccgcg    240
aaaagtgctg ggagcggtgg tgggagtggc gacgctcaca agtctgaagt ggcacatagg    300
ttcaaagatc tgggcgaaga gaactttaag gccctcgtcc tgatcgcttt cgcacagtac    360
ctccagcagt ctccctttga agatcacgtg aaactggtca atgaggtgac cgaatttgcc    420
aagacatgcg tggctgatga gagtgcagaa actgtgacaa atcactgca tactctcttt     480 ggagataagc tgtgcaccgt cgccacactc agagagactt atggggaaat ggctgactgt    540
tgcgcaaaac aggagcctga acggaatgag tgtttcctcc agcacaagga tgacaaccca    600
aatctgcccc gcctcgtgcg acctgaggtc gatgtgatgt gcaccgcctt tcatgacaac    660
gaagagacat tcctgaagaa atacctgtat gaaattgctc gtaggcaccc atacttttat    720
gcccccgagc tcctgttctt tgcaaagaga tacaaagctg ccttcactga atgttgccag    780
gcagctgata aggccgcatg tctcctgcct aaactggacg agctccggga tgaaggtaag    840
gcttccagcg ccaaacagcg cctgaagtgc gcttctctcc agaagtttgg cgagcgagca    900
ttcaaagcct gggctgtggc ccgtctcagt cagaggtttc caaaggcaga atttgctgag    960
gtgtcaaaac tggtgaccga cctcacaaag gtccatactg agtgttgcca cggagatctg    1020
ctggaatgtg ccgacgatag agcagacctc gctaaatata tctgcgagaa tcaggattcc    1080
attagctcta agctgaaaga atgttgcgag aagccccctcc tggaaaagag tcattgtatc    1140
gccgaggtgg aaaacgacga gatgccagca gatctgccat cactcgctgc cgactttgtg    1200
gaatccaaag atgtctgcaa gaattacgca gaggctaaag acgtgttcct ggggatgttt    1260
ctgtatgagt acgcccggcg tcaccccgat tatagcgtcg tgctcctgct ccgactggca    1320
aagacctacg aaacaactct ggagaaatgt tgcgctgccg cagaccctca tgaatgttat    1380
gctaaggtgt tcgatgagtt taagccactc gtcgaagagc cccagaacct gattaaacag    1440
aattgcgaac tgttcgagca gctcggtgaa tacaagtttc agaacgccct gctcgtgcgt    1500
tataccaaaa aggtccctca ggtgtctaca ccaactctgg tggaggtcag taggaatctg    1560
ggcaaagtgg gatcaaagtg ttgcaaacac cccgaggcaa agagaatgcc ttgtgctgaa    1620
gattacctct ccgtcgtgct gaaccagctc tgcgtgctgc atgaaaagac cccagtcagc    1680
gaccgggtga caaaatgttg caccgaatct ctggtcaatc gccgaccctg tttcagtgcc    1740
ctcgaagtga cgaaactta tgtgcctaag gagtttcagg ctgaaacatt caccctttcac   1800 gccgatatct gcactctgtc cgagaaagaa aggcagatta agaaacagac agcactggtc    1860
gagctcgtga agcataaacc aaaggctacc aaggagcagc tgaaagccgt catggacgat    1920
ttcgcagctt ttgtggaaaa gtgttgcaaa gccgacgata aggagacttg tttcgcagaa    1980
gaggggaaaa agctcgtggc tgccagccag gcagctctgg gtctggggag cggtggtggg    2040
agtggcgctc aagtcttgcg tggtacggtg acagacttcc caggcttcga tgaaagagcg    2100
gacgcggaaa cacttcgaaa ggcgatgaaa gggctcggta ctgacgaaga gtccattttg    2160
acccttctta cgagcaggtc aaacgctcag aggcaagaaa tctctgcagc ctttaagaca    2220
ctctttggac gtgaccttct tgatgacctc aaatctgagc tgacgggaaa gtttgagaaa    2280
ctcatcgtag ctttgatgaa gcccagccga ttgtatgatg cttacgaact gaaacacgcc    2340
ctgaaaggag cgggaacgaa cgagaaagtt ttgactgaga tcatcgcatc gcggaccccg    2400
```

```
gaagagctca gagccatcaa acaagtctac gaggaggagt acggatcgtc attggaagat     2460
gacgtggtgg gggatacgtc gggttactac caacgaatgc ttgtcgtgct tttgcaggca     2520
aatcgcgacc cggatgcggg gatcgacgag gcccaagtgg agcaagatgc gcaagcactc     2580
ttccaggccg gtgaactcaa atgggggacc gatgaagaga agtttatcac catctttggc     2640
acgaggagtg taagtcatct gcgtaaagta ttcgataagt atatgacaat ctcagggttt     2700
cagattgagg agacaattga cagggaaacc tccggtaact tggagcagct cttgcttgcc     2760
gtcgtcaagt ccattcgctc gatccctgcg tatctggctg aaacactgta ttacgccatg     2820 aaagggggcag gcactgatga ccacaccttg attagagtta tggtgtcgcg atcagaaatt     2880
gacttgttca atatccggaa agagttccgg aagaatttcg caacgagcct ctatagcatg     2940
atcaaagggg acacttcggg agattacaag aaagcgttgc tccttctttg cggagaggat     3000
gactgataa                                                             3009
```

<210> SEQ ID NO 97
<211> LENGTH: 3045
<212> TYPE: DNA
<213> ORGANISM: Artificial Sequence
<220> FEATURE:
<223> OTHER INFORMATION: Syntehtic construct

<400> SEQUENCE: 97

```
atgttcccag ccatgccctt gtccagcctg tttgttaacg gcccaagaac actttgtgga       60
gccgaactgg tggatgctct ccaattcgtt tgcggcgacc gcggattcta ctttaacaag      120
cccaccggtt acgggtcttc aagccgggcc ccgcagactg gcatcgtcga cgagtgctgt      180
tttagaagct gcgatctgcg acggttggag atgtattgtg cacctctgaa gcccgcgggt      240
tccgagggga gcgtggtggg gagtggcgga tctggtggag gagacgctca caagtctgaa      300
gtggcacata ggttcaaaga tctgggcgaa gagaacttta aggccctcgt cctgatcgct      360
ttcgcacagt acctccagca gtctcccttt gaagatcacg tgaaactggt caatgaggtg      420
accgaatttg ccaagacatg cgtggctgat gagagtgcag aaaactgtga caaatcactg      480
catactctct ttggagataa gctgtgcacc gtcgccacac tcagagagac ttatggggaa      540
atggctgact gttgcgcaaa acaggagcct gaacggaatg agtgtttcct ccagcacaag      600
gatgacaacc caaatctgcc ccgcctcgtg cgacctgagg tcgatgtgat gtgcaccgcc      660
tttcatgaca cgaagagac attcctgaag aaatacctgt atgaaattgc tcgtaggcac      720
ccatactttt atgcccccga gctcctgttc tttgcaaaga gatacaaagc tgccttcact      780
gaatgttgcc aggcagctga taaggccgca tgtctcctgc ctaaactgga cgagctccgg      840
gatgaaggta aggcttccag cgccaaacag cgcctgaagt gcgcttctct ccagaagttt      900
ggcgagcgag cattcaaagc ctgggctgtg gcccgtctca gtcagaggtt ccaaaggca      960 gaatttgctg aggtgtcaaa actggtgacc gacctcacaa aggtcctac tgagtgttgc     1020 cacgagatc tgctggaatg tgccgacgat agagcagacc tcgctaaata tatctgcgag     1080
aatcaggatt ccattagctc taagctgaaa gaatgttgcg agaagcccct cctggaaaag     1140
agtcattgta tcgccgaggt ggaaaacgac gagatgccag cagatctgcc atcactcgct     1200
gccgactttg tggaatccaa agatgtctgc aagaattacg cagaggctaa agacgtgttc     1260
ctggggatgt ttctgtatga gtacgcccgg cgtcaccccg attatagcgt cgtgctcctg     1320
ctccgactgg caaagaccta cgaaacaact ctggagaaat gttgcgctgc gcagaccct     1380 catgaatgtt atgctaaggt gttcgatgag tttaagccac tcgtcgaaga gcccagaac     1440
```

```
ctgattaaac agaattgcga actgttcgag cagctcggtg aatacaagtt tcagaacgcc    1500
ctgctcgtgc gttataccaa aaaggtccct caggtgtcta caccaactct ggtggaggtc    1560
agtaggaatc tgggcaaagt gggatcaaag tgttgcaaac accccgaggc aaagagaatg    1620
ccttgtgctg aagattacct ctccgtcgtg ctgaaccagc tctgcgtgct gcatgaaaag    1680
accccagtca gcgaccgggt gacaaaatgt tgcaccgaat ctctggtcaa tcgccgaccc    1740
tgtttcagtg ccctcgaagt ggacgaaact tatgtgccta aggagtttca ggctggaaca    1800
ttcacctttc acgccgatat ctgcactctg tccgagaaag aaaggcagat taagaaacag    1860
acagcactgg tcgagctcgt gaagcataaa ccaaaggcta ccaaggagca gctgaaagcc    1920
gccatggacg atttcgcagc ttttgtggaa aagtgttgca agccgacga taaggagact    1980 tgtttcgcag aagaggggaa aaagctcgtg gctgccagcc aggcagctct gggtctgggg    2040
tctggcggtt caggggagg aagtggaggc tcaggaggtg gtgctcaagt cttgcgtggt    2100
acggtgacag acttcccagg cttcgatgaa agagcggacg cggaaacact tcgaaaggcg    2160
atgaaagggc tcggtactga cgaagagtcc attttgaccc ttcttacgag caggtcaaac    2220 gctcagagc aagaaatctc tgcagccttt aagacactct ttggagctga ccttcttgat    2280
gacctcgcat ctgagctgac gggaaagttt gagaaactca tcgtagcttt gatgaagccc    2340
agccgattgt atgatgctta cgaactgaaa cacgccctgg ctggagcggg aacgaacgag    2400
aaagttttga ctgagatcat cgcatcgcgg accccggaag agctcagagc catcaaacaa    2460
gtctacgagg aggagtacgg atcgtcattg gcaggagacg tggtgggga tacgtcgggt    2520 tactaccaac gaatgcttgt cgtgcttttg caggcagctc gcgacccgga tgcggggatc    2580
gacgaggccc aagtggagca agatgcgcaa gcactcttcc aggccggtga actcaaatgg    2640
gggaccgatg aagagaagtt tatcaccatc tttggcacga ggagtgtaag tcatctgcgt    2700
aaagtattcg ataagtatat gacaatctca gggtttcaga ttgaggagac aattgacagg    2760
gaaacctccg gtaacttgga gcagctcttg cttgccgtcg tcaagtccat tcgctcgatc    2820
cctgcgtatc tggctgaaac actgtattac gccatgaaag gggcaggcac tgatgaccac    2880
accttgatta gagttatggt gtcgcgatca gaaattgact tgttcaatat ccggaaagag    2940
ttccggaaga atttcgcaac gagcctctat agcatgatca aggggacac ttcgggagat    3000 tacaagaaag cgttgctcct tctttgcgga gaggatgact aatga                    3045
```

<210> SEQ ID NO 98
<211> LENGTH: 3057
<212> TYPE: DNA
<213> ORGANISM: Artificial Sequence
<220> FEATURE:
<223> OTHER INFORMATION: Synthetic construct

<400> SEQUENCE: 98

```
atgttcccag ccatgccctt gtccagcctg tttgttaacg gcccaagaac actttgtgga     60
gccgaactgg tggatgctct ccaattcgtt tgcggcgacc gcggattcct ctttaacaag    120
cccaccggtg ccgggtcttc aagccggagg gccccgcaga ctggcatcgt cgacgagtgc    180
tgttttagaa gctgcgatct gcgacggttg agatgtatt tgcacctct gaagcccgcg    240 aaaagtgctg gttccggagg gagcggtggt gggagtggcg gatctggtgg aggagacgct    300
cacaagtctg aagtggcaca taggttcaaa gatctgggcg aagagaactt taaggccctc    360
gtcctgatcg cttttcgcaca gtacctccag cagtctccct ttgaagatca cgtgaaactg    420
```

```
gtcaatgagg tgaccgaatt tgccaagaca tgcgtggctg atgagagtgc agaaaactgt    480
gacaaatcac tgcatactct ctttggagat aagctgtgca ccgtcgccac actcagagag    540
acttatgggg aaatggctga ctgttgcgca aaacaggagc ctgaacggaa tgagtgtttc    600
ctccagcaca aggatgacaa cccaaatctg ccccgcctcg tgcgacctga ggtcgatgtg    660
atgtgcaccg cctttcatga caacgaagag acattcctga agaaatacct gtatgaaatt    720
gctcgtaggc acccatactt ttatgccccc gagctcctgt tctttgcaaa agatacaaaa    780
gctgccttca ctgaatgttg ccaggcagct gataaggccg catgtctcct gcctaaactg    840
gacgagctcc gggatgaagg taaggcttcc agcgccaaac agcgcctgaa gtgcgcttct    900
ctccagaagt ttggcgagcg agcattcaaa gcctgggctg tggcccgtct cagtcagagg    960
tttccaaagg cagaatttgc tgaggtgtca aaactggtga ccgacctcac aaaggtccat   1020
actgagtgtt gccacggaga tctgctggaa tgtgccgacg atagagcaga cctcgctaaa   1080
tatatctgcg agaatcagga ttccattagc tctaagctga agaatgttgc gagaagccc    1140 ctcctggaaa gagtcattg tatcgccgag gtggaaaacg acgagatgcc agcagatctg   1200
ccatcactcg ctgccgactt tgtggaatcc aaagatgtct gcaagaatta cgcagaggct   1260
aaagacgtgt tcctggggat gtttctgtat gagtacgccc ggcgtcaccc cgattatagc   1320
gtcgtgctcc tgctccgact ggcaaagacc tacgaaacaa ctctggagaa atgttgcgct   1380
gccgcagacc ctcatgaatg ttatgctaag gtgttcgatg agtttaagcc actcgtcgaa   1440 gagcccccaga acctgattaa acagaattgc gaactgttcg agcagctcgg tgaatacaag   1500
tttcagaacg ccctgctcgt gcgttatacc aaaaaggtcc ctcaggtgtc tacaccaact   1560
ctggtggagg tcagtaggaa tctgggcaaa gtgggatcaa agtgttgcaa acaccccgag   1620
gcaaagagaa tgccttgtgc tgaagattac ctctccgtcg tgctgaacca gctctgcgtg   1680
ctgcatgaaa agaccccagt cagcgaccgg gtgacaaaat gttgcaccga atctctggtc   1740
aatcgccgac cctgtttcag tgccctcgaa gtggacgaaa cttatgtgcc taaggagttt   1800
caggctggaa cattcacctt tcacgccgat atctgcactc tgtccgagaa agaaaggcag   1860
attaagaaac agacagcact ggtcgagctc gtgaagcata aaccaaaggc taccaaggag   1920
cagctgaaag ccgccatgga cgatttcgca gcttttgtgg aaaagtgttg caaagccgac   1980
gataaggaga cttgtttcgc agaagagggg aaaaagctcg tggctgccag ccaggcagct   2040
ctgggtctgg ggtctggcgg ttcaggggga ggaagtggag gctcaggagg tggtgctcaa   2100
gtcttgcgtg gtacggtgac agacttccca ggcttcgatg aaagagcgga cgcggaaaca   2160
cttcgaaagg cgatgaaagg gctcggtact gacgaagagt ccattttgac ccttcttacg   2220
agcaggtcaa acgctcagag gcaagaaatc tctgcagcct ttaagacact ctttggagct   2280
gaccttcttg atgacctcgc atctgagctg acgggaaagt ttgagaaact catcgtagct   2340
ttgatgaagc ccagccgatt gtatgatgct tacgaactga acacgcccct ggctggagcg   2400
ggaacgaacg agaaagtttt tgactgagatc atcgcatcgc ggaccccgga agagctcaga   2460
gccatcaaac aagtctacga ggaggagtac ggatcgtcat ggcaggaga cgtggtgggg   2520 gatacgtcgg gttactacca acgaatgctt gtcgtgcttt tgcaggcagc tcgcgacccg   2580
gatgcgggga tcgacgaggc ccaagtggag caagatgcgc aagcactctt ccaggccggt   2640
gaactcaaat gggggaccga tgaagagaag tttatcacca tctttggcac gaggagtgta   2700
agtcatctgc gtaaagtatt cgataagtat atgacaatct cagggtttca gattgaggag   2760
acaattgaca gggaaacctc cggtaacttg gagcagctct tgcttgccgt cgtcaagtcc   2820
```

| | |
|---|---|
| attcgctcga tccctgcgta tctggctgaa acactgtatt acgccatgaa aggggcaggc | 2880 |
| actgatgacc acaccttgat tagagttatg gtgtcgcgat cagaaattga cttgttcaat | 2940 |
| atccggaaag agttccggaa gaatttcgca acgagcctct atagcatgat caaaggggac | 3000 |
| acttcgggag attacaagaa agcgttgctc cttctttgcg gagaggatga ctaatga | 3057 |

<210> SEQ ID NO 99
<211> LENGTH: 3057
<212> TYPE: DNA
<213> ORGANISM: Artificial Sequence
<220> FEATURE:
<223> OTHER INFORMATION: Synthetic construct

<400> SEQUENCE: 99

| | |
|---|---|
| atgttcccag ccatgccctt gtccagcctg tttgttaacg cccaagaac actttgtgga | 60 |
| gccgaactgg tggatgctct ccaattcgtt tgcggcgacc gcggattcct ctttaacaag | 120 |
| cccaccggtt acgggtcttc aagccggagg ccccgcaga ctggcatcgt cgacgagtgc | 180 |
| tgttttagaa gctgcgatct gcgacggttg gagatgtatt gtgcacctct gaagcccgcg | 240 |
| aaaagtgctg gttccggagg gagcggtggt gggagtggcg gatctggtgg aggagacgct | 300 |
| cacaagtctg aagtggcaca taggttcaaa gatctgggcg aagagaactt taaggccctc | 360 |
| gtcctgatcg ctttcgcaca gtacctccag cagtctccct ttgaagatca cgtgaaactg | 420 |
| gtcaatgagg tgaccgaatt tgccaagaca tgcgtggctg atgagagtgc agaaaactgt | 480 |
| gacaaatcac tgcatactct ctttggagat aagctgtgca ccgtcgccac actcagagag | 540 |
| acttatgggg aaatggctga ctgttgcgca aaacaggagc ctgaacggaa tgagtgtttc | 600 |
| ctccagcaca aggatgacaa cccaaatctg ccccgcctcg tgcgacctga ggtcgatgtg | 660 |
| atgtgcaccg cctttcatga caacgaagag acattcctga gaaatacct gtatgaaatt | 720 |
| gctcgtaggc acccatactt ttatgccccc gagctcctgt tctttgcaaa gagatacaaa | 780 |
| gctgccttca ctgaatgttg ccaggcagct gataaggccg catgtctcct gcctaaactg | 840 |
| gacgagctcc gggatgaagg taaggcttcc agcgccaaac agcgcctgaa gtgcgcttct | 900 |
| ctccagaagt ttggcgagcg agcattcaaa gcctgggctg tggcccgtct cagtcagagg | 960 |
| tttccaaagg cagaatttgc tgaggtgtca aaactggtga ccgacctcac aaaggtccat | 1020 |
| actgagtgtt gccacggaga tctgctggaa tgtgccgacg atagagcaga cctcgctaaa | 1080 |
| tatatctgcg agaatcagga ttccattagc tctaagctga agaatgttg cgagaagccc | 1140 |
| ctcctggaaa agagtcattg tatcgccgag gtggaaaacg acgagatgcc agcagatctg | 1200 |
| ccatcactcg ctgccgactt tgtggaatcc aaagatgtct gcaagaatta cgcagaggct | 1260 |
| aaagacgtgt tcctggggat gtttctgtat gagtacgccc ggcgtcaccc cgattatagc | 1320 |
| gtcgtgctcc tgctccgact ggcaaagacc tacgaaacaa ctctggagaa atgttgcgct | 1380 |
| gccgcagacc tcatgaatg ttatgctaag gtgttcgatg agtttaagcc actcgtcgaa | 1440 |
| gagcccaga acctgattaa acagaattgc gaactgttcg agcagctcgg tgaatacaag | 1500 |
| tttcagaacg ccctgctcgt gcgttatacc aaaaaggtcc ctcaggtgtc tacaccaact | 1560 |
| ctggtggagg tcagtaggaa tctgggcaaa gtgggatcaa agtgttgcaa acaccccgag | 1620 |
| gcaaagagaa tgccttgtgc tgaagattac ctctccgtcg tgctgaacca gctctgcgtg | 1680 |
| ctgcatgaaa agaccccagt cagcgaccgg gtgacaaaat gttgcaccga atctctggtc | 1740 |
| aatcgccgac cctgtttcag tgccctcgaa gtggacgaaa cttatgtgcc taaggagttt | 1800 |

| | |
|---|---|
| caggctggaa cattcacctt tcacgccgat atctgcactc tgtccgagaa agaaaggcag | 1860 |
| attaagaaac agacagcact ggtcgagctc gtgaagcata aaccaaaggc taccaaggag | 1920 |
| cagctgaaag ccgccatgga cgatttcgca gcttttgtgg aaaagtgttg caaagccgac | 1980 |
| gataaggaga cttgtttcgc agaagagggg aaaaagctcg tggctgccag ccaggcagct | 2040 |
| ctgggtctgg ggtctggcgg ttcaggggga ggaagtggag gctcaggagg tggtgctcaa | 2100 |
| gtcttgcgtg gtacggtgac agacttccca ggcttcgatg aaagagcgga cgcggaaaca | 2160 |
| cttcgaaagg cgatgaaagg gctcggtact gacgaagagt ccattttgac ccttcttacg | 2220 |
| agcaggtcaa acgctcagag gcaagaaatc tctgcagcct ttaagacact ctttggagct | 2280 |
| gaccttcttg atgacctcgc atctgagctg acgggaaagt ttgagaaact catcgtagct | 2340 |
| ttgatgaagc ccagccgatt gtatgatgct tacgaactga acacgccct ggctggagcg | 2400 |
| ggaacgaacg agaaagtttt gactgagatc atcgcatcgc ggaccccgga gagctcaga | 2460 |
| gccatcaaac aagtctacga ggaggagtac ggatcgtcat ggcaggaga cgtggtgggg | 2520 |
| gatacgtcgg gttactacca acgaatgctt gtcgtgcttt tgcaggcagc tcgcgacccg | 2580 |
| gatgcgggga tcgacgaggc ccaagtggag caagatgcgc aagcactctt ccaggccggt | 2640 |
| gaactcaaat gggggaccga tgaagagaag tttatcacca tctttggcac gaggagtgta | 2700 |
| agtcatctgc gtaaagtatt cgataagtat atgacaatct cagggtttca gattgaggag | 2760 |
| acaattgaca gggaaacctc cggtaacttg gagcagctct tgcttgccgt cgtcaagtcc | 2820 |
| attcgctcga tccctgcgta tctggctgaa acactgtatt acgccatgaa aggggcaggc | 2880 |
| actgatgacc acaccttgat tagagttatg gtgtcgcgat cagaaattga cttgttcaat | 2940 |
| atccggaaag agttccggaa gaatttcgca acgagcctct atagcatgat caaaggggac | 3000 |
| acttcgggag attacaagaa agcgttgctc cttctttgcg gagaggatga ctaatga | 3057 |

<210> SEQ ID NO 100
<211> LENGTH: 3057
<212> TYPE: DNA
<213> ORGANISM: Artificial Sequence
<220> FEATURE:
<223> OTHER INFORMATION: Synthetic construct

<400> SEQUENCE: 100

| | |
|---|---|
| atgttcccag ccatgccctt gtccagcctg tttgttaacg cccaagaac actttgtgga | 60 |
| gccgaactgg tggatgctct ccaattcgtt tgcggcgacc gcggattcta ctttaacaag | 120 |
| cccaccggtg ccgggtcttc aagccggagg gccccgcaga ctggcatcgt cgacgagtgc | 180 |
| tgttttagaa gctgcgatct gcgacggttg gagatgtatt gtgcacctct gaagcccgcg | 240 |
| aaaagtgctg gttccggagg gagcggtggt gggagtggcg atctggtgg aggagacgct | 300 |
| cacaagtctg aagtggcaca taggttcaaa gatctgggcg aagagaactt taaggccctc | 360 |
| gtcctgatcg ctttcgcaca gtacctccag cagtctccct ttgaagatca cgtgaaactg | 420 |
| gtcaatgagg tgaccgaatt tgccaagaca tgcgtggctg atgagagtgc agaaaactgt | 480 |
| gacaaatcac tgcatactct ctttggagat aagctgtgca ccgtcgccac actcagagag | 540 |
| acttatgggg aaatggctga ctgttgcgca aaacaggagc tgaacggaa tgagtgtttc | 600 |
| ctccagcaca aggatgacaa cccaaatctg ccccgcctcg tgcgacctga ggtcgatgtg | 660 |
| atgtgcaccg cctttcatga caacgaagag acattcctga gaaataccct gtatgaaatt | 720 |
| gctcgtaggc acccatactt ttatgccccc gagctcctgt tctttgcaaa agatacaaa | 780 |
| gctgccttca ctgaatgttg ccaggcagct gataaggccg catgtctcct gcctaaactg | 840 |

```
gacgagctcc gggatgaagg taaggcttcc agcgccaaac agcgcctgaa gtgcgcttct    900
ctccagaagt ttggcgagcg agcattcaaa gcctgggctg tgcccgtct cagtcagagg    960 tttccaaagg cagaatttgc tgaggtgtca aaactggtga ccgacctcac aaaggtccat   1020
actgagtgtt gccacggaga tctgctggaa tgtgccgacg atagagcaga cctcgctaaa   1080
tatatctgcg agaatcagga ttccattagc tctaagctga agaatgttg cgagaagccc    1140 ctcctggaaa agagtcattg tatcgccgag gtggaaaacg acgagatgcc agcagatctg   1200
ccatcactcg ctgccgactt tgtggaatcc aaagatgtct gcaagaatta cgcagaggct   1260
aaagacgtgt tcctggggat gtttctgtat gagtacgccc ggcgtcaccc cgattatagc   1320
gtcgtgctcc tgctccgact ggcaaagacc tacgaaacaa ctctggagaa atgttgcgct   1380
gccgcagacc tcatgaatg ttatgctaag gtgttcgatg agtttaagcc actcgtcgaa    1440
gagccccaga acctgattaa acagaattgc gaactgttcg agcagctcgg tgaatacaag   1500
tttcagaacg ccctgctcgt gcgttatacc aaaaaggtcc ctcaggtgtc tacaccaact   1560
ctggtggagg tcagtaggaa tctgggcaaa gtgggatcaa agtgttgcaa acaccccgag   1620
gcaaagagaa tgccttgtgc tgaagattac ctctccgtcg tgctgaacca gctctgcgtg   1680
ctgcatgaaa agaccccagt cagcgaccgg gtgacaaaat gttgcaccga atctctggtc   1740
aatcgccgac cctgtttcag tgccctcgaa gtggacgaaa cttatgtgcc taaggagttt   1800
caggctggaa cattcacctt tcacgccgat atctgcactc tgtccgagaa agaaaggcag   1860
attaagaaac agacagcact ggtcgagctc gtgaagcata aaccaaaggc taccaaggag   1920
cagctgaaag ccgccatgga cgatttcgca gcttttgtgg aaaagtgttg caaagccgac   1980
gataaggaga cttgtttcgc agaagagggg aaaaagctcg tggctgccag ccaggcagct   2040
ctgggtctgg ggtctggcgg ttcagggga ggaagtggag gctcaggagg tggtgctcaa    2100
gtcttgcgtg gtacggtgac agacttccca ggcttcgatg aaagagcgga cgcggaaaca   2160
cttcgaaagg cgatgaaagg gctcggtact gacgaagagt ccattttgac ccttcttacg   2220
agcaggtcaa acgctcagag gcaagaaatc tctgcagcct ttaagacact ctttggagct   2280
gaccttcttg atgacctcgc atctgagctg acgggaaagt ttgagaaact catcgtagct   2340
ttgatgaagc ccagccgatt gtatgatgct tacgaactga acacgccct ggctggagcg    2400 ggaacgaacg agaaagtttt tgactgagatc atcgcatcgc ggaccccgga agagctcaga   2460
gccatcaaac aagtctacga ggaggagtac ggatcgtcat ggcaggaga cgtggtgggg    2520 gatacgtcgg gttactacca acgaatgctt gtcgtgcttt tgcaggcagc tcgcgacccg   2580
gatgcgggga tcgacgaggc ccaagtggag caagatgcgc aagcactctt ccaggccggt   2640
gaactcaaat gggggaccga tgaagagaag tttatcacca tctttggcac gaggagtgta   2700
agtcatctgc gtaaagtatt cgataagtat atgacaatct cagggtttca gattgaggag   2760
acaattgaca gggaaacctc cggtaacttg agcagctctc tgcttgccgt cgtcaagtcc   2820
attcgctcga tccctgcgta tctggctgaa acactgtatt acgccatgaa aggggcaggc   2880
actgatgacc acaccttgat tagagttatg gtgtcgcgat cagaaattga cttgttcaat   2940
atccggaaag agttccggaa gaatttcgca acgagcctct atagcatgat caagggggac   3000
acttcgggag attacaagaa agcgttgctc cttctttgcg gagaggatga ctaatga      3057
```

<210> SEQ ID NO 101
<211> LENGTH: 3009
<212> TYPE: DNA

<213> ORGANISM: Artificial Sequence
<220> FEATURE:
<223> OTHER INFORMATION: Synthetic construct

<400> SEQUENCE: 101

```
atgttcccag ccatgccctt gtccagcctg tttgttaacg cccaagaac actttgtgga      60
gccgaactgg tggatgctct ccaattcgtt tgcggcgacc gcggattcct ctttaacaag     120
cccaccggtt acgggtcttc aagccggagg gccccgcaga ctggcatcgt cgacgagtgc     180
tgttttagaa gctgcgatct cgacggttg gagatgtatt gtgcacctct gaagcccgcg      240
aaaagtgctg ggagcggtgg tgggagtggc gacgctcaca agtctgaagt ggcacatagg     300
ttcaaagatc tgggcgaaga gaactttaag gccctcgtcc tgatcgcttt cgcacagtac     360
ctccagcagt ctccctttga agatcacgtg aaactggtca atgaggtgac cgaatttgcc     420
aagacatgcg tggctgatga gagtgcagaa actgtgaca atcactgca tactctcttt       480
ggagataagc tgtgcaccgt cgccacactc agagagactt atgggaaat ggctgactgt      540
tgcgcaaaac aggagcctga acggaatgag tgtttcctcc agcacaagga tgacaaccca     600
aatctgcccc gcctcgtgcg acctgaggtc gatgtgatgt gcaccgcctt tcatgacaac     660
gaagagacat tcctgaagaa atacctgtat gaaattgctc gtaggcaccc atactttat     720
gcccccgagc tcctgttctt tgcaaagaga tacaaagctg ccttcactga atgttgccag     780
gcagctgata aggccgcatg tctcctgcct aaactgacg agctccggga tgaaggtaag     840
gcttccagcg ccaaacagcg cctgaagtgc gcttctctcc agaagtttgg cgagcgagca     900
ttcaaagcct gggctgtggc ccgtctcagt cagaggtttc caaaggcaga atttgctgag     960
gtgtcaaaac tggtgaccga cctcacaaag gtccatactg agtgttgcca cggagatctg    1020
ctggaatgtg ccgacgatag agcagacctc gctaaatata tctgcgagaa tcaggattcc    1080
attagctcta agctgaaaga atgttgcgag aagcccctcc tggaaaagag tcattgtatc    1140
gccgaggtga aaaacgacga gatgccagca gatctgccat cactcgctgc cgactttgtg    1200
gaatccaaag atgtctgcaa gaattacgca gaggctaaag acgtgttcct ggggatgttt    1260
ctgtatgagt acgcccggcg tcaccccgat tatagcgtcg tgctcctgct ccgactggca    1320
aagacctacg aaacaactct ggagaaatgt tgcgctgccg cagaccctca tgaatgttat    1380
gctaaggtgt tcgatgagtt taagccactc gtcgaagagc cccagaacct gattaaacag    1440
aattgcgaac tgttcgagca gctcggtgaa tacaagtttc agaacgccct gctcgtgcgt    1500
tataccaaaa aggtccctca ggtgtctaca ccaactctgg tggaggtcag taggaatctg    1560
ggcaaagtgg atcaaagtg ttgcaaacac cccgaggcaa agagaatgcc ttgtgctgaa     1620
gattacctct ccgtcgtgct gaaccagctc tgcgtgctgc atgaaaagac cccagtcagc    1680
gaccgggtga caaaatgttg caccgaatct ctggtcaatc gccgaccctg tttcagtgcc    1740
ctcgaagtgg acgaaactta tgtgcctaag gagtttcagg ctgaaacatt caccttcac    1800
gccgatatct gcactctgtc cgagaaagaa aggcagatta gaaacagac agcactggtc    1860
gagctcgtga agcataaacc aaaggctacc aaggagcagc tgaaagccgt catggacgat    1920
ttcgcagctt ttgtggaaaa gtgttgcaaa gccgacgata ggagacttg tttcgcagaa    1980
gaggggaaaa agctcgtggc tgccagccag gcagctctgg gtctggggag cggtggtggg    2040
agtggcgctc aagtcttgcg tggtacggtg acagacttcc caggcttcga tgaaagagcg    2100
gacgcggaaa cacttcgaaa ggcgatgaaa gggctcggta ctgacgaaga gtccattttg    2160
accccttctta cgagcaggtc aaacgctcag aggcaagaaa tctctgcagc ctttaagaca    2220
```

```
ctctttggag ctgaccttct tgatgacctc gcatctgagc tgacgggaaa gtttgagaaa    2280
ctcatcgtag ctttgatgaa gcccagccga ttgtatgatg cttacgaact gaaacacgcc    2340
ctggctggag cgggaacgaa cgagaaagtt ttgactgaga tcatcgcatc gcggaccccg    2400
gaagagctca gagccatcaa acaagtctac gaggaggagt acggatcgtc attggcagga    2460
gacgtggtgg gggatacgtc gggttactac caacgaatgc ttgtcgtgct tttgcaggca    2520
gctcgcgacc cggatgcggg gatcgacgag gcccaagtgg agcaagatgc gcaagcactc    2580
ttccaggccg gtgaactcaa atggggggacc gatgaagaga agttaatcac catctttggc    2640
```
```
ctctttggag ctgaccttct tgatgacctc gcatctgagc tgacgggaaa gtttgagaaa    2280
ctcatcgtag ctttgatgaa gcccagccga ttgtatgatg cttacgaact gaaacacgcc    2340
ctggctggag cgggaacgaa cgagaaagtt ttgactgaga tcatcgcatc gcggaccccg    2400
gaagagctca gagccatcaa acaagtctac gaggaggagt acggatcgtc attggcagga    2460
gacgtggtgg gggatacgtc gggttactac caacgaatgc ttgtcgtgct tttgcaggca    2520
gctcgcgacc cggatgcggg gatcgacgag gcccaagtgg agcaagatgc gcaagcactc    2580
ttccaggccg gtgaactcaa atggggggacc gatgaagaga agttaatcac catctttggc    2640
acgaggagtg taagtcatct gcgtaaagta ttcgataagt atatgacaat ctcagggttt    2700
cagattgagg agacaattga cagggaaacc tccggtaact tggagcagct cttgcttgcc    2760
gtcgtcaagt ccattcgctc gatccctgcg tatctggctg aaacactgta ttcgccatg     2820
aaagggcag gcactgatga ccacaccttg attagagtta tggtgtcgcg atcagaaatt    2880
gacttgttca atatccggaa agagttccgg aagaatttcg caacgagcct ctatagcatg    2940
atcaaagggg acacttcggg agattacaag aaagcgttgc tccttctttg cggagaggat    3000
gactgataa                                                              3009

<210> SEQ ID NO 102
<211> LENGTH: 3009
<212> TYPE: DNA
<213> ORGANISM: Artificial Sequence
<220> FEATURE:
<223> OTHER INFORMATION: Synthetic construct

<400> SEQUENCE: 102
atgttcccag ccatgccctt gtccagcctg tttgttaacg cccaagaac actttgtgga      60
gccgaactgg tggatgctct ccaattcgtt tgcggcgacc gcggattcta ctttaacaag    120
cccaccggtg ccgggtcttc aagccggagg gccccgcaga ctggcatcgt cgacgagtgc    180
tgttttagaa gctgcgatct gcgacggttg gagatgtatt gtgcacctct gaagcccgcg    240
aaaagtgctg ggagcggtgg tgggagtggc gacgctcaca agtctgaagt ggcacatagg    300
ttcaaagatc tgggcgaaga gaactttaag gccctcgtcc tgatcgcttt cgcacagtac    360
ctccagcagt ctcccttgga agatcacgtg aaactggtca atgaggtgac cgaatttgcc    420
aagacatgcg tggctgatga gagtgcagaa aactgtgaca aatcactgca tactctcttt    480
ggagataagc tgtgcaccgt cgccacactc agagagactt atggggaaat ggctgactgt    540
tgcgcaaaac aggagcctga acggaatgag tgtttcctcc agcacaagga tgacaaccca    600
aatctgcccc gcctcgtgcg acctgaggtc gatgtgatgt gcaccgcctt tcatgacaac    660
gaagagacat tcctgaagaa atacctgtat gaaattgctc gtaggcaccc atacttttat    720
gcccccgagc tcctgttctt tgcaaagaga tacaaagctg ccttcactga atgttgccag    780
gcagctgata ggccgcatg tctcctgcct aaactggacg agctccggga tgaaggtaag    840
gcttccagcg ccaaacagcg cctgaagtgc gcttctctcc agaagtttgg cgagcgagca    900
ttcaaagcct gggctgtggc ccgtctcagt cagaggtttc caaaggcaga atttgctgag    960
gtgtcaaaac tggtgaccga cctcacaaag gtccatactg agtgttgcca cggagatctg    1020
ctggaatgtg ccgacgatag agcagacctc gctaaatata tctgcgagaa tcaggattcc    1080
attagctcta agctgaaaga atgttgcgag aagcccctcc tggaaaagag tcattgtatc    1140
gccgaggtgg aaaacgacga gatgccagca gatctgccat cactcgctgc cgactttgtg    1200
```

```
gaatccaaag atgtctgcaa gaattacgca gaggctaaag acgtgttcct ggggatgttt    1260
ctgtatgagt acgcccggcg tcaccccgat tatagcgtcg tgctcctgct ccgactggca    1320
aagacctacg aaacaactct ggagaaatgt tgcgctgccg cagaccctca tgaatgttat    1380
gctaaggtgt tcgatgagtt taagccactc gtcgaagagc cccagaacct gattaaacag    1440
aattgcgaac tgttcgagca gctcggtgaa tacaagtttc agaacgccct gctcgtgcgt    1500
tataccaaaa aggtccctca ggtgtctaca ccaactctgg tggaggtcag taggaatctg    1560
ggcaaagtgg gatcaaagtg ttgcaaacac cccgaggcaa agagaatgcc ttgtgctgaa    1620
gattacctct ccgtcgtgct gaaccagctc tgcgtgctgc atgaaaagac cccagtcagc    1680
gaccgggtga caaaatgttg caccgaatct ctggtcaatc gccgaccctg tttcagtgcc    1740
ctcgaagtgg acgaaactta tgtgcctaag gagtttcagg ctgaaacatt caccttcac    1800 gccgatatct gcactctgtc cgagaaagaa aggcagatta gaaacagac agcactggtc    1860 gagctcgtga agcataaacc aaaggctacc aaggagcagc tgaaagccgt catggacgat    1920
ttcgcagctt ttgtggaaaa gtgttgcaaa gccgacgata aggagacttg tttcgcagaa    1980
gaggggaaaa agctcgtggc tgccagccag gcagctctgg gtctggggag cggtggtggg    2040
agtggcgctc aagtcttgcg tggtacggtg acagacttcc caggcttcga tgaaagagcg    2100
gacgcgaaaa cacttcgaaa ggcgatgaaa gggctcggta ctgacgaaga gtccattttg    2160 accttctta cgagcaggtc aaacgctcag aggcaagaaa tctctgcagc ctttaagaca    2220
ctctttggag ctgaccttct tgatgacctc gcatctgagc tgacgggaaa gtttgagaaa    2280
ctcatcgtag ctttgatgaa gcccagccga ttgtatgatg cttacgaact gaaacacgcc    2340
ctggctggag cgggaacgaa cgagaaagtt ttgactgaga tcatcgcatc gcggaccccg    2400
gaagagctca gagccatcaa acaagtctac gaggaggagt acggatcgtc attggcagga    2460
gacgtggtgg gggatacgtc gggttactac caacgaatgc ttgtcgtgct tttgcaggca    2520
gctcgcgacc cggatgcggg gatcgacgag gcccaagtgg agcaagatgc gcaagcactc    2580
ttccaggccg gtgaactcaa atgggggacc gatgaagaga gtttatcac catctttggc    2640 acgaggagtg taagtcatct gcgtaaagta ttcgataagt atatgacaat ctcagggttt    2700
cagattgagg agacaattga cagggaaacc tccggtaact tggagcagct cttgcttgcc    2760
gtcgtcaagt ccattcgctc gatccctgcg tatctggctg aaacactgta ttacgccatg    2820
aaaggggcag gcactgatga ccacaccttg attagagtta tggtgtcgcg atcagaaatt    2880
gacttgttca atatccggaa agagttccgg aagaatttcg caacgagcct ctatagcatg    2940
atcaaagggg acacttcggg agattacaag aaagcgttgc tccttctttg cggagaggat    3000
gactgataa                                                            3009
```

<210> SEQ ID NO 103
<211> LENGTH: 3009
<212> TYPE: DNA
<213> ORGANISM: Artificial Sequence
<220> FEATURE:
<223> OTHER INFORMATION: Synthetic construct

<400> SEQUENCE: 103

```
atgttcccag ccatgccctt gtccagcctg tttgttaacg gcccaagaac actttgtgga     60
gccgaactgg tggatgctct ccaattcgtt tgcggcgacc gcggattcta ctttaacaag    120
cccaccggtt acgggtcttc aagccggagg gccccgcaga ctggcatcgt cgacgagtgc    180
tgttttagaa gctgcgatct gcgacggttg gagatgttgt gtgcacctct gaagcccgcg    240
```

```
aaaagtgctg ggagcggtgg tgggagtggc gacgctcaca agtctgaagt ggcacatagg    300
ttcaaagatc tgggcgaaga gaactttaag gccctcgtcc tgatcgcttt cgcacagtac    360
ctccagcagt ctccctttga agatcacgtg aaactggtca atgaggtgac cgaatttgcc    420
aagacatgcg tggctgatga gagtgcagaa actgtgacaa atcactgca tactctcttt     480 ggagataagc tgtgcaccgt cgccacactc agagagactt atggggaaat ggctgactgt    540
tgcgcaaaac aggagcctga acggaatgag tgtttcctcc agcacaagga tgacaaccca    600
aatctgcccc gcctcgtgcg acctgaggtc gatgtgatgt gcaccgcctt tcatgacaac    660
gaagagacat tcctgaagaa atacctgtat gaaattgctc gtaggcaccc atacttttat    720
gcccccgagc tcctgttctt tgcaaagaga tacaaagctg ccttcactga atgttgccag    780
gcagctgata aggccgcatg tctcctgcct aaactggacg agctccggga tgaaggtaag    840
gcttccagcg ccaaacagcg cctgaagtgc gcttctctcc agaagtttgg cgagcgagca    900
ttcaaagcct gggctgtggc ccgtctcagt cagaggtttc caaaggcaga atttgctgag    960
gtgtcaaaac tggtgaccga cctcacaaag gtccatactg agtgttgcca cggagatctg   1020
ctggaatgtg ccgacgatag agcagacctc gctaaatata tctgcagaa tcaggattcc    1080 attagctcta agctgaaaga atgttgcgag aagcccctcc tggaaaagag tcattgtatc   1140
gccgaggtgg aaaacgacga gatgccagca gatctgccat cactcgctgc cgactttgtg   1200
gaatccaaag atgtctgcaa gaattacgca gaggctaaag acgtgttcct ggggatgttt   1260
ctgtatgagt acgcccggcg tcaccccgat tatagcgtcg tgctcctgct ccgactggca   1320
aagacctacg aaacaactct ggagaaatgt tgcgctgccg cagaccctca tgaatgttat   1380
gctaaggtgt tcgatgagtt taagccactc gtcgaagagc cccagaacct gattaaacag   1440
aattgcgaac tgttcgagca gctcggtgaa tacaagtttc agaacgccct gctcgtgcgt   1500
tataccaaaa aggtccctca ggtgtctaca ccaactctgg tggaggtcag taggaatctg   1560
ggcaaagtgg atcaaagtg ttgcaaacac cccgaggcaa agagaatgcc ttgtgctgaa    1620
gattacctct ccgtcgtgct gaaccagctc tgcgtgctgc atgaaaagac cccagtcagc   1680
gaccgggtga caaaatgttg caccgaatct ctggtcaatc gccgaccctg tttcagtgcc   1740
ctcgaagtgg acgaaactta tgtgcctaag gagtttcagg ctgaaacatt caccttttcac  1800 gccgatatct gcactctgtc cgagaaagaa aggcagatta gaaacagac agcactggtc    1860 gagctcgtga agcataaacc aaaggctacc aaggagcagc tgaaagccgt catggacgat   1920
ttcgcagctt ttgtgaaaaa gtgttgcaaa gccgacgata ggagacttg tttcgcagaa    1980 gaggggaaaa agctcgtggc tgccagccag gcagctctgg gtctggggag cggtggtggg   2040
agtggcgctc aagtcttgcg tggtacggtg acagacttcc caggcttcga tgaaagagcg   2100
gacgcggaaa cacttcgaaa ggcgatgaaa gggctcggta ctgacgaaga gtccattttg   2160
acccttctta cgagcaggtc aaacgctcag aggcaagaaa tctctgcagc ctttaagaca   2220
ctctttggag ctgaccttct tgatgacctc gcatctgagc tgacgggaaa gtttgagaaa   2280
ctcatcgtag ctttgatgaa gcccagccga ttgtatgatg cttacgaact gaaacacgcc   2340
ctggctggag cggaacgaa cgagaaagtt ttgactgaga tcatcgcatc gcggaccccg    2400
gaagagctca gagccatcaa acaagtctac gaggaggagt acggatcgtc attggcagga   2460
gacgtggtgg gggatacgtc gggttactac caacgaatgc ttgtcgtgct tttgcaggca   2520
gctcgcgacc cggatgcggg gatcgacgag gcccaagtgg agcaagatgc gcaagcactc   2580
```

| | | | | |
|---|---|---|---|---|
| ttccaggccg | gtgaactcaa | atgggggacc | gatgaagaga | agtttatcac catctttggc | 2640 |
| acgaggagtg | taagtcatct | gcgtaaagta | ttcgataagt | atatgacaat ctcagggttt | 2700 |
| cagattgagg | agacaattga | cagggaaacc | tccggtaact | tggagcagct cttgcttgcc | 2760 |
| gtcgtcaagt | ccattcgctc | gatccctgcg | tatctggctg | aaacactgta ttacgccatg | 2820 |
| aaaggggcag | gcactgatga | ccacaccttg | attagagtta | tggtgtcgcg atcagaaatt | 2880 |
| gacttgttca | atatccggaa | agagttccgg | aagaatttcg | caacgagcct ctatagcatg | 2940 |
| atcaaagggg | acacttcggg | agattacaag | aaagcgttgc | tccttctttg cggagaggat | 3000 |
| gactgataa | | | | | 3009 |

<210> SEQ ID NO 104
<211> LENGTH: 2997
<212> TYPE: DNA
<213> ORGANISM: Artificial Sequence
<220> FEATURE:
<223> OTHER INFORMATION: Synthetic construct

<400> SEQUENCE: 104

| | | | | |
|---|---|---|---|---|
| atgttcccag | ccatgccctt | gtccagcctg | tttgttaacg | gcccaagaac actttgtgga | 60 |
| gccgaactgg | tggatgctct | ccaattcgtt | tgcggcgacc | gcggattcta ctttaacaag | 120 |
| cccaccggtt | acgggtcttc | aagccggggcc | ccgcagactg | gcatcgtcga cgagtgctgt | 180 |
| tttagaagct | gcgatctgcg | acggttggag | atgtattgtg | cacctctgaa gcccgcgggg | 240 |
| agcggtggtg | ggagtggcga | cgctcacaag | tctgaagtgg | cacataggtt caaagatctg | 300 |
| ggcgaagaga | actttaaggc | cctcgtcctg | atcgctttcg | cacagtacct ccagcagtct | 360 |
| cccttttgaag | atcacgtgaa | actggtcaat | gaggtgaccg | aatttgccaa gacatgcgtg | 420 |
| gctgatgaga | gtgcagaaaa | actgtgacaaa | tcactgcata | ctctctttgg agataagctg | 480 |
| tgcaccgtcg | ccacactcag | agagacttat | ggggaaatgg | ctgactgttg cgcaaaacag | 540 |
| gagcctgaac | ggaatgagtg | tttcctccag | cacaaggatg | acaacccaaa tctgccccgc | 600 |
| ctcgtgcgac | ctgaggtcga | tgtgatgtgc | accgcctttc | atgacaacga agagacattc | 660 |
| ctgaagaaat | acctgtatga | aattgctcgt | aggcacccat | acttttatgc ccccgagctc | 720 |
| ctgttctttg | caaagagata | caaagctgcc | ttcactgaat | gttgccaggc agctgataag | 780 |
| gccgcatgtc | tcctgcctaa | actggacgag | ctccggggatg | aaggtaaggc ttccagcgcc | 840 |
| aaacagcgcc | tgaagtgcgc | ttctctccag | aagtttggcg | agcgagcatt caaagcctgg | 900 |
| gctgtggccc | gtctcagtca | gaggtttcca | aaggcagaat | ttgctgaggt gtcaaaactg | 960 |
| gtgaccgacc | tcacaaaggt | ccatactgag | tgttgccacg | gagatctgct ggaatgtgcc | 1020 |
| gacgatagag | cagacctcgc | taaatatatc | tgcgagaatc | aggattccat tagctctaag | 1080 |
| ctgaaagaat | gttgcgagaa | gcccctcctg | gaaaagagtc | attgtatcgc cgaggtggaa | 1140 |
| aacgacgaga | tgccagcaga | tctgccatca | ctcgctgccg | actttgtgga atccaaagat | 1200 |
| gtctgcaaga | attacgcaga | ggctaaagac | gtgttcctgg | gatgtttct gtatgagtac | 1260 |
| gcccggcgtc | accccgatta | tagcgtcgtg | ctcctgctcc | gactggcaaa gacctacgaa | 1320 |
| acaactctgg | agaaatgttg | cgctgccgca | gaccctcatg | aatgttatgc taaggtgttc | 1380 |
| gatgagttta | agccactcgt | cgaagagccc | cagaacctga | ttaaacagaa ttgcgaactg | 1440 |
| ttcgagcagc | tcggtgaata | caagtttcag | aacgccctgc | tcgtgcgtta taccaaaaag | 1500 |
| gtccctcagg | tgtctacacc | aactctggtg | gaggtcagta | ggaatctggg caaagtggga | 1560 |
| tcaaagtgtt | gcaaacaccc | cgaggcaaag | agaatgcctt | gtgctgaaga ttacctctcc | 1620 |

```
gtcgtgctga accagctctg cgtgctgcat gaaaagaccc cagtcagcga ccgggtgaca    1680
aaatgttgca ccgaatctct ggtcaatcgc cgaccctgtt tcagtgccct cgaagtggac    1740
gaaacttatg tgcctaagga gtttcaggct gaaacattca cctttcacgc cgatatctgc    1800
actctgtccg agaaagaaag gcagattaag aaacagacag cactggtcga gctcgtgaag    1860
cataaaccaa aggctaccaa ggagcagctg aaagccgtca tggacgattt cgcagctttt    1920
gtggaaaagt gttgcaaagc cgacgataag gagacttgtt tcgcagaaga ggggaaaaag    1980
ctcgtggctg ccagccaggc agctctgggt ctggggagcg tggtgggag tggcgctcaa    2040 gtcttgcgtg gtacggtgac agacttccca ggcttcgatg aaagagcgga cgcggaaaca    2100
cttcgaaagg cgatgaaagg gctcggtact gacgaagagt ccattttgac ccttcttacg    2160
agcaggtcaa acgctcagag gcaagaaatc tctgcagcct taagacact ctttggagct    2220 gaccttcttg atgacctcgc atctgagctg acgggaaagt ttgagaaact catcgtagct    2280
ttgatgaagc ccagccgatt gtatgatgct tacgaactga acacgccct ggctggagcg    2340 ggaacgaacg agaaagtttt gactgagatc atcgcatcgc ggaccccgga gagctcaga    2400 gccatcaaac aagtctacga ggaggagtac ggatcgtcat ggcaggaga cgtggtgggg    2460 gatacgtcgg gttactacca acgaatgctt gtcgtgcttt tgcaggcagc tcgcgacccg    2520
gatgcgggga tcgacgaggc ccaagtggag caagatgcgc aagcactctt ccaggccggt    2580
gaactcaaat gggggaccga tgaagagaag tttatcacca tctttggcac gaggagtgta    2640
agtcatctgc gtaaagtatt cgataagtat atgacaatct cagggttttca gattgaggag    2700 acaattgaca gggaaacctc cggtaacttg gagcagctct tgcttgccgt cgtcaagtcc    2760
attcgctcga tccctgcgta tctggctgaa acactgtatt acgccatgaa aggggcaggc    2820
actgatgacc acaccttgat tagagttatg gtgtcgcgat cagaaattga cttgttcaat    2880
atccggaaag agttccggaa gaatttcgca acgagcctct atagcatgat caaaggggac    2940
acttcgggag attacaagaa agcgttgctc cttctttgcg gagaggatga ctgataa      2997
```

<210> SEQ ID NO 105
<211> LENGTH: 21
<212> TYPE: PRT
<213> ORGANISM: Artificial Sequence
<220> FEATURE:
<223> OTHER INFORMATION: Synthetic construct

<400> SEQUENCE: 105

Met Ala Trp Arg Leu Trp Trp Leu Leu Leu Leu Leu Leu Leu Leu Trp
1               5                   10                  15

Pro Met Val Trp Ala
            20

<210> SEQ ID NO 106
<211> LENGTH: 63
<212> TYPE: DNA
<213> ORGANISM: Artificial Sequence
<220> FEATURE:
<223> OTHER INFORMATION: Synthetic construct

<400> SEQUENCE: 106

```
atggcctggc ggctgtggtg gctgctgctc ctgctcctgt tgctttggcc tatggtgtgg    60
gcc                                                                  63
```

<210> SEQ ID NO 107

```
<211> LENGTH: 683
<212> TYPE: PRT
<213> ORGANISM: Artificial Sequence
<220> FEATURE:
<223> OTHER INFORMATION: Synthetic construct

<400> SEQUENCE: 107
```

| | | | | | | | | | | | | | | |
|---|---|---|---|---|---|---|---|---|---|---|---|---|---|---|
| Met | Phe | Pro | Ala | Met | Pro | Leu | Ser | Ser | Leu | Phe | Val | Asn | Gly | Pro | Arg |
| 1 | | | | 5 | | | | | 10 | | | | | 15 | |
| Thr | Leu | Cys | Gly | Ala | Glu | Leu | Val | Asp | Ala | Leu | Gln | Phe | Val | Cys | Gly |
| | | | 20 | | | | | 25 | | | | | 30 | | |
| Asp | Arg | Gly | Phe | Tyr | Phe | Asn | Lys | Pro | Thr | Gly | Tyr | Gly | Ser | Ser | Ser |
| | | 35 | | | | | 40 | | | | | 45 | | | |
| Arg | Arg | Ala | Pro | Gln | Thr | Gly | Ile | Val | Asp | Glu | Cys | Cys | Phe | Arg | Ser |
| 50 | | | | | 55 | | | | | 60 | | | | | |
| Cys | Asp | Leu | Arg | Arg | Leu | Glu | Met | Tyr | Cys | Ala | Pro | Leu | Lys | Pro | Ala |
| 65 | | | | 70 | | | | | 75 | | | | | 80 | |
| Lys | Ser | Ala | Gly | Ser | Gly | Gly | Ser | Gly | Gly | Ser | Gly | Gly | Ser | Gly |
| | | | | 85 | | | | | 90 | | | | | 95 | |
| Gly | Gly | Asp | Ala | His | Lys | Ser | Glu | Val | Ala | His | Arg | Phe | Lys | Asp | Leu |
| | | | 100 | | | | | 105 | | | | | 110 | | |
| Gly | Glu | Glu | Asn | Phe | Lys | Ala | Leu | Val | Leu | Ile | Ala | Phe | Ala | Gln | Tyr |
| | | | 115 | | | | | 120 | | | | | 125 | | |
| Leu | Gln | Gln | Ser | Pro | Phe | Glu | Asp | His | Val | Lys | Leu | Val | Asn | Glu | Val |
| | | 130 | | | | | 135 | | | | | 140 | | | |
| Thr | Glu | Phe | Ala | Lys | Thr | Cys | Val | Ala | Asp | Glu | Ser | Ala | Glu | Asn | Cys |
| 145 | | | | | 150 | | | | | 155 | | | | | 160 |
| Asp | Lys | Ser | Leu | His | Thr | Leu | Phe | Gly | Asp | Lys | Leu | Cys | Thr | Val | Ala |
| | | | | 165 | | | | | 170 | | | | | 175 | |
| Thr | Leu | Arg | Glu | Thr | Tyr | Gly | Glu | Met | Ala | Asp | Cys | Cys | Ala | Lys | Gln |
| | | | 180 | | | | | 185 | | | | | 190 | | |
| Glu | Pro | Glu | Arg | Asn | Glu | Cys | Phe | Leu | Gln | His | Lys | Asp | Asp | Asn | Pro |
| | | | 195 | | | | | 200 | | | | | 205 | | |
| Asn | Leu | Pro | Arg | Leu | Val | Arg | Pro | Glu | Val | Asp | Val | Met | Cys | Thr | Ala |
| | | 210 | | | | | 215 | | | | | 220 | | | |
| Phe | His | Asp | Asn | Glu | Glu | Thr | Phe | Leu | Lys | Lys | Tyr | Leu | Tyr | Glu | Ile |
| 225 | | | | | 230 | | | | | 235 | | | | | 240 |
| Ala | Arg | Arg | His | Pro | Tyr | Phe | Tyr | Ala | Pro | Glu | Leu | Leu | Phe | Phe | Ala |
| | | | | 245 | | | | | 250 | | | | | 255 | |
| Lys | Arg | Tyr | Lys | Ala | Ala | Phe | Thr | Glu | Cys | Cys | Gln | Ala | Ala | Asp | Lys |
| | | | 260 | | | | | 265 | | | | | 270 | | |
| Ala | Ala | Cys | Leu | Leu | Pro | Lys | Leu | Asp | Glu | Leu | Arg | Asp | Glu | Gly | Lys |
| | | 275 | | | | | 280 | | | | | 285 | | | |
| Ala | Ser | Ser | Ala | Lys | Gln | Arg | Leu | Lys | Cys | Ala | Ser | Leu | Gln | Lys | Phe |
| | 290 | | | | | 295 | | | | | 300 | | | | |
| Gly | Glu | Arg | Ala | Phe | Lys | Ala | Trp | Ala | Val | Ala | Arg | Leu | Ser | Gln | Arg |
| 305 | | | | | 310 | | | | | 315 | | | | | 320 |
| Phe | Pro | Lys | Ala | Glu | Phe | Ala | Glu | Val | Ser | Lys | Leu | Val | Thr | Asp | Leu |
| | | | | 325 | | | | | 330 | | | | | 335 | |
| Thr | Lys | Val | His | Thr | Glu | Cys | Cys | His | Gly | Asp | Leu | Leu | Glu | Cys | Ala |
| | | | 340 | | | | | 345 | | | | | 350 | | |
| Asp | Asp | Arg | Ala | Asp | Leu | Ala | Lys | Tyr | Ile | Cys | Glu | Asn | Gln | Asp | Ser |
| | | 355 | | | | | 360 | | | | | 365 | | | |
| Ile | Ser | Ser | Lys | Leu | Lys | Glu | Cys | Cys | Glu | Lys | Pro | Leu | Leu | Glu | Lys |
| | 370 | | | | | 375 | | | | | 380 | | | | |

```
Ser His Cys Ile Ala Glu Val Glu Asn Asp Glu Met Pro Ala Asp Leu
385                 390                 395                 400

Pro Ser Leu Ala Ala Asp Phe Val Glu Ser Lys Asp Val Cys Lys Asn
                405                 410                 415

Tyr Ala Glu Ala Lys Asp Val Phe Leu Gly Met Phe Leu Tyr Glu Tyr
            420                 425                 430

Ala Arg Arg His Pro Asp Tyr Ser Val Val Leu Leu Leu Arg Leu Ala
                435                 440                 445

Lys Thr Tyr Glu Thr Thr Leu Glu Lys Cys Cys Ala Ala Ala Asp Pro
        450                 455                 460

His Glu Cys Tyr Ala Lys Val Phe Asp Glu Phe Lys Pro Leu Val Glu
465                 470                 475                 480

Glu Pro Gln Asn Leu Ile Lys Gln Asn Cys Glu Leu Phe Glu Gln Leu
                485                 490                 495

Gly Glu Tyr Lys Phe Gln Asn Ala Leu Leu Val Arg Tyr Thr Lys Lys
            500                 505                 510

Val Pro Gln Val Ser Thr Pro Thr Leu Val Glu Val Ser Arg Asn Leu
        515                 520                 525

Gly Lys Val Gly Ser Lys Cys Cys Lys His Pro Glu Ala Lys Arg Met
530                 535                 540

Pro Cys Ala Glu Asp Tyr Leu Ser Val Leu Asn Gln Leu Cys Val
545                 550                 555                 560

Leu His Glu Lys Thr Pro Val Ser Asp Arg Val Thr Lys Cys Cys Thr
                565                 570                 575

Glu Ser Leu Val Asn Arg Arg Pro Cys Phe Ser Ala Leu Glu Val Asp
            580                 585                 590

Glu Thr Tyr Val Pro Lys Glu Phe Gln Ala Gly Thr Phe Thr Phe His
        595                 600                 605

Ala Asp Ile Cys Thr Leu Ser Glu Lys Glu Arg Gln Ile Lys Lys Gln
610                 615                 620

Thr Ala Leu Val Glu Leu Val Lys His Lys Pro Lys Ala Thr Lys Glu
625                 630                 635                 640

Gln Leu Lys Ala Ala Met Asp Asp Phe Ala Ala Phe Val Glu Lys Cys
                645                 650                 655

Cys Lys Ala Asp Asp Lys Glu Thr Cys Phe Ala Glu Glu Gly Lys Lys
            660                 665                 670

Leu Val Ala Ala Ser Gln Ala Ala Leu Gly Leu
        675                 680

<210> SEQ ID NO 108
<211> LENGTH: 1001
<212> TYPE: PRT
<213> ORGANISM: Artificial Sequence
<220> FEATURE:
<223> OTHER INFORMATION: Synthetic construct

<400> SEQUENCE: 108

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Leu Phe Asn Lys Pro Thr Gly Ala Gly Ser Ser Ser
        35                  40                  45

Arg Arg Ala Pro Gln Thr Gly Ile Val Asp Glu Cys Cys Phe Arg Ser
    50                  55                  60
```

```
Cys Asp Leu Arg Arg Leu Glu Met Tyr Cys Ala Pro Leu Lys Pro Ala
 65                  70                  75                  80

Lys Ser Ala Gly Ser Gly Gly Ser Gly Asp Ala His Lys Ser Glu
                 85                  90                  95

Val Ala His Arg Phe Lys Asp Leu Gly Glu Glu Asn Phe Lys Ala Leu
                100                 105                 110

Val Leu Ile Ala Phe Ala Gln Tyr Leu Gln Gln Ser Pro Phe Glu Asp
            115                 120                 125

His Val Lys Leu Val Asn Glu Val Thr Glu Phe Ala Lys Thr Cys Val
        130                 135                 140

Ala Asp Glu Ser Ala Glu Asn Cys Asp Lys Ser Leu His Thr Leu Phe
145                 150                 155                 160

Gly Asp Lys Leu Cys Thr Val Ala Thr Leu Arg Glu Thr Tyr Gly Glu
                165                 170                 175

Met Ala Asp Cys Cys Ala Lys Gln Glu Pro Glu Arg Asn Glu Cys Phe
            180                 185                 190

Leu Gln His Lys Asp Asp Asn Pro Asn Leu Pro Arg Leu Val Arg Pro
        195                 200                 205

Glu Val Asp Val Met Cys Thr Ala Phe His Asp Asn Glu Glu Thr Phe
210                 215                 220

Leu Lys Lys Tyr Leu Tyr Glu Ile Ala Arg Arg His Pro Tyr Phe Tyr
225                 230                 235                 240

Ala Pro Glu Leu Leu Phe Phe Ala Lys Arg Tyr Lys Ala Ala Phe Thr
                245                 250                 255

Glu Cys Cys Gln Ala Ala Asp Lys Ala Ala Cys Leu Leu Pro Lys Leu
            260                 265                 270

Asp Glu Leu Arg Asp Glu Gly Lys Ala Ser Ser Ala Lys Gln Arg Leu
        275                 280                 285

Lys Cys Ala Ser Leu Gln Lys Phe Gly Glu Arg Ala Phe Lys Ala Trp
        290                 295                 300

Ala Val Ala Arg Leu Ser Gln Arg Phe Pro Lys Ala Glu Phe Ala Glu
305                 310                 315                 320

Val Ser Lys Leu Val Thr Asp Leu Thr Lys Val His Thr Glu Cys Cys
                325                 330                 335

His Gly Asp Leu Leu Glu Cys Ala Asp Asp Arg Ala Asp Leu Ala Lys
            340                 345                 350

Tyr Ile Cys Glu Asn Gln Asp Ser Ile Ser Ser Lys Leu Lys Glu Cys
        355                 360                 365

Cys Glu Lys Pro Leu Leu Glu Lys Ser His Cys Ile Ala Glu Val Glu
        370                 375                 380

Asn Asp Glu Met Pro Ala Asp Leu Pro Ser Leu Ala Ala Asp Phe Val
385                 390                 395                 400

Glu Ser Lys Asp Val Cys Lys Asn Tyr Ala Glu Ala Lys Asp Val Phe
                405                 410                 415

Leu Gly Met Phe Leu Tyr Glu Tyr Ala Arg Arg His Pro Asp Tyr Ser
            420                 425                 430

Val Val Leu Leu Leu Arg Leu Ala Lys Thr Tyr Glu Thr Thr Leu Glu
        435                 440                 445

Lys Cys Cys Ala Ala Ala Asp Pro His Glu Cys Tyr Ala Lys Val Phe
        450                 455                 460

Asp Glu Phe Lys Pro Leu Val Glu Glu Pro Gln Asn Leu Ile Lys Gln
465                 470                 475                 480
```

```
Asn Cys Glu Leu Phe Glu Gln Leu Gly Glu Tyr Lys Phe Gln Asn Ala
            485                 490                 495

Leu Leu Val Arg Tyr Thr Lys Lys Val Pro Gln Val Ser Thr Pro Thr
        500                 505                 510

Leu Val Glu Val Ser Arg Asn Leu Gly Lys Val Gly Ser Lys Cys Cys
        515                 520                 525

Lys His Pro Glu Ala Lys Arg Met Pro Cys Ala Glu Asp Tyr Leu Ser
        530                 535                 540

Val Val Leu Asn Gln Leu Cys Val Leu His Glu Lys Thr Pro Val Ser
545                 550                 555                 560

Asp Arg Val Thr Lys Cys Cys Thr Glu Ser Leu Val Asn Arg Arg Pro
                565                 570                 575

Cys Phe Ser Ala Leu Glu Val Asp Glu Thr Tyr Val Pro Lys Glu Phe
            580                 585                 590

Gln Ala Gly Thr Phe Thr Phe His Ala Asp Ile Cys Thr Leu Ser Glu
            595                 600                 605

Lys Glu Arg Gln Ile Lys Lys Gln Thr Ala Leu Val Glu Leu Val Lys
            610                 615                 620

His Lys Pro Lys Ala Thr Lys Glu Gln Leu Lys Ala Ala Met Asp Asp
625                 630                 635                 640

Phe Ala Ala Phe Val Glu Lys Cys Cys Lys Ala Asp Asp Lys Glu Thr
                645                 650                 655

Cys Phe Ala Glu Glu Gly Lys Lys Leu Val Ala Ala Ser Gln Ala Ala
                660                 665                 670

Leu Gly Leu Gly Ser Gly Gly Ser Gly Ala Gln Val Leu Arg Gly
            675                 680                 685

Thr Val Thr Asp Phe Pro Gly Phe Asp Glu Arg Ala Asp Ala Glu Thr
            690                 695                 700

Leu Arg Lys Ala Met Lys Gly Leu Gly Thr Asp Glu Glu Ser Ile Leu
705                 710                 715                 720

Thr Leu Leu Thr Ser Arg Ser Asn Ala Gln Arg Gln Glu Ile Ser Ala
                725                 730                 735

Ala Phe Lys Thr Leu Phe Gly Ala Asp Leu Leu Asp Asp Leu Ala Ser
            740                 745                 750

Glu Leu Thr Gly Lys Phe Glu Lys Leu Ile Val Ala Leu Met Lys Pro
            755                 760                 765

Ser Arg Leu Tyr Asp Ala Tyr Glu Leu Lys His Ala Leu Ala Gly Ala
        770                 775                 780

Gly Thr Asn Glu Lys Val Leu Thr Glu Ile Ile Ala Ser Arg Thr Pro
785                 790                 795                 800

Glu Glu Leu Arg Ala Ile Lys Gln Val Tyr Glu Glu Glu Tyr Gly Ser
                805                 810                 815

Ser Leu Ala Gly Asp Val Val Gly Asp Thr Ser Gly Tyr Tyr Gln Arg
            820                 825                 830

Met Leu Val Val Leu Leu Gln Ala Ala Arg Asp Pro Asp Ala Gly Ile
            835                 840                 845

Asp Glu Ala Gln Val Glu Gln Asp Ala Gln Ala Leu Phe Gln Ala Gly
        850                 855                 860

Glu Leu Lys Trp Gly Thr Asp Glu Glu Lys Phe Ile Thr Ile Phe Gly
865                 870                 875                 880

Thr Arg Ser Val Ser His Leu Arg Lys Val Phe Asp Lys Tyr Met Thr
                885                 890                 895

Ile Ser Gly Phe Gln Ile Glu Glu Thr Ile Asp Arg Glu Thr Ser Gly
```

```
                900               905                910
Asn Leu Glu Gln Leu Leu Ala Val Val Lys Ser Ile Arg Ser Ile
            915                 920                925

Pro Ala Tyr Leu Ala Glu Thr Leu Tyr Tyr Ala Met Lys Gly Ala Gly
            930                 935                940

Thr Asp Asp His Thr Leu Ile Arg Val Met Val Ser Arg Ser Glu Ile
945                 950                 955                960

Asp Leu Phe Asn Ile Arg Lys Glu Phe Arg Lys Asn Phe Ala Thr Ser
            965                 970                975

Leu Tyr Ser Met Ile Lys Gly Asp Thr Ser Gly Asp Tyr Lys Lys Ala
            980                 985                990

Leu Leu Leu Leu Cys Gly Glu Asp  Asp
            995                  1000

<210> SEQ ID NO 109
<211> LENGTH: 675
<212> TYPE: PRT
<213> ORGANISM: Artificial Sequence
<220> FEATURE:
<223> OTHER INFORMATION: Synthetic construct

<400> SEQUENCE: 109

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Tyr Phe Asn Lys Pro Thr Gly Ala Gly Ser Ser Ser
        35                  40                  45

Arg Arg Ala Pro Gln Thr Gly Ile Val Asp Glu Cys Cys Phe Arg Ser
    50                  55                  60

Cys Asp Leu Arg Arg Leu Glu Met Tyr Cys Ala Pro Leu Lys Pro Ala
65                  70                  75                  80

Lys Ser Ala Gly Ser Gly Gly Ser Gly Asp Ala His Lys Ser Glu
            85                  90                  95

Val Ala His Arg Phe Lys Asp Leu Gly Glu Glu Asn Phe Lys Ala Leu
            100                 105                 110

Val Leu Ile Ala Phe Ala Gln Tyr Leu Gln Gln Ser Pro Phe Glu Asp
            115                 120                 125

His Val Lys Leu Val Asn Glu Val Thr Glu Phe Ala Lys Thr Cys Val
        130                 135                 140

Ala Asp Glu Ser Ala Glu Asn Cys Asp Lys Ser Leu His Thr Leu Phe
145                 150                 155                 160

Gly Asp Lys Leu Cys Thr Val Ala Thr Leu Arg Glu Thr Tyr Gly Glu
            165                 170                 175

Met Ala Asp Cys Cys Ala Lys Gln Glu Pro Glu Arg Asn Glu Cys Phe
            180                 185                 190

Leu Gln His Lys Asp Asp Asn Pro Asn Leu Pro Arg Leu Val Arg Pro
        195                 200                 205

Glu Val Asp Val Met Cys Thr Ala Phe His Asp Asn Glu Glu Thr Phe
    210                 215                 220

Leu Lys Lys Tyr Leu Tyr Glu Ile Ala Arg Arg His Pro Tyr Phe Tyr
225                 230                 235                 240

Ala Pro Glu Leu Leu Phe Phe Ala Lys Arg Tyr Lys Ala Ala Phe Thr
            245                 250                 255

Glu Cys Cys Gln Ala Ala Asp Lys Ala Ala Cys Leu Leu Pro Lys Leu
```

```
                260             265             270
Asp Glu Leu Arg Asp Glu Gly Lys Ala Ser Ala Lys Gln Arg Leu
            275             280             285

Lys Cys Ala Ser Leu Gln Lys Phe Gly Glu Arg Ala Phe Lys Ala Trp
290             295             300

Ala Val Ala Arg Leu Ser Gln Arg Phe Pro Lys Ala Glu Phe Ala Glu
305             310             315             320

Val Ser Lys Leu Val Thr Asp Leu Thr Lys Val His Thr Glu Cys Cys
                325             330             335

His Gly Asp Leu Leu Glu Cys Ala Asp Asp Arg Ala Asp Leu Ala Lys
            340             345             350

Tyr Ile Cys Glu Asn Gln Asp Ser Ile Ser Ser Lys Leu Lys Glu Cys
        355             360             365

Cys Glu Lys Pro Leu Leu Glu Lys Ser His Cys Ile Ala Glu Val Glu
    370             375             380

Asn Asp Glu Met Pro Ala Asp Leu Pro Ser Leu Ala Ala Asp Phe Val
385             390             395             400

Glu Ser Lys Asp Val Cys Lys Asn Tyr Ala Glu Ala Lys Asp Val Phe
                405             410             415

Leu Gly Met Phe Leu Tyr Glu Tyr Ala Arg Arg His Pro Asp Tyr Ser
            420             425             430

Val Val Leu Leu Leu Arg Leu Ala Lys Thr Tyr Glu Thr Thr Leu Glu
        435             440             445

Lys Cys Cys Ala Ala Ala Asp Pro His Glu Cys Tyr Ala Lys Val Phe
    450             455             460

Asp Glu Phe Lys Pro Leu Val Glu Glu Pro Gln Asn Leu Ile Lys Gln
465             470             475             480

Asn Cys Glu Leu Phe Glu Gln Leu Gly Glu Tyr Lys Phe Gln Asn Ala
                485             490             495

Leu Leu Val Arg Tyr Thr Lys Lys Val Pro Gln Val Ser Thr Pro Thr
            500             505             510

Leu Val Glu Val Ser Arg Asn Leu Gly Lys Val Gly Ser Lys Cys Cys
        515             520             525

Lys His Pro Glu Ala Lys Arg Met Pro Cys Ala Glu Asp Tyr Leu Ser
    530             535             540

Val Val Leu Asn Gln Leu Cys Val Leu His Glu Lys Thr Pro Val Ser
545             550             555             560

Asp Arg Val Thr Lys Cys Cys Thr Glu Ser Leu Val Asn Arg Arg Pro
                565             570             575

Cys Phe Ser Ala Leu Glu Val Asp Glu Thr Tyr Val Pro Lys Glu Phe
            580             585             590

Gln Ala Glu Thr Phe Thr Phe His Ala Asp Ile Cys Thr Leu Ser Glu
        595             600             605

Lys Glu Arg Gln Ile Lys Lys Gln Thr Ala Leu Val Glu Leu Val Lys
    610             615             620

His Lys Pro Lys Ala Thr Lys Glu Gln Leu Lys Ala Val Met Asp Asp
625             630             635             640

Phe Ala Ala Phe Val Glu Lys Cys Cys Lys Ala Asp Asp Lys Glu Thr
                645             650             655

Cys Phe Ala Glu Glu Gly Lys Lys Leu Val Ala Ala Ser Gln Ala Ala
            660             665             670

Leu Gly Leu
        675
```

<210> SEQ ID NO 110
<211> LENGTH: 985
<212> TYPE: PRT
<213> ORGANISM: Artificial Sequence
<220> FEATURE:
<223> OTHER INFORMATION: Synthetic construct

<400> SEQUENCE: 110

Thr Gly Ser His Leu Val Lys Cys Ala Glu Lys Glu Lys Thr Phe Cys
1               5                   10                  15

Val Asn Gly Gly Glu Cys Phe Met Val Lys Asp Leu Ser Asn Pro Ser
            20                  25                  30

Arg Tyr Leu Cys Lys Cys Gln Pro Gly Phe Thr Gly Ala Arg Cys Thr
        35                  40                  45

Glu Asn Val Pro Met Lys Val Gln Asn Gln Lys Ala Glu Glu Leu
    50                  55                  60

Tyr Gln Lys Gly Ser Gly Gly Ser Gly Asp Ala His Lys Ser Glu
65                  70                  75                  80

Val Ala His Arg Phe Lys Asp Leu Gly Glu Glu Asn Phe Lys Ala Leu
                85                  90                  95

Val Leu Ile Ala Phe Ala Gln Tyr Leu Gln Gln Ser Pro Phe Glu Asp
            100                 105                 110

His Val Lys Leu Val Asn Glu Val Thr Glu Phe Ala Lys Thr Cys Val
        115                 120                 125

Ala Asp Glu Ser Ala Glu Asn Cys Asp Lys Ser Leu His Thr Leu Phe
    130                 135                 140

Gly Asp Lys Leu Cys Thr Val Ala Thr Leu Arg Glu Thr Tyr Gly Glu
145                 150                 155                 160

Met Ala Asp Cys Cys Ala Lys Gln Glu Pro Glu Arg Asn Glu Cys Phe
                165                 170                 175

Leu Gln His Lys Asp Asp Asn Pro Asn Leu Pro Arg Leu Val Arg Pro
            180                 185                 190

Glu Val Asp Val Met Cys Thr Ala Phe His Asp Asn Glu Glu Thr Phe
        195                 200                 205

Leu Lys Lys Tyr Leu Tyr Glu Ile Ala Arg Arg His Pro Tyr Phe Tyr
    210                 215                 220

Ala Pro Glu Leu Leu Phe Phe Ala Lys Arg Tyr Lys Ala Ala Phe Thr
225                 230                 235                 240

Glu Cys Cys Gln Ala Ala Asp Lys Ala Ala Cys Leu Leu Pro Lys Leu
                245                 250                 255

Asp Glu Leu Arg Asp Glu Gly Lys Ala Ser Ser Ala Lys Gln Arg Leu
            260                 265                 270

Lys Cys Ala Ser Leu Gln Lys Phe Gly Glu Arg Ala Phe Lys Ala Trp
        275                 280                 285

Ala Val Ala Arg Leu Ser Gln Arg Phe Pro Lys Ala Glu Phe Ala Glu
    290                 295                 300

Val Ser Lys Leu Val Thr Asp Leu Thr Lys Val His Thr Glu Cys Cys
305                 310                 315                 320

His Gly Asp Leu Leu Glu Cys Ala Asp Asp Arg Ala Asp Leu Ala Lys
                325                 330                 335

Tyr Ile Cys Glu Asn Gln Asp Ser Ile Ser Ser Lys Leu Lys Glu Cys
            340                 345                 350

Cys Glu Lys Pro Leu Leu Glu Lys Ser His Cys Ile Ala Glu Val Glu
        355                 360                 365

```
Asn Asp Glu Met Pro Ala Asp Leu Pro Ser Leu Ala Ala Asp Phe Val
    370                 375                 380
Glu Ser Lys Asp Val Cys Lys Asn Tyr Ala Glu Ala Lys Asp Val Phe
385                 390                 395                 400
Leu Gly Met Phe Leu Tyr Glu Tyr Ala Arg Arg His Pro Asp Tyr Ser
                405                 410                 415
Val Val Leu Leu Leu Arg Leu Ala Lys Thr Tyr Glu Thr Thr Leu Glu
            420                 425                 430
Lys Cys Cys Ala Ala Ala Asp Pro His Glu Cys Tyr Ala Lys Val Phe
                435                 440                 445
Asp Glu Phe Lys Pro Leu Val Glu Glu Pro Gln Asn Leu Ile Lys Gln
    450                 455                 460
Asn Cys Glu Leu Phe Glu Gln Leu Gly Glu Tyr Lys Phe Gln Asn Ala
465                 470                 475                 480
Leu Leu Val Arg Tyr Thr Lys Lys Val Pro Gln Val Ser Thr Pro Thr
                485                 490                 495
Leu Val Glu Val Ser Arg Asn Leu Gly Lys Val Gly Ser Lys Cys Cys
            500                 505                 510
Lys His Pro Glu Ala Lys Arg Met Pro Cys Ala Glu Asp Tyr Leu Ser
                515                 520                 525
Val Val Leu Asn Gln Leu Cys Val Leu His Glu Lys Thr Pro Val Ser
    530                 535                 540
Asp Arg Val Thr Lys Cys Cys Thr Glu Ser Leu Val Asn Arg Arg Pro
545                 550                 555                 560
Cys Phe Ser Ala Leu Glu Val Asp Glu Thr Tyr Val Pro Lys Glu Phe
                565                 570                 575
Gln Ala Glu Thr Phe Thr Phe His Ala Asp Ile Cys Thr Leu Ser Glu
            580                 585                 590
Lys Glu Arg Gln Ile Lys Lys Gln Thr Ala Leu Val Glu Leu Val Lys
                595                 600                 605
His Lys Pro Lys Ala Thr Lys Glu Gln Leu Lys Ala Val Met Asp Asp
    610                 615                 620
Phe Ala Ala Phe Val Glu Lys Cys Cys Lys Ala Asp Asp Lys Glu Thr
625                 630                 635                 640
Cys Phe Ala Glu Glu Gly Lys Lys Leu Val Ala Ala Ser Gln Ala Ala
                645                 650                 655
Leu Gly Leu Gly Ser Gly Gly Ser Gly Ala Gln Val Leu Arg Gly
            660                 665                 670
Thr Val Thr Asp Phe Pro Gly Phe Asp Glu Arg Ala Asp Ala Glu Thr
                675                 680                 685
Leu Arg Lys Ala Met Lys Gly Leu Gly Thr Asp Glu Glu Ser Ile Leu
    690                 695                 700
Thr Leu Leu Thr Ser Arg Ser Asn Ala Gln Arg Gln Glu Ile Ser Ala
705                 710                 715                 720
Ala Phe Lys Thr Leu Phe Gly Ala Asp Leu Leu Asp Asp Leu Ala Ser
                725                 730                 735
Glu Leu Thr Gly Lys Phe Glu Lys Leu Ile Val Ala Leu Met Lys Pro
            740                 745                 750
Ser Arg Leu Tyr Asp Ala Tyr Glu Leu Lys His Ala Leu Ala Gly Ala
                755                 760                 765
Gly Thr Asn Glu Lys Val Leu Thr Glu Ile Ile Ala Ser Arg Thr Pro
    770                 775                 780
```

| | | | | | | | | | | | | | | |
|---|---|---|---|---|---|---|---|---|---|---|---|---|---|---|
|Glu|Glu|Leu|Arg|Ala|Ile|Lys|Gln|Val|Tyr|Glu|Glu|Tyr|Gly|Ser|
|785| | | |790| | | |795| | | |800| | |

Ser Leu Ala Gly Asp Val Val Gly Asp Thr Ser Gly Tyr Tyr Gln Arg
             805                   810                815

Met Leu Val Val Leu Leu Gln Ala Ala Arg Asp Pro Asp Ala Gly Ile
        820                   825                   830

Asp Glu Ala Gln Val Glu Gln Asp Ala Gln Ala Leu Phe Gln Ala Gly
           835                   840               845

Glu Leu Lys Trp Gly Thr Asp Glu Glu Lys Phe Thr Ile Phe Gly
    850                 855                 860

Thr Arg Ser Val Ser His Leu Arg Lys Val Phe Asp Lys Tyr Met Thr
865               870                 875               880

Ile Ser Gly Phe Gln Ile Glu Glu Thr Ile Asp Arg Glu Thr Ser Gly
           885                   890               895

Asn Leu Glu Gln Leu Leu Ala Val Val Lys Ser Ile Arg Ser Ile
        900                   905               910

Pro Ala Tyr Leu Ala Glu Thr Leu Tyr Tyr Ala Met Lys Gly Ala Gly
        915                 920               925

Thr Asp Asp His Thr Leu Ile Arg Val Met Val Ser Arg Ser Glu Ile
    930                 935                 940

Asp Leu Phe Asn Ile Arg Lys Glu Phe Arg Lys Asn Phe Ala Thr Ser
945               950                 955               960

Leu Tyr Ser Met Ile Lys Gly Asp Thr Ser Gly Asp Tyr Lys Lys Ala
           965                   970               975

Leu Leu Leu Leu Cys Gly Glu Asp Asp
    980                 985

<210> SEQ ID NO 111
<211> LENGTH: 2055
<212> TYPE: DNA
<213> ORGANISM: Artificial Sequence
<220> FEATURE:
<223> OTHER INFORMATION: Synthetic construct

<400> SEQUENCE: 111

| | | |
|---|---|---|
|atgttcccag ccatgccctt gtccagcctg tttgttaacg cccaagaac actttgtgga|60|
|gccgaactgg tggatgctct ccaattcgtt tgcggcgacc gcggattcta ctttaacaag|120|
|cccaccggtt acgggtcttc aagccggagg cccccgcaga ctggcatcgt cgacgagtgc|180|
|tgttttagaa gctgcgatct gcgacggttg gagatgtatt gtgcacctct gaagcccgcg|240|
|aaaagtgctg gttccggagg gagcggtggt gggagtggcg atctggtgg aggagacgct|300|
|cacaagtctg aagtggcaca taggttcaaa gatctgggcg aagagaactt taaggccctc|360|
|gtcctgatcg ctttcgcaca gtacctccag cagtctccct tgaagatca cgtgaaactg|420|
|gtcaatgagg tgaccgaatt tgccaagaca tgcgtggctg atgagagtgc agaaaactgt|480|
|gacaaatcac tgcatactct ctttggagat aagctgtgca ccgtcgccac actcagagag|540|
|acttatgggg aaatggctga ctgttgcgca aaacaggagc tgaacggaa tgagtgtttc|600|
|ctccagcaca aggatgacaa cccaaatctg ccccgcctcg tgcgacctga ggtcgatgtg|660|
|atgtgcaccg cctttcatga caacgaagag acattcctga gaaatacct gtatgaaatt|720|
|gctcgtaggc acccatactt ttatgccccc gagctcctgt tctttgcaaa gagatacaaa|780|
|gctgccttca ctgaatgttg ccaggcagct gataaggccg catgtctcct gcctaaactg|840|
|gacgagctcc gggatgaagg taaggcttcc agcgccaaac agcgcctgaa gtgcgcttct|900|

```
ctccagaagt ttggcgagcg agcattcaaa gcctgggctg tggcccgtct cagtcagagg      960
tttccaaagg cagaatttgc tgaggtgtca aaactggtga ccgacctcac aaaggtccat     1020
actgagtgtt gccacggaga tctgctggaa tgtgccgacg atagagcaga cctcgctaaa     1080
tatatctgcg agaatcagga ttccattagc tctaagctga agaatgttg cgagaagccc      1140 ctcctggaaa agagtcattg tatcgccgag gtggaaaacg acgagatgcc agcagatctg     1200
ccatcactcg ctgccgactt tgtggaatcc aaagatgtct gcaagaatta cgcagaggct     1260
aaagacgtgt tcctggggat gtttctgtat gagtacgccc ggcgtcaccc cgattatagc     1320
gtcgtgctcc tgctccgact ggcaaagacc tacgaaacaa ctctggagaa atgttgcgct     1380
gccgcagacc ctcatgaatg ttatgctaag gtgttcgatg agtttaagcc actcgtcgaa     1440
gagccccaga acctgattaa acagaattgc gaactgttcg agcagctcgg tgaatacaag     1500
tttcagaacg ccctgctcgt gcgttatacc aaaaaggtcc ctcaggtgtc tacaccaact     1560 ctggtgagg tcagtaggaa tctgggcaaa gtgggatcaa agtgttgcaa cacccccgag      1620
gcaaagagaa tgccttgtgc tgaagattac ctctccgtcg tgctgaacca gctctgcgtg     1680
ctgcatgaaa agaccccagt cagcgaccgg gtgacaaaat gttgcaccga atctctggtc     1740
aatcgccgac cctgtttcag tgccctcgaa gtggacgaaa cttatgtgcc taaggagttt     1800
caggctggaa cattcacctt tcacgccgat atctgcactc tgtccgagaa agaaaggcag     1860
attaagaaac agacagcact ggtcgagctc gtgaagcata aaccaaaggc taccaaggag     1920
cagctgaaag ccgccatgga cgatttcgca gcttttgtgg aaaagtgttg caaagccgac     1980
gataaggaga cttgtttcgc agaagagggg aaaaagctcg tggctgccag ccaggcagct     2040
ctgggtctgt aatga                                                     2055
```

<210> SEQ ID NO 112
<211> LENGTH: 3009
<212> TYPE: DNA
<213> ORGANISM: Artificial Sequence
<220> FEATURE:
<223> OTHER INFORMATION: Synthetic construct

<400> SEQUENCE: 112

```
atgttcccag ccatgccctt gtccagcctg tttgttaacg cccaagaac actttgtgga       60 gccgaactgg tggatgctct ccaattcgtt tgcggcgacc gcggattcct ctttaacaag     120
cccaccggtg ccgggtcttc aagccggagg gccccgcaga ctggcatcgt cgacgagtgc     180
tgttttagaa gctgcgatct gcgacggttg gagatgtatt gtgcacctct gaagcccgcg     240
aaaagtgctg ggagcggtgg tgggagtggc gacgctcaca gtctgaagt ggcacatagg      300 ttcaaagatc tgggcgaaga gactttaag gccctcgtcc tgatcgcttt cgcacagtac      360
ctccagcagt ctccctttga agatcacgtg aaactggtca atgaggtgac cgaatttgcc     420
aagacatgcg tggctgatga gagtgcagaa aactgtgaca aatcactgca tactctcttt     480
ggagataagc tgtgcaccgt cgccacactc agagagactt atgggaaat ggctgactgt      540 tgcgcaaaac aggagcctga acggaatgag tgtttcctcc agcacaagga tgacaaccca     600
aatctgcccc gcctcgtgcg acctgaggtc gatgtgatgt gcaccgcctt tcatgacaac     660
gaagagacat tcctgaagaa atacctgtat gaaattgctc gtaggcaccc atactttat     720 gcccccgagc tcctgttctt tgcaaagaga tacaaagctg ccttcactga atgttgccag    780
gcagctgata ggccgcatg tctcctgcct aaactggacg agctccggga tgaaggtaag    840
gcttccagcg ccaaacagcg cctgaagtgc gcttctctcc agaagtttgg cgagcgagca    900
```

```
ttcaaagcct gggctgtggc ccgtctcagt cagaggtttc caaaggcaga atttgctgag    960
gtgtcaaaac tggtgaccga cctcacaaag gtccatactg agtgttgcca cggagatctg   1020
ctggaatgtg ccgacgatag agcagacctc gctaaatata tctgcgagaa tcaggattcc   1080
attagctcta agctgaaaga atgttgcgag aagcccctcc tggaaaagag tcattgtatc   1140
gccgaggtgg aaaacgacga gatgccagca gatctgccat cactcgctgc cgactttgtg   1200
gaatccaaag atgtctgcaa gaattacgca gaggctaaag acgtgttcct ggggatgttt   1260
ctgtatgagt acgcccggcg tcaccccgat tatagcgtcg tgctcctgct ccgactggca   1320
aagacctacg aaacaactct ggagaaatgt tgcgctgccg cagaccctca tgaatgttat   1380
gctaaggtgt tcgatgagtt taagccactc gtcgaagagc cccagaacct gattaaacag   1440
aattgcgaac tgttcgagca gctcggtgaa tacaagtttc agaacgccct gctcgtgcgt   1500
tataccaaaa aggtccctca ggtgtctaca ccaactctgg tggaggtcag taggaatctg   1560
ggcaaagtgg gatcaaagtg ttgcaaacac cccgaggcaa agagaatgcc ttgtgctgaa   1620
gattacctct ccgtcgtgct gaaccagctc tgcgtgctgc atgaaaagac cccagtcagc   1680
gaccgggtga caaaatgttg caccgaatct ctggtcaatc gccgaccctg tttcagtgcc   1740
ctcgaagtgg acgaaactta tgtgcctaag gagtttcagg ctggaacatt caccttcac   1800 gccgatatct gcactctgtc cgagaaaaga aggcagatta gaaacagac agcactggtc   1860 gagctcgtga agcataaacc aaaggctacc aaggagcagc tgaaagccgc catggacgat   1920
ttcgcagctt ttgtggaaaa gtgttgcaaa gccgacgata aggagacttg tttcgcagaa   1980
gaggggaaaa agctcgtggc tgccagccag gcagctctgg gtctggggag cggtggtggg   2040
agtggcgctc aagtcttgcg tggtacggtg acagacttcc caggcttcga tgaaagagcg   2100
gacgcggaaa cacttcgaaa ggcgatgaaa gggctcggta ctgacgaaga gtccattttg   2160
acccttctta cgagcaggtc aaacgctcag aggcaagaaa tctctgcagc ctttaagaca   2220
ctctttggag ctgaccttct tgatgacctc gcatctgagc tgacgggaaa gtttgagaaa   2280
ctcatcgtag ctttgatgaa gcccagccga ttgtatgatg cttacgaact gaaacacgcc   2340
ctggctgagc cggaacgaa cgagaaagtt ttgactgaga tcatcgcatc gcggaccccg   2400
gaagagctca gagccatcaa acaagtctac gaggaggagt acggatcgtc attggcagga   2460
gacgtggtgg gggatacgtc gggttactac caacgaatgc ttgtcgtgct tttgcaggca   2520
gctcgcgacc cggatgcggg gatcgacgag gcccaagtgg agcaagatgc gcaagcactc   2580
ttccaggccg tgaactcaa atgggggacc gatgaagaga gtttatcac catctttggc   2640 acgaggagtg taagtcatct gcgtaaagta ttcgataagt atatgacaat ctcagggttt   2700
cagattgagg agacaattga cagggaaacc tccggtaact tggagcagct cttgcttgcc   2760
gtcgtcaagt ccattcgctc gatccctgcg tatctggctg aaacactgta ttacgccatg   2820 aaagggcag gcactgatga ccacaccttg attagagtta tggtgtcgcg atcagaaatt   2880
gacttgttca atatccggaa agagttccgg aagaatttcg caacgagcct ctatagcatg   2940
atcaaagggg acacttcggg agattacaag aaagcgttgc tccttctttg cggagaggat   3000
gactaatga                                                          3009
```

<210> SEQ ID NO 113
<211> LENGTH: 2037
<212> TYPE: DNA
<213> ORGANISM: Artificial Sequence
<220> FEATURE:

<223> OTHER INFORMATION: Synthetic construct

<400> SEQUENCE: 113

```
atgttcccag ccatgccctt gtccagcctg tttgttaacg gcccaagaac actttgtgga      60
gccgaactgg tggatgctct ccaattcgtt tgcggcgacc gcggattcta ctttaacaag     120
cccaccggtg ccgggtcttc aagccggagg gccccgcaga ctggcatcgt cgacgagtgc     180
tgttttagaa gctgcgatct gcgacggttg gagatgtatt gtgcacctct gaagcccgcg     240
aaaagtgctg ggagcggtgg tgggagtggc gacgctcaca agtctgaagt ggcacatagg     300
ttcaaagatc tgggcgaaga gaactttaag gccctcgtcc tgatcgcttt cgcacagtac     360
ctccagcagt ctcccttga agatcacgtg aaactggtca atgaggtgac cgaatttgcc     420
aagacatgcg tggctgatga gagtgcagaa actgtgaca atcactgca tactctcttt      480
ggagataagc tgtgcaccgt cgccacactc agagagactt atggggaaat ggctgactgt    540
tgcgcaaaac aggagcctga acggaatgag tgtttcctcc agcacaagga tgacaaccca    600
aatctgcccc gcctcgtgcg acctgaggtc gatgtgatgt gcaccgcctt tcatgacaac    660
gaagagacat tcctgaagaa atacctgtat gaaattgctc gtaggcaccc atactttat    720
gcccccgagc tcctgttctt tgcaaagaga tacaaagctg ccttcactga atgttgccag    780
gcagctgata aggccgcatg tctcctgcct aaactggacg agctccggga tgaaggtaag    840
gcttccagcg ccaaacagcg cctgaagtgc gcttctctcc agaagtttgg cgagcgagca    900
ttcaaagcct gggctgtggc ccgtctcagt cagaggtttc caaaggcaga atttgctgag    960
gtgtcaaaac tggtgaccga cctcacaaag gtccatactg agtgttgcca cggagatctg   1020
ctggaatgtg ccgacgatag agcagacctc gctaaatata tctgcgagaa tcaggattcc   1080
attagctcta agctgaaaga atgttgcgag aagcccctcc tggaaaagag tcattgtatc   1140
gccgaggtgg aaaacgacga gatgccagca gatctgccat cactcgctgc cgactttgtg   1200
gaatccaaag atgtctgcaa gaattacgca gaggctaaag acgtgttcct ggggatgttt   1260
ctgtatgagt acgcccggcg tcaccccgat tatagcgtcg tgctcctgct ccgactggca   1320
aagacctacg aaacaactct ggagaaatgt tgcgctgccg cagaccctca tgaatgttat   1380
gctaaggtgt tcgatgagtt taagccactc gtcgaagagc cccagaacct gattaaacag   1440
aattgcgaac tgttcgagca gctcggtgaa tacaagtttc agaacgccct gctcgtgcgt   1500
tataccaaaa aggtccctca ggtgtctaca ccaactctgg tggaggtcag taggaatctg   1560
ggcaaagtgg gatcaaagtg ttgcaaacac cccgaggcaa agagaatgcc ttgtgctgaa   1620
gattacctct ccgtcgtgct gaaccagctc tgcgtgctgc atgaaaagac cccagtcagc   1680
gaccgggtga caaatgttg caccgaatct ctggtcaatc gccgaccctg tttcagtgcc   1740
ctcgaagtgg acgaaactta tgtgcctaag gagtttcagg ctgaaacatt caccttcac   1800
gccgatatct gcactctgtc cgagaaagaa aggcagatta gaaacagac agcactggtc   1860
gagctcgtga agcataaacc aaaggctacc aaggagcagc tgaaagccgt catggacgat   1920
ttcgcagctt ttgtggaaaa gtgttgcaaa gccgacgata ggagacttg tttcgcagaa   1980
gagggggaaaa agctcgtggc tgccagccag gcagctctgg gtctgtaatg aggatcc     2037
```

<210> SEQ ID NO 114
<211> LENGTH: 2961
<212> TYPE: DNA
<213> ORGANISM: Artificial Sequence
<220> FEATURE:
<223> OTHER INFORMATION: Synthetic construct

<400> SEQUENCE: 114

```
accggtagcc accttgtgaa atgtgcggag aaagaaaaga cattctgtgt taatggcggg      60
gagtgcttca tggtaaaaga cctgtcgaat ccgtcaagat atctctgcaa atgccagccc     120
ggttttacgg gagcccgatg taccgagaac gtgcctatga agtccaaaa ccaggaaaag     180
gcagaagaat tgtaccaaaa ggggagcggt ggtgggagtg gcgacgctca caagtctgaa    240
gtggcacata ggttcaaaga tctgggcgaa gagaacttta aggccctcgt cctgatcgct    300
ttcgcacagt acctccagca gtctcccttt gaagatcacg tgaaactggt caatgaggtg   360
accgaatttg ccaagacatg cgtggctgat gagagtgcag aaaactgtga caaatcactg   420
catactctct ttggagataa gctgtgcacc gtcgccacac tcagagagac ttatggggaa   480
atggctgact gttgcgcaaa acaggagcct gaacggaatg agtgtttcct ccagcacaag   540
gatgacaacc caaatctgcc ccgcctcgtg cgacctgagg tcgatgtgat gtgcaccgcc   600
tttcatgaca cgaagagac attcctgaag aaatacctgt atgaaattgc tcgtaggcac    660
ccatactttt atgcccccga gctcctgttc tttgcaaaga gatacaaagc tgccttcact   720
gaatgttgcc aggcagctga taaggccgca tgtctcctgc ctaaactgga cgagctccgg   780
gatgaaggta aggcttccag cgccaaacag cgcctgaagt gcgcttctct ccagaagttt   840
ggcgagcgag cattcaaagc ctgggctgtg gcccgtctca gtcagaggtt tccaaaggca   900
gaatttgctg aggtgtcaaa actggtgacc gacctcacaa aggtccatac tgagtgttgc   960
cacggagatc tgctggaatg tgccgacgat agagcagacc tcgctaaata tatctgcgag  1020
aatcaggatt ccattagctc taagctgaaa gaatgttgcg agaagcccct cctggaaaag  1080
agtcattgta tcgccgaggt ggaaaacgac gagatgccag cagatctgcc atcactcgct  1140
gccgactttg tggaatccaa agatgtctgc aagaattacg cagaggctaa agacgtgttc  1200
ctggggatgt ttctgtatga gtacgcccgg cgtcaccccg attatagcgt cgtgctcctg  1260
ctccgactgg caaagaccta cgaaacaact ctggagaaat gttgcgctgc cgcagaccct  1320
catgaatgtt atgctaaggt gttcgatgag tttaagccac tcgtcgaaga gccccagaac  1380
ctgattaaac agaattgcga actgttcgag cagctcggtg aatacaagtt tcagaacgcc  1440
ctgctcgtgc gttataccaa aaaggtccct caggtgtcta caccaactct ggtggaggtc  1500
agtaggaatc tgggcaaagt gggatcaaag tgttgcaaac accccgaggc aaagagaatg  1560
ccttgtgctg aagattacct ctccgtcgtg ctgaaccagc tctgcgtgct gcatgaaaag  1620
acccccagtca gcgaccgggt gacaaaatgt gcaccgaat ctctggtcaa tcgccgaccc  1680
tgtttcagtg ccctcgaagt ggacgaaact tatgtgccta aggagtttca ggctgaaaca  1740
ttcacctttc acgccgatat ctgcactctg tccgagaaag aaaggcagat taagaaacag  1800
acagcactgg tcgagctcgt gaagcataaa ccaaggcta ccaaggagca gctgaaagcc  1860
gtcatggacg atttcgcagc ttttgtggaa aagtgttgca aagccgacga taaggagact  1920
tgtttcgcag aagaggggaa aaagctcgtg gctgccagcc aggcagctct gggtctgggg  1980
agcggtggtg ggagtggcgc tcaagtcttg cgtggtacgg tgacagactt cccaggcttc  2040
gatgaaagag cggacgcgga aacacttcga aaggcgatga agggctcgg tactgacgaa  2100
gagtccattt tgacccttct tacgagcagg tcaaacgctc agaggcaaga aatctctgca  2160
gcctttaaga cactctttgg agctgacctt cttgatgacc tcgcatctga gctgacggga  2220
aagtttgaga aactcatcgt agctttgatg aagcccagcc gattgtatga tgcttacgaa  2280
```

```
ctgaaacacg ccctggctgg agcgggaacg aacgagaaag ttttgactga gatcatcgca    2340
tcgcggaccc cggaagagct cagagccatc aaacaagtct acgaggagga gtacggatcg    2400
tcattggcag agacgtggt gggggatacg tcgggttact accaacgaat gcttgtcgtg    2460
cttttgcagg cagctcgcga cccggatgcg gggatcgacg aggcccaagt ggagcaagat    2520
gcgcaagcac tcttccaggc cggtgaactc aaatggggga ccgatgaaga gaagtttatc    2580
accatctttg gcacgaggag tgtaagtcat ctgcgtaaag tattcgataa gtatatgaca    2640
atctcagggt ttcagattga ggagacaatt gacagggaaa cctccggtaa cttggagcag    2700
ctcttgcttg ccgtcgtcaa gtccattcgc tcgatccctg cgtatctggc tgaaacactg    2760
tattacgcca tgaaaggggc aggcactgat gaccacacct tgattagagt tatggtgtcg    2820
cgatcagaaa ttgacttgtt caatatccgg aaagagttcc ggaagaattt cgcaacgagc    2880
ctctatagca tgatcaaagg ggacacttcg ggagattaca agaaagcgtt gctccttctt    2940
tgcggagagg atgactgata a                                              2961

<210> SEQ ID NO 115
<211> LENGTH: 678
<212> TYPE: DNA
<213> ORGANISM: Artificial Sequence
<220> FEATURE:
<223> OTHER INFORMATION: Synthetic construct

<400> SEQUENCE: 115
gataagaccc atacatgccc tccgtgcccc gcaccggaac tcttgggtgg cccatcagtc      60
tttctgttcc cgccaaagcc caaagacaca ctgatgattt cgcgcacgcc cgaagtcact     120
tgcgtcgtgg tggatgtgtc gcatgaggac ccggaggtca agttcaactg gtacgtcgat     180
ggtgtagaag tccacaacgc caagaccaag cctcgggagg agcagtatca gtccacctac     240
cgggtagtga gcgtgcttac agtgctccat caggactggc tgaacggcaa agaatacaaa     300
tgcaaagtca gcaacaaagc gctgccagcg cccatcgaga aaacaattag caaagcgaaa     360
gggcagccca gagaacctca agtgtataca ttgccgccgt cgcgggagga aatgacaaag     420
aatcaggtat ccctgacgtg tcttgtgaaa ggcttttacc catccgacat tgcggtagag     480
tgggagtcga atgggcaacc cgagaacaac tataagacga ctccccccagt cttggattca     540 gacggatcct ttttcttgta ctcgaaactc acagtcgaca gtccagatg cagcagggg     600 aacgtgttca gctgcagcgt gatgcacgag gcccttcaca accactatac gcagaaatca     660
ttaagcttat cgcctggg                                                  678

<210> SEQ ID NO 116
<211> LENGTH: 1001
<212> TYPE: PRT
<213> ORGANISM: Artificial Sequence
<220> FEATURE:
<223> OTHER INFORMATION: Synthetic construct

<400> SEQUENCE: 116

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Tyr Phe Asn Lys Pro Thr Gly Ala Gly Ser Ser Ser
        35                  40                  45

Arg Arg Ala Pro Gln Thr Gly Ile Val Asp Glu Cys Cys Phe Arg Ser
    50                  55                  60
```

-continued

Cys Asp Leu Arg Arg Leu Glu Met Tyr Cys Ala Pro Leu Lys Pro Ala
65                  70                  75                  80

Lys Ser Ala Gly Ser Gly Gly Ser Gly Asp Ala His Lys Ser Glu
            85                  90                  95

Val Ala His Arg Phe Lys Asp Leu Gly Glu Glu Asn Phe Lys Ala Leu
            100                 105                 110

Val Leu Ile Ala Phe Ala Gln Tyr Leu Gln Gln Ser Pro Phe Glu Asp
            115                 120                 125

His Val Lys Leu Val Asn Glu Val Thr Glu Phe Ala Lys Thr Cys Val
            130                 135                 140

Ala Asp Glu Ser Ala Glu Asn Cys Asp Lys Ser Leu His Thr Leu Phe
145                 150                 155                 160

Gly Asp Lys Leu Cys Thr Val Ala Thr Leu Arg Glu Thr Tyr Gly Glu
            165                 170                 175

Met Ala Asp Cys Cys Ala Lys Gln Glu Pro Glu Arg Asn Glu Cys Phe
            180                 185                 190

Leu Gln His Lys Asp Asp Asn Pro Asn Leu Pro Arg Leu Val Arg Pro
            195                 200                 205

Glu Val Asp Val Met Cys Thr Ala Phe His Asp Asn Glu Glu Thr Phe
210                 215                 220

Leu Lys Lys Tyr Leu Tyr Glu Ile Ala Arg Arg His Pro Tyr Phe Tyr
225                 230                 235                 240

Ala Pro Glu Leu Leu Phe Phe Ala Lys Arg Tyr Lys Ala Ala Phe Thr
            245                 250                 255

Glu Cys Cys Gln Ala Ala Asp Lys Ala Ala Cys Leu Leu Pro Lys Leu
            260                 265                 270

Asp Glu Leu Arg Asp Glu Gly Lys Ala Ser Ser Ala Lys Gln Arg Leu
            275                 280                 285

Lys Cys Ala Ser Leu Gln Lys Phe Gly Glu Arg Ala Phe Lys Ala Trp
            290                 295                 300

Ala Val Ala Arg Leu Ser Gln Arg Phe Pro Lys Ala Glu Phe Ala Glu
305                 310                 315                 320

Val Ser Lys Leu Val Thr Asp Leu Thr Lys Val His Thr Glu Cys Cys
            325                 330                 335

His Gly Asp Leu Leu Glu Cys Ala Asp Asp Arg Ala Asp Leu Ala Lys
            340                 345                 350

Tyr Ile Cys Glu Asn Gln Asp Ser Ile Ser Ser Lys Leu Lys Glu Cys
            355                 360                 365

Cys Glu Lys Pro Leu Leu Glu Lys Ser His Cys Ile Ala Glu Val Glu
            370                 375                 380

Asn Asp Glu Met Pro Ala Asp Leu Pro Ser Leu Ala Ala Asp Phe Val
385                 390                 395                 400

Glu Ser Lys Asp Val Cys Lys Asn Tyr Ala Glu Ala Lys Asp Val Phe
            405                 410                 415

Leu Gly Met Phe Leu Tyr Glu Tyr Ala Arg Arg His Pro Asp Tyr Ser
            420                 425                 430

Val Val Leu Leu Leu Arg Leu Ala Lys Thr Tyr Glu Thr Thr Leu Glu
            435                 440                 445

Lys Cys Cys Ala Ala Ala Asp Pro His Glu Cys Tyr Ala Lys Val Phe
            450                 455                 460

Asp Glu Phe Lys Pro Leu Val Glu Glu Pro Gln Asn Leu Ile Lys Gln
465                 470                 475                 480

```
Asn Cys Glu Leu Phe Glu Gln Leu Gly Glu Tyr Lys Phe Gln Asn Ala
                485                 490                 495
Leu Leu Val Arg Tyr Thr Lys Lys Val Pro Gln Val Ser Thr Pro Thr
            500                 505                 510
Leu Val Glu Val Ser Arg Asn Leu Gly Lys Val Gly Ser Lys Cys Cys
            515                 520                 525
Lys His Pro Glu Ala Lys Arg Met Pro Cys Ala Glu Asp Tyr Leu Ser
            530                 535                 540
Val Val Leu Asn Gln Leu Cys Val Leu His Glu Lys Thr Pro Val Ser
545                 550                 555                 560
Asp Arg Val Thr Lys Cys Cys Thr Glu Ser Leu Val Asn Arg Arg Pro
                565                 570                 575
Cys Phe Ser Ala Leu Glu Val Asp Glu Thr Tyr Val Pro Lys Glu Phe
            580                 585                 590
Gln Ala Glu Thr Phe Thr Phe His Ala Asp Ile Cys Thr Leu Ser Glu
            595                 600                 605
Lys Glu Arg Gln Ile Lys Lys Gln Thr Ala Leu Val Glu Leu Val Lys
            610                 615                 620
His Lys Pro Lys Ala Thr Lys Glu Gln Leu Lys Ala Val Met Asp Asp
625                 630                 635                 640
Phe Ala Ala Phe Val Glu Lys Cys Cys Lys Ala Asp Asp Lys Glu Thr
                645                 650                 655
Cys Phe Ala Glu Glu Gly Lys Lys Leu Val Ala Ala Ser Gln Ala Ala
                660                 665                 670
Leu Gly Leu Gly Ser Gly Gly Ser Gly Ala Gln Val Leu Arg Gly
            675                 680                 685
Thr Val Thr Asp Phe Pro Gly Phe Asp Glu Arg Ala Asp Ala Glu Thr
    690                 695                 700
Leu Arg Lys Ala Met Lys Gly Leu Gly Thr Asp Glu Glu Ser Ile Leu
705                 710                 715                 720
Thr Leu Leu Thr Ser Arg Ser Asn Ala Gln Arg Gln Glu Ile Ser Ala
                725                 730                 735
Ala Phe Lys Thr Leu Phe Gly Arg Asp Leu Leu Asp Asp Leu Lys Ser
            740                 745                 750
Glu Leu Thr Gly Lys Phe Glu Lys Leu Ile Val Ala Leu Met Lys Pro
            755                 760                 765
Ser Arg Leu Tyr Asp Ala Tyr Glu Leu Lys His Ala Leu Lys Gly Ala
            770                 775                 780
Gly Thr Asn Glu Lys Val Leu Thr Glu Ile Ile Ala Ser Arg Thr Pro
785                 790                 795                 800
Glu Glu Leu Arg Ala Ile Lys Gln Val Tyr Glu Glu Glu Tyr Gly Ser
                805                 810                 815
Ser Leu Glu Asp Asp Val Val Gly Asp Thr Ser Gly Tyr Tyr Gln Arg
            820                 825                 830
Met Leu Val Val Leu Leu Gln Ala Asn Arg Asp Pro Asp Ala Gly Ile
            835                 840                 845
Asp Glu Ala Gln Val Glu Gln Asp Ala Gln Ala Leu Phe Gln Ala Gly
    850                 855                 860
Glu Leu Lys Trp Gly Thr Asp Glu Glu Lys Phe Ile Thr Ile Phe Gly
865                 870                 875                 880
Thr Arg Ser Val Ser His Leu Arg Lys Val Phe Asp Lys Tyr Met Thr
                885                 890                 895
Ile Ser Gly Phe Gln Ile Glu Glu Thr Ile Asp Arg Glu Thr Ser Gly
```

```
                900           905           910
Asn Leu Glu Gln Leu Leu Ala Val Val Lys Ser Ile Arg Ser Ile
            915                 920                 925

Pro Ala Tyr Leu Ala Glu Thr Leu Tyr Tyr Ala Met Lys Gly Ala Gly
            930                 935                 940

Thr Asp Asp His Thr Leu Ile Arg Val Met Val Ser Arg Ser Glu Ile
945                 950                 955                 960

Asp Leu Phe Asn Ile Arg Lys Glu Phe Arg Lys Asn Phe Ala Thr Ser
            965                 970                 975

Leu Tyr Ser Met Ile Lys Gly Asp Thr Ser Gly Asp Tyr Lys Lys Ala
            980                 985                 990

Leu Leu Leu Leu Cys Gly Glu Asp  Asp
            995                 1000

<210> SEQ ID NO 117
<211> LENGTH: 3009
<212> TYPE: DNA
<213> ORGANISM: Artificial Sequence
<220> FEATURE:
<223> OTHER INFORMATION: Synthetic construct

<400> SEQUENCE: 117
```

| | | | | | |
|---|---|---|---|---|---|
| atgttcccag | ccatgccctt | gtccagcctg | tttgttaacg | gcccaagaac | actttgtgga | 60 |
| gccgaactgg | tggatgctct | ccaattcgtt | tgcggcgacc | gcggattcta | ctttaacaag | 120 |
| cccaccggtg | ccgggtcttc | aagccggagg | gccccgcaga | ctggcatcgt | cgacgagtgc | 180 |
| tgttttagaa | gctgcgatct | gcgacggttg | agatgtgatt | gtgcacctct | gaagcccgcg | 240 |
| aaaagtgctg | ggagcggtgg | tgggagtggc | gacgctcaca | agtctgaagt | ggcacatagg | 300 |
| ttcaaagatc | tgggcgaaga | gaactttaag | gccctcgtcc | tgatcgcttt | cgcacagtac | 360 |
| ctccagcagt | ctcccttgta | agatcacgtg | aaactggtca | atgaggtgac | cgaatttgcc | 420 |
| aagacatgcg | tggctgatga | gagtgcagaa | actgtgaca | atcactgca | tactctcttt | 480 |
| ggagataagc | tgtgcaccgt | cgccacactc | agagagactt | atggggaaat | ggctgactgt | 540 |
| tgcgcaaaac | aggagcctga | acggaatgag | tgtttcctcc | agcacaagga | tgacaaccca | 600 |
| aatctgcccc | gcctcgtgcg | acctgaggtc | gatgtgatgt | gcaccgcctt | tcatgacaac | 660 |
| gaagagacat | tcctgaagaa | atacctgtat | gaaattgctc | gtaggcaccc | atactttta | 720 |
| gccccgagc | tcctgttctt | tgcaaagaga | tacaaagctg | ccttcactga | atgttgccag | 780 |
| gcagctgata | aggccgcatg | tctcctgcct | aaactggacg | agctccggga | tgaaggtaag | 840 |
| gcttccagcg | ccaaacagcg | cctgaagtgc | gcttctctcc | agaagtttgg | cgagcgagca | 900 |
| ttcaaagcct | gggctgtggc | ccgtctcagt | cagaggtttc | caaaggcaga | atttgctgag | 960 |
| gtgtcaaaac | tggtgaccga | cctcacaaag | gtccatactg | agtgttgcca | cggagatctg | 1020 |
| ctggaatgtg | ccgacgatag | agcagacctc | gctaaatata | tctgcgagaa | tcaggattcc | 1080 |
| attagctcta | agctgaaaga | atgttgcgag | aagcccctcc | tggaaaagag | tcattgtatc | 1140 |
| gccgaggtgg | aaaacgacga | gatgccagca | gatctgccat | cactcgctgc | cgactttgtg | 1200 |
| gaatccaaag | atgtctgcaa | gaattacgca | gaggctaaag | acgtgttcct | ggggatgttt | 1260 |
| ctgtatgagt | acgcccggcg | tcaccccgat | tatagcgtcg | tgctcctgct | ccgactggca | 1320 |
| aagacctacg | aaacaactct | ggagaaatgt | tgcgctgccg | cagaccctca | tgaatgttat | 1380 |
| gctaaggtgt | tcgatgagtt | taagccactc | gtcgaagagc | cccagaacct | gattaaacag | 1440 |
| aattgcgaac | tgttcgagca | gctcggtgaa | tacaagtttc | agaacgccct | gctcgtgcgt | 1500 |

-continued

```
tataccaaaa aggtccctca ggtgtctaca ccaactctgg tggaggtcag taggaatctg    1560
ggcaaagtgg gatcaaagtg ttgcaaacac cccgaggcaa agagaatgcc ttgtgctgaa    1620
gattacctct ccgtcgtgct gaaccagctc tgcgtgctgc atgaaaagac cccagtcagc    1680
gaccgggtga caaaatgttg caccgaatct ctggtcaatc gccgaccctg tttcagtgcc    1740
ctcgaagtgg acgaaactta tgtgcctaag gagtttcagg ctgaaacatt cacctttcac    1800
gccgatatct gcactctgtc cgagaaagaa aggcagatta gaaacagac agcactggtc     1860 gagctcgtga agcataaacc aaaggctacc aaggagcagc tgaaagccgt catggacgat    1920
ttcgcagctt ttgtggaaaa gtgttgcaaa gccgacgata aggagacttg tttcgcagaa    1980
gaggggaaaa agctcgtggc tgccagccag gcagctctgg gtctggggag cggtggtggg    2040
agtggcgctc aagtcttgcg tggtacggtg acagacttcc caggcttcga tgaaagagcg    2100
gacgcggaaa cacttcgaaa ggcgatgaaa gggctcggta ctgacgaaga gtccattttg    2160
acccttctta cgagcaggtc aaacgctcag aggcaagaaa tctctgcagc ctttaagaca    2220
ctctttggac gtgaccttct tgatgacctc aaatctgagc tgacgggaaa gtttgagaaa    2280
ctcatcgtag ctttgatgaa gcccagccga ttgtatgatg cttacgaact gaaacacgcc    2340
ctgaaaggag cgggaacgaa cgagaaagtt ttgactgaga tcatcgcatc gcggacccc g   2400 gaagagctca gagccatcaa acaagtctac gaggaggagt acggatcgtc attggaagat    2460
gacgtggtgg gggatacgtc gggttactac caacgaatgc ttgtcgtgct tttgcaggca    2520
aatcgcgacc cggatgcggg gatcgacgag gcccaagtgg agcaagatgc gcaagcactc    2580
ttccaggccg gtgaactcaa atgggggacc gatgaagaga gtttatcac catctttggc     2640 acgaggagtg taagtcatct gcgtaaagta ttcgataagt atatgacaat ctcagggttt    2700
cagattgagg agacaattga cagggaaacc tccggtaact tggagcagct cttgcttgcc    2760
gtcgtcaagt ccattcgctc gatccctgcg tatctggctg aaacactgta ttacgccatg    2820
aaaggggcag gcactgatga ccacaccttg attagagtta tggtgtcgcg atcagaaatt    2880
gacttgttca atatccggaa agagttccgg aagaatttcg caacgagcct ctatagcatg    2940
atcaaagggg acacttcggg agattacaag aaagcgttgc tccttctttg cggagaggat    3000
gactgataa                                                            3009
```

<210> SEQ ID NO 118
<211> LENGTH: 988
<212> TYPE: PRT
<213> ORGANISM: Artificial Sequence
<220> FEATURE:
<223> OTHER INFORMATION: Synthetic construct

<400> SEQUENCE: 118

```
Gly Pro Arg Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Ala Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala Gly Ser Gly Gly Ser Gly Asp Ala His
65                  70                  75                  80

Lys Ser Glu Val Ala His Arg Phe Lys Asp Leu Gly Glu Glu Asn Phe
```

-continued

```
                    85                  90                  95
Lys Ala Leu Val Leu Ile Ala Phe Ala Gln Tyr Leu Gln Gln Ser Pro
                100                 105                 110

Phe Glu Asp His Val Lys Leu Val Asn Glu Val Thr Glu Phe Ala Lys
                115                 120                 125

Thr Cys Val Ala Asp Glu Ser Ala Glu Asn Cys Asp Lys Ser Leu His
130                 135                 140

Thr Leu Phe Gly Asp Lys Leu Cys Thr Val Ala Thr Leu Arg Glu Thr
145                 150                 155                 160

Tyr Gly Glu Met Ala Asp Cys Cys Ala Lys Gln Glu Pro Glu Arg Asn
                165                 170                 175

Glu Cys Phe Leu Gln His Lys Asp Asp Asn Pro Asn Leu Pro Arg Leu
                180                 185                 190

Val Arg Pro Glu Val Asp Val Met Cys Thr Ala Phe His Asp Asn Glu
                195                 200                 205

Glu Thr Phe Leu Lys Lys Tyr Leu Tyr Glu Ile Ala Arg Arg His Pro
                210                 215                 220

Tyr Phe Tyr Ala Pro Glu Leu Leu Phe Phe Ala Lys Arg Tyr Lys Ala
225                 230                 235                 240

Ala Phe Thr Glu Cys Cys Gln Ala Ala Asp Lys Ala Ala Cys Leu Leu
                245                 250                 255

Pro Lys Leu Asp Glu Leu Arg Asp Glu Gly Lys Ala Ser Ser Ala Lys
                260                 265                 270

Gln Arg Leu Lys Cys Ala Ser Leu Gln Lys Phe Gly Glu Arg Ala Phe
                275                 280                 285

Lys Ala Trp Ala Val Ala Arg Leu Ser Gln Arg Phe Pro Lys Ala Glu
                290                 295                 300

Phe Ala Glu Val Ser Lys Leu Val Thr Asp Leu Thr Lys Val His Thr
305                 310                 315                 320

Glu Cys Cys His Gly Asp Leu Leu Glu Cys Ala Asp Asp Arg Ala Asp
                325                 330                 335

Leu Ala Lys Tyr Ile Cys Glu Asn Gln Asp Ser Ile Ser Ser Lys Leu
                340                 345                 350

Lys Glu Cys Cys Glu Lys Pro Leu Leu Glu Lys Ser His Cys Ile Ala
                355                 360                 365

Glu Val Glu Asn Asp Glu Met Pro Ala Asp Leu Pro Ser Leu Ala Ala
                370                 375                 380

Asp Phe Val Glu Ser Lys Asp Val Cys Lys Asn Tyr Ala Glu Ala Lys
385                 390                 395                 400

Asp Val Phe Leu Gly Met Phe Leu Tyr Glu Tyr Ala Arg Arg His Pro
                405                 410                 415

Asp Tyr Ser Val Val Leu Leu Leu Arg Leu Ala Lys Thr Tyr Glu Thr
                420                 425                 430

Thr Leu Glu Lys Cys Cys Ala Ala Ala Asp Pro His Glu Cys Tyr Ala
                435                 440                 445

Lys Val Phe Asp Glu Phe Lys Pro Leu Val Glu Glu Pro Gln Asn Leu
                450                 455                 460

Ile Lys Gln Asn Cys Glu Leu Phe Glu Gln Leu Gly Glu Tyr Lys Phe
465                 470                 475                 480

Gln Asn Ala Leu Leu Val Arg Tyr Thr Lys Lys Val Pro Gln Val Ser
                485                 490                 495

Thr Pro Thr Leu Val Glu Val Ser Arg Asn Leu Gly Lys Val Gly Ser
                500                 505                 510
```

```
Lys Cys Cys Lys His Pro Glu Ala Lys Arg Met Pro Cys Ala Glu Asp
            515                 520                 525

Tyr Leu Ser Val Val Leu Asn Gln Leu Cys Val Leu His Glu Lys Thr
        530                 535                 540

Pro Val Ser Asp Arg Val Thr Lys Cys Cys Thr Glu Ser Leu Val Asn
545                 550                 555                 560

Arg Arg Pro Cys Phe Ser Ala Leu Glu Val Asp Glu Thr Tyr Val Pro
                565                 570                 575

Lys Glu Phe Gln Ala Glu Thr Phe Thr Phe His Ala Asp Ile Cys Thr
            580                 585                 590

Leu Ser Glu Lys Glu Arg Gln Ile Lys Lys Gln Thr Ala Leu Val Glu
        595                 600                 605

Leu Val Lys His Lys Pro Lys Ala Thr Lys Glu Gln Leu Lys Ala Val
    610                 615                 620

Met Asp Asp Phe Ala Ala Phe Val Glu Lys Cys Cys Lys Ala Asp Asp
625                 630                 635                 640

Lys Glu Thr Cys Phe Ala Glu Glu Gly Lys Lys Leu Val Ala Ala Ser
                645                 650                 655

Gln Ala Ala Leu Gly Leu Gly Ser Gly Gly Ser Gly Ala Gln Val
            660                 665                 670

Leu Arg Gly Thr Val Thr Asp Phe Pro Gly Phe Asp Glu Arg Ala Asp
        675                 680                 685

Ala Glu Thr Leu Arg Lys Ala Met Lys Gly Leu Gly Thr Asp Glu Glu
    690                 695                 700

Ser Ile Leu Thr Leu Leu Thr Ser Arg Ser Asn Ala Gln Arg Gln Glu
705                 710                 715                 720

Ile Ser Ala Ala Phe Lys Thr Leu Phe Gly Ala Asp Leu Leu Asp Asp
                725                 730                 735

Leu Ala Ser Glu Leu Thr Gly Lys Phe Glu Lys Leu Ile Val Ala Leu
            740                 745                 750

Met Lys Pro Ser Arg Leu Tyr Asp Ala Tyr Glu Leu Lys His Ala Leu
        755                 760                 765

Ala Gly Ala Gly Thr Asn Glu Lys Val Leu Thr Glu Ile Ile Ala Ser
    770                 775                 780

Arg Thr Pro Glu Glu Leu Arg Ala Ile Lys Gln Val Tyr Glu Glu Glu
785                 790                 795                 800

Tyr Gly Ser Ser Leu Ala Gly Asp Val Val Gly Asp Thr Ser Gly Tyr
                805                 810                 815

Tyr Gln Arg Met Leu Val Val Leu Leu Gln Ala Ala Arg Asp Pro Asp
            820                 825                 830

Ala Gly Ile Asp Glu Ala Gln Val Glu Gln Asp Ala Gln Ala Leu Phe
        835                 840                 845

Gln Ala Gly Glu Leu Lys Trp Gly Thr Asp Glu Glu Lys Phe Ile Thr
    850                 855                 860

Ile Phe Gly Thr Arg Ser Val Ser His Leu Arg Lys Val Phe Asp Lys
865                 870                 875                 880

Tyr Met Thr Ile Ser Gly Phe Gln Ile Glu Glu Thr Ile Asp Arg Glu
                885                 890                 895

Thr Ser Gly Asn Leu Glu Gln Leu Leu Leu Ala Val Val Lys Ser Ile
            900                 905                 910

Arg Ser Ile Pro Ala Tyr Leu Ala Glu Thr Leu Tyr Tyr Ala Met Lys
        915                 920                 925
```

```
Gly Ala Gly Thr Asp Asp His Thr Leu Ile Arg Val Met Val Ser Arg
            930                 935                 940

Ser Glu Ile Asp Leu Phe Asn Ile Arg Lys Glu Phe Arg Lys Asn Phe
945                 950                 955                 960

Ala Thr Ser Leu Tyr Ser Met Ile Lys Gly Asp Thr Ser Gly Asp Tyr
                965                 970                 975

Lys Lys Ala Leu Leu Leu Ala Gly Glu Asp Asp
                980                 985

<210> SEQ ID NO 119
<211> LENGTH: 3043
<212> TYPE: DNA
<213> ORGANISM: Artificial Sequence
<220> FEATURE:
<223> OTHER INFORMATION: Synthetic construct

<400> SEQUENCE: 119
```

| | | | | | |
|---|---|---|---|---|---|
| atggcctggc | ggctgtggtg | gctgctgctc | ctgctcctgt | tgctttggcc | tatggtgtgg | 60 |
| gccggcccaa | gaacactttg | tggagccgaa | ctggtggatg | ctctccaatt | cgtttgcggc | 120 |
| gaccgcggat | tctactttaa | caagcccacc | ggtgccgggt | cttcaagccg | gagggccccg | 180 |
| cagactggca | tcgtcgacga | gtgctgtttt | agaagctgcg | atctgcgacg | gttggagatg | 240 |
| tattgtgcac | tcctgaagcc | cgcgaaaagt | gctgggagcg | tggtgggag | tggcgacgct | 300 |
| cacaagtctg | aagtggcaca | taggttcaaa | gatctgggcg | aagagaactt | taaggccctc | 360 |
| gtcctgatcg | ctttcgcaca | gtacctccag | cagtctccct | ttgaagatca | cgtgaaactg | 420 |
| gtcaatgagg | tgaccgaatt | tgccaagaca | tgcgtggctg | atgagagtgc | agaaaactgt | 480 |
| gacaaatcac | tgcatactct | ctttggagat | aagctgtgca | ccgtcgccac | actcagagag | 540 |
| acttatgggg | aaatggctga | ctgttgcgca | aacaggagc | ctgaacggaa | tgagtgtttc | 600 |
| ctccagcaca | aggatgacaa | cccaaatctg | ccccgcctcg | tgcgacctga | ggtcgatgtg | 660 |
| atgtgcaccg | cctttcatga | caacgaagag | acattcctga | gaaataacct | gtatgaaatt | 720 |
| gctcgtaggc | acccatactt | ttatgccccc | gagctcctgt | tctttgcaaa | gagatacaaa | 780 |
| gctgccttca | ctgaatgttg | ccaggcagct | gataaggccg | catgtctcct | gcctaaactg | 840 |
| gacgagctcc | gggatgaagg | taaggcttcc | agcgccaaac | agcgcctgaa | gtgcgcttct | 900 |
| ctccagaagt | ttggcgagcg | agcattcaaa | gcctgggctg | tggcccgtct | cagtcagagg | 960 |
| tttccaaagg | cagaatttgc | tgaggtgtca | aaactggtga | ccgacctcac | aaaggtccat | 1020 |
| actgagtgtt | gccacggaga | tctgctggaa | tgtgccgacg | atagagcaga | cctcgctaaa | 1080 |
| tatatctgcg | agaatcagga | ttccattagc | tctaagctga | agaatgttg | cgagaagccc | 1140 |
| ctcctggaaa | agagtcattg | tatcgccgag | gtggaaaacg | acgagatgcc | agcagatctg | 1200 |
| ccatcactcg | ctgccgactt | tgtggaatcc | aaagatgtct | gcaagaatta | cgcagaggct | 1260 |
| aaagacgtgt | tcctgggat | gtttctgtat | gagtacgccc | ggcgtcaccc | cgattatagc | 1320 |
| gtcgtgctcc | tgctccgact | ggcaaagacc | tacgaaacaa | tctggagaa | tgttgcgct | 1380 |
| gccgcagacc | tcatgaatg | ttatgctaag | gtgttcgatg | agtttaagcc | actcgtcgaa | 1440 |
| gagccccaga | acctgattaa | acagaattgc | gaactgttcg | agcagctcgg | tgaatacaag | 1500 |
| tttcagaacg | ccctgctcgt | gcgttatacc | aaaaaggtcc | ctcaggtgtc | tacaccaact | 1560 |
| ctggtggagg | tcagtaggaa | tctgggcaaa | gtgggatcaa | agtgttgcaa | acaccccgag | 1620 |
| gcaaagagaa | tgccttgtgc | tgaagattac | ctctccgtcg | tgctgaacca | gctctgcgtg | 1680 |
| ctgcatgaaa | agacccccagt | cagcgaccgg | gtgacaaaat | gttgcaccga | atctctggtc | 1740 |

-continued

```
aatcgccgac cctgtttcag tgccctcgaa gtggacgaaa cttatgtgcc taaggagttt   1800
caggctgaaa cattcacctt tcacgccgat atctgcactc tgtccgagaa agaaaggcag   1860
attaagaaac agacagcact ggtcgagctc gtgaagcata aaccaaaggc taccaaggag   1920
cagctgaaag ccgtcatgga cgatttcgca gcttttgtgg aaaagtgttg caaagccgac   1980
gataaggaga cttgtttcgc agaagagggg aaaaagctcg tggctgccag ccaggcagct   2040
ctgggtctgg ggagcggtgg tgggagtggc gctcaagtct tgcgtggtac ggtgacagac   2100
ttcccaggct tcgatgaaag agcggacgcg gaaacacttc gaaaggcgat gaaagggctc   2160
ggtactgacg aagagtccat tttgaccctt cttacgagca ggtcaaacgc tcagaggcaa   2220
gaaatctctg cagcctttaa gacactcttt ggagctgacc ttcttgatga cctcgcatct   2280
gagctgacgg gaaagtttga gaaactcatc gtagctttga tgaagcccag ccgattgtat   2340
gatgcttacg aactgaaaca cgccctggct ggagcgggaa cgaacgagaa agttttgact   2400
gagatcatcg catcgcggac cccggaagag ctcagagcca tcaaacaagt ctacgaggag   2460
gagtacggat cgtcattggc aggagacgtg gtggggata cgtcgggtta ctaccaacga   2520
atgcttgtcg tgcttttgca ggcagctcgc gacccggatg cggggatcga cgaggcccaa   2580
gtggagcaag atgcgcaagc actcttccag gccggtgaac tcaaatgggg gaccgatgaa   2640
gagaagttta tcaccatctt tggcacgagg agtgtaagtc atctgcgtaa agtattcgat   2700
aagtatatga caatctcagg gtttcagatt gaggagacaa ttgacaggga aacctccggt   2760
aacttggagc agctcttgct tgccgtcgtc aagtccattc gctcgatccc tgcgtatctg   2820
gctgaaacac tgtattacgc catgaaaggg gcaggcactg atgaccacac cttgattaga   2880
gttatggtgt cgcgatcaga aattgacttg ttcaatatcc ggaaagagtt ccggaagaat   2940
ttcgcaacga gcctctatag catgatcaaa ggggacactt cgggagatta caagaaagcg   3000
ttgctccttc ttgccggaga ggatgactga taaggatcct agc                    3043
```

<210> SEQ ID NO 120
<211> LENGTH: 70
<212> TYPE: PRT
<213> ORGANISM: Artificial Sequence
<220> FEATURE:
<223> OTHER INFORMATION: Synthetic construct

<400> SEQUENCE: 120

Gly Pro Arg Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Ala Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70

<210> SEQ ID NO 121
<211> LENGTH: 210
<212> TYPE: DNA
<213> ORGANISM: Artificial Sequence
<220> FEATURE:
<223> OTHER INFORMATION: Synthetic construct

<400> SEQUENCE: 121

```
ggcccaagaa cactttgtgg agccgaactg gtggatgctc tccaattcgt ttgcggcgac    60
cgcggattct actttaacaa gcccaccggt gccgggtctt caagccggag ggccccgcag   120
actggcatcg tcgacgagtg ctgttttaga agctgcgatc tgcgacggtt ggagatgtat   180
tgtgcacctc tgaagcccgc gaaaagtgct                                    210
```

<210> SEQ ID NO 122  
<211> LENGTH: 319  
<212> TYPE: PRT  
<213> ORGANISM: Artificial Sequence  
<220> FEATURE:  
<223> OTHER INFORMATION: Synthetic construct

<400> SEQUENCE: 122

```
Ala Gln Val Leu Arg Gly Thr Val Thr Asp Phe Pro Gly Phe Asp Glu
1               5                   10                  15

Arg Ala Asp Ala Glu Thr Leu Arg Lys Ala Met Lys Gly Leu Gly Thr
                20                  25                  30

Asp Glu Glu Ser Ile Leu Thr Leu Leu Thr Ser Arg Ser Asn Ala Gln
            35                  40                  45

Arg Gln Glu Ile Ser Ala Ala Phe Lys Thr Leu Phe Gly Ala Asp Leu
        50                  55                  60

Leu Asp Asp Leu Ala Ser Glu Leu Thr Gly Lys Phe Glu Lys Leu Ile
65                  70                  75                  80

Val Ala Leu Met Lys Pro Ser Arg Leu Tyr Asp Ala Tyr Glu Leu Lys
                85                  90                  95

His Ala Leu Ala Gly Ala Gly Thr Asn Glu Lys Val Leu Thr Glu Ile
            100                 105                 110

Ile Ala Ser Arg Thr Pro Glu Glu Leu Arg Ala Ile Lys Gln Val Tyr
        115                 120                 125

Glu Glu Glu Tyr Gly Ser Ser Leu Ala Gly Asp Val Val Gly Asp Thr
    130                 135                 140

Ser Gly Tyr Tyr Gln Arg Met Leu Val Val Leu Leu Gln Ala Ala Arg
145                 150                 155                 160

Asp Pro Asp Ala Gly Ile Asp Glu Ala Gln Val Glu Gln Asp Ala Gln
                165                 170                 175

Ala Leu Phe Gln Ala Gly Glu Leu Lys Trp Gly Thr Asp Glu Glu Lys
            180                 185                 190

Phe Ile Thr Ile Phe Gly Thr Arg Ser Val Ser His Leu Arg Lys Val
        195                 200                 205

Phe Asp Lys Tyr Met Thr Ile Ser Gly Phe Gln Ile Glu Glu Thr Ile
    210                 215                 220

Asp Arg Glu Thr Ser Gly Asn Leu Glu Gln Leu Leu Leu Ala Val Val
225                 230                 235                 240

Lys Ser Ile Arg Ser Ile Pro Ala Tyr Leu Ala Glu Thr Leu Tyr Tyr
                245                 250                 255

Ala Met Lys Gly Ala Gly Thr Asp Asp His Thr Leu Ile Arg Val Met
            260                 265                 270

Val Ser Arg Ser Glu Ile Asp Leu Phe Asn Ile Arg Lys Glu Phe Arg
        275                 280                 285

Lys Asn Phe Ala Thr Ser Leu Tyr Ser Met Ile Lys Gly Asp Thr Ser
    290                 295                 300

Gly Asp Tyr Lys Lys Ala Leu Leu Leu Leu Ala Gly Glu Asp Asp
305                 310                 315
```

<210> SEQ ID NO 123
<211> LENGTH: 957
<212> TYPE: DNA
<213> ORGANISM: Artificial Sequence
<220> FEATURE:
<223> OTHER INFORMATION: Synthetic construct

<400> SEQUENCE: 123

```
gctcaagtct tgcgtggtac ggtgacagac ttcccaggct tcgatgaaag agcggacgcg        60
gaaacacttc gaaaggcgat gaaagggctc ggtactgacg aagagtccat tttgacccttt     120
cttacgagca ggtcaaacgc tcagaggcaa gaaatctctg cagcctttaa gacactcttt       180
ggagctgacc ttcttgatga cctcgcatct gagctgacgg gaaagtttga gaaactcatc      240
gtagctttga tgaagcccag ccgattgtat gatgcttacg aactgaaaca cgccctggct       300
ggagcgggaa cgaacgagaa agttttgact gagatcatcg catcgcggac cccggaagag      360
ctcagagcca tcaaacaagt ctacgaggag gagtacggat cgtcattggc aggagacgtg       420
gtggggata cgtcgggtta ctaccaacga atgcttgtcg tgcttttgca ggcagctcgc          480
gacccggatg cggggatcga cgaggcccaa gtggagcaag atgcgcaagc actcttccag      540
gccggtgaac tcaaatgggg gaccgatgaa gagaagttta tcaccatctt tggcacgagg     600
agtgtaagtc atctgcgtaa agtattcgat aagtatatga caatctcagg gtttcagatt      660
gaggagacaa ttgacaggga aacctccggt aacttggagc agctcttgct tgccgtcgtc       720
aagtccattc gctcgatccc tgcgtatctg gctgaaacac tgtattacgc catgaaaggg       780
gcaggcactg atgaccacac cttgattaga gttatggtgt cgcgatcaga aattgacttg       840
ttcaatatcc ggaaagagtt ccggaagaat tcgcaacga gcctctatag catgatcaaa       900
ggggacactt cggagattaa caagaaagcg ttgctccttc tgccggaga ggatgac             957
```

<210> SEQ ID NO 124
<211> LENGTH: 585
<212> TYPE: PRT
<213> ORGANISM: Artificial Sequence
<220> FEATURE:
<223> OTHER INFORMATION: Synthetic construct

<400> SEQUENCE: 124

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140
```

```
Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Gln Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
```

Ala Ala Ser Gln Ala Ala Leu Gly Leu
        580                 585

<210> SEQ ID NO 125
<211> LENGTH: 1755
<212> TYPE: DNA
<213> ORGANISM: Artificial Sequence
<220> FEATURE:
<223> OTHER INFORMATION: Synthetic construct

<400> SEQUENCE: 125

```
gacgctcaca agtctgaagt ggcacatagg ttcaaagatc tgggcgaaga gaactttaag      60
gccctcgtcc tgatcgcttt cgcacagtac ctccagcagt ctcccttgga agatcacgtg     120
aaactggtca atgaggtgac cgaatttgcc aagacatgcg tggctgatga gagtgcagaa     180
aactgtgaca atcactgca tactctcttt ggagataagc tgtgcaccgt cgccacactc     240
agagagactt atgggaaat ggctgactgt tgcgcaaaac aggagcctga acggaatgag     300
tgtttcctcc agcacaagga tgacaaccca atctgcccc gcctcgtgcg acctgaggtc     360
gatgtgatgt gcaccgcctt tcatgacaac gaagagacat cctgaagaa atacctgtat     420
gaaattgctc gtaggcaccc atactttat gcccccgagc tcctgttctt tgcaaagaga     480
tacaaagctg ccttcactga atgttgccag gcagctgata aggccgcatg tctcctgcct     540
aaactggacg agctccggga tgaaggtaag gcttccagcg ccaaacagcg cctgaagtgc     600
gcttctctcc agaagtttgg cgagcgagca ttcaaagcct gggctgtggc ccgtctcagt     660
cagaggtttc caaaggcaga atttgctgag gtgtcaaaac tggtgaccga cctcacaaag     720
gtccatactg agtgttgcca cggagatctg ctggaatgtg ccgacgatag agcagacctc     780
gctaaatata tctgcgagaa tcaggattcc attagctcta agctgaaaga atgttgcgag     840
aagccctcc tggaaaagag tcattgtatc gccgaggtgg aaaacgacga gatgccagca     900
gatctgccat cactcgctgc cgactttgtg aatccaaag atgtctgcaa gaattacgca     960
gaggctaaag acgtgttcct ggggatgttt ctgtatgagt acgcccggcg tcaccccgat    1020
tatagcgtcg tgctcctgct ccgactggca aagacctacg aaacaactct ggagaaatgt    1080
tgcgctgccg cagaccctca tgaatgttat gctaaggtgt tcgatgagtt aagccactc    1140
gtcgaagagc cccagaacct gattaaacag aattgcgaac tgttcgagca gctcggtgaa    1200
tacaagtttc agaacgccct gctcgtgcgt tataccaaaa aggtccctca ggtgtctaca    1260
ccaactctgg tggaggtcag taggaatctg ggcaaagtgg atcaaagtg ttgcaaacac    1320
cccgaggcaa agagaatgcc ttgtgctgaa gattacctct ccgtcgtgct gaaccagctc    1380
tgcgtgctgc atgaaaagac cccagtcagc gaccgggtga caaatgttg caccgaatct    1440
ctggtcaatc gccgaccctg tttcagtgcc ctcgaagtgg acgaaactta tgtgcctaag    1500
gagtttcagg ctgaaacatt caccttcac gccgatatct gcactctgtc cgagaaagaa    1560
aggcagatta agaaacagac agcactggtc gagctcgtga agcataaacc aaaggctacc    1620
aaggagcagc tgaaagccgt catggacgat ttcgcagctt ttgtggaaaa gtgttgcaaa    1680
gccgacgata aggagacttg tttcgcagaa gagggaaaa agctcgtggc tgccagccag    1740
gcagctctgg gtctg                                                    1755
```

<210> SEQ ID NO 126
<211> LENGTH: 7
<212> TYPE: PRT

```
<213> ORGANISM: Artificial Sequence
<220> FEATURE:
<223> OTHER INFORMATION: Synthetic construct

<400> SEQUENCE: 126

Gly Glu Gly Gly Gly Glu Gly
1               5

<210> SEQ ID NO 127
<211> LENGTH: 7
<212> TYPE: PRT
<213> ORGANISM: Artificial Sequence
<220> FEATURE:
<223> OTHER INFORMATION: Synthetic construct

<400> SEQUENCE: 127

Ala Ala Ala Leu Ala Ala Ala
1               5

<210> SEQ ID NO 128
<211> LENGTH: 245
<212> TYPE: PRT
<213> ORGANISM: Artificial Sequence
<220> FEATURE:
<223> OTHER INFORMATION: Synthetic construct

<400> SEQUENCE: 128

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Lys Trp Val Lys Gln Ser His Gly Lys Asn Leu Glu Trp Ile
        35                  40                  45

Gly Leu Ile Asn Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Asp Asp Ser Ala Val Tyr Tyr Cys
                85                  90                  95

Ala Arg Glu Gly Asp Tyr Asp Gly Ala Met Asp Tyr Trp Gly Gln Gly
            100                 105                 110

Thr Ser Val Thr Val Ser Gly Gly Gly Ser Gly Gly Gly Gly Ser
        115                 120                 125

Gly Gly Gly Gly Ser Gly Gly Gly Ser Gly Gly Ser Asp Ile Gln
    130                 135                 140

Met Thr Gln Ser Pro Ser Ser Leu Ser Ala Ser Leu Gly Gly Lys Val
145                 150                 155                 160

Thr Ile Thr Cys Lys Ser Ser Gln Asp Ile Asn Lys Tyr Ile Ala Trp
                165                 170                 175

Tyr Gln His Lys Pro Gly Lys Gly Pro Gly Leu Leu Ile His Tyr Thr
            180                 185                 190

Ser Thr Leu Gln Pro Gly Ile Pro Ser Arg Phe Ser Gly Ser Gly Ser
        195                 200                 205

Gly Arg Asp Tyr Ser Phe Ser Ile Ser Asn Leu Asp Pro Glu Asn Ile
    210                 215                 220

Ala Ala Tyr Tyr Cys Leu Gln Tyr Asp Asn Leu Tyr Thr Phe Gly Gly
225                 230                 235                 240

Gly Thr Arg Leu Glu
                245
```

```
<210> SEQ ID NO 129
<211> LENGTH: 249
<212> TYPE: PRT
<213> ORGANISM: Artificial Sequence
<220> FEATURE:
<223> OTHER INFORMATION: Synthetic construct

<400> SEQUENCE: 129

Leu Glu Ser Gly Gly Gly Leu Val Gln Pro Gly Gly Ser Leu Arg Leu
1               5                   10                  15

Ser Cys Ala Gly Ser Gly Phe Thr Phe Ser Ser Tyr Ala Met Ser Trp
            20                  25                  30

Val Arg Gln Ala Pro Gly Lys Gly Leu Glu Trp Val Ser Ser Ile Ser
        35                  40                  45

Gly Ser Gly Gly Ser Thr Tyr Tyr Ala Asp Ser Val Lys Gly Arg Phe
    50                  55                  60

Thr Ile Ser Arg Asp Asn Ser Lys Lys Thr Leu Tyr Leu Gln Met Asn
65                  70                  75                  80

Ser Leu Arg Ala Glu Asp Thr Ala Val Tyr Tyr Cys Ala Arg Lys Arg
                85                  90                  95

Gly Arg Thr Thr Val Ser Trp Gly Leu Val Tyr Phe Asp Tyr Trp Gly
            100                 105                 110

Gln Gly Thr Val Val Thr Val Ser Ser Gly Gly Gly Ser Gly Gly Gly
        115                 120                 125

Gly Gly Ser Gly Gly Gly Ser Gly Gly Gly Ser Gly Gly Ser
    130                 135                 140

Glu Leu Thr Gln Ser Pro Gly Thr Leu Ser Leu Ser Pro Gly Glu Arg
145                 150                 155                 160

Ala Thr Leu Ser Cys Arg Ala Ser His Ser Val Ser Arg Ala Tyr Leu
                165                 170                 175

Ala Trp Tyr Gln Gln Lys Pro Gly Gln Ala Pro Arg Leu Leu Ile Tyr
            180                 185                 190

Gly Thr Ser Ser Arg Ala Thr Gly Ile Pro Asp Arg Phe Ser Gly Ser
        195                 200                 205

Gly Ser Gly Thr Asp Phe Thr Leu Thr Ile Ser Arg Leu Glu Pro Glu
    210                 215                 220

Asp Phe Ala Val Tyr Tyr Cys Gln Gln Tyr Gly Gly Ser Pro Trp Phe
225                 230                 235                 240

Gly Gln Gly Thr Lys Val Glu Leu Lys
                245

<210> SEQ ID NO 130
<211> LENGTH: 251
<212> TYPE: PRT
<213> ORGANISM: Artificial Sequence
<220> FEATURE:
<223> OTHER INFORMATION: Synthetic construct

<400> SEQUENCE: 130

Leu Glu Gln Ser Gly Gly Gly Val Val Gln Pro Gly Gly Ser Leu Arg
1               5                   10                  15

Leu Ser Cys Thr Ala Ser Gly Phe Thr Phe Ser Ser Tyr Gly Met His
            20                  25                  30

Trp Val Arg Gln Ala Pro Gly Lys Gly Leu Glu Trp Val Thr Phe Ile
        35                  40                  45

Arg Tyr Asp Gly Ser Ser Lys Tyr Ser Ala Asp Ser Val Lys Gly Arg
```

```
            50                  55                  60
Phe Thr Ile Ser Arg Asp Asn Ser Lys Asn Thr Leu Phe Leu Gln Met
 65                  70                  75                  80

Asn Ser Leu Arg Ala Glu Asp Thr Ala Val Tyr Tyr Cys Ala Arg Ala
                 85                  90                  95

Arg Trp Arg Asp Tyr Tyr Tyr Met Asp Val Trp Gly Lys Gly Thr
            100                 105                 110

Thr Val Thr Val Ser Ser Gly Gly Gly Gly Ser Gly Gly Gly Gly Ser
            115                 120                 125

Gly Gly Gly Gly Ser Gly Gly Gly Ser Gly Gly Ser Glu Leu Thr
            130                 135                 140

Gln Glu Pro Ser Val Ser Gly Ala Pro Gly Gln Arg Val Thr Ile Ser
145                 150                 155                 160

Cys Thr Gly Ser Ser Ser Asn Ile Gly Ala Gly Tyr Asp Val His Trp
                165                 170                 175

Tyr Gln Gln Leu Pro Gly Thr Ala Pro Lys Leu Leu Ile Tyr Gly Asn
                180                 185                 190

Ser Asn Arg Pro Ser Gly Val Pro Asp Arg Phe Ser Gly Ser Lys Ser
                195                 200                 205

Gly Thr Ser Ala Ser Leu Ala Ile Thr Gly Leu Gln Ala Glu Asp Glu
            210                 215                 220

Ala Asp Tyr Tyr Cys Gln Ser Tyr Asp Ser Ser Leu Ser Gly Val Val
225                 230                 235                 240

Phe Gly Gly Gly Thr Lys Leu Thr Val Leu Gly
                245                 250

<210> SEQ ID NO 131
<211> LENGTH: 252
<212> TYPE: PRT
<213> ORGANISM: Artificial Sequence
<220> FEATURE:
<223> OTHER INFORMATION: Synthetic construct

<400> SEQUENCE: 131

Glu Val Gln Leu Val Glu Ser Gly Gly Gly Leu Val Gln Pro Gly Gly
 1               5                  10                  15

Ser Leu Arg Leu Ser Cys Ser Ala Ser Gly Phe Thr Phe Ser Ser Tyr
                20                  25                  30

Ala Met His Trp Val Arg Gln Ala Pro Gly Lys Gly Leu Glu Tyr Val
             35                  40                  45

Ser Ala Ile Ser Ser Asn Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Ser Ser Leu Arg Ala Glu Asp Thr Ala Val Tyr Tyr Cys
                 85                  90                  95

Val Lys Ile Thr Gly Ala Tyr Ser Ser Trp Tyr Tyr Asp Asn Trp
            100                 105                 110

Phe Asp Pro Trp Gly Gln Gly Thr Leu Val Thr Val Ser Ser Gly Gly
            115                 120                 125

Gly Gly Ser Gly Gly Gly Gly Ser Gly Gly Gly Gly Ser Gly Gly Ser
            130                 135                 140

Ser Tyr Glu Leu Thr Gln Pro Pro Ser Val Ser Val Ser Pro Gly Gln
145                 150                 155                 160

Thr Ala Ser Ile Thr Cys Ser Gly Asp Lys Leu Gly Asp Lys Tyr Ala
```

```
                165                 170                 175
Cys Trp Tyr Gln Gln Lys Pro Gly Gln Ser Pro Val Leu Val Ile Tyr
            180                 185                 190

Gln Asp Ser Lys Arg Pro Ser Gly Ile Pro Glu Arg Phe Ser Gly Ser
        195                 200                 205

Asn Ser Gly Asn Thr Ala Thr Leu Thr Ile Ser Gly Thr Gln Ala Met
    210                 215                 220

Asp Glu Ala Asp Tyr Tyr Cys Gln Ala Trp Asp Ser Ser Thr Ala Val
225                 230                 235                 240

Phe Gly Gly Gly Thr Lys Leu Thr Val Leu Gly Gln
                245                 250

<210> SEQ ID NO 132
<211> LENGTH: 247
<212> TYPE: PRT
<213> ORGANISM: Artificial Sequence
<220> FEATURE:
<223> OTHER INFORMATION: Synthetic construct

<400> SEQUENCE: 132

Glu Val Gln Leu Val Glu Ser Gly Gly Gly Val Val Gln Pro Gly Gly
1               5                   10                  15

Ser Leu Arg Leu Phe Cys Ala Ala Ser Gly Phe Thr Phe Asp Gly Tyr
            20                  25                  30

Ala Met His Trp Val Arg Gln Ala Pro Gly Lys Gly Leu Glu Trp Val
        35                  40                  45

Ser Leu Ile Ser Gly Asp Gly Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Lys Val Thr Thr Ile Tyr Asp Arg Phe Asp Ile Trp Gly
            100                 105                 110

Gln Gly Thr Met Val Thr Val Ser Ser Gly Gly Gly Gly Ser Gly Gly
        115                 120                 125

Gly Gly Ser Gly Gly Gly Ser Gly Gly Ser Asp Ile Gln Met Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Gly Ile Ser Asn Tyr Leu Ala Trp Tyr Gln
                165                 170                 175

Gln Lys Pro Gly Lys Val Pro Lys Ser Leu Ile Tyr Ala Ala Ser Thr
            180                 185                 190

Leu Gln Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Val Ala Thr
    210                 215                 220

Tyr Tyr Cys Gln Lys Tyr Asn Ser Ala Pro Arg Thr Phe Gly Pro Gly
225                 230                 235                 240

Thr Lys Leu Glu Ile Lys Arg
                245

<210> SEQ ID NO 133
<211> LENGTH: 243
<212> TYPE: PRT
```

<213> ORGANISM: Artificial Sequence
<220> FEATURE:
<223> OTHER INFORMATION: Synthetic construct

<400> SEQUENCE: 133

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Thr Ile Ile Thr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Ser Ser Glu Ala Phe Asp Ile Trp Gly Gln Gly Thr
            100                 105                 110

Met Val Thr Val Ser Leu Gly Gly Gly Gly Ser Gly Gly Gly Gly Ser
        115                 120                 125

Gly Gly Gly Gly Ser Gly Gly Ser Ser Tyr Glu Leu Thr Gln Pro Ser
    130                 135                 140

Ser Val Ser Val Ser Pro Gly Gln Thr Ala Arg Ile Thr Cys Ser Gly
145                 150                 155                 160

Asp Leu Leu Ala Lys Lys Tyr Ala Arg Trp Phe Gln Gln Lys Pro Gly
                165                 170                 175

Gln Ala Pro Ile Leu Val Ile Phe Lys Asp Thr Glu Arg Pro Ser Gly
            180                 185                 190

Ile Pro Glu Arg Phe Ser Gly Ser Ser Ser Gly Thr Thr Val Thr Leu
        195                 200                 205

Thr Ile Ser Gly Ala Gln Val Glu Asp Glu Ala Asp Tyr Tyr Cys Tyr
    210                 215                 220

Ser Ala Ser Asp Asn Asn Gly Arg Val Phe Gly Gly Gly Thr Lys Leu
225                 230                 235                 240

Thr Val Leu
```

<210> SEQ ID NO 134
<211> LENGTH: 256
<212> TYPE: PRT
<213> ORGANISM: Artificial Sequence
<220> FEATURE:
<223> OTHER INFORMATION: Synthetic construct

<400> SEQUENCE: 134

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Lys Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Leu Thr Ile Ser Arg Asp Ser Ser Lys Asn Thr
65                  70                  75                  80
```

```
Leu Tyr Leu Arg Met Asn Ser Leu Lys Thr Glu Asp Thr Ala Val Tyr
                85                  90                  95

Tyr Cys Thr Thr Gly Ile Thr Met Ile Ile Val Val Ile Thr Thr Ser
            100                 105                 110

Ser Lys Arg Thr Ser Phe Glu Tyr Trp Gly Gln Gly Thr Leu Val Thr
        115                 120                 125

Val Ser Ser Gly Gly Gly Gly Ser Gly Gly Gly Ser Gly Gly Gly
    130                 135                 140

Gly Ser Gly Gly Ser Asp Ile Gln Met Thr Gln Ser Pro Ser Ser Leu
145                 150                 155                 160

Ser Ala Ser Val Gly Asp Arg Val Thr Ile Thr Cys Arg Ala Ser Gln
            165                 170                 175

Ser Ile Ser Asn Tyr Leu Asn Trp Tyr Gln Gln Lys Pro Gly Lys Ala
        180                 185                 190

Pro Asn Leu Leu Ile Tyr Ala Ala Ser Ser Leu Gln Ser Gly Val Pro
    195                 200                 205

Ser Arg Phe Ser Gly Ser Gly Ser Gly Thr Asp Phe Thr Leu Thr Ile
    210                 215                 220

Ser Gly Leu Gln Ala Glu Asp Phe Ala Thr Tyr Tyr Cys Gln Gln Ser
225                 230                 235                 240

Tyr Ser Ala Leu Thr Phe Gly Pro Gly Thr Lys Val Asp Ile Arg Arg
                245                 250                 255

<210> SEQ ID NO 135
<211> LENGTH: 229
<212> TYPE: PRT
<213> ORGANISM: Artificial Sequence
<220> FEATURE:
<223> OTHER INFORMATION: Synthetic construct

<400> SEQUENCE: 135

Gly Leu Val Lys Pro Ser Gln Thr Leu Ser Leu Thr Cys Ala Ile Ser
1               5                   10                  15

Gly Asp Ser Val Ser Ser Asn Ser Ala Ala Trp Asn Cys Ile Arg Pro
            20                  25                  30

Val Pro Ser Arg Gly Leu Glu Trp Leu Gly Arg Thr Thr Tyr Arg Ser
        35                  40                  45

Lys Trp Tyr Asn Asp Tyr Ala Val Ser Val Lys Ser Arg Ile Thr Ile
    50                  55                  60

Asn Pro Asp Thr Ser Lys Asn Gln Phe Ser Leu Gln Leu Asn Ser Val
65                  70                  75                  80

Thr Pro Glu Asp Thr Ala Val Tyr Tyr Cys Ala Ser Thr Thr Leu Asn
                85                  90                  95

Trp Gly Tyr Glu Lys Asp Asp Ala Phe Asp Ile Trp Gly Gln Gly Thr
            100                 105                 110

Met Val Thr Val Ser Ser Gly Gly Gly Gly Ser Gly Gly Gly Gly Ser
        115                 120                 125

Gly Gly Gly Gly Ser Gly Gly Ser Gln Ala Val Leu Thr Gln Pro Ala
    130                 135                 140

Ser Leu Ser Ala Ser Pro Gly Ala Ser Ala Ser Leu Thr Cys Thr Leu
145                 150                 155                 160

Arg Ser Gly Ile Asn Val Cys Thr Pro Arg Ile Tyr Trp Gln Gly Ser
                165                 170                 175

Gly Val Pro Ser Arg Phe Ser Gly Ser Lys Asn Ala Ser Ala Asn Ala
            180                 185                 190
```

Gly Ile Leu Leu Ile Ser Gly Leu Gln Ser Glu Asp Glu Ala Asp Tyr
        195                 200                 205

Tyr Cys Met Ile Trp His Ser Ser Ala Leu Val Phe Gly Gly Gly Thr
210                 215                 220

Lys Leu Thr Val Leu
225

<210> SEQ ID NO 136
<211> LENGTH: 244
<212> TYPE: PRT
<213> ORGANISM: Artificial Sequence
<220> FEATURE:
<223> OTHER INFORMATION: Syntehtic construct

<400> SEQUENCE: 136

Leu Glu Ser Gly Gly Gly Leu Val Gln Pro Gly Gly Ser Leu Arg Leu
1               5                   10                  15

Ser Cys Ala Gly Ser Gly Phe Thr Phe Ser Ser Tyr Ala Met Ser Trp
            20                  25                  30

Val Arg Gln Ala Pro Gly Lys Gly Leu Glu Trp Val Ser Ser Ile Ser
        35                  40                  45

Gly Ser Gly Gly Ser Thr Tyr Tyr Ala Asp Ser Val Lys Gly Arg Phe
    50                  55                  60

Thr Ile Ser Arg Asp Asn Ser Lys Lys Thr Leu Tyr Leu Gln Met Asn
65                  70                  75                  80

Ser Leu Arg Ala Glu Asp Thr Ala Val Tyr Tyr Cys Ala Arg Lys Arg
                85                  90                  95

Gly Arg Thr Thr Val Ser Trp Gly Leu Val Tyr Phe Asp Tyr Trp Gly
            100                 105                 110

Gln Gly Thr Val Val Thr Val Ser Ser Gly Gly Gly Ser Gly Gly
        115                 120                 125

Gly Gly Ser Gly Gly Gly Ser Gly Gly Ser Glu Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser His Ser Val Ser Arg Ala Tyr Leu Ala Trp Tyr Gln Gln
                165                 170                 175

Lys Pro Gly Gln Ala Pro Arg Leu Leu Ile Tyr Gly Thr Ser Ser Arg
            180                 185                 190

Ala Thr Gly Ile Pro Asp Arg Phe Ser Gly Ser Gly Ser Gly Thr Asp
        195                 200                 205

Phe Thr Leu Thr Ile Ser Arg Leu Glu Pro Glu Asp Phe Ala Val Tyr
    210                 215                 220

Tyr Cys Gln Gln Tyr Gly Gly Ser Pro Trp Phe Gly Gln Gly Thr Lys
225                 230                 235                 240

Val Glu Leu Lys

<210> SEQ ID NO 137
<211> LENGTH: 20
<212> TYPE: PRT
<213> ORGANISM: Artificial Sequence
<220> FEATURE:
<223> OTHER INFORMATION: Synthetic construct

```
<400> SEQUENCE: 137

Ala Ser Pro Ala Ala Pro Ala Pro Ala Ser Pro Ala Ala Pro Ala Pro
1               5                   10                  15

Ser Ala Pro Ala
            20

<210> SEQ ID NO 138
<211> LENGTH: 107
<212> TYPE: PRT
<213> ORGANISM: Artificial Sequence
<220> FEATURE:
<223> OTHER INFORMATION: Synthetic construct

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ser Gln
            20                  25                  30

Leu Ser Trp Tyr Gln Gln Lys Pro Gly Lys Ala Pro Lys Leu Leu Ile
        35                  40                  45

Met Trp Arg Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Gly Ala Ala Leu Pro Arg
                85                  90                  95

Thr Phe Gly Gln Gly Thr Lys Val Glu Ile Lys
                100                 105
```